United States Patent
Nazare et al.

(10) Patent No.: US 7,741,341 B2
(45) Date of Patent: Jun. 22, 2010

(54) BENZIMIDAZOLE-DERIVATIVES AS FACTOR XA INHIBITORS

(75) Inventors: Marc Nazare, Idstein (DE); Michael Wagner, Alsbach (DE); Volkmar Wehner, Sandberg (DE); Hans Matter, Langenselbold (DE); Matthias Urmann, Eschborn (DE); Kurt Ritter, Frankfurt am Main (DE)

(73) Assignee: sanofi-aventis Deutschland GmbH, Frankfurt am Main (DE)

(*) Notice: Subject to any disclaimer, the term of this patent is extended or adjusted under 35 U.S.C. 154(b) by 591 days.

(21) Appl. No.: 10/849,436

(22) Filed: May 19, 2004

(65) Prior Publication Data

US 2005/0009829 A1 Jan. 13, 2005

Related U.S. Application Data

(60) Provisional application No. 60/507,201, filed on Sep. 30, 2003.

(30) Foreign Application Priority Data

May 19, 2003 (EP) .................. 03011305

(51) Int. Cl.
A61K 31/4523 (2006.01)
C07D 401/14 (2006.01)
C07D 409/14 (2006.01)

(52) U.S. Cl. ............ 514/318; 548/309.4; 548/247; 514/378; 514/394; 514/322; 546/199; 546/193

(58) Field of Classification Search ............ 546/199; 548/309.4
See application file for complete search history.

(56) References Cited

U.S. PATENT DOCUMENTS

| | | | |
|---|---|---|---|
| 4,269,846 A | 5/1981 | Huang et al. | |
| 6,562,828 B1 | 5/2003 | Katoh et al. | |
| 6,906,084 B2 | 6/2005 | Nazaré et al. | |
| 6,953,857 B2 | 10/2005 | Nazaré et al. | |
| 7,067,665 B2 | 6/2006 | Nazaré et al. | |
| 2004/0171604 A1 | 9/2004 | Nazaré et al. | |
| 2004/0204406 A1 | 10/2004 | Nazaré et al. | |
| 2004/0235824 A1 | 11/2004 | Nazaré et al. | |
| 2005/0009827 A1 | 1/2005 | Nazaré et al. | |
| 2005/0033049 A1 | 2/2005 | Nazaré et al. | |
| 2005/0043302 A1 | 2/2005 | Nazaré et al. | |

FOREIGN PATENT DOCUMENTS

| | | |
|---|---|---|
| DE | 3828537 | 3/1990 |
| DE | 4304650 | 8/1994 |
| EP | 0 254 322 | 1/1988 |
| EP | 0987274 | 3/2000 |
| GB | 1 377 642 | 12/1974 |
| JP | 03184043 | 8/1991 |
| JP | 8295667 | 11/1996 |
| JP | 09124609 | 5/1997 |
| JP | 10182459 | 7/1998 |
| JP | 08208640 | 8/1998 |
| WO | WO 92/06711 | 4/1992 |
| WO | WO 95/29189 | 11/1995 |
| WO | WO 98/12800 | 5/1996 |
| WO | 97/47651 | 12/1997 |
| WO | WO01/07436 | 2/2001 |
| WO | WO 2004/022060 | 3/2004 |

OTHER PUBLICATIONS

Natsukari et al., CA 126:89269, 1997.*
An English translation of Nishi et al., JP 10-182459, 1998.*
An English translation of Tanigawa et al., JP 09-124609, 1997.*
An English translation of Natsukari et al., JP 08-295667, 1996.*
Abdelhamid, Abdou O. et al., Synthesis of Fused Ring Heterocycles from Aromatic Amines with Hydroximoyl Chlorides [1], Journal of Heterocyclic Chemistry. (1988), vol. 25. pp. 403-405.
Adang, Anton E. P. et al., A New Generation of Orally Active Antithrombotic: Comparing Strategies in the GPIIb/IIIa, Thrombin and Factor Xa Areas, Drugs of the Future, (2000). vol. 24. No. 4, pp. 369-383.
Akiko, Yamamoto, Benzimidazole Derivative, Patent Abstract of Japan Publication No. 09124609; Pub. Date Jul. 11, 1995, p. 1.
Ambinter, Ambinter: Exploratory Library, XP-002256743; Database Chemcats; Apr. 30, 2003 pp. 1-4.
Baudy, et al., Design, synthesis, SAR, and biological evaluation of highly potent benzimidazole-spaced phosphono-alpha-amino acid competitive NMDA antagonists of the AP-6 type, J. Med. Chem.; 44; 2001; pp. 1516-1529.

(Continued)

Primary Examiner—Laura L. Stockton
(74) Attorney, Agent, or Firm—Ronald G. Ort; Jiang Lin

(57) ABSTRACT

The present invention relates to compounds of the formula I,

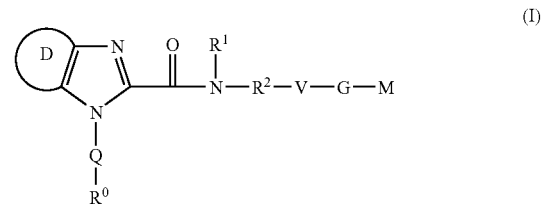

wherein $R^0$, $R^1$, $R^2$, Q, V, G and M are as defined herein. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

19 Claims, No Drawings

OTHER PUBLICATIONS

Brain, Christopher T. et al., An Intramolecular Palladium-Catalysed Aryl Amination Reaction to Produce Benzimidazoles, Tetrahedron Letters, (2002), vol. 43, pp. 1893-1895.

Breslow, et al., Synthesis Of Some Polyimidazole Ligands Related To Zinc Enzymes, J. Am. Chem. Soc. 1983, 105, 5337-5342.

Buchwald, et al., A General And Efficient Copper Catalyst For The Amidation Of Aryl Halides And the N-Arylation of Nitrogen Heterocycles, J. Am. Chem. Soc, 2001, 123, 7727-7729.

Bundgaard, Hans, Novel Chemical Approaches in Prodrug Design, Drugs of the Future, (1991), vol. 16, No. 5, pp. 443-458.

Chan, et al., New N- and O-Alylations With Phenylboronic Acids and Cupric Acetate, Tetrahedron Letters 39 (1998) 2933-2936.

Cheng, et al, Relationship Between the Inhibition Constant (KI) and the Concentation Of Inhibitor Which Causes 50 Per Cent Inhibition (150) Of An Enzymatic Reaction, Biochem. Pharmacol. (1973), 22, 3099-3108.

Collman, et al., Catalytic Activities of Cu(II) Complexes with Nitrogen-Chelating Bidentate Ligands in the Coupling of Imidazoles with Arylboronic Acids, J. Org. Chem.; 66; 2001; pp. 7892-7897.

Cozzi, et al., Ethyl 2- {[5,6-Dihydro-7-(1H-Imidazol-1-YL)-2-Naphthatenyl] Oxy]-2-Methytpropanonate As A New Potent Oxyisobutyrate Hypolipidaemic With Unusual Features, Farmaco (1987) 42, 205-218.

Crank, George et al., Photochemistry of Hetrocyclis. III Phtolysis of Various 2-Substituted Benzimidazoles, Aust. J. Chem., (1982), vol. 35. pp. 775-784.

Dannhardt, Gerd et al., Benzimidazoles as NMDA Glycine-Site Antagonists: Study on the Structural Requirements in 2-Position of the Ligand, Arch. Pharm. Pharm. Med. Chem., pp. 123-129, 2000.

Fleisher, David et al., Improved Oral Drug Delivery: Solubility Limitations Overcome by the Use of Prodrugs, Advanced Drug Delivery Reviews, (1996), vol. 19, pp. 115-130.

Fuchikami, et al., A Novel and Convenient Method for Trifluoromethylation of Organic Halides Using CF3SiR'3/KF/Cu(I) System, Tetrahedron Lett., 1991, 32(1), 91-94.

Goker, et al., Synthesis and Antimicrobial Activity of Some New 2-Phenyl-N-substituted Carboxamido-1H-benzimidazole Derivatives, Arch. Pharm. Pharm. Med. Chem.; 344; 2001; pp. 148-152.

Hartwig, John, Ubergangsmetall-Katalysierte Synthese Von Arylaminen Und Arylethern Aus Arylhalogeniden Und—Triflaten: Anwendungen Und Reaktionsmechanismus, Angew. Chem., 1998, 110, 2154-2177.

Hartwig, et al., Room-Temperature Palladium-Catalyzed Amination of Aryl Bromides And Chlorides And Extended Scope of Aromatic C-N Bond Formation With a Commercial Ligand, J. Org. Chem. (1999) 64, 5575-5580.

Holan, G. et al., 2-Trihalogenomethylbenzazoles, Part I Formation, Journal of Chemical Society. (1967), pp. 20-25.

Holan, G. et al., 2-Trihalogenomethylbenzazoles. Part II. Reactions of 2-Trihalogenomethylbenzimidazoles with Ammonia and Amines, J. Chem. Soc., (1967). pp. 25-29.

Huang, Zhi-Tang et al., The Synthesis and Tautomedzation of Ketene Animals with Benzimidazoline Ring, Tetrahedron, (1992), vol. 48, No. 12, pp. 2325-2332.

Jones, et al., N-Multilabeled Adenine and Guanine Nucleosides. Syntheses Of [1,3,NH2-15N3]- and [2-13C-1,3,NH2-15N3]-Labeled Adenosine, Guanosine, 2'-Deoxyadenosine, and 2'-Deoxyguanosine, J. Org. Chem. 1999, 64, 6575-6582.

Kang, et al., Copper-Catalyzed N-Arylation of Aryl Iodides With Benzamides Or Nitrogen Heterocycles In The Presence Of Ethylenediamine, Synlett, 2002, 3, 427-430.

Kwong, et al., Copper-Catalyzed Coupling Of Alkylamines And Aryl Iodides: An Efficient System Even In An Air Atmosphere, Organic Lett, 2002, 4 (4), 581-584.

Knochel, et al., Preparation Of New Polyfunctional Magnesiated Heterocycles Using A Chlorine-, Bromine-, or Iodine -Magnesium Exchange, J. Org. Chem, 2000, 65, 4618-4634.

Lam, et al., New Aryl/Heteroaryl C-N Bond Cross-coupling Reactions Via Arylboronic Acid/Cupric Acetate Arylation, Tetrahedron Letters 39 (1998) 2941-2944.

Louvet, P. et al., Novel Benzimidazoles as Ligands for the Strychnine-Insensitive N-Methyl-d-aspartate-linked Glycine Receptor, Eur. Journal Med. Chem., (1993), vol. 28, pp. 71-75.

Mann, et al., Palladium-Catalyzed C-N(sp2) Bond Formation: N-Arylation Of Aromatic And Unsaturated Nitrogen And The Reductive Elimination Chemistry Of Palladium Azolyl And Methyleneamido Complexes, J. Am. Chem. Soc. (1998), 120, 827-828.

Matter, Hans et al., Design and Quantitative Structure—Activity Relationship of 3-Amidinobenzyl-1H-indole-2-carboxamides as Potent, Nonchiral, and Selective Inhibitors of Blood Congestion Factor Xa, Journal of Medicinal Chemistry, (2002), vol. 45, pp. 2749-2769.

Mederski Werner W K R et al., N-Aryl Heterocycles via Coupling Reactions with Arylboronic Acids, Tetrahedron, 1999, vol. 55, pp. 12757-12770.

Musser, J. H. at al., A Simple One-Step Synthesis of Alkyl Benzazol-2-Carboxylates, Synthetic Communications, (1984), vol. 14, No. 10, pp. 947-953.

Nabulsi, et al., Optimizations in the preparation of the first benzimidazolyl salicylic acid derivatives., J. Org. Chem.; 56; 1991; pp. 2260-2262.

Natsukari, et al., Preparation of Heterocyclic Compounds as Cholesterol Acyltransferase, XP-002256741; Database Chemabs, Chemical Abstract Services; pp. 1-3, 1997.

Nichols, et al., 1-(2,5-Dimethoxy-4-(Trifluoromethyl)Phenyl)-2-Aminopropane: A Potent Serotonin 5-HT2A/2C Agonist. J. Med. Chem. 1994,37, 4346-4351.

Nobuyuki, Koga, CGMP Phosphodiesrerase Inhibitor, Patent Abstract of Japan Pub. No. 10182459; Pub. Date Jul. 7, 1998; p. 1.

O'Connell, et al., Convenient Synthesis Of Methyl 1-Methyl-2,4-dibromo-5-imidazoiecarboxylate, Synthesis 1988, 767-771.

Ohmori, et al., Novel AMPA Receptor Antagonists: Synthesis and Structure-Activity Relationships of 1-Hydroxy-7-(1H-imidazol-1-yl)-6-nitro-2,3(1H,4H)-quinoxalinedione and Related Compounds, J. Med. Chem.; 39; 1996; pp. 3971-3979.

Ohta, et al., Total Synthesis Of Nortopsentins A-D, Marine Alkaloids, Chem. Pharm. Bull. 44(10) 1831-1839, 1996.

Old David W et al., Efficient Palladium-Catalyzed N-Arylation of Indoles, Organic Letters, 2000, vol. 2, No. 10, pp. 1403-1406.

Orjales, et al., Benzimidazole-2-carboxlic acid amides and esters: a new structural class of 5-HT3 ligands, Eur. J. Med. Chem.; 34; 1999; pp. 415-422.

Ostrem James A et al., Discovery of a Novel, Potent, and Specific Family of Factor Xa inhibitors via Combinatorial Chemistry, Biochemistry, 1998, vol. 37, pp. 1053-1059.

Otava, Otava Chemical Collection, XP-002256742; Database Chemcats; Apr. 21, 2003; pp. 1-2.

Petyunin, P. A. et al., Synthesis of Benzimidazole-2-Carboxylic Acid Amides from o-Phenylenediamine and Oxamic Acid Esters, Khimiya Geterotsiklicheskikh Soedinenii, (1982), No. 5, pp. 684-686.

Qing, et al., First Synthesis Of Ortho-Trifluoromethylated Aryl Triflates, J. Chem Soc. Perkin Trans. I, 1997, 20, 3053-3057.

Reissert, et al., Ueber einige aus 2-Amido-4-nitro-diphenylamin erhaltliche Chinoxalin-und Benzimidazol-Verbindungen, Chem. Ber.; Dec. 12, 1904; 38; pp. 90-104.

Sakamoto, et al., Palladium-Catalyzed Cyanation Of Aryl and Heterozuyl Iodides With Copper (I) Cyanide, J. Chem. Soc. Perkin Trans I, 1999, 2323-2326.

Segel Irwin H, Behavior and Analysis of Rapid Equilibrium and Steady-State Enzyme Systems, Enzyme Kinetics, 1975, John Wiley & Sons, New York, pp. 100-125.

Sessler, et al., Self-Assembled Helices From 2,2'-Biimidazoles, Chem. Eur. J, 2001, 7(3), 721-729.

Shi, et al., A Practical Synthesis Of 2-Butyl-4-(5)-Chloro-5(4)-Hydroxymethyl-1H-Imidazole, Synthetic Communications, 1993, 23(18), 2623-2630.

Su, et al., Methyl Chlorodifluoroacetate A Convenient Trifluoromethylating Agent, Tetrahedron Letters, (1991), 32(52), 7689-7690.

Tokmakov Gennadii P et al., Rearrangement of 1-Arylindoles to 5H-Dibenz[b,f]azepines, Tetrahedron, 1995, vol. 51, No. 7. pp. 2091-2098.

Umemoto, et al., Power And Structure-Variable Fluorinating Agents. The N-Fluoropyridinium Salt System, J. Am. Chem. Soc. (1990), 112, 8563-8575.

Unangst Paul C et al., Synthesis of Novel 1-Phenyl-1H-indole-2-carboxylic Acids. I. Utilization of Ullmann and Dieckmann Reactions for the Preparation of 3-Hydroxy, 3-Alkoxy, and 3-Alkyl Derivatives, J. Heterocyclic Chem., 1987, vol. 24, pp. 811-815.

Usherwood, Edith Hilda et al., The Oxime of Mesozamide (isoNitrosomalonamide) and Some Allied Compounds. Part II. Ring Formation in the Tetra-substituted Series, Journal of The Chemical Society, (1923), vol. 23, pp. 1069-1089.

Wolfe, et al., Simple, Efficient Catalyst System For The Palladium-Catalyzed Amination Of Aryl Chlorides, Bromides, and Triflates, J. Org. Chem., 2000, 65, 1158-1174.

Yamada, et al., 2-[(2-Aminobenzyl)sulfinyl]-1-(2-pyridyl)-1,4,5,6-tetrahydrocyclopent[d]imidazoles As A Novel Class Of Gastric H+/K+−ATPase Inhibitors, J. Med. Chem., 1996, 39, 598-604.

Yasushi, Ichijima, Silver Halide Color Photographic Sensitive Material, Patent Abstract of Japan Publication No. 03184043; Pub. Date Dec. 8, 1991, p. 1.

Young, Jonathan R. et al., 2-Arylindoles as Gonadotropin Releasing Hormone (GnRH) Antagonists: Optimization of the Tryptamine Side Chain, Bioorganic & Medicinal Chemistry Letters, (2002), vol. 12, pp. 827-832.

Yukawa, Hirotaka et al., Practical Synthetic Route To Benzimidazole-2-Carboxylate Derivatives Via 12-Induced Overall 5-ENDO-TRIG Cyclization, Bioorganic & Medicinal Chemistry Letters, (1997), vol. 7, No. 10, pp. 1267-1268.

Yun, et al., Polymer-assisted parallel solution phase synthesis of substituted benzimidazoles, Synlett, 2002; 5; pp. 739-742.

Yang, et al., Palladium-Catalyzed Amination Of Aryl Halides and Sulfonates, J. Organomet. Chem., 1999, 576, 125.

Garuti, et al., Synthesis and antiviral assays of some 2-substituted benzimidazole-N-carbamates, FARMACO, 55(1); 2000; pp. 35-39.

U.S. Appl. No. 11/467,277, filed Aug. 25, 2006, Bauer et al.

U.S. Appl. No. 11/469,513, filed Sep. 1, 2006, Urmann et al.

* cited by examiner

BENZIMIDAZOLE-DERIVATIVES AS FACTOR XA INHIBITORS

This application claims the benefit of U.S. Provisional Application No. 60/507,201, filed Sep. 30, 2003.

FIELD OF THE INVENTION

The present invention relates to compounds of the formula I,

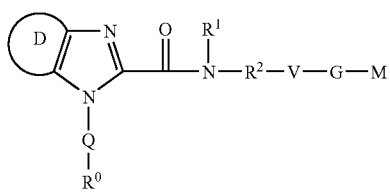

in which $R^0$, $R^1$, $R^2$, Q, V, G and M have the meanings indicated below. The compounds of the formula I are valuable pharmacologically active compounds. They exhibit a strong anti-thrombotic effect and are suitable, for example, for the therapy and prophylaxis of cardio-vascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of athereoslerotic plaque a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383). Low molecular weight, factor Xa-specific blood clotting inhibitors that are effective but do not cause unwanted side effects have been described, for example, in WO-A-95/29189. However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors The present invention satisfies the above needs by providing novel compounds of the formula I, which exhibit better factor Xa and/or factor VIIa inhibitory activity and are favorable agents with high bioavailability.

A process for the preparation of benzoimidazole-anilide-derivatives is described in DE 3708292. Said compounds were prepared under strong acidic conditions and with yields of about 50%. Similar processes are also described in DE 4304650 or in the Journal of Medicinal Chemistry (1984, Vol. 27, No. 2, pages 121-125), wherein the compounds were prepared in the presence of sodium bicarbonate. These conditions gave the products in only low yields.

Another object of the present invention is to find a process for the amination of the compounds of the formula V in high yields and purity.

SUMMARY OF THE INVENTION

The present invention relates to a compound of the formula I,

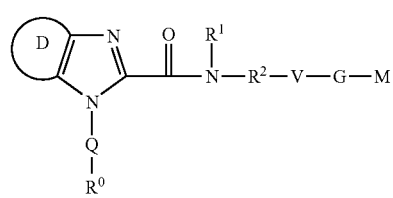

wherein
$R^0$ is 1) a monocyclic or bicyclic 6- to 14-membered aryl, wherein aryl is mono-, di- or trisubstituted independently of one another by R8,
2) a monocyclic or bicyclic 4- to 15-membered heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or methoxy,
10) —O—($C_1$-$C_8$)-alkyl, wherein alkyl is unsubstituted or mono-, di- or trisubstituted independently of one another by halogen, $NH_2$, —OH or methoxy,
11) —$SO_2$—$CH_3$ or
12) —$SO_2$—$CF_3$, provided that R8 is at least one halogen, —C(O)—$NH_2$ or —O—($C_1$-$C_8$)-alkyl residue, if $R^0$ is a monocyclic or bicyclic 6- to 14-membered aryl, provided that R8 is not a —O—($C_1$-$C_8$)-alkyl residue, if $R^0$ and V are a monocyclic or bicyclic 6- to 14-membered aryl, the substructure

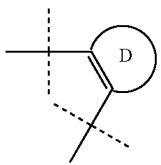

in formulae I is a 4- to 8 membered saturated, partially unsaturated or aromatic cyclic group containing zero, 1, 2, 3 or 4 heteroatoms chosen from nitrogen, sulfur or oxygen and is unsubstituted or substituted 1, 2, 3, 4, 5 or 6 times by R3 or substituted 1 or 2 times by =O, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, methylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —($C_3$-$C_6$)-cycloalkylen, wherein cycloalkylen is unsubstituted or mono-, di- or trisubstituted independently of one another by halogen, —$NH_2$ or —OH;

$R^1$ is hydrogen, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—$R^{15}$, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, $R^{4'}$ and $R^{5'}$ are independent of one another are identical or different and are hydrogen or —($C_1$-$C_4$)-alkyl, $R^2$ is a direct bond, or —($C_1$-$C_4$)-alkylene, or $R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$, wherein $R^{18}$ and $R^{21}$ are independently from each other hydrogen, —($C_1$-$C_3$)-perfluoroalkyl or —($C_1$-$C_6$)-alkyl, V is 1) a 6- to 14-membered aryl, wherein aryl is unsubstituted or mono-, di- or trisubstituted independently of one another by R14, or 2) a heterocyclyl out of the group acridinyl, 8-aza-bicyclo [3.2.1]oct-3-yl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, 1λ6-thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, $-(CH_2)_m-NR^{10}-SO_2-NR^{10}-(CH_2)_n-$, $-(CH_2)_m-CH(OH)-(CH_2)_n-$, $-(CH_2)_m-$, $-(CH_2)_m-O-(CH_2)_n-$, $-(CH_2)_m-C(O)-NR^{10}-(CH_2)_n-$, $-(CH_2)-SO_2-(CH_2)_n-$, $-(CH_2)_m-NR^{10}-C(O)-NR^{10}-(CH_2)_n-$, $-(CH_2)_m-NR^{10}-C(O)-(CH_2)_n-$, $-(CH_2)_m-C(O)-(CH_2)_n-$, $-(CH_2)-S-(CH_2)_n-$, $-(CH_2)_m-SO_2-NR^{10}-(CH_2)_n-$, $-(CH_2)_m-NR^{10}-SO_2-(CH_2)_n-$, $-(CH_2)_m-NR^{10}-$, $-(CH_2)_m-O-C(O)-NR^{10}-(CH_2)_n-$ or $-(CH_2)_m-NR^{10}-C(O)-O-(CH_2)_n-$, n and m are independently of one another identical or different and are the integers zero, 1, 2, 3, 4, 5 or 6, M is 1) hydrogen,
2) $-(C_1-C_8)$-alkyl, wherein alkyl is unsubstituted or mono-, di- or trisubstituted independently of one another by R14,
3) $-C(O)-N(R11)-R12$,
4) $-(CH_2)_m-NR^{10}$,
5) a 6- to 14-membered aryl, wherein aryl is unsubstituted or mono-, di- or trisubstituted independently of one another by R14,
6) a monocyclic or bicyclic 4- to 15-membered heterocyclyl, wherein heterocyclyl is unsubstituted or mono-, di- or trisubstituted independently of one another by R14,
7) $-(C_3-C_8)$-cycloalkyl, wherein said cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R3 is 1) hydrogen,
2) halogen,
3) $-(C_1-C_4)$-alkyl, wherein alkyl is unsubstituted or mono-, di- or trisubstituted independently of one another by R13,
4) $-(C_1-C_3)$-perfluoroalkyl,
5) phenyl, wherein phenyl is unsubstituted or mono-, di- or trisubstituted independently of one another by R13,
6) $-(C_0-C_4)$-alkylene-O—R19, wherein R19 is
  a) hydrogen,
  b) $-(C_1-C_4)$-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) $-CF_3$, or
  e) $-CHF_2$,
7) $-NO_2$,
8) $-CN$,
9) $-SO_s-R^{11}$, wherein s is 1 or 2,
10) $-SO_t-N(R^{11})-R^{12}$, wherein t is 1 or 2,
11) $-(C_0-C_4)$-alkylene-C(O)—$R^{11}$,
12) $-(C_0-C_4)$-alkylene-C(O)—O—$R^{11}$,
13) $-(C_0-C_4)$-alkylene-C(O)—N($R^{11}$)—$R^{12}$,
14) $-(C_0-C_4)$-alkylene-N($R^{11}$)—$R^{12}$,
15) $-NR^{10}-SO_2-R^{10}$,
16) $-S-R^{10}$,
17) $-(C_0-C_2)$alkylene-C(O)—O—$(C_2-C_4)$-alkylene-O—C(O)—$(C_1-C_4)$-alkyl,
18) $-C(O)-O-C(R15, R16)-O-C(O)-R17$,
19) $-(C_0-C_2)$alkylene-C(O)—O—$(C_2-C_4)$-alkylene-O—C(O)—O—$(C_1-C_6)$-alkyl,
20) $-C(O)-O-C(R15, R16)-O-C(O)-O-R17$,
21) $-(C_0-C_4)$-alkylene-$(C_6-C_{14})$-aryl, wherein aryl is mono-, di- or trisubstituted independently of one another by R13,
22) $-(C_0-C_4)$-alkylene-$(C_4-C_{15})$-heterocyclyl, wherein heterocyclyl is unsubstituted or mono-, di- or trisubstituted independently of one another by R13
23) $-(C_0-C_4)$-alkylene-$(C_3-C_8)$-cycloalkyl, wherein cycloalkyl is unsubstituted or mono-, di- or trisubstituted independently of one another by R13,
24) $-(C_0-C_4)$-alkylene-het, wherein het is unsubstituted or mono-, di- or trisubstituted independently of one another by R13,
25) $-(C_0-C_4)$-alkylene-O—$CH_2$—$(C_1-C_3)$-perfluoro-alkylene-$CH_2$—O—$(C_0-C_4)$-alkyl,
26) $-SO_w-N(R^{11})-R^{13}$, wherein w is 1 or 2,
27) $-(C_0-C_4)$-alkylene-C(O)—N($R^{11}$)—$R^{13}$,
28) $-(C_0-C_4)$-alkylene-N($R^{11}$)—$R^{13}$, or
29) a residue from the following list

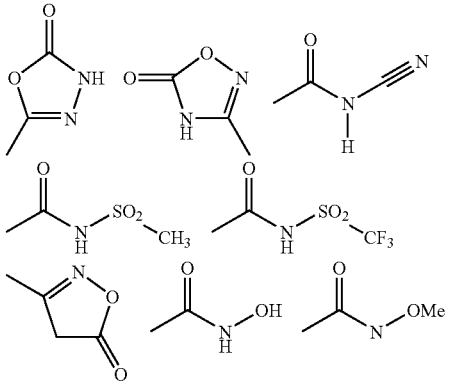

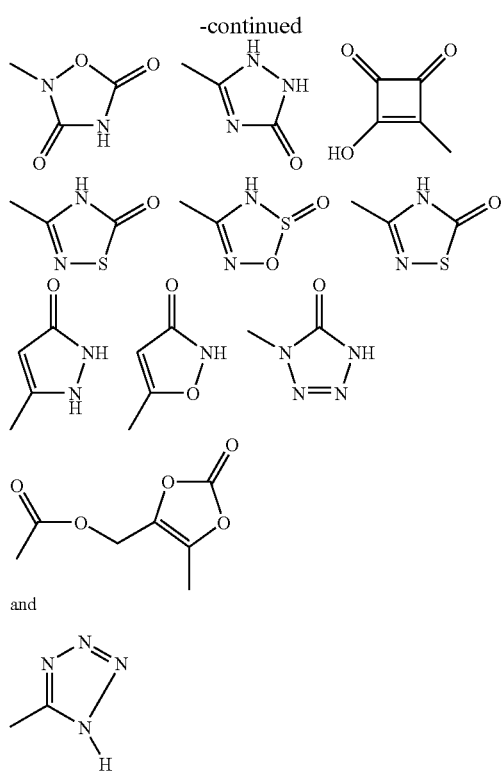

and

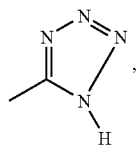

wherein Me is methyl, or if two —OR19 residues are attached to adjacent atoms they can form together with the atoms which they are attached to a 5- or 6-membered ring, which is unsubstituted or substituted one, two, three or four times by R13, R11 and R12 are independently of one another identical or different and are
1) hydrogen,
2) —($C_1$-$C_6$)-alkyl, wherein alkyl is unsubstituted or mono-, di- or trisubstituted independently of one another by R13,
3) —($C_0$-$C_6$)-alkyl-($C_3$-$C_8$)-cycloalkyl,
4) —$SO_t$—$R^{10}$, wherein t is 1 or 2,
5) —($C_0$-$C_6$)-alkyl-($C_6$-$C_{14}$)-aryl, wherein alkyl and aryl independently from one another are unsubstituted or mono-, di- or trisubstituted by R13,
6) —($C_1$-$C_3$)-perfluoroalkyl,
7) —O—$R^{17}$, or
8) —($C_0$-$C_6$)-alkyl-($C_4$-$C_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen;
wherein said heterocyclic ring is unsubstituted or mono-, di- or trisubstituted independently of one another by R13, R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_3$-$C_8$)-cycloalkyl, —($C_0$-$C_3$)-alkylene-O—$R^{10}$, —Si—($CH_3$)$_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$-$C_8$)-alkyl, —($C_1$-$C_8$)-alkoxy, phenyl, phenyloxy-, —O—$CF_3$, —($C_0$-$C_4$)-alkyl-C(O)—O—C(R15, R16)-O—C(O)—R17, —($C_1$-$C_4$)-alkoxy-phenyl, —($C_0$-$C_4$)-alkyl-C(O)—O—C(R15, R16)-O—C(O)—O—R17, —($C_1$-$C_3$)-perfluoroalkyl, —O—R15, —NH—C(O)—NH—$R^{10}$, —NH—C(O)—O—$R^{10}$, or a residue from the following list

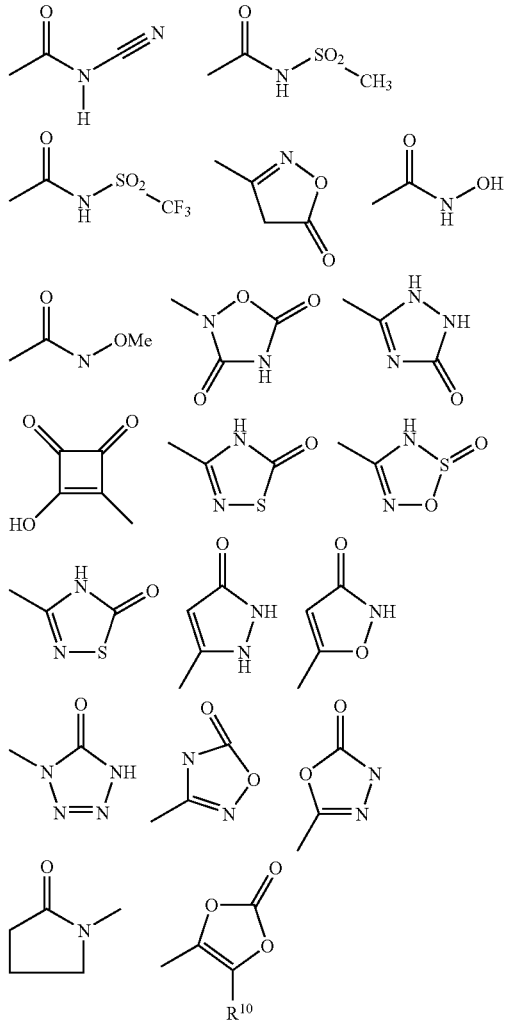

and wherein Me is methyl, or
$R^{10}$ and $R^{20}$ are independently of one another hydrogen, —($C_1$-$C_6$)-alkyl, —($C_0$-$C_4$)-alkyl-OH, —($C_0$-$C_4$)-alkyl-O—($C_1$-$C_4$)-akyl or —($C_1$-$C_3$)-perfluoroalkyl,
R15 and R16 are independently of one another hydrogen, —($C_1$-$C_6$)-alkyl, or together with the carbon atom to which they are bonded they can form a 3- to 6 membered carbocyclic ring which is unsubstituted or substituted one to three times by $R^{10}$, and
R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-

$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts.

The invention also relates to a process for producing the compound of formula IV,

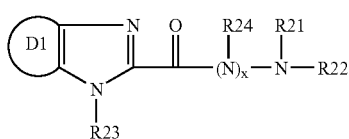

(IV)

wherein x is the integer zero or 1,

R21 and R24 are identical or different and are independent from each other
- a) hydrogen,
- b) —($C_1$-$C_4$)-alkyl, wherein alkyl is unsubstituted or substituted one to three times by R13,
- c) —($C_1$-$C_3$)-alkylene-C(O)—NH—$R^O$,
- d) —($C_1$-$C_3$)-alkylene-C(O)—O—$R^{10}$,
- e) —($C_0$-$C_4$)-alkyl-aryl, wherein aryl is a monocyclic or bicyclic 6- to 14-membered aryl and is mono-, di- or trisubstituted independently of one another by R8,
- f) —($C_0$-$C_4$)-alkyl-heteroaryl, wherein heteroaryl is a monocyclic or bicyclic 4- to 15-membered heterocyclyl, containing one, two, three or four heteroatoms chosen from nitrogen, sulphur or oxygen and is mono-, di- or trisubstituted independently of one another by R8,
- g) —($C_1$-$C_4$)-alkyl-heterocyclyl, wherein heterocyclyl is a monocyclic or bicyclic 4- to 15-membered heterocyclyl, containing one, two, three or four heteroatoms chosen from nitrogen, sulphur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulphur or oxygen, wherein heterocyclyl is unsubstituted or mono-, di- or trisubstituted independently of one another by R8,
- h) —($C_1$-$C_3$)-perfluoroalkylene,
- i) —($C_1$-$C_3$)-alkylene-S(O)—($C_1$-$C_4$)-alkyl,
- j) —($C_1$-$C_3$)-alkylene-S(O)$_2$—($C_1$-$C_3$)-alkyl,
- k) —($C_1$-$C_3$)-alkylene-S(O)$_2$—N($R^{4'}$)—$R^{5'}$,
- l) —($C_1$-$C_3$)-alkylene-O—($C_1$-$C_4$)-alkyl,
- m) —($C_0$-$C_3$)-alkylene-($C_3$-$C_8$)-cycloalkyl or
- n) —($C_0$-$C_3$)-alkylene-het, wherein het is a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14, wherein $R^O$, $R^{4'}$, $R^{5'}$, R8, $R^{10}$, $R^{13}$ and $R^{14}$ are as defined in formula I, R22 is a) hydrogen,
- b) —($C_1$-$C_4$)-alkyl, wherein alkyl is unsubstituted or substituted one to three times by R13,
- c) —($C_1$-$C_3$)-alkylene-C(O)—NH—$R^{10}$,
- d) —($C_1$-$C_3$)-alkylene-C(O)—O—$R^{10}$,
- e) —($C_0$-$C_4$)-alkyl-aryl, wherein aryl is a monocyclic or bicyclic 6- to 14-membered aryl and is mono-, di- or trisubstituted independently of one another by R8,
- f) —($C_0$-$C_4$)-alkyl-heteroaryl, wherein heteroaryl is a monocyclic or bicyclic 4- to 15-membered heterocyclyl, containing one, two, three or four heteroatoms chosen from nitrogen, sulphur or oxygen and is mono-, di- or trisubstituted independently of one another by R8,
- g) —($C_0$-$C_4$)-alkyl-heterocyclyl, wherein heterocyclyl is a monocyclic or bicyclic 4- to 15-membered heterocyclyl, containing one, two, three or four heteroatoms chosen from nitrogen, sulphur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulphur or oxygen, wherein heterocyclyl is unsubstituted or mono-, di- or trisubstituted independently of one another by R8,
- h) —($C_1$-$C_3$)-perfluoroalkylene,
- i) —($C_0$-$C_3$)-alkylene-S(O)—($C_1$-$C_4$)-alkyl,
- j) —($C_0$-$C_3$)-alkylene-S(O)$_2$—($C_1$-$C_3$)-alkyl,
- k) —($C_0$-$C_3$)-alkylene-S(O)$_2$—N($R^{4'}$)—$R^{5'}$,
- l) —($C_1$-$C_3$)-alkylene-O—($C_1$-$C_4$)-alkyl,
- m) —($C_0$-$C_3$)-alkylene-($C_3$-$C_8$)-cycloalkyl,
- n) —($C_0$-$C_3$)-alkylene-het, wherein het is a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14, or
- o) $R^2$—V-G-M, wherein $R^O$, $R^2$, $R^{4'}$, $R^{5'}$, R8, $R^{10}$, R13, R14, V, G and M are as defined in formula I, or the substructure R21-N—$R^2$—V in formula IV can form a 4- to 8-membered cyclic group, containing 1, 2, 3 or 4 heteroatoms chosen from nitrogen, sulphur or oxygen, wherein said cyclic group is unsubstituted or mono-, di- or trisubstituted independently of one another by R14, wherein the residue R14 is as defined as in formula I, R23 is a) hydrogen,
- b) —($C_1$-$C_4$)-alkyl, wherein alkyl is unsubstituted or substituted one to three times by R13,
- c) —($C_1$-$C_3$)-alkylene-C(O)—NH—$R^O$,
- d) —($C_1$-$C_3$)-alkylene-C(O)—O—$R^{10}$,
- e) a monocyclic or bicyclic 6- to 14-membered aryl, wherein aryl is mono-, di- or trisubstituted independently of one another by R8,
- f) a monocyclic or bicyclic 4- to 15-membered heterocyclyl, containing one, two, three or four heteroatoms chosen from nitrogen, sulphur or oxygen,
- g) —($C_1$-$C_3$)-perfluoroalkylene,
- h) —($C_1$-$C_3$)-alkylene-S(O)—($C_1$-$C_4$)-alkyl,
- j) —($C_1$-$C_3$)-alkylene-S(O)$_2$—($C_1$-$C_3$)-alkyl,
- k) —($C_1$-$C_3$)-alkylene-S(O)$_2$—N($R^{4'}$)—$R^{5'}$,
- l) —($C_1$-$C_3$)-alkylene-O—($C_1$-$C_4$)-alkyl,
- m) —($C_0$-$C_3$)-alkylene-($C_3$-$C_8$)-cycloalkyl,
- n) —($C_0$-$C_3$)-alkylene-het, wherein het is a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14, or
- o) -Q-$R^O$, wherein $R^0$, $R^2$, $R^{4'}$, $R^{5'}$, R8, $R^{10}$, R13, R14, Q, V, G and M are as defined in formula I, and substructure

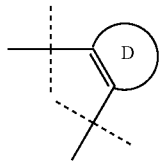

in formula IV is a 4-to 8 membered saturated, partially unsaturated or aromatic cyclic group containing zero, 1, 2, 3 or 4 heteroatoms chosen from nitrogen, sulphur or oxygen and is unsubstituted or substituted 1, 2, 3, 4, 5 or 6 times by R3, wherein R3 is as defined in formula I, which comprises reacting a compound of formula V

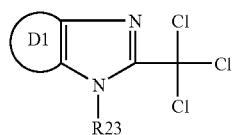

wherein R23 is as defined in formula IV and substructure

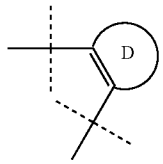

in formula V is as defined in formula IV, with a primary amine or a secondary amine in the presence of water, at least one base and at least one water-miscible organic solvent.

DETAILED DESCRIPTION OF THE INVENTION

Definition of Terms

As used above, and throughout the description of the invention, the following terms, unless otherwise indicated, shall be understood to have the following meanings.

In general, the meaning of any group, residue, heteroatom, number etc., which can occur more than once in the compounds of the formula I, is independent of the meaning of this group, residue, heteroatom, number etc. in any other occurrence. All groups, residues, heteroatoms, numbers etc., which can occur more than once in the compounds of the formula I can be identical or different.

As used herein, the term alkyl is to be understood in the broadest sense to mean hydrocarbon residues which can be linear, e.g. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—$(C_0-C_6)$-alkyl" or "—$(C_0-C_8)$-alkylene" is a hydrocarbon residues containing 1, 2, 3, 4, 5, 6, 7 or 8 carbon atoms. The term "—$C_0$-alkyl" or "—$C_0$-alkylene" is a covalent bond.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted. Examples of —$(C_3-C_8)$-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The terms "a monocyclic or bicyclic 6- to 14-membered aryl" or "—$(C_6-C_{14})$-aryl" are understood as meaning aromatic hydrocarbon radicals containing from 6 to 14 carbon atoms in the ring. Examples of —$(C_6-C_{14})$-aryl radicals are phenyl, naphthyl, for example 1-Naphthyl and 2-Naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—$(C_4-C_{15})$-heterocyclyl" refer to heterocycles in which one or more of the 4 to 15 ring carbon atoms are replaced by heteroatoms such as nitrogen, oxygen or sulfur. Examples are acridinyl, 8-aza-bicyclo[3.2.1]oct-3-yl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, such as benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

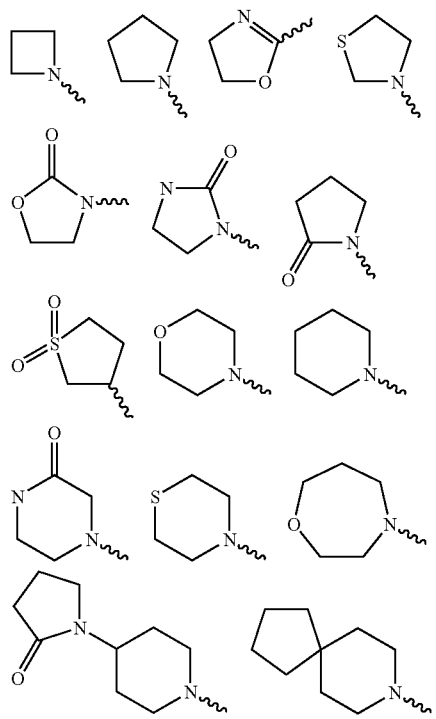

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "$R^1$—N—$R^2$—V can form a 4- to 8-membered cyclic group" or "$R^{11}$ and $R^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, 2,3 dihydroindole, imidazole, imidazoline, imidazolidine, indole, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "$R^{15}$ and $R^{16}$ together with the carbon atom to which they are bonded can form a 3- to 6 membered carbocyclic ring" refer to structures, which can be derived from compounds such as cyclopropyl, cyclobutyl, cyclopentyl or cyclohexyl.

The term "substructure

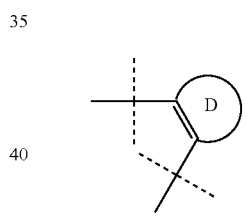

in formula I or the "substructure D" is a 4-to 8 membered saturated, partially unsaturated or aromatic cyclic group containing zero, 1, 2, 3 or 4 heteroatoms chosen from nitrogen, sulfur or oxygen" refer to structures, which can be derived from compounds such as azepane, azetidine, azetine, azocane, azocane-2-one, cyclobutyl, cyclooctane, cyclooctene, cyclopentyl, cyclohexyl, cycloheptyl, cyclooctyl, 1,2-diazepane, 1,2-diazepine, 1,3-diazepine, 1,4-diazepine, [1,4]diazocane, [1,2]diazocan-3-one, [1,3]diazocan-2-one, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxaazepane, 1,2-oxa-thiepane, 1,2-oxathiolan, 1,2-oxazine, 1,3-oxazine, 1,4-oxazine, oxazole, [1,4]oxazocane, [1,3]oxazocan-2-one, oxetan, oxocane, oxocan-2-one, piperazine, piperidine, phenyl, pyran, pyrazine, pyrazole, pyrazoline, pyrazolidine, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, thiadiazine thiadiazole, 1,2-thiazine, 1,3-thiazine, 1,4-thiazine, 1,3-thiazole, thiazole, thiazolidine, thiazoline, thietan, thiocane, thiocane-1,1-dioxide, thiocane- 1-oxide, thiocan-2-one, thiomorpholine, thiophen, thiopyran, 1,2,3-triazine, 1,2,4-triazine, 1,3,5-triazine, 1,2,3-triazole or 1,2,4-triazole.

The term "substructure D" is a 5 to 6 membered saturated, partially unsaturated or aromatic cyclic group containing zero, 1, 2, 3 or 4 heteroatoms chosen from nitrogen, sulfur or oxygen" refer to structures, which can be derived from compounds such as cyclopentyl, cyclohexyl, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxathiolan, 1,2-oxazine, 1,3-oxazine, 1,4-oxazine, oxazole, piperazine, piperidine, phenyl, pyran, pyrazine, pyrazole, pyrazoline, pyrazolidine, pyrazine, pyrazinone, pyridazine, pyridazone, pyridine, pyridone, pyrimidine, pyrimidone, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thiomorpholine, thiophen, thiopyran, tetrazine, tetrazole, 1,2,3-triazine, 1,2,4-triazine, 1,3,5-triazine, 1,2,3-triazole or 1,2,4-triazole.

The term "$R^1$ and $R^3$ together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxa-thiepane, 1,4-oxazepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The term "oxo-residue" or "=O" refers to residues such as carbonyl (—C(O)—) or nitroso (—N=O).

The fact that many of the before-listed names of heterocycles are the chemical names of unsaturated or aromatic ring systems does not imply that the, the 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The term "—($C_1$-$C_3$)-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—($C_1$-$C_3$)-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—, —$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—, —$CF_2$—$CH_2$—$CHF$—, —$CF_2$—$CF_2$—$CF_2$—, or —$CF_2$—$CF_2$—$CHF$.

Halogen is fluorine, chlorine, bromine or iodine, preferably fluorine, chlorine or bromine, particularly preferably chlorine or bromine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines) which are likewise included in the present invention.

The term "water-miscible organic solvent" is taken to mean, for example, organic solvents such as:

Tetrahydrofuran, acetonitrile, dimethylsulfoxide, dioxane, 1,2-dimethoxyethane, N,N-dimethylformamide, N-methylpyrrolidone, acetone or sulfolane.

The term "base" is taken to mean alkali metal carbonates, for example sodium bicarbonate or potassium bicarbonate, in solid form or in the form of solutions of differing concentrations. Basically all inorganic salts, particularly bicarbonates, which have a basicity comparable to sodium bicarbonate, can be used for the above described process. Also, the term "base" is taken to mean tertiary amines, such as triethylamine or diisopropylethylamine.

The term "primary amine" is taken to mean an amine which is substituted by one residue at the nitrogen atom. The term "secondary amine" is taken to mean an amine, which is substituted by two residues at the nitrogen atom.

The term

wherein x is zero" in formula IV is a covalent bond and wherein x is 1 is a —N(R24)- residue.

Patient includes both human and other mammals.

Pharmaceutically effective amount means an amount of the compound according to the invention effective in producing the desired therapeutic effect.

Preferred or Particular Embodiment

One particular embodiment of the present invention relates to a compound of the formula I, wherein $R^0$ is 1) a monocyclic or bicyclic 6- to 14-membered aryl out of the group phenyl, naphthyl, biphenylyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl, wherein heterocyclyl is selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R8, and which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1) halogen,
2) —NO$_2$,
3) —CN,
4) —C(O)—NH$_2$,
5) —OH,
6) —NH$_2$,
7) —O—CF$_3$
8) a monocyclic or bicyclic 6- to 14-membered aryl, wherein aryl is as defined above and wherein aryl is mono-, di- or trisubstituted independently of one another by halogen or —O—(C$_1$-C$_8$)-alkyl,
9) —(C$_1$-C$_8$)-alkyl, wherein alkyl is unsubstituted or mono-, di- or trisubstituted independently of one another by halogen, NH$_2$, —OH or methoxy, or
10) —O—(C$_1$-C$_8$)-alkyl, wherein alkyl is unsubstituted or mono-, di- or trisubstituted independently of one another by halogen, NH$_2$, —OH or methoxy,
11) —SO$_2$—CH$_3$ or
12) —SO$_2$—CF$_3$, provided that R8 is at least one halogen, —C(O)—NH$_2$ or —O—(C$_1$-C$_8$)-alkyl residue, if R$^0$ is a monocyclic or bicyclic 6- to 14-membered aryl, wherein aryl is as defined above, provided that R8 is not a —O—(C$_1$-C$_8$)-alkyl residue, if R$^0$ and V are a monocyclic or bicyclic 6- to 14-membered aryl, substructure D is a residue selected out of the group azetidine, azetine, azocane, azocane-2-one, cyclobutyl, cyclooctane, cyclooctene, cyclopentyl, cyclohexyl, cycloheptyl, cyclooctyl, 1,4-diazepane, 1,2-diazepine, 1,3-diazepine, 1,4-diazepine, [1,4]diazocane, [1,2]diazocan-3-one, [1,3]diazocan-2-one, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolan, 1,2-oxazine, 1,3-oxazine, 1,4-oxazine, oxazole, [1,4]oxazocane, [1,3]oxazocan-2-one, oxetan, oxocane, oxocan-2-one, piperazine, piperidine, phenyl, pyran, pyrazine, pyrazole, pyrazoline, pyrazolidine, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, thiadiazine, thiadiazole, 1,2-thiazine, 1,3-thiazine, 1,4-thiazine, 1,3-thiazole, thiazole, thiazolidine, thiazoline, thietan, thiocane, thiocane-1,1-dioxide, thiocane-1-oxide, thiocan-2-one, thiomorpholine, thiophene, thiopyran, 1,2,3-triazine, 1,2,4-triazine, 1,3,5-triazine, 1,2,3-triazole or 1,2,4-triazole and is unsubstituted or substituted 1, 2, 3, 4, 5 or 6 times by R3 or is substituted 1 or 2 times by =O, Q is a direct bond, —(C$_0$-C$_2$)-alkylene-C(O)—NR$^{10}$—, —NR$^{10}$—C(O)—NR$^{10}$—, —NR$^{10}$—C(O)—, —SO$_2$—, methylene, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—S—(CH$_2$)$_n$—, —(CH$_2$)$_m$—C(O)—(CH$_2$)$_n$—, —(CH$_2$)$_m$—SO$_2$—NR$^{10}$—(CH$_2$)$_n$—, —(CH$_2$)$_m$—NR$^{10}$—SO$_2$—(CH$_2$)$_n$—, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—O—C(O)—NR$^{10}$—(CH$_2$)$_n$—, —(C$_2$-C$_3$)-alkylene-O—(C$_0$-C$_3$)-alkylene-, —(C$_2$-C$_3$)-alkylene-S(O)—, —(C$_2$-C$_3$)-alkylene-S(O)$_2$—, —(CH$_2$)$_m$—NR$^{10}$—C(O)—O—(CH$_2$)$_n$—, —(C$_2$-C$_3$)-alkylene-S(O)$_2$—NH—(R$^{10}$)—, —(C$_2$-C$_3$)-alkylene-N(R$^{10}$)— or —(C$_0$-C$_3$)-alkylene-C(O)—O—(CH$_2$)$_m$—, wherein R$^{10}$ is as defined below, and wherein n and m are independently of one another identical or different and are the integers zero, 1, 2, 3, 4, 5 or 6, wherein the alkylene residues which are formed by —(CH$_2$)$_m$— or —(CH$_2$)$_n$— are unsubstituted or mono-, di- or trisubstituted independently of one another by halogen, —NH$_2$ or —OH; or —(C$_3$-C$_6$)-cycloalkylen, wherein cycloalkylen is unsubstituted or mono-, di- or trisubstituted independently of one another by halogen, —NH$_2$ or —OH;

R$^1$ is hydrogen, —(C$_1$-C$_4$)-alkyl, wherein alkyl is unsubstituted or substituted one to three times by R13; —(C$_1$-C$_3$)-alkylene-C(O)—NH—R$^0$, —(C$_1$-C$_3$)-alkylene-C(O)—O—R15, an aryl out of the group phenyl, naphthyl, biphenylyl, anthryl or fluorenyl, wherein aryl is mono-, di- or trisubstituted independently of one another by R8, wherein R8 is as defined above;

a monocyclic or bicyclic 4- to 15-membered heterocyclyl, which is as defined above; —(C$_1$-C$_3$)-perfluoroalkylene, —(C$_1$-C$_3$)-alkylene-S(O)—(C$_1$-C$_4$)-alkyl, —(C$_1$-C$_3$)-alkylene-S(O)$_2$—(C$_1$-C$_3$)-alkyl, —(C$_1$-C$_3$)-alkylene-S(O)$_2$—N(R$^{4'}$)—R$^{5'}$, —(C$_1$-C$_3$)-alkylene-O—(C$_1$-C$_4$)-alkyl, —(C$_0$-C$_3$)-alkylene-(C$_3$-C$_8$)-cycloalkyl, or —(C$_0$-C$_3$)-alkylene-het, wherein het is a residue selected out of the group azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, R$^{4'}$ and R$^{5'}$ are independent of one another are identical or different and are hydrogen or —(C$_1$-C$_4$)-alkyl, R$^2$ is a direct bond, R$^1$—N—R$^2$—V can form a 4- to 8-membered cyclic group selected out of the group azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$, wherein $R^{18}$ and $R^{21}$ are independently from each other hydrogen, —($C_1$-$C_3$)-perfluoroalkyl or —($C_1$-$C_6$)-alkyl, V is 1) a monocyclic or bicyclic 6- to 14-membered aryl out of the group phenyl, naphthyl, biphenylyl, anthryl or fluorenyl, wherein aryl is mono-, di- or trisubstituted independently of one another by R14, 2) a heterocyclyl out of the group acridinyl, 8-aza-bicyclo[3.2.1]oct-3-yl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, 1λ6-thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, —($CH_2$)$_m$—$NR^{10}$—$SO_2$—$NR^{10}$—($CH_2$)$_n$—, —($CH_2$)$_m$—CH(OH)—($CH_2$)$_n$—, —($CH_2$)$_m$—, —($CH_2$)$_m$—O—($CH_2$)$_n$—, —($CH_2$)$_m$—C(O)—$NR^{10}$—($CH_2$)$_n$—, —($CH_2$)—$SO_2$—($CH_2$)$_n$—, —($CH_2$)$_m$—$NR^{10}$—C(O)—$NR^{10}$—($CH_2$)$_n$—, —($CH_2$)$_m$—$NR^{10}$—C(O)—($CH_2$)$_n$—, —($CH_2$)$_m$—C(O)—($CH_2$)$_n$—, —($CH_2$)—S—($CH_2$)$_n$—, —($CH_2$)$_m$—$SO_2$—$NR^{10}$—($CH_2$)$_n$—, —($CH_2$)$_m$—$NR^{10}$—$SO_2$—($CH_2$)$_n$—, —($CH_2$)$_m$—$NR^{10}$—, —($CH_2$)$_m$—O—C(O)—$NR^{10}$—($CH_2$)$_n$— or —($CH_2$)$_m$—$NR^{10}$—C(O)—O—($CH_2$)$_n$—, n and m are independently of one another identical or different and are the integers zero, 1, 2, 3, 4, 5 or 6, M is 1) hydrogen,
2) —($C_1$-$C_8$)-alkyl, wherein alkyl is unsubstituted or mono-, di- or trisubstituted independently of one another by R14,
3) —C(O)—N(R11)-R12,
4) —($CH_2$)$_m$—$NR^{10}$,
5) —($C_6$-$C_{14}$)-aryl, wherein aryl is as defined above and wherein aryl is unsubstituted or mono-, di- or trisubstituted independently of one another by R14,
6) —($C_4$-$C_{15}$)-heterocyclyl, wherein heterocyclyl is as defined above and is unsubstituted or mono-, di- or trisubstituted independently of one another by R14, or
7) —($C_3$-$C_8$)-cycloalkyl, wherein said cycloalkyl is unsubstituted or mono-, di- or trisubstituted independently of one another by R14, R3 is
1) hydrogen,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
  a) hydrogen,
  b) —($C_1$-$C_4$)-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) —$CF_3$, or
  e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —$NR^{10}$—$SO_2$—$R^{10}$,
16) —S—$R^{10}$,
17) —($C_0$-$C_2$)alkylene-C(O)—O—($C_2$-$C_4$)-alkylene-O—C(O)—($C_1$-$C_4$)-alkyl,
18) —C(O)—O—C(R15, R16)-O—C(O)—R17,
19) —$C_0$-$C_2$)alkylene-C(O)—O—($C_2$-$C_4$)-alkylene-O—C(O)—O—($C_1$-$C_6$)-alkyl,
20) —C(O)—O—C(R15, R16)-O—C(O)—O—R17,
21) —($C_0$-$C_4$)-alkylene-($C_6$-$C_{14}$)-aryl, wherein aryl is mono-, di- or tri substituted independently of one another by R13, 22) —(C$_0$-C$_4$)-alkylene-(C$_4$-C$_{15}$)-heterocyclyl, wherein heterocyclyl is unsubstituted or mono-, di- or trisubstituted independently of one another by R13
23) —(C$_0$-C$_4$)-alkylene-(C$_3$-C$_8$)-cycloalkyl, wherein cycloalkyl is unsubstituted or mono-, di- or trisubstituted independently of one another by R13,
24) —(C$_0$-C$_4$)-alkylene-het, wherein het is unsubstituted or mono-, di- or trisubstituted independently of one another by R13,
25) —(C$_0$-C$_3$)-alkylene-O—CH$_2$—(C$_1$-C$_3$)-perfluoroalkylene-CH$_2$—O—(C$_0$-C$_3$)-alkyl,
26) —SO$_w$—N(R$^{11}$)—R$^{13}$ wherein w is 1 or 2,
27) —(C$_0$-C$_4$)-alkylene-C(O)—N(R$^{11}$)—R$^{13}$,
28) —(C$_0$-C$_4$)-alkylene-N(R$^{11}$)—R$^{13}$, or
29) a residue from the following list

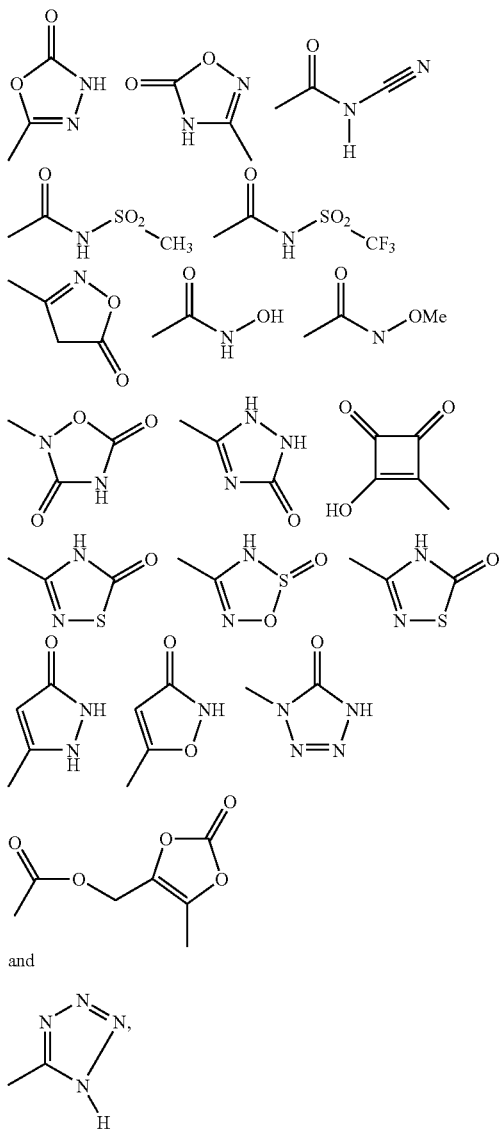

wherein Me is methyl, or if two —OR19 residues are attached to adjacent atoms they can form together with the atoms which they are attached to a 1,3-dioxole ring or a 2,3-dihydro-[1,4]dioxine ring, which is substituted one, two, three or four times by R13, R11 and R12 are independently of one another identical or different and are
1) hydrogen,
2) —(C$_1$-C$_6$)-alkyl, wherein alkyl is unsubstituted or mono-, di- or trisubstituted independently of one another by R13,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R13,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl are as defined above and are independently from one another unsubstituted or mono-, di- or trisubstituted by R13, or R11 and R12 together with the nitrogen atom to which they are bonded form a heterocyclic ring out of the group azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R13, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —(C$_1$-C$_3$)-perfluoroalkyl, —O—R15, —NH—C(O)—NH—R$^{10}$, —NH—C(O)—O—R$^{10}$, or a residue from the following list

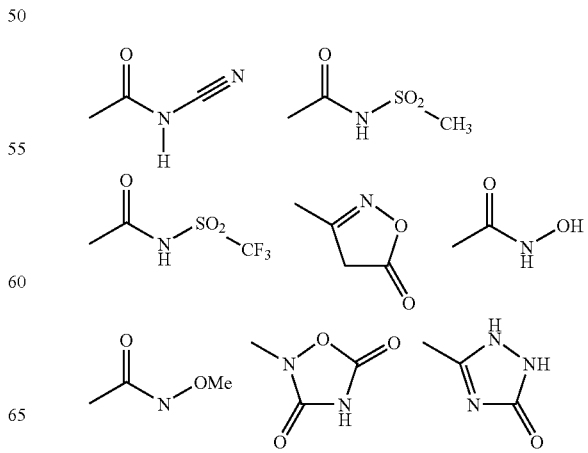

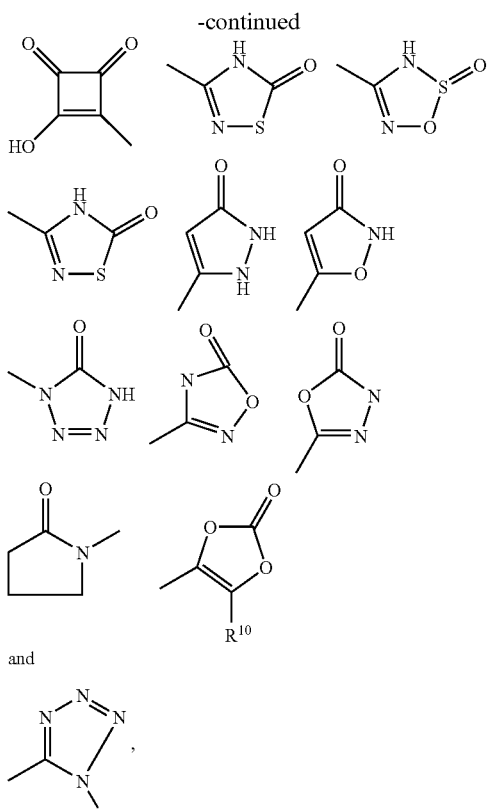

and wherein Me is methyl,

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl, R15 and R16 are independently of one another hydrogen, —(C$_1$-C$_6$)-alkyl, cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts Another particular embodiment of the present invention also relates to a compound of the formula I, wherein R$^0$ is 1) a monocyclic or bicyclic 6- to 14-membered aryl out of the group phenyl, naphthyl, biphenyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl out of the group azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiadiazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1. F, Cl or Br,
   2. —NO$_2$,
   3. —CN,
   4. —C(O)—NH$_2$,
   5. —OH,
   6. —NH$_2$,
   7. —OCF$_3$
   8. a monocyclic or bicyclic 6- to 14-membered aryl, wherein aryl is as defined above and is mono-, di- or trisubstituted independently of one another by halogen or —O—(C$_1$-C$_8$)-alkyl, 9. —($C_1$-$C_8$)-alkyl, wherein alkyl is unsubstituted or mono-, di- or trisubstituted independently of one another by halogen, $NH_2$, —OH or methoxy, or 10. —O—($C_1$-$C_8$)-alkyl, wherein alkyl is unsubstituted or mono-, di- or trisubstituted independently of one another by halogen, $NH_2$, —OH or methoxy, 11. —$SO_2CH_3$ or

12. —$SO_2CF_3$, provided that R8 is at least one halogen, —C(O)—$NH_2$ or —O—($C_1$-$C_8$)-alkyl residue, if R0 is a aryl or a heterocyclyl, which are as defined above, provided that R8 is not a —O—($C_1$-$C_8$)-alkyl residue, if $R^0$ and V are phenyl, substructure D is a residue selected out of the group phenyl, pyridyl, pyridyl-N-oxide pyridyl, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R3 or is substituted 1 or 2 times by =O, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, methylene or —($C_0$-$C_3$)-alkylene-C(O)—O—($C_0$-$C_2$)-alkylene, $R^1$ is hydrogen, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—R15, —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen or —($C_1$-$C_4$)-alkyl, $R^2$ is a direct bond, $R^1$—N—$R^2$—V form a 4- to 8-membered cyclic group selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$, wherein $R^{18}$ and $R^{21}$ are independently from each other hydrogen, —($C_1$-$C_3$)-perfluoroalkyl or —($C_1$-$C_6$)-alkyl, V is 1) a het residue out of the group 8-aza-bicyclo[3.2.1]oct-3-yl, azaindole (1H-pyrrolopyridine), azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14, or 2) phenyl, wherein phenyl is unsubstituted or mono-, di- or trisubstituted independently of one another by R14, G is a direct bond, —($CH_2$)$_m$—$NR^{10}$—$SO_2$—$NR^{10}$—($CH_2$)$_n$—, —($CH_2$)$_m$—CH(OH)—($CH_2$)$_n$—, —($CH_2$)$_m$—, —($CH_2$)$_m$—O—($CH_2$)$_n$—, —($CH_2$)$_m$—C(O)—$NR^{10}$—($CH_2$)$_n$—, —($CH_2$)—$SO_2$—($CH_2$)$_n$—, —($CH_2$)$_m$—$NR^{10}$—C(O)—$NR^{10}$—($CH_2$)$_n$—, —($CH_2$)$_m$—$NR^{10}$—C(O)—($CH_2$)$_n$—, —($CH_2$)$_m$—C(O)—($CH_2$)$_n$—, —($CH_2$)—S—($CH_2$)$_n$—, —($CH_2$)$_m$—$SO_2$—$NR^{10}$—($CH_2$)$_n$—, —($CH_2$)$_m$—$NR^{10}$—$SO_2$—($CH_2$)$_n$—, —($CH_2$)$_m$—$NR^{10}$—, —($CH_2$)$_m$—O—C(O)—$NR^{10}$—($CH_2$)$_n$— or —($CH_2$)$_m$—$NR^{10}$—C(O)—O—($CH_2$)$_n$—, n and m are independently of one another identical or different and are the integers zero, 1, 2, 3, 4, 5 or 6, M is 1) hydrogen, 2) —($C_1$-$C_8$)-alkyl, wherein alkyl is unsubstituted or mono-, di- or trisubstituted independently of one another by R14,

3) —C(O)—N(R11)-R12,

4) —($CH_2$)$_m$—$NR^{10}$, 5) phenyl or naphthyl, wherein phenyl or naphthyl are unsubstituted or mono-, di- or trisubstituted independently of one another by R14, 6) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketopiperazine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, 1λ6-thiomorpholinyl, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, or 7) —($C_3$-$C_8$)-cycloalkyl, wherein said cycloalkyl is unsubstituted or mono-, di- or trisubstituted independently of one another by R14, R3 is
1) hydrogen,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
   a) hydrogen,
   b) —($C_1$-$C_4$)-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —$CF_3$, or
   e) $CHF_2$,
7) —CN,
8) —($C_0$-$C_4$)-alkylene-($C_4$-$C_{15}$)-heterocyclyl, wherein heterocyclyl is as defined above and is unsubstituted or mono-, di- or trisubstituted independently of one another by R13,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —$NR^{10}$—$SO_2$—$R^{10}$,
16) —($C_0$-$C_4$)-alkylene-het, wherein het is as defined above and is unsubstituted or mono-, di- or trisubstituted independently of one another by R13,
17) —($C_0$-$C_2$)alkylene-C(O)—O—($C_2$-$C_4$)-alkylene-O—C(O)—($C_1$-$C_4$)-alkyl,
18) —C(O)—O—C(R15, R16)-O—C(O)—R17,
19) —($C_0$-$C_2$)alkylene-C(O)—O—($C_2$-$C_4$)-alkylene-O—C(O)—O—($C_1$-$C_6$)-alkyl,
20) —C(O)—O—C(R15, R16)-O—C(O)—O—R17,
21) —($C_0$-$C_4$)-alkylene-($C_6$-$C_{14}$)-aryl, wherein aryl is as defined above and is mono-, di- or trisubstituted independently of one another by R13,
22) —($C_0$-$C_4$)-alkylene-($C_3$-$C_8$)-cycloalkyl, wherein cycloalkyl is unsubstituted or mono-, di- or trisubstituted independently of one another by R13,
23) —($C_0$-$C_3$)-alkylene-O—$CH_2$—$CF_2$—$CH_2$—O—($C_0$-$C_3$)-alkyl,
24) —($C_0$-$C_3$)-alkylene-O—$CH_2$—$CF_2$—$CF_2$—$CH_2$—O—($C_0$-$C_3$)-alkyl,
25) —($C_0$-$C_3$)-alkylene-O—$CH_2$—($C_1$-$C_3$)-perfluoroalkylene-$CH_2$—OH,
26) —$SO_w$—N($R^{11}$)—$R^{13}$, wherein w is 1 or 2,
27) —($C_0$-$C_4$)-alkylene-C(O)—N($R^{11}$)—$R^{13}$,
28) —($C_0$-$C_4$)-alkylene-N($R^{11}$)—$R^{13}$, or
29) a residue from the following list

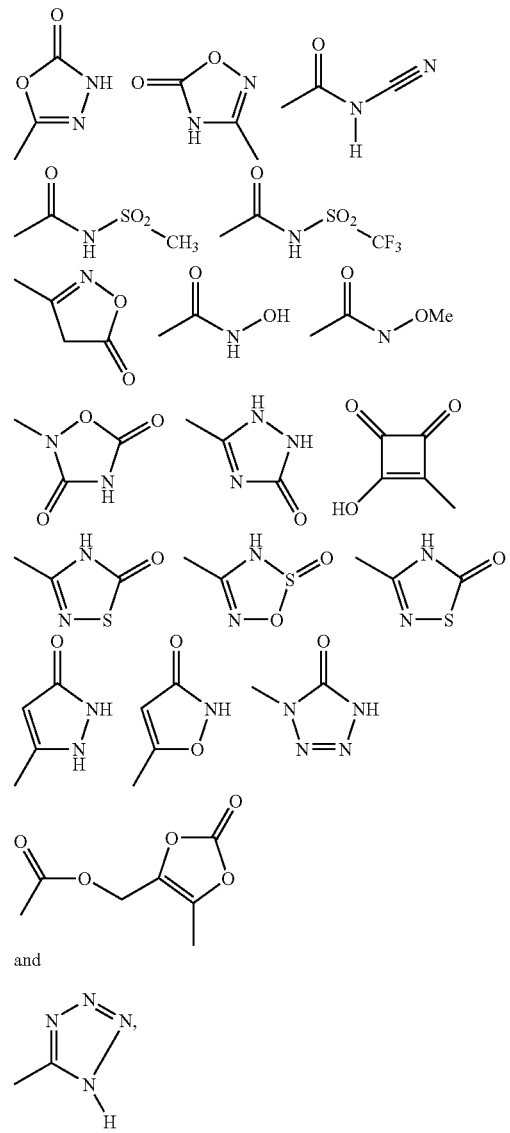

and wherein Me is methyl, if two —OR19 residues are attached to adjacent atoms they can form together with atoms which they are attached to a 1,3-dioxole ring or a 2,3-dihydro-[1,4]dioxine ring, which is substituted one, two, three or four times by R13, R11 and R12 are independently of one another identical or different and are
1) hydrogen,
2) —($C_1$-$C_6$)-alkyl, wherein alkyl is unsubstituted or mono-, di- or trisubstituted independently of one another by R13,
3) —($C_0$-$C_6$)-alkyl-($C_6$-$C_{14}$)-aryl, wherein aryl is as defined above and wherein alkyl and aryl are independently from one another are unsubstituted or mono-, di- or trisubstituted by R13,
4) —O—$R^{17}$, or
5) —($C_0$-$C_6$)-alkyl-($C_4$-$C_{15}$)-heterocyclyl, wherein alkyl and heterocyclyl is as defined above and independently from one another are unsubstituted or mono-, di- or trisubstituted by R13, or R11 and R12 together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, which is unsubstituted or mono-, di- or trisubstituted independently of one another by R13, R13 is fluorine, chlorine, bromine, iodine, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_0$-$C_3$)-alkylene-O—$R^{10}$, —Si—$(CH_3)_3$, —N($R^{10}$)—S(O)$_2$—$R^{10}$, —S—$R^{10}$, —$SO_2$—$R^{10}$, —S(O)$_2$—N($R^{10}$)—$R^{20}$, —C(O)—$R^{10}$, —($C_1$-$C_8$)-alkyl, —($C_1$-$C_8$)-alkoxy, phenyl, phenyloxy-, —O—$CF_3$, —($C_1$-$C_3$)-perfluoroalkyl, —($C_0$-$C_4$)-alkyl-C(O)—O—C(R15, R16)-O—C(O)—R17, —($C_1$-$C_4$)-alkoxy-phenyl, —($C_0$-$C_4$)-alkyl-C(O)—O—C(R15, R16)-O—C(O)—O—R17, —O—R15, —NH—C(O)—NH—$R^{10}$, —NH—C(O)—O—$R^{10}$, or a residue from the following list

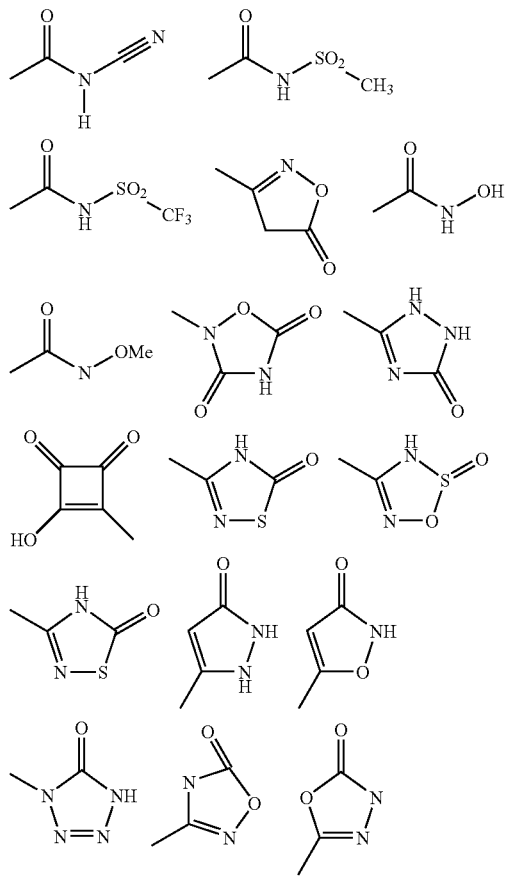

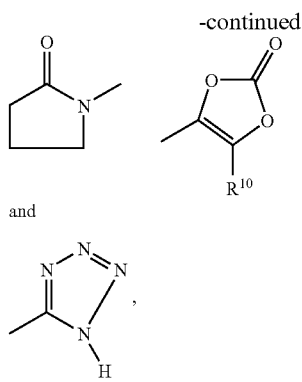

and wherein Me is methyl, $R^{10}$ and $R^{20}$ are independently of one another hydrogen, —($C_1$-$C_6$)-alkyl, —($C_0$-$C_4$)-alkyl-OH, —($C_0$-$C_4$)-alkyl-O—($C_1$-$C_4$)-alkyl or —($C_1$-$C_3$)-perfluoroalkyl, R15 and R16 are independently of one another hydrogen, —($C_1$-$C_6$)-alkyl, or together form a ring out of the group cyclopropyl, cyclobutyl, cyclopentyl or cyclohexyl, wherein each ring is unsubstituted or substituted one to three times by $R^{10}$, and R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts.

Another particular embodiment of the present invention also relates to a compound of the formula I, wherein R0 is 1) phenyl, wherein phenyl is unsubstituted or mono-, di- or trisubstituted independently of one another by R8,
  2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
  3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. F, Cl, Br or I,
2. —C(O)—NH$_2$,
3. —(C$_1$-C$_4$)-alkyl, wherein alkyl is unsubstituted or mono-, di- or trisubstituted independently of one another by halogen, —OH or methoxy, or
4. —O—(C$_1$-C$_4$)-alkyl, wherein alkyl is unsubstituted or mono-, di- or trisubstituted independently of one another by halogen or methoxy,
provided that R8 is at least one halogen, —C(O)—NH$_2$ or —O—(C$_1$-C$_8$)-alkyl residue, if R0 is a aryl or a heterocyclyl, which are as defined above,
provided that R8 is not a —O—(C$_1$-C$_8$)-alkyl residue, if R$^0$ and V are phenyl, substructure D is a residue selected out of the group phenyl, pyridyl, pyridyl-N-oxide, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R3 or is substituted 1 or 2 times by =O,
Q is a direct bond, —C(O)—; —SO$_2$—, methylene, —(C$_0$-C$_2$)-alkylene-C(O)—NR$^{10}$— or —(C$_0$-C$_3$)-alkylene-C(O)—O—(C$_0$-C$_2$)-alkylene,
R$^1$ is hydrogen, —(C$_1$-C$_2$)-alkyl, —(C$_1$-C$_3$)-alkylene-C(O)—NH—R$^0$, —(C$_1$-C$_3$)-perfluoroalkylene, —(C$_1$-C$_3$)-alkylene-C(O)—O—R$^{15}$, —(C$_1$-C$_3$)-alkylene-S(O)$_2$—(C$_1$-C$_3$)-alkyl or —(C$_1$-C$_3$)-alkylene-S(O)$_2$—N(R$^{4'}$)—R$^{5'}$, wherein R$^{4'}$ and R$^{5'}$ are independent of one another are identical or different and are hydrogen or —(C$_1$-C$_4$)-alkyl,
R$^2$ is a direct bond,
R$^1$—N—R$^2$—V can form a 4- to 7-membered cyclic group out of the group azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazapane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14,
R14 is fluorine, chlorine, —OH, =O, —(C$_1$-C$_8$)-alkyl, —C(O)—OH, —CN, —NH$_2$, —C(O)—O—(C$_1$-C$_4$)-alkyl, —C(O)—NH—(C$_1$-C$_8$)-alkyl, —C(O)—N—[(C$_1$-C$_8$)-alkyl]$_2$, —C(O)—NH$_2$ or —N(R$^{18}$)—R$^{21}$, wherein R$^{18}$ and R$^{21}$ are independently from each other hydrogen, —(C$_1$-C$_3$)-perfluoroalkyl or —(C$_1$-C$_4$)-alkyl,
V is 1. a cyclic residue out of the group containing compounds which are derived from 8-aza-bicyclo[3.2.1]oct-3-yl, azaindole (1H-pyrrolopyridine), aziridine, azirine, azetidine, azetidinone, 1,4-diazapane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine,
wherein said cyclic residue is unsubstituted or mono-, di- or trisubstituted independently of one another by R14, or
2. phenyl, wherein phenyl is unsubstituted or mono-, di- or trisubstituted independently of one another by R14, or G is a direct bond, —(CH$_2$)$_m$—, or —(CH$_2$)$_m$—NR$^{10}$—,
m is the integers zero, 1, 2, 3 or 4,
M is 1. hydrogen,
2. heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, 1λ6-thiomorpholinyl, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14,
3. —(C$_1$-C$_6$)-alkyl, wherein alkyl is unsubstituted or mono-, di- or trisubstituted independently of one another by R14,
4. (C$_3$-C$_6$)-cycloalkyl or
5. —C(O)—N(R$^{11}$)—R$^{12}$,
R3 is
1) hydrogen,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
a) hydrogen,
b) —(C$_1$-C$_4$)-alkyl, wherein alkyl is unsubstituted or mono-, di- or trisubstituted independently of one another by R13, or
c) phenyl, wherein phenyl is unsubstituted or mono-, di- or trisubstituted independently of one another by R13,
d) —CF$_3$, or
e) CHF$_2$,
7) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)-O—C(O)—R17,
17) —(C$_0$-C$_2$)alkylene-C(O)—O—(C$_2$-C$_4$)-alkylene-O—C(O)—O—(C$_1$-C$_6$)-alkyl,
18) —C(O)—O—C(R15, R16)-O—C(O)—O—R17,
19) —(C$_0$-C$_3$)-alkylene-O—CH$_2$—CF$_2$—CH$_2$—O—(C$_0$-C$_3$)-alkyl,
20) —(C$_0$-C$_3$)-alkylene-O—CH$_2$—CF$_2$—CF$_2$—CH$_2$—O—(C$_0$-C$_3$)-alkyl,
21) —(C$_0$-C$_3$)-alkylene-O—CH$_2$—(C$_1$-C$_3$)-perfluoroalkylene-CH$_2$—OH,
22) —SO$_w$—N(R$^{11}$)—R$^{13}$, wherein w is 1 or 2,
23) —(C$_0$-C$_4$)-alkylene-C(O)—N(R$^{11}$)—R$^{13}$,
24) —(C$_0$-C$_4$)-alkylene-N(R$^{11}$)—R$^{13}$, or 25) a residue from the following list

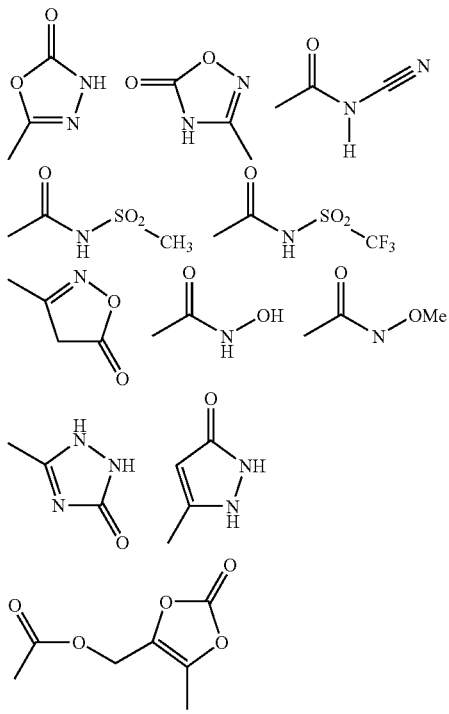

and

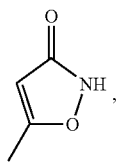

wherein Me is methyl,
if two —OR19 residues are attached to adjacent atoms they can form together with the atoms which they are attached to a 1,3-dioxole ring or a 2,3-dihydro-[1,4]dioxine ring, which is substituted one, two, three or four times by R13,
$R^{11}$ and $R^{12}$ together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said ring is unsubstituted or mono-, di- or trisubstituted independently of one another by R13,
R13 is fluorine, chlorine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —NH—C(O)—NH—R$^{10}$, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17—O—R15, —NH—C(O)—O—R$^{10}$, or a residue from the following list

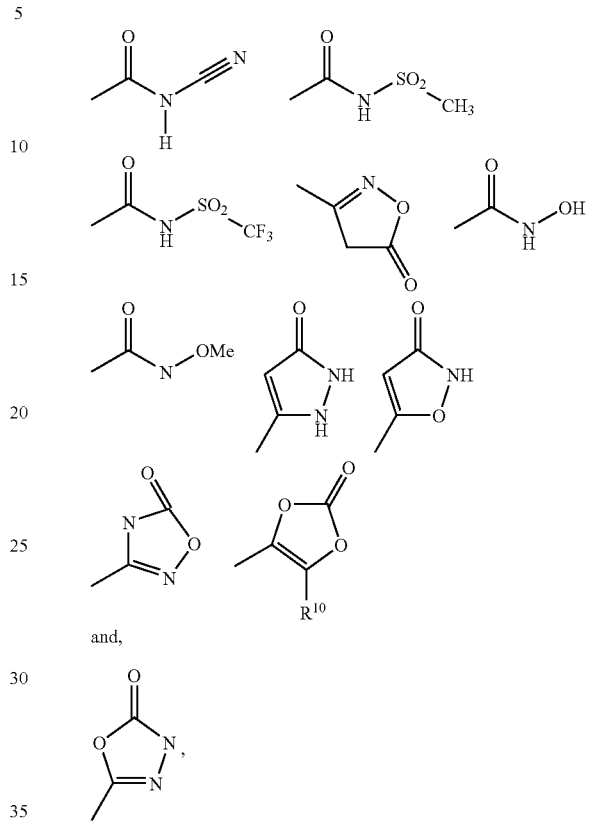

and, wherein Me is methyl,
$R^{10}$ and $R^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl,
R15 and R16 are independently of one another hydrogen, —(C$_1$-C$_6$)-alkyl, or together form a ring out of the group cyclopropyl, cyclobutyl, cyclopentyl or cyclohexyl, wherein each ring is unsubstituted or substituted one to three times by R$^{10}$, and
R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.
Another particular embodiment of the present invention also relates to a compound of the formula I, wherein
R0 is 1. phenyl, wherein phenyl is unsubstituted or mono-, di- or trisubstituted independently of one another by R8,
2. a heterocyclyl selected out of the group indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridyl, purinyl and pteridinyl,
wherein said heterocyclyl is unsubstituted or mono-, di- or trisubstituted independently of one another by R8, 3. a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. is F, Cl, Br, J,
2. —C(O)—$NH_2$,
3. —($C_1$-$C_4$)-alkyl, wherein alkyl is unsubstituted or mono-, di- or trisubstituted independently of one another by halogen, —OH or methoxy, or
4. —O—($C_1$-$C_4$)-alkyl, wherein alkyl is unsubstituted or mono-, di- or trisubstituted independently of one another by halogen or methoxy, provided that R8 is at least one halogen, —C(O)—$NH_2$ or —($C_1$-$C_8$)-alkyl residue, if R0 is a aryl or a heterocyclyl, which are as defined above, provided that R8 is not a —O—($C_1$-$C_8$)-alkyl residue, if $R^0$ and V are phenyl, substructure D is a residue selected out of the group phenyl, pyridyl, pyridyl-N-oxide, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by $R^3$ or is substituted 1 or 2 times by ═O, Q is a direct bond, —C(O)—; —$SO_2$—, —C(O)—O-methylene, methylene or —($C_0$-$C_2$)-alkylene-C(O)—$NR^{10}$—,
$R^1$ is hydrogen or —($C_1$-$C_2$)-alkyl,
$R^2$ is a direct bond,
$R^1$—N—$R^2$—V can form a 4- to 7-membered cyclic group out of the group piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluorine, chlorine, —($C_1$-$C_4$)-alkyl or —$NH_2$, V is 1. a cyclic residue out of the group containing compounds, which are derived from 8-aza-bicyclo[3.2.1]oct-3-yl, azaindolyl (1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole, wherein said cyclic residue is unsubstituted or mono-, di- or trisubstituted independently of one another by R14, or
2. phenyl, wherein phenyl is unsubstituted or mono-, di- or trisubstituted independently of one another by R14, G is a direct bond, —$(CH_2)_m$—, or —$(CH_2)_m$—$NR^{10}$—,
m is the integers zero, 1, 2, 3 or 4,
M is 1. hydrogen,
2. heterocyclyl, wherein heterocyclyl is a residue out of the group which can be derived from 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole, 1λ6-thiomorpholinyl or thiomorpholine, wherein said heterocyclyl is unsubstituted or mono-, di- or trisubstituted independently of one another by R14,
3. —($C_1$-$C_6$)-alkyl, wherein alkyl is unsubstituted or mono-, di- or trisubstituted independently of one another by R14, or
4. ($C_3$-$C_6$)-cycloalkyl, R3 is
1) hydrogen,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
a) hydrogen,
b) —($C_1$-$C_4$)-alkyl, wherein alkyl is unsubstituted or mono-, di- or trisubstituted independently of one another by R3, or
c) phenyl, wherein phenyl is unsubstituted or mono-, di- or trisubstituted independently of one another by R13,
d) —$CF_3$, or
e) —$CHF_2$,
7) —CN,
8) —$NR^{10}$—$SO_2$—$R^{10}$,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —($C_0$-$C_2$)alkylene-C(O)—O—($C_2$-$C_4$)-alkylene-O—C(O)—($C_1$-$C_4$)-alkyl,
16) —C(O)—O—C(R15, R16)-O—C(O)—R17,
17) —($C_0$-$C_2$)alkylene-C(O)—O—($C_2$-$C_4$)-alkylene-O—C(O)—O—($C_1$-$C_6$)-alkyl,
18) —C(O)—O—C(R15, R16)-O—C(O)—O—R17, or
19) a residue from the following list

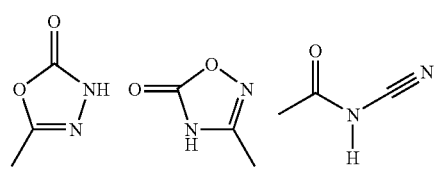

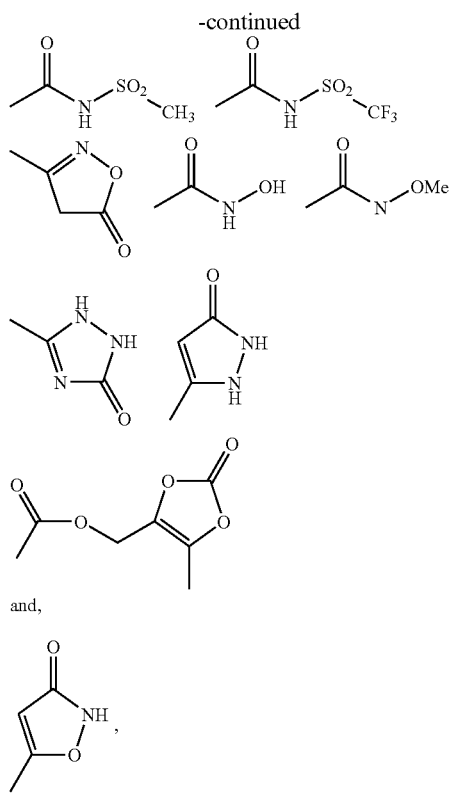

and,

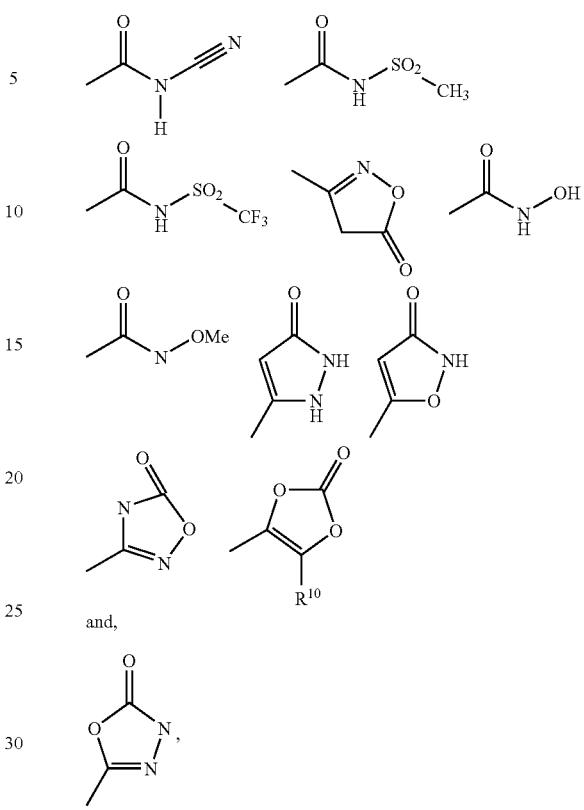

and, wherein Me is methyl, $R^{11}$ and $R^{12}$ are independently of one another identical or different and are 1) hydrogen,
2) —($C_1$-$C_4$)-alkyl, wherein alkyl is unsubstituted or mono-, di- or trisubstituted independently of one another by R13,
3) —($C_0$-$C_6$)-alkyl-($C_3$-$C_6$)-cycloalkyl,
4) —O—$R^{17}$, or
5) —($C_0$-$C_6$)-alkyl-($C_4$-$C_{15}$)-heterocyclyl, wherein alkyl and heterocyclyl independently from one another are unsubstituted or mono-, di- or trisubstituted by R13 and wherein heterocyclyl is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, or $R^{11}$ and $R^{12}$ together with the nitrogen atom to which they are bonded form a heterocyclic ring, which is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, wherein said ring is unsubstituted or mono-, di- or trisubstituted by R13, R13 is fluorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—($CH_3$)$_3$, —S—$R^{10}$, —$SO_2$—$R^{10}$, —($C_1$-$C_3$)-perfluoroalkyl, or a residue from the following list wherein Me is methyl, $R^{10}$ and $R^{20}$ are independently of one another hydrogen, —($C_1$-$C_4$)-alkyl or —($C_1$-$C_3$)-perfluoroalkyl, $R^{15}$ and $R^{16}$ are independently of one another hydrogen, —($C_1$-$C_4$)-alkyl, or together form a ring out of the group cyclopropyl, cyclobutyl, cyclopentyl or cyclohexyl, wherein each ring is unsubstituted or substituted one to three times by $R^{10}$, and R17 is —($C_1$-$C_6$)-alkyl, —($C_1$-$C_6$)-alkyl-OH, —($C_1$-$C_6$)-alkyl-O—($C_1$-$C_8$)-alkyl-($C_3$-$C_8$)-cycloalkyl, —($C_1$-$C_6$)-alkyl-O—($C_1$-$C_6$)-alkyl or —($C_0$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts.

Another particular embodiment of the present invention also relates to a compound of the formula I, wherein R0 is 1. phenyl, wherein phenyl is unsubstituted or mono- or disubstituted independently of one another by R8,
2. pyridyl or 1H-indazolyl, wherein pyridyl and 1H-indazolyl are unsubstituted or mono- or disubstituted independently of one another by R8, or
3. a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8, R8 is F, Cl, Br, —O—$CH_3$ or —C(O)—$NH_2$, provided that R8 is not a —O—($C_1$-$C_8$)-alkyl residue, if $R^0$ and V are phenyl, substructure D is a residue selected out of the group phenyl, pyridyl, pyridyl-N-oxide, pyrrolyl, thienyl, imidazolyl, pyrazolyl, oxazolyl, isoxazolyl, thiazolyl, isothiazolyl, thiadiazolyl, pyrimidinyl, pyridazinyl or pyrazinyl and is unsubstituted or substituted 1, 2, 3 or 4 times by R3 or is substituted 1 or 2 times by =O, Q is a direct bond, —C(O)—; —SO$_2$—, —C(O)—O-methylene, —CH$_2$—C(O)—NH— or methylene, $R^1$ is hydrogen, $R^2$ is a direct bond, $R^1$—N—$R^2$—V can form a 4- to 8-membered cyclic group out of the group azetidine, pyrrolidine, piperidine and piperazine, R14 is fluorine, chlorine, methyl, ethyl, =O, —SO$_2$—CH$_3$ or —NH$_2$, V is 1. a residue out of the group containing compounds which is derived from 8-aza-bicyclo[3.2.1]oct-3-yl, azaindolyl (1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane, wherein said cyclic residue is unsubstituted or mono- or disubstituted independently of one another by R14, or 2. phenyl, wherein phenyl is unsubstituted or mono- or disubstituted independently of one another by R14, G is a direct bond, —(CH$_2$)$_m$—, —C(O)— or —(CH$_2$)$_m$—NR$^{10}$—, m is the integers zero, 1 or 2, M is hydrogen, (C$_2$-C$_4$)-alkyl, azepanyl, cyclopropyl, cyclobutyl, cyclopentyl, cyclohexyl, imidazolyl, ketomorpholinyl, morpholinyl, [1,4]Oxazepanyl, piperazinyl, piperidinyl, piperidonyl, pyrazinyl, pyrazolyl, pyridazinyl, pyridyl, pyrimidyl, pyrrolidinyl, 1λ6-thiomorpholinyl, 1,4,5,6-tetrahydro-pyridazinyl, or tetrahydropyranyl, wherein the residues are unsubstituted or mono- or disubstituted independently of one another by R14

R3 is
1) hydrogen,
2) fluorine, chlorine,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_2$)-alkylene-O—R19, wherein R19 is
  a) hydrogen,
  b) —(C$_1$-C$_4$)-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) —CF$_3$, or
  e) —CHF$_2$,
7) —CN,
8) —NR$^{10}$—SO$_2$—R$^{10}$,
9) —SO$_S$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)-O—C(O)—R$^{17}$,
17) —(C$_0$-C$_2$)alkylene-C(O)—O—(C$_2$-C$_4$)-alkylene-O—C(O)—O—(C$_1$-C$_6$)-alkyl or
18) —C(O)—O—C(R15, R16)-O—C(O)—O—R$^{17}$, or R11 and R12 are independently of one another identical or different and are
1) hydrogen,
2) —(C$_1$-C$_4$)-alkyl, wherein alkyl is unsubstituted or mono-, di- or trisubstituted independently of one another by R13,
3) —(C$_0$-C$_6$)-alkyl-(C$_3$-C$_6$)-cycloalkyl,
4) —O—R$^{17}$, or
5) —(C$_0$-C$_6$)-alkyl-heterocyclyl, wherein alkyl and heterocyclyl independently from one another are unsubstituted or mono-, di- or trisubstituted by R13 and wherein heterocyclyl is selected out of the group azetidine, imidazolidine, morpholine, (1,4)-oxazepane or pyrrolidine or R11 and R12 together with the nitrogen atom to which they are bonded can form a ring, which is selected out of the group azetidine, imidazolidine, morpholine, (1,4)-oxazepane piperazine, piperidine, pyrrolidine or thiomorpholine, wherein said ring is unsubstituted or mono-, di- or trisubstituted by R13, R13 is fluorine, —CN, =O, —OH, —CF$_3$, —C(O)—O—R$^{10}$, —C(O)—N(R$^{10}$)—R$^{20}$, —N(R$^{10}$)—R$^{20}$, —(C$_1$-C$_3$)-alkyl,
—(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, —SO$_2$—NH, or
—(C$_1$-C$_3$)-perfluoroalkyl, R$^{10}$ and R$^{20}$ are independently of one another hydrogen, —(C$_1$-C$_4$)-alkyl or —(C$_1$-C$_3$)-perfluoroalkyl, R$^{15}$ and R$^{16}$ are independently of one another hydrogen, —(C$_1$-C$_4$)-alkyl, or together form a ring out of the group cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_8$)-alkyl-(C$_3$-C$_8$)-cycloalkyl, —(C$_1$-C$_6$)-alkyl-O—(C$_1$-C$_6$)-alkyl or —(C$_0$-C$_4$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

Another particular embodiment of the present invention also relates to a compound of the formula I, wherein R0 is 1. phenyl, wherein phenyl is unsubstituted or mono- or disubstituted independently of one another by R8,
2. pyridyl or 1H-indazolyl, wherein pyridyl and 1H-indazolyl are unsubstituted or mono- or disubstituted independently of one another by R8, or
3. a heterocyclyl out of the group thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8, R8 is Cl or —O—CH$_3$, provided that R8 is not a —O—(C$_1$-C$_8$)-alkyl residue, if R$^0$ and V are phenyl, substructure D is a residue selected out of the group phenyl, pyridyl, thienyl or pyrimidinyl, and is unsubstituted or substituted 1, 2, 3 or 4 times by R3 or is substituted 1 or 2 times by =O, Q is —CH$_2$—C(O)—NH— or methylene, $R^1$ is hydrogen, $R^2$ is a direct bond, R14 is fluorine or =O, V is piperidinyl or phenyl, wherein phenyl is unsubstituted or mono- or disubstituted independently of one another by R14, G is a direct bond or —C(O)—, M is hydrogen, $(C_2-C_4)$-alkyl, isopropyl, cyclopropyl, morpholinyl, piperazinyl, piperidinyl, pyrazinyl, pyridyl, pyrimidyl, pyrrolidinyl or 1λ6-thiomorpholinyl, wherein the residues are unsubstituted or mono- or disubstituted independently of one another by R14

R3 is
1) hydrogen,
2) fluorine, chlorine,
3) —$(C_1-C_4)$-alkyl, wherein alkyl is unsubstituted or mono-, di- or trisubstituted independently of one another by R13,
4) —$(C_0-C_2)$-alkylene-O—R19, wherein R19 is
   a) hydrogen,
   b) —$(C_1-C_4)$-alkyl, wherein alkyl is unsubstituted or mono-, di- or trisubstituted independently of one another by R13, or
   c) —$CF_3$,
5) —$SO_2$—$R^{11}$,
6) —$(C_0-C_4)$-alkylene-C(O)—O—$R^{11}$,
7) —$(C_0-C_4)$-alkylene-C(O)—N($R^{11}$)—$R^{12}$,
8) —$(C_0-C_2)$-alkylene-C(O)—O—$(C_2-C_4)$-alkylene-O—C(O)—O—$(C_1-C_6)$-alkyl or
9) —C(O)—O—C(R15, R16)-O—C(O)—O—R17, R11 and R12 are independently of one another identical or different and are
1) hydrogen,
2) —$(C_1-C_4)$-alkyl, wherein alkyl is unsubstituted or mono-, di- or trisubstituted independently of one another by R13, or
3) —$(C_0-C_6)$-alkyl-$(C_3-C_6)$-cycloalkyl or R11 and R12 together with the nitrogen atom to which they are bonded can form a ring, which is selected out of the group azetidine, morpholine, (1,4)-oxazepane or piperidine, wherein said ring is unsubstituted or mono-, di- or trisubstituted by R13, R13 is fluorine, =O, —OH, —$CF_3$, —C(O)—O—$R^{10}$, —$(C_1-C_3)$-alkyl, —$(C_3-C_6)$-cycloalkyl or —$(C_0-C_3)$-alkylene-O—$R^{10}$, $R^{10}$ is hydrogen or —$(C_1-C_4)$-alkyl, $R^{15}$ and $R^{16}$ are independently of one another hydrogen or —$(C_1-C_4)$-alkyl, and R17 is —$(C_1-C_6)$-alkyl, —$(C_1-C_6)$-alkyl-OH or —$(C_0-C_4)$-alkyl-$(C_3-C_8)$-cycloalkyl, in all its stereoisomeric forms and mixtures thereof in any ratio, and its physiologically tolerable salts.

Another particular embodiment of the present invention also relates to a compound of the formula I, which is 1-[5-(5-Chloro-thiophen-2-yl)-isoxazol-3-ylmethyl]-1H-benzoimidazole-2-carboxylic acid (1-isopropyl-piperidin-4-yl)-amide, 1-[(4-Chloro-phenylcarbamoyl)-methyl]-1H-benzoimidazole-2-carboxylic acid (1-isopropyl-piperidin-4-yl)-amide, 1-[(5-Chloro-pyridin-2-ylcarbamoyl)-methyl]-1H-benzoimidazole-2-carboxylic acid (1-isopropyl-piperidine-4-yl)-amide, 1-[5-(5-Chloro-thiophen-2-yl)-isoxazol-3-ylmethyl]-1H-benzoimidazole-2-carboxylic acid (1-pyrimidine-4-yl-piperidine-4-yl)-amide, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid methyl ester, 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid methyl ester, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid, 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid, 1-[2-(5-Chloro-thiophen-2-yl)-thiazol-5-ylmethyl]-2-(1-isopropyl-piperidin-4-ylcarbamoyl)-1H-benzoimidazole-5-carboxylic acid methyl ester, 3-[2-(5-Chloro-thiophen-2-yl)-thiazol-5-ylmethyl]-2-(1-isopropyl-piperidin-4-ylcarbamoyl)-3H-benzoimidazole-5-carboxylic acid methyl ester, 1-[2-(5-Chloro-thiophen-2-yl)-thiazol-5-ylmethyl]-2-(1-isopropyl-piperidin-4-ylcarbamoyl)-1H-benzoimidazole-5-carboxylic acid, 3-[2-(5-Chloro-thiophen-2-yl)-thiazol-5-ylmethyl]-2-(1-isopropyl-piperidin-4-ylcarbamoyl)-3H-benzoimidazole-5-carboxylic acid, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid methyl ester, 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid methyl ester, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid, 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid, 3-[5-(5-Chloro-thiophen-2-yl)-isoxazol-3-ylmethyl]-3H-imidazo[4,5-b]pyridine-2-carboxylic acid (1-isopropyl-piperidin-4-yl)-amide, 1-[(5-Chloro-pyridin-2-ylcarbamoyl)-methyl]-2-(1-isopropyl-piperidin-4-ylcarbamoyl)-1H-benzoimidazole-4-carboxylic acid methyl ester, 1-[(5-Chloro-pyridin-2-ylcarbamoyl)-methyl]-2-(1-isopropyl-piperidin-4-ylcarbamoyl)-1H-benzoimidazole-4-carboxylic acid, 1-[(5-Chloro-pyridin-2-ylcarbamoyl)-methyl]-2-(1-isopropyl-piperidin-4-ylcarbamoyl)-1H-benzoimidazole-5-carboxylic acid methyl ester, 3-[(5-Chloro-pyridin-2-ylcarbamoyl)-methyl]-2-(1-isopropyl-piperidin-4-ylcarbamoyl)-3H-benzoimidazole-5-carboxylic acid methyl ester, 1-[(5-Chloro-pyridin-2-ylcarbamoyl)-methyl]-2-(1-isopropyl-piperidin-4-ylcarbamoyl)-1H-benzoimidazole-5-carboxylic acid, 3-[(5-Chloro-pyridin-2-ylcarbamoyl)-methyl]-2-(1-isopropyl-piperidin-4-ylcarbamoyl)-3H-benzoimidazole-5-carboxylic acid, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-ethoxycarbonyloxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-cyclohexyloxycarbonyloxy-ethyl ester, 1-[5-(5-Chloro-thiophen-2-yl)-isoxazol-3-ylmethyl]-1H-benzoimidazole-2,4-dicarboxylic acid 4-[(2-hydroxy-ethyl)-amide]2-[(1-isopropyl-piperidin-4-yl)-amide], 1-[5-(5-Chloro-thiophen-2-yl)-isoxazol-3-ylmethyl]-4-(3-hydroxy-azetidine-1-carbonyl)-1H-benzoimidazole-2-carboxylic acid (1-isopropyl-piperidin-4-yl)-amide, 1-[5-(5-Chloro-thiophen-2-yl)-isoxazol-3-ylmethyl]-1H-benzoimidazole-2,4-dicarboxylic acid 4-[(2-hydroxy-ethyl)-methyl-amide]2-[(1-isopropyl-piperidin-4-yl)-amide], 1-[5-(5-Chloro-thiophen-2-yl)-isoxazol-3-ylmethyl]-1H-benzoimidazole-2,5-dicarboxylic acid 5-[(2-hydroxy-ethyl)-methyl-amide]2-[(1-isopropyl-piperidin-4-yl)-amide], 1-[5-(5-Chloro-thiophen-2-yl)-isoxazol-3-ylmethyl]-5-(3-hydroxy-azetidine-1-carbonyl)-1H-benzoimidazole-2-carboxylic acid (1-isopropyl-piperidin-4-yl)-amide, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-ethoxycarbonyloxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-cyclohexyloxycarbonyloxy-ethyl ester, 1-[5-(5-Chloro-thiophen-2-yl)-isoxazol-3-ylmethyl]-5-(2-hydroxy-ethanesulfonyl)-1H-benzoimidazole-2-carboxylic acid (1-isopropyl-piperidin-4-yl)-amide, 1-[5-(5-Chloro-thiophen-2-yl)-isoxazol-3-ylmethyl]-6-(2-hydroxy-ethanesulfonyl)-1H-benzoimidazole-2-carboxylic acid (1-isopropyl-piperidin-4-yl)-amide, 1-[(5-Chloro-pyridin-2-ylcarbamoyl)-methyl]-1H-benzoimidazole-2,4-dicarboxylic acid 4-[(2-hydroxy-ethyl)-amide]2-[(1-isopropyl-piperidin-4-yl)-amide], 1-[(5-Chloro-pyridin-2-ylcarbamoyl)-methyl]-1H-benzoimidazole-2,4-dicarboxylic acid 4-[(2-hydroxy-ethyl)-methyl-amide]2-[(1-isopropyl-piperidin-4-yl)-amide], 1-[(5-Chloro-pyridin-2-ylcarbamoyl)-methyl]-4-(3-hydroxy-azetidine-1-carbonyl)-1H-benzoimidazole-2-carboxylic acid (1-isopropyl-piperidin-4-yl)-amide, 1-[(5-Chloro-pyridin-2-ylcarbamoyl)-methyl]-2-(1-isopropyl-piperidin-4-ylcarbamoyl)-1H-benzoimidazole-4-carboxylic acid 1-ethoxycarbonyloxy-ethyl ester, 1-[(5-Chloro-pyridin-2-ylcarbamoyl)-methyl]-2-(1-isopropyl-piperidin-4-ylcarbamoyl)-1H-benzoimidazole-4-carboxylic acid 1-cyclohexyloxycarbonyloxy-ethyl ester, 1-[(5-Chloro-pyridin-2-ylcarbamoyl)-methyl]-1H-benzoimidazole-2-carboxylic acid [4-(3-oxo-morpholin-4-yl)-phenyl]-amide, 1-[(5-Chloro-pyridin-2-ylcarbamoyl)-methyl]-2-[4-(3-oxo-morpholin-4-yl)-phenylcarbamoyl]-1H-benzoimidazole-4-carboxylic acid methyl ester, 1-[5-(5-Chloro-thiophen-2-yl)-isoxazol-3-ylmethyl]-1H-benzoimidazole-2-carboxylic acid [4-(4-oxo-4H-pyridin-1-yl)-phenyl]-amide, 1-(3-Methoxy-benzyl)-1H-benzoimidazole-2-carboxylic acid [4-(4-oxo-4H-pyridin-1-yl)-phenyl]-amide, 1-[(5-Chloro-pyridin-2-ylcarbamoyl)-methyl]-1H-benzoimidazole-2-carboxylic acid [4-(4-oxo-4H-pyridin-1-yl)-phenyl]-amide, 1-[5-(5-Chloro-thiophen-2-yl)-isoxazol-3-ylmethyl]-1H-benzoimidazole-2-carboxylic acid (8-methyl-8-aza-bicyclo[3.2.1]oct-3-yl)-amide, 1-[5-(5-Chloro-thiophen-2-yl)-isoxazol-3-ylmethyl]-1H-benzoimidazole-2-carboxylic acid [4-(2,4-dioxo-3,4-dihydro-2H-pyrimidin-1-yl)-phenyl]-amide, 1-[5-(5-Chloro-thiophen-2-yl)-isoxazol-3-ylmethyl]-1H-benzoimidazole-2-carboxylic acid [4-(2-oxo-oxazolidin-3-yl)-phenyl]-amide, 1-[(5-Chloro-pyridin-2-ylcarbamoyl)-methyl]-1H-benzoimidazole-2-carboxylic acid [4-(2-oxo-oxazolidin-3-yl)-phenyl]-amide, 1-[(5-Chloro-pyridin-2-ylcarbamoyl)-methyl]-1H-benzoimidazole-2-carboxylic acid [4-(2,4-dioxo-3,4-dihydro-2H-pyrimidin-1-yl)-phenyl]-amide, 1-[5-(5-Chloro-thiophen-2-yl)-isoxazol-3-ylmethyl]-1H-benzoimidazole-2-carboxylic acid [4-(4-oxo-piperidin-1-yl)-phenyl]-aminde, 1-[5-(5-Chloro-thiophen-2-yl)-isoxazol-3-ylmethyl]-1H-benzoimidazole-2-carboxylic acid [4-(1,1-dioxo-1l6-thiomorpholin-4-yl)-phenyl]-amide, 1-[(5-Chloro-pyridin-2-ylcarbamoyl)-methyl]-1H-benzoimidazole-2-carboxylic acid [4-(1,1-dioxo-116-thiomorpholin-4-yl)-phenyl]-amide, 1-[5-(5-Chloro-thiophen-2-yl)-isoxazol-3-ylmethyl]-1H-benzoimidazole-2-carboxylic acid [4-(2-oxo-2H-pyrazin-1-yl)-phenyl]-amide, 1-[(5-Chloro-pyridin-2-ylcarbamoyl)-methyl]-1H-benzoimidazole-2-carboxylic acid [4-(2-oxo-2H-pyrazin-1-yl)-phenyl]-amide, 1-[5-(5-Chloro-thiophen-2-yl)-isoxazol-3-ylmethyl]-1H-benzoimidazole-2-carboxylic acid [4-(2-oxo-piperazin-1-yl)-phenyl]-amide, 1-[(5-Chloro-pyridin-2-ylcarbamoyl)-methyl]-1H-benzoimidazole-2-carboxylic acid [4-(2-oxo-piperazin-1-yl)-phenyl]-amide, 1-[(5-Chloro-pyridin-2-ylcarbamoyl)-methyl]-4-(2-methoxy-ethoxy)-1H-benzoimidazole-2-carboxylic acid [4-(3-oxo-morpholin-4-yl)-phenyl]-amide, 1-[(5-Chloro-pyridin-2-ylcarbamoyl)-methyl]-2-[4-(3-oxo-morpholin-4-yl)-phenylcarbamoyl]-11H-benzoimidazole-4-carboxylic acid, 1-[(5-Chloro-pyridin-2-ylcarbamoyl)-methyl]-5-(3-hydroxy-azetidine-1-carbonyl)-1H-benzoimidazole-2-carboxylic acid (1-isopropyl-piperidin-4-yl)-amide, 1-[(5-Chloro-pyridin-2-ylcarbamoyl)-methyl]-6-(3-hydroxy-azetidine-1-carbonyl)-1H-benzoimidazole-2-carboxylic acid (1-isopropyl-piperidin-4-yl)-amide, 1-[(5-Chloro-pyridin-2-ylcarbamoyl)-methyl]-1H-benzoimidazole-2,5-dicarboxylic acid 5-[(2-hydroxy-ethyl)-amide]2-[(1-isopropyl-piperidin-4-yl)-amide], 3-[(5-Chloro-pyridin-2-ylcarbamoyl)-methyl]-3H-benzoimidazole-2,5-dicarboxylic acid 5-[(2-hydroxy-ethyl)-amide]2-[(1-isopropyl-piperidin-4-yl)-amide], 1-[(5-Chloro-pyridin-2-ylcarbamoyl)-methyl]-1H-benzoimidazole-2,5-dicarboxylic acid 5-[(2-hydroxy-ethyl)-methyl-amide]2-[(1-isopropyl-piperidin-4-yl)-amide], 3-[(5-Chloro-pyridin-2-ylcarbamoyl)-methyl]-3H-benzoimidazole-2,5-dicarboxylic acid 5-[(2-hydroxy-ethyl)-methyl-amide]2-[(1-isopropyl-piperidin-4-yl)-amide], 1-[(5-Chloro-pyridin-2-ylcarbamoyl)-methyl]-2-(1-isopropyl-piperidin-4-ylcarbamoyl)-1H-benzoimidazole-5-carboxylic acid 1-cyclohexyloxycarbonyloxy-ethyl ester, 3-[(5-Chloro-pyridin-2-ylcarbamoyl)-methyl]-2-(1-isopropyl-piperidin-4-ylcarbamoyl)-3H-benzoimidazole-5-carboxylic acid 1-cyclohexyloxycarbonyloxy-ethyl ester, 1-[(5-Chloro-pyridin-2-ylcarbamoyl)-methyl]-2-(1-isopropyl-piperidin-4-ylcarbamoyl)-1H-benzoimidazole-5-carboxylic acid 1-ethoxycarbonyloxy-ethyl ester, 3-[(5-Chloro-pyridin-2-ylcarbamoyl)-methyl]-2-(1-isopropyl-piperidin-4-ylcarbamoyl)-3H-benzoimidazole-5-carboxylic acid 1-ethoxycarbonyloxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 2-hydroxy-ethyl ester, 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid 2-hydroxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid carboxymethyl ester, 1-(3-Methoxy-benzyl)-2-[4-(3-oxo-morpholin-4-yl)-phenylcarbamoyl]-1H-benzoimidazole-4-carboxylic acid, 1-[(5-Chloro-pyridin-2-ylcarbamoyl)-methyl]-5-(2-hydroxy-ethanesulfonyl)-1H-benzoimidazole-2-carboxylic acid (1-isopropyl-piperidin-4-yl)-amide, 1-[(5-Chloro-pyridin-2-ylcarbamoyl)-methyl]-6-(2-hydroxy-ethanesulfonyl)-1H-benzoimidazole-2-carboxylic acid (1-isopropyl-piperidin-4-yl)-amide, 1-[(5-Chloro-pyridin-2-ylcarbamoyl)-methyl]-2-(1-isopropyl-piperidin-4-ylcarbamoyl)-1H-benzoimidazole-4-carboxylic acid cyclopropylmethyl ester, 1-[(5-Chloro-pyridin-2-ylcarbamoyl)-methyl]-2-(1-isopropyl-piperidin-4-ylcarbamoyl)-1H-benzoimidazole-4-carboxylic acid 2-methoxy-ethyl ester, 1-[(5-Chloro-pyridin-2-ylcarbamoyl)-methyl]-4-hydroxymethyl-1H-benzoimidazole-2-carboxylic acid (1-isopropyl-piperidin-4-yl)-amide, 1-[(5-Chloro-pyridin-2-ylcarbamoyl)-methyl]-4-(2-methoxy-ethoxymethyl)-1H-benzoimidazole-2-carboxylic acid (1-isopropyl-piperidin-4-yl)-amide, 1-[(5-Chloro-pyridin-2-ylcarbamoyl)-methyl]-4-(morpholine-4-carbonyl)-1H-benzoimidazole-2-carboxylic acid (1-isopropyl-piperidin-4-yl)-amide, 1-[(5-Chloro-pyridin-2-ylcarbamoyl)-methyl]-4-([1,4]oxazepane-4-carbonyl)-1H-benzoimidazole-2-carboxylic acid (1-isopropyl-piperidin-4-yl)-amide, 1-[(5-Chloro-pyridin-2-ylcarbamoyl)-methyl]-4-(2,6-dimethyl-piperidine-1-carbonyl)-1H-benzoimidazole-2-carboxylic acid (1-isopropyl-piperidin-4-yl)-amide, 1-[(5-Chloro-pyridin-2-ylcarbamoyl)-methyl]-4-(4,4-difluoro-piperidine-1-carbonyl)-1H-benzoimidazole-2-carboxylic acid (1-isopropyl-piperidin-4-yl)-amide, 1-[(5-Chloro-pyridin-2-ylcarbamoyl)-methyl]-5-([1,4]oxazepane-4-carbonyl)-1H-benzoimidazole-2-carboxylic acid (1-isopropyl-piperidin-4-yl)-amide, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 2-hydroxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid carboxymethyl ester, 1-[5-(5-Chloro-thiophen-2-yl)-isoxazol-3-ylmethyl]-4-(3-methoxy-azetidine-1-carbonyl)-1H-benzoimidazole-2-carboxylic acid (1-isopropyl-piperidin-4-yl)-amide, 2-(1-Isopropyl-piperidin-4-ylcarbamoyl)-1-(3-methoxy-benzyl)-1H-benzoimidazole-4-carboxylic acid, 2-(1-Isopropyl-piperidin-4-ylcarbamoyl)-3-(3-methoxy-benzyl)-3H-benzoimidazole-4-carboxylic acid, 1-[2-(4-Chloro-phenyl)-ethyl]-2-(1-isopropyl-piperidin-4-ylcarbamoyl)-1H-benzoimidazole-4-carboxylic acid, 3-[2-(4-Chloro-phenyl)-ethyl]-2-(1-isopropyl-piperidin-4-ylcarbamoyl)-3H-benzoimidazole-4-carboxylic acid, 4-(3-Hydroxy-azetidine-1-carbonyl)-1-(3-methoxy-benzyl)-1H-benzoimidazole-2-carboxylic acid (1-isopropyl-piperidin-4-yl)-amide, 1-[2-(4-Chloro-phenyl)-ethyl]-4-(3-hydroxy-azetidine-1-carbonyl)-1H-benzoimidazole-2-carboxylic acid (1-isopropyl-piperidin-4-yl)-amide, 1-[2-(4-Chloro-phenyl)-ethyl]-4-(3-methoxy-azetidine-1-carbonyl)-1H-benzoimidazole-2-carboxylic acid (1-isopropyl-piperidin-4-yl)-amide, 2-(1-Isopropyl-piperidin-4-ylcarbamoyl)-1-(3-methoxy-benzyl)-1H-benzoimidazole-5-carboxylic acid methyl ester, 2-(1-Isopropyl-piperidin-4-ylcarbamoyl)-3-(3-methoxy-benzyl)-3H-benzoimidazole-5-carboxylic acid methyl ester, 1-[2-(4-Chloro-phenyl)-ethyl]-2-(1-isopropyl-piperidin-4-ylcarbamoyl)-1H-benzoimidazole-5-carboxylic acid methyl ester, 3-[2-(4-Chloro-phenyl)-ethyl]-2-(1-isopropyl-piperidin-4-ylcarbamoyl)-3H-benzoimidazole-5-carboxylic acid methyl ester, 1-[2-(4-Chloro-phenyl)-ethyl]-2-(1-isopropyl-piperidin-4-ylcarbamoyl)-1H-benzoimidazole-5-carboxylic acid, 1-(5-Chloro-benzo[b]thiophen-2-ylmethyl)-2-(1-isopropyl-piperidin-4-ylcarbamoyl)-1H-benzoimidazole-4-carboxylic acid, 3-(5-Chloro-benzo[b]thiophen-2-ylmethyl)-2-(1-isopropyl-piperidin-4-ylcarbamoyl)-3H-benzoimidazole-4-carboxylic, acid, 1-(5-Chloro-1H-indazol-3-ylmethyl)-2-(1-isopropyl-piperidin-4-ylcarbamoyl)-1H-benzoimidazole-4-carboxylic acid, 1-[5-(5-Chloro-thiophen-2-yl)-isoxazol-3-ylmethyl]-4-(4-hydroxy-piperidine-1-carbonyl)-1H-benzoimidazole-2-carboxylic acid (1-isopropyl-piperidin-4-yl)-amide, 7-[5-(5-Chloro-thiophen-2-yl)-isoxazol-3-ylmethyl]-1,3-dimethyl-2,6-dioxo-2,3,6,7-tetrahydro-1H-purine-8-carboxylic acid (1-isopropyl-piperidin-4-yl)-amide, 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid methyl ester, 3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid methyl ester, 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid, 3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid, 1-[5-(5-Chloro-thiophen-2-yl)-isoxazol-3-ylmethyl]-2-(1-cyclopropyl-piperidin-4-ylcarbamoyl)-1H-benzoimidazole-4-carboxylic acid, 3-[5-(5-Chloro-thiophen-2-yl)-isoxazol-3-ylmethyl]-2-(1-cyclopropyl-piperidin-4-ylcarbamoyl)-3H-benzoimidazole-4-carboxylic acid, 1-[(5-Chloro-pyridin-2-ylcarbamoyl)-methyl]-2-(1-cyclopropyl-piperidin-4-ylcarbamoyl)-1H-benzoimidazole-4-carboxylic acid methyl ester, 1-[(5-Chloro-pyridin-2-ylcarbamoyl)-methyl]-2-(1-cyclopropyl-piperidin-4-ylcarbamoyl)-1H-benzoimidazole-4-carboxylic acid, 1-[(5-Chloro-pyridin-2-ylcarbamoyl)-methyl]-2-(1-cyclopropyl-piperidin-4-ylcarbamoyl)-1H-benzoimidazole-4-carboxylic acid cyclopropylmethyl ester, 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid, 3-[5-(5-Chloro-thiophen-2-yl)-isoxazol-3-ylmethyl]-2-(1-isopropyl-piperidin-4-ylcarbamoyl)-3H-thieno[3,4-d]imidazole-4-carboxylic acid, 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid, 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-4-carboxylic acid, 3-[5-(5-Chloro-thiophen-2-yl)-isoxazol-3-ylmethyl]-3H-thieno[3,4-d]imidazole-2,6-dicarboxylic acid 6-[(2-hydroxy-ethyl)-amide]2-[(1-isopropyl-piperidin-4-yl)-amide], 3-[(5-Chloro-pyridin-2-ylcarbamoyl)-methyl]-2-(1-isopropyl-piperidin-4-ylcarbamoyl)-3H-thieno[3,4-d]imidazole-6-carboxylic acid, 3-[(5-Chloro-pyridin-2-ylcarbamoyl)-methyl]-2-(1-isopropyl-piperidin-4-ylcarbamoyl)-3H-thieno[3,4-d]imidazole-4-carboxylic acid, 3-[(5-Chloro-pyridin-2-ylcarbamoyl)-methyl]-6-([1,4]oxazepane-4-carbonyl)-3H-thieno[3,4-d]imidazole-2-carboxylic acid (1-isopropyl-piperidin-4-yl)-amide, 3-[5-(5-Chloro-thiophen-2-yl)-isoxazol-3-ylmethyl]-2-(1-isopropyl-piperidin-4-ylcarbamoyl)-6-(2,2,2-trifluoro-ethoxy)-3H-thieno[3,4-d]imidazole-4-carboxylic acid methyl ester, 1-[3-(5-Chloro-thiophen-2-yl)-isoxazol-5-ylmethyl]-2-(1-cyclopropyl-piperidin-4-ylcarbamoyl)-1H-benzoimidazole-5-carboxylic acid, 3-[3-(5-Chloro-thiophen-2-yl)-isoxazol-5-ylmethyl]-2-(1-cyclopropyl-piperidin-4-ylcarbamoyl)-3H-benzoimidazole-5-carboxylic acid 1-[5-(5-Chloro-thiophen-2-yl)-[1,3,4]thiadiazol-2-ylmethyl]-2-(1-cyclopropyl-piperidin-4-ylcarbamoyl)-1H-benzoimidazole-5-carboxylic acid, 3-[5-(5-Chloro-thiophen-2-yl)-[1,3,4]thiadiazol-2-ylmethyl]-2-(1-cyclopropyl-piperidin-4-ylcarbamoyl)-3H-benzoimidazole-5-carboxylic acid, 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide, 1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide, 1-[(5-Chloro-pyridin-2-ylcarbamoyl)-methyl]-4-(2-hydroxy-ethoxy)-1H-benzoimidazole-2-carboxylic acid (1-isopropyl-piperidin-4-yl)-amide, 1-[(5-Chloro-pyridin-2-ylcarbamoyl)-methyl]-2-[2-fluoro-4-(pyrrolidine-1-carbonyl)-phenylcarbamoyl]-1H-benzoimidazole-4-carboxylic acid methyl ester, 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid, 3-[5-(5-Chloro-thiophen-2-yl)-isoxazol-3-ylmethyl]-2-(1-cyclopropyl-piperidin-4-ylcarbamoyl)-7-methyl-3H-benzoimidazole-5-carboxylic acid, 1-[5-(5-Chloro-thiophen-2-yl)-isoxazol-3-ylmethyl]-5-fluoro-2-(1-isopropyl-piperidin-4-ylcarbamoyl)-1H-benzoimidazole-4-carboxylic acid, 1-[5-(5-Chloro-thiophen-2-yl)-isoxazol-3-ylmethyl]-2-(1-isopropyl-piperidin-4-ylcarbamoyl)-5-(2,2,2-trifluoro-ethoxy)-1H-benzoimidazole-4-carboxylic acid, or 1-[5-(5-Chloro-thiophen-2-yl)-isoxazol-3-ylmethyl]-4-(3-hydroxy-azetidine-1-carbonyl)-5-(2,2,2-trifluoro-ethoxy)-1H-benzoimidazole-2-carboxylic acid (1-isopropyl-piperidin-4-yl)-amide.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i. e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogens on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_8$)-alkyl, ($C_3$-$C_8$)-cycloalkyl, ($C_3$-$C_8$)-cycloalkyl-($C_1$-$C_4$)-alkyl-, ($C_6$-$C_{14}$)-aryl, Het-, ($C_6$-$C_{14}$)-aryl-($C_1$-$C_4$)-alkyl- or Het-($C_1$-$C_4$)-alkyl- and in which $R^{p2}$ has the meanings indicated for $R^{p1}$ with the exception of hydrogen.

Especially preferred compounds of the formula I are those wherein two or more residues are defined as indicated before for preferred compounds of the formula I, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

The compounds of the formula I can be prepared by utilising procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I can be prepared, for example in the course of a convergent synthesis, by linking two or more fragments which can be derived retrosynthetically from the formula I. More specifically, suitably substituted starting benzoimidazole derivatives are employed as building blocks in the preparation of the compounds of formula I. If not commercially available, such benzoimidazole derivatives can be prepared according to the well-known standard procedures for the formation of the benzoimidazole ring system. By choosing suitable precursor molecules, these benzoimidazole syntheses allow the introduction of a variety of substituents into the various positions of the benzoimidazole system, which can be chemically modified in order to finally arrive at the molecule of the formula I having the desired substituent pattern. As one of the comprehensive reviews in which numerous details and literature references on the chemistry of benzoimidazole and on synthetic procedures for their preparation can be found, J. Backes, B. Heinz, W. G. Ried in Houben-Weyl, "Methoden der Organischen Chemie" (Methods of Organic Chemistry), Georg Thieme Verlag, Stuttgart, Germany 1994, Vol. E8c Hetarene. If starting benzoimidazole derivatives are not commercially available and have to be synthesized this can be done, for example, according to the well-known benzoimidazole syntheses mentioned above. In the following procedures of particuluar interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modem separation techniques like, for example, preparative HPLC.

1) J. H. Musser et al., Synth. Commun. 1984, 10, 947.

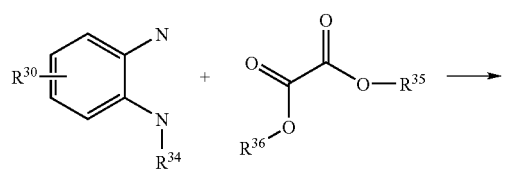

2) Reissert et al., Chem. Ber. 1905, 38, 93.

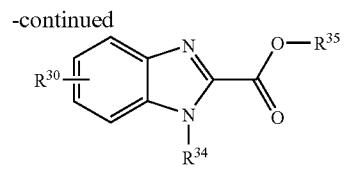

3) a) Usherwood et al., J. Chem. Soc. 1923, 123, 1082
   b) J. R. Young et al., Bioorg. Med. Chem Lett. 2002, 12, 827.
   c) H. Yukawa et al., Bioorg. Med. Chem Lett. 1997, 10, 1267.

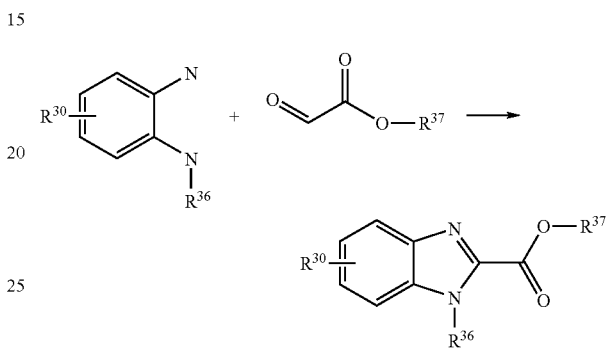

4) Z.-T. Huang et al., Tetrahedron 1992, 48, 2325.

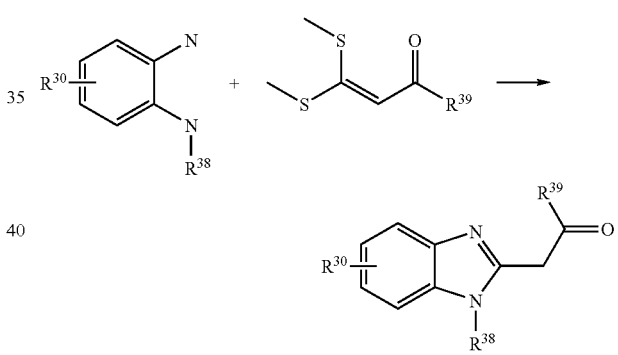

5) A. O. Abdelhamid et al., J. Heterocycl. Chem. 1988, 25, 403.

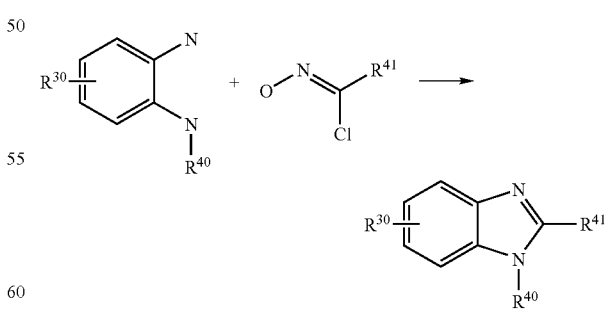

6) a) G. Holan et al., J. Chem. Soc. 1967, 20.
   b) G. Crank et al., Aust. J. Chem. 1982, 35, 775.
   c) G. Dannhardt et al., Arch. Pharm. 2000, 333, 123.
   d) P. Louvet et al., Eur. J. Med. Chem. 1993, 28, 71.
   e) E. L. Samuel et al., J. Chem. Soc. C, 1967, 25.

7) P. A. Petyunin et al., Khim. Geterosikl Soedin 19982, 5, 684.
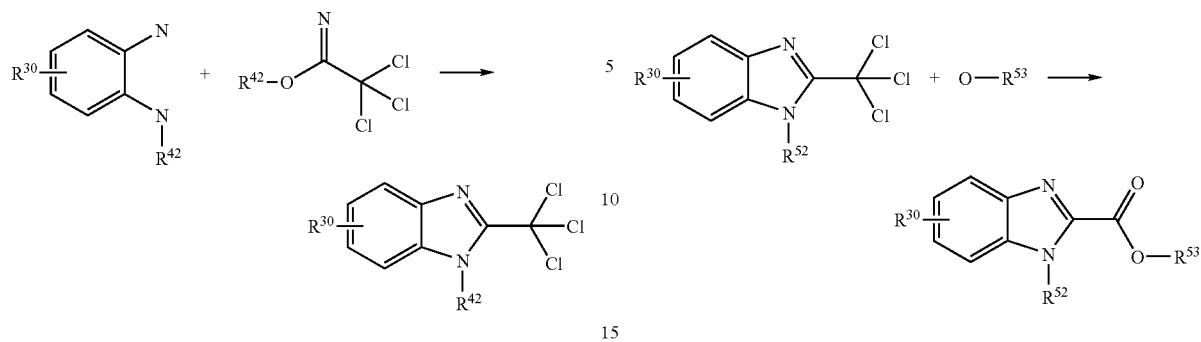
8) C. T. Brain et al., Tetrahedron Lett., 2002, 43, 1893.
9) E. L. Samuel et al., J. Chem. Soc. C, 1967, 25.
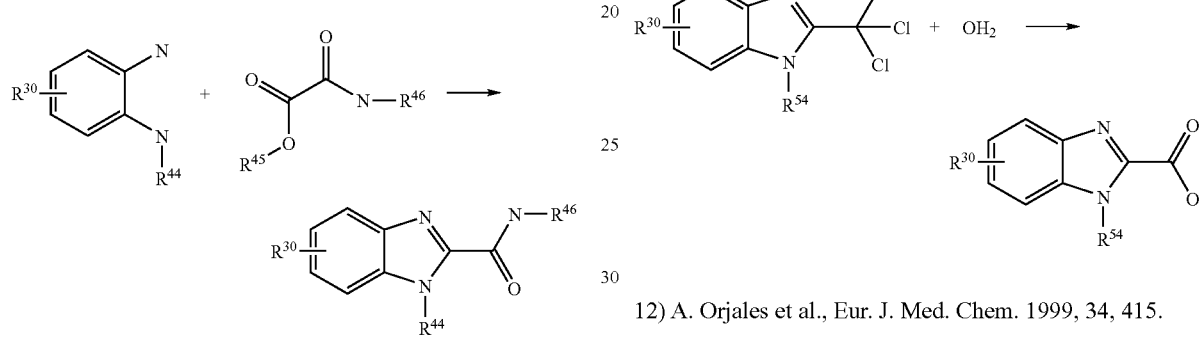
10) E. L. Samuel et al., J. Chem. Soc. C, 1967, 25.
11) G. Dannhardt et al, Arch. Pharm. 2000, 333, 123.
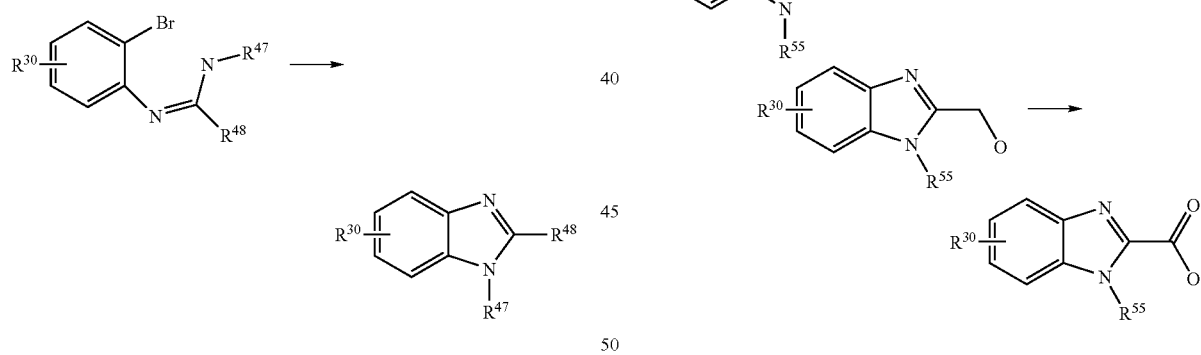
12) A. Orjales et al., Eur. J. Med. Chem. 1999, 34, 415.
13) H. Göker et al., Arch. Pharm. Pharm. Med. Chem. 2001, 334, 148.
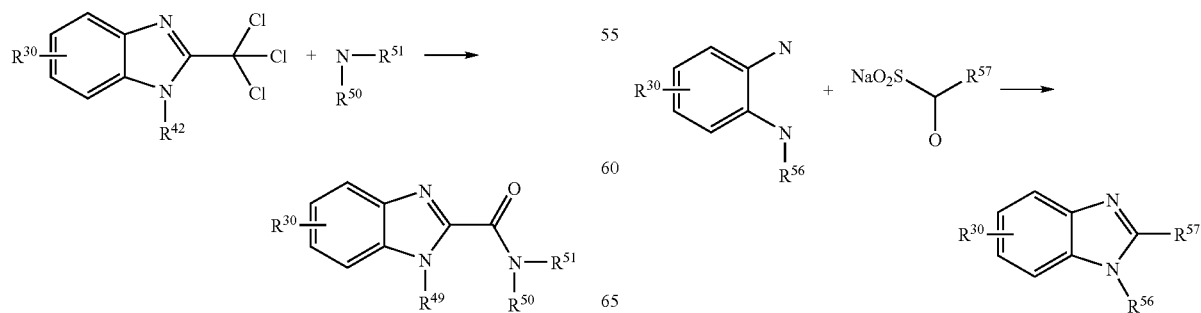

14) a) R. B. Baudy et al., J. Med. Chem. 2001, 44, 1516.
b) Y. K. Yun et al., Synlett 2002, No. 5, 739.

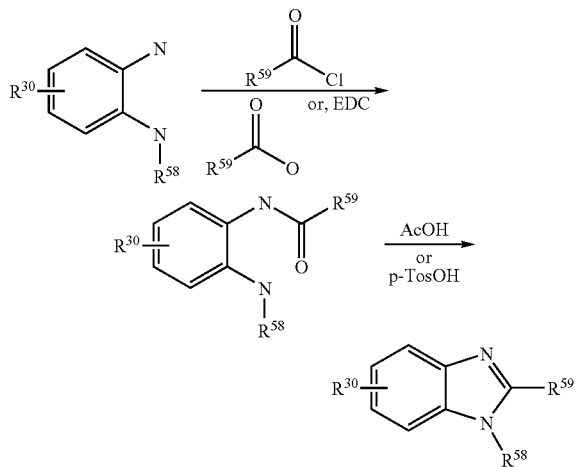

15) N. Nabulsi, R. Gandour, J. Org. Chem. 1991, 56, 2260.

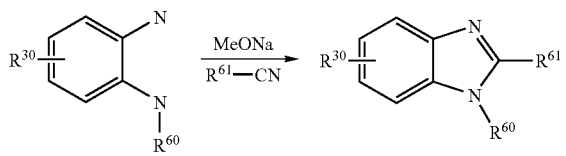

Depending on the substituents in the starting materials, in certain benzoimidazole syntheses mixtures of positional isomers may be obtained, which, however, can be separated by modem separation techniques like, for example, preparative HPLC.

Further, in order to obtain the desired substituents at the benzoimidazole ring system in the formula I, the functional groups introduced into the ring system during the benzoimidazole synthesis can be chemically modified. Especially the groups present in the benzoimidazole ring system can be modified by a variety of reactions and thus the desired residues $R^{30}$ be obtained. For example, a benzoimidazole carrying hydrogen in the 2-position can also be obtained by saponification and subsequent decarboxylation of benzoimidazole carrying an ester group in the respective position. Carboxylic acid groups and acetic acid groups in the 2-position, the 4-position, 5-position, 6-position and the 7-position can be converted into their homologues by usual reactions for chain elongation of carboxylic acids. Halogen atoms can be introduced, for example according to procedures described in the literature like the following. For the fluorination of benzoimidazoles N-fluoro-2,4,6-trimethylpyridinium triflate is the reagent of choice (T. Umemoto, S. Fukami, G. Tomizawa, K. Harasawa, K. Kawada, K. Tomita, J. Am. Chem. Soc. 1990, 112, 8563) but is not limited to this reagent. The chlorination, bromination, or iodination of benzoimidazoles can be accomplished by the reaction of the elemental halogens or by the use of NCS, NBS or NIS and many other reagents well known to those skilled in the art. These procedures are for example referred in Y. Shi et al., Synth. Commun. 1993, 23, 2623; H. Rapoport et al., Synthesis 1988, 767; R. Jones et al., J. Org. Chem. 1999, 64, 6575; J. Sessler et al., Chem. Eur. J. 2001, 7, 721. Depending on the reaction conditions, reagent, stochiometry and substitution pattern the halogen is introduced in the 2-position and/or 4-position and/or 5-position and/or 6-position and/or 7-position. By selective halogen/metal exchange or metalation by selective hydrogen/metal exchange and subsequent reaction with a wide range of electrophiles various substituents can be introduced at the heterocyclic nucleus. (R. Breslow et al., J. Am. Chem. Soc. 1983, 105, 5337; P. Knochel et al., J. Org. Chem. 2000, 65, 4618; S. Ohta et al., Chem. Pharm. Bull. 1996, 44, 1831).

Halogens or hydroxy groups—via the triflate or nonaflate—or primary amines—via its diazonium salt—or after interconversion to the corresponding stannane, or boronic acid—present in the benzoimidazole structure can be converted into a variety of other functional groups like for example—CN, —CF$_3$, —C$_2$F$_5$, ethers, acids, amides, amines, alkyl- or aryl-groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. I 1997, 3053; S. Buchwald et al. J. Am. Chem Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689). For example, nitro groups can be reduced to amino group with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce the residues $R^{30}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the benzoimidazole nucleus can be hydrolyzed to the corresponding carboxylic acids, which after activation can then be reacted with amines or alcohols under standard conditions. Furthermore these ester or acid groups can be reduced to the corresponding alcohols by many standard procedures. Ether groups present at the benzoimidazole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{62}$ or $R^{8'}$ attached to the benzoimidazole ring system by application of parallel synthesis methodology, beside a variety of reactions, palladium, nickel or copper catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; P. Lam, C. Clark, S. Saubern, J. Adams, M. Winters, D. Chan, A. Combs, Tetrahedron Lett. 1998, 39, 2941; D. Chan, K. Monaco, R. Wang, M. Winters, Tetrahedron Lett. 1998, 39, 2933; J. Wolfe, H. Tomori, J. Sadight, J. Yin, S. Buchwald, J. Org. Chem. 2000, 65, 1158; V. Farina, V. Krishnamurthy, W. Scott, The Stille Reaction, Wiley, 1994; S. Buchwald et al., J. Am. Chem Soc. 2001, 123, 7727; S. Kang et al., Synlett 2002, 3, 427; S. Buchwald et al., Org. Lett. 2002, 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to a benzoimidazole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues in the 1-position of the benzoimidazole ring in the compounds of the formula I and in the $COR^{8'}$ group present in the 2-position of the benzoimidazole ring can be introduced into the starting benzoimidazole derivative obtainable as outlined above by consecutive reaction steps using parallel synthesis methodologies like those outlined below using procedures which per se are well known to one skilled in the art.

The residues $R^{8'}$ that can be introduced in formula 2, for example, by condensing a corresponding carboxylic acid of the formula 2 with a compound of the formula $HR^{8'}$, i.e. with an amine of the formula $HN(R^{1'})R^{2'}$—V-G-M to give a compound of the formula 3. The compound of the formula 3 thus obtained can already contain the desired final groups, i.e. the groups $R^{8'}$ and $R^{62}$ can be the groups —$N(R^1)$—$R^2$—V-G-M and $R^0$-Q- as defined in the formula I, or optionally in the compound of the formula 3 thus obtained subsequently the residue or the residues $R^{8'}$ and the residue R are converted into the residues —$N(R^1)$—$R^2$—V-G-M and $R^0$-Q-, respectively, to give the desired compound of the formula I.

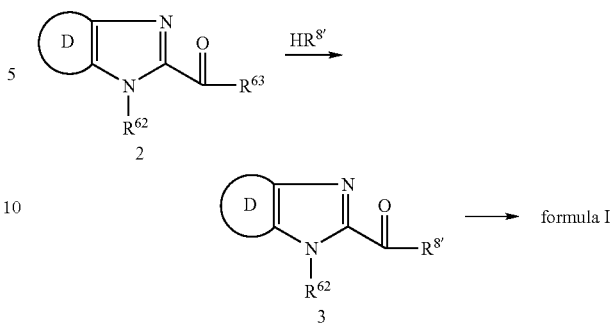

Thus, the residues $R^{8'}$ and the residues $R^{1'}$ and $R^{2'}$—V-G-M contained therein can have the denotations of $R^1$ and $R^2$—V-G-M, respectively, given above or in addition in the residues $R^{1'}$ and $R^{2'}$—V-G-M functional groups can also be present in the form of groups that can subsequently be transformed into the final groups $R^1$ and $R^2$—V-G-M, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Examples of precursor groups are cyano groups and nitro groups. The cyano group can in a later step be transformed into carboxylic acid derivatives or by reduction into aminomethyl groups, or the nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{62}$ in the compounds of the formulae 2 and 3 can denote the group -Q-$R^0$ as defined above which finally is to be present in the desired target molecule of the formula I, or it can denote a group which can subsequently be transformed into the group -Q-$R^0$, for example a precursor group or a derivative of the group -Q-$R^0$ in which functional groups are present in protected form, or $R^{62}$ can denote hydrogen or a protective group for the nitrogen atom of the benzoimidazole ring. Similarly, the residues $R^{30}$ have the corresponding definitions of $R^3$ in formula I as defined above, however, for the synthesis of the compounds of the formula I these residues, too, can in principle be present at the stage of the condensation of a compound of the formula 2 with a compound of the formula $HR^{8'}$ giving a compound of the formula 3 in the form of precursor groups or in protected form.

The residues $R^{63}$ in the compounds of the formula 2 which can be identical or different, can be, for example, hydroxy or $(C_1-C_4)$-alkoxy, i.e., the groups $COR^{63}$ present in the compounds of the formula 2 can be, for example, the free carboxylic acids or esters thereof like alkyl esters as can be the groups COR⁸' in the compounds of the formula I. The groups COR⁶³ can also be any other activated derivative of a carboxylic acid which allows amide formation, ester formation or thioester formation with a compound of the formula HR⁸'. The group COR⁶³ can be, for example, an acid chloride, an activated ester like a substituted phenyl ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula HR⁸' under standard conditions. A carboxylic acid group COOH representing COR⁶³ in a compound of the formula 2 can be obtained, for example, from an ester group introduced into the benzoimidazole system during a benzoimidazole synthesis by standard hydrolysis procedures.

Compounds of the formula I in which a group COR⁸' is an ester group can also be prepared from compounds of the formula 2 in which COR⁶³ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formula I in which a group COR⁸ is an amide group can be prepared from amines and compounds of the formula 2 in which COR⁶³ is a carboxylic acid group or an ester thereof by common amination reactions. Especially for the preparation of amides the compounds of the formula 2 in which COR⁶³ is a carboxylic acid group can be condensed under standard conditions with compounds of the formula HR⁸' which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene) amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others.

If the residue -Q-R⁰ present in a benzoimidazole of the formula I or the residue R⁶³ present in a benzoimidazole of the formula 2, or a residue in which functional groups within the residue -Q-R⁰ or R⁶³ are present in protected form or in the form of a precursor group, have not already been introduced during a preceding step, for example during a synthesis of the benzoimidazole nucleus, these residues can, for example, be introduced into the 1-position of the benzoimidazole system by conventional literature procedures well known to one skilled in the art for N-alkylation, reductive amination, N-arylation, N-acylation or N-sulfonylation of ring nitrogen atoms of heterocycles. The starting benzoimidazole derivative that is to be employed in such a reaction carries hydrogen in the 1-position. N-Alkylation of a ring nitrogen atom can, for example, be performed under standard conditions, preferably in the presence of a base like K₂CO₃, Cs₂CO₃, NaH or KOᵗBu, using an alkylating compound of the formula LG-Q-R⁰ or of the formula R⁶²-LG, wherein the atom in the group Q or in the group R⁶² bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated by a conventional activating agent. For the preparation of compounds in which A is a direct linkage and an aromatic group is directly bonded to the 1-position of the benzoimidazole system, conventional arylation procedures can be used. For example aryl fluorides like alkyl fluorobenzoates or 4-fluorophenyl methyl sulfones can be employed as arylating agents. Such processes are described, for example, by M. Yamada et al. J. Med. Chem. 1996, 39, 596; J. Ohmori et al. J. Med. Chem. 1996, 39, 3971. Alternatively a wide variety of substituted aryl iodides, aryl bromides or aryl triflates can serve as arylating agents at the 1-position of the heterocyclic nitrogen in a copper salt or palladium mediated reaction according for example to P. Cozzi et al. Farmaco 1987, 42, 205; P. Unangst, D. Connor, R. Stabler, R. Weikert, J. Heterocycl. Chem. 1987, 24, 811; G. Tokmakov, I. Grandberg, Tetrahedron 1995, 51, 2091; D. Old, M. Harris, S. Buchwald, Org. Lett. 2000, 2, 1403, G. Mann, J. Hartwig, M. Driver, C. Fernandez-Rivas, J. Am. Chem. Soc. 1998, 120, 827; J. Hartwig, M. Kawatsura, S. Hauk, K. Shaughnessy, L. J. Org. Chem. 1999, 64, 5575; S. Buchwald et al., J. Am. Chem. Soc. 2001, 123, 7727. Moreover such arylations can also be accomplished by reaction of a wide range of substituted aryl boronic acids as demonstrated for example by W. Mederski, M. Lefort, M. Germann, D. Kux, Tetrahedron 1999, 55, 12757; J. Collman et al., J. Org. Chem. 2001, 66, 7892. During the above-mentioned transformations positional isomers may occur, nevertheless these mixtures of positional isomers can be separated by modern separation techniques like, for example, preparative HPLC.

Another particular embodiment of the present invention is a process for the preparation of a compound of formula IV, wherein the primary amine is
a) NH₂—R21, wherein R21 is as defined in formula IV,
b) NH₂—R²—V-G-M, wherein R², V, G and M are as defined in formula IV,
c) NH₂—N(R21)-R22, wherein R21 and R22 are as defined in formula IV or
d) a compound of formula VI

(VI)

wherein R², R21, V, G and M are as defined as in formula IV.

Another particular embodiment of the present invention is a process for the preparation of a compound of formula IV, wherein the secondary amine is
a)

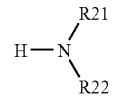

wherein R21 and R22 are as defined in formula IV,
b) a compound of formula VII

(VII)

wherein R21, R², V, G and M are as defined in formula IV, or c) a compound of formula VIII

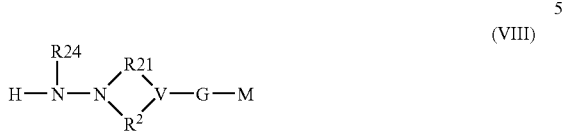

(VIII)

wherein R², R21, R24, V, G and M are as defined in formula IV.

Introducing a primary or secondary amine into a mixture of water and a water miscible organic solvent starts the preparation of the compound of the formula IV. Then a base, particularly sodium bicarbonate, is added and the resulting solution or suspension is stirred or shaken at room temperature. Finally the compound of the formula V is added either in solid form or dissolved in an appropriate organic solvent. The resulting reaction mixture is then stirred or shaken under temperature control. After an appropriate reaction time the compound of the formula IV is isolated by precipitation, e.g. by removing the organic solvent by evaporation. Alternatively, the compound of the formula IV can be extracted using an organic solvent such as dichloromethane, ethyl acetate, toluene, tertiary-butyl methyl ether or diethyl ether.

Preferably, for the inventive reaction, 2 mol to 12 mol of a base are used per 1 mol of the compound of the formula V.

Preferably, for the inventive reaction, 1 mol to 1.5 mol of a primary amine or a secondary amine are used per 1 mol of the compound of the formula V.

The amount of water-miscible organic solvent used is generally from 5 g to 300 g per 1 g of the compound of the formula V, preferably from 10 g to 200 g.

The reaction time is generally between a few minutes and 24 hours, preferably 1 to 5 hours, depending on the composition of the mixture and the temperature range selected.

The reaction temperature is from 5° C. to 120° C., preferably from 10° C. to 35° C., in particular 25° C. In case of 1-substitued imidazole-derivatives (compounds wherein R23 is not hydrogen) the reaction temperature is from 50° C. to 120° C., preferably from 70° C. to 100° C., in particular 90° C.

The residual content of starting substrate of the compound of the formula V was reduced to a content, which is below 0.5% in the isolated compound of formula IV.

Advantageous features in the inventive process are the very short reaction times, the omission of additional purification steps, the high yields and the high purity of the products prepared.

Further advantageous features in the inventive process are:

easy accessibility of diversely substituted imidazole-2-carboxylic acid amides, particularly benzoimidazole-2-carboxylic acid amides. The preparation of these structural classes is difficult when using standard procedures such as coupling of benzoimidazole-2-carboxylic acids with amines. Very often the synthesis of substituted benzoimidazole-2-carboxylic acids is laborious. Furthermore, benzoimidazole-2-carboxylic acids, especially 1-substituted benzoimidazole-2-carboxylic acids, tend to decarboxylate during their synthesis but also under typical amide coupling conditions.

easy accessibility of yet completely unknown structural classes, for example thieno-[3,4]-imidazole-2-carboxylic acid amides.

amines with a very low reactivity, for example amines which even do not react with the corresponding benzoimidazole-2-carboxylic acid chlorides, such as (4-amino-3-fluoro-phenyl)-pyrrolidin-1-yl-methanone (example 165) or 2-amino-3-nitro-benzoic acid methyl ester (example 167), react in a smooth way (under very mild conditions) allowing the construction of special imidazole-2-carboxylic acid anilides, which are difficult to synthesize by other existing methods. For example, the acylation of 2-amino-3-nitro-benzoic acid methyl ester with even a sterically not hindered acid chloride, for example acetyl chloride, requires a large excess of the corresponding acid chloride and elevated temperatures (100° C., toluene as solvent).

Preferred methods include, but are not limited to those described in the examples.

The compounds of the present invention are serine protease inhibitors, which inhibit the activity of the blood coagulation enzyme factors Xa and/or factor VIIa In particular, they are highly active inhibitors of factor Xa. They are specific serine protease inhibitors inasmuch as they do not substantially inhibit the activity of other proteases whose inhibition is not desired. The activity of the compounds of the formula I can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and/or factor VIIa the compounds of the formula I and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i. e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatine capsules it is possible to use, for example, lactose, cornstarch or derivatives thereof, talc, stearic acid or its salts, etc. Carriers for soft gelatine capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of factor Xa and/or factor VIIa or to isolate factor Xa and/or factor VIIa in a substantially purified form. A compound of the invention can be labelled with, for example, a radioisotope, and the labelled compound bound to factor Xa and/or factor VIIa is then detected using a routine method useful for detecting the particular label. Thus, a compound of the formula I or a salt thereof can be used as a probe to detect the location or amount of factor Xa and/or factor VIIa activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

| Abbreviations used: | |
|---|---|
| tert-Butyl | tBu |
| 2,2'-bis(diphenylphoshino-1,1'-binaphthyl | Binap |
| Bis-(oxo-3-oxazolidinyl)-phosphoiyl chloride | BOP-Cl |
| dibenzylidenacetone | dba |
| Dichloromethane | DCM |
| Dicyclohexyl-carbodiimide | DCC |
| Diethylphosphoryl cyanide | DEPC |
| Diisopropylethyl amine | DIPEA |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| O-(7-Azabenzotriazol-1-yl)-N,N,N',N'-tetramethyluronium-hexafluorophosphate | HATU |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

1-[5-(5-Chloro-thiophen-2-yl)-isoxazol-3-ylmethyl]-1H-benzoimidazole-2-carboxylic acid (1-isopropyl-piperidin-4-yl)-amide (i) (1-Isopropyl-piperidin-4-yl)-carbamic acid tert-butyl ester To a solution of 5.0 g Piperidin-4-yl-carbamic acid tert-butyl ester in 15 mL methanol, 7.34 mL acetone, 3.14 g Na(CN)BH$_3$ and 0.3 mL acetic acid were added. After stirring for 16 h at room temperature the solvent was removed under reduced pressure and the residue was partitioned between 30 mL water and 30 mL ethyl acetate. The organic layer was washed with saturated Na$_2$CO$_3$ solution, water and then dried over Na$_2$SO$_4$. The solvent was removed under reduced pressure to give the product as a white solid. Yield: 4.8 g MS (ES$^+$): m/e=243.

(ii) 1-Isopropyl-piperidin-4-ylamine

To 4.8 g (1-Isopropyl-piperidin-4-yl)-carbamic acid tert-butyl ester in 15 mL methanol, 20 mL methanolic hydrochloric acid (8 M) were added and the mixture was stirred for 16 h. Removal of the solvent under reduced pressure, followed by removal of residual volatiles by twice coevaporating with toluene, gave the product. Yield: 5.42 g MS (ES$^+$): m/e=143.

(iii) 1H-Benzoimidazole-2-carboxylic acid (1-isopropyl-piperidin-4-yl)-amide

To a solution of 300 mg 1H-Benzoimidazole-2-carboxylic acid in 3 mL DMF and 1 mL NEt$_3$, 398 mg 1-Isopropyl-piperidin-4-ylamine hydrochloride and 470 mg BOP-Cl were added and the mixture was stirred for 3 h. Finally, 3 mL saturated NaHCO$_3$ solution were added and the mixture was filtered through a chem elut® cartridge by elution with ethyl acetate. After removal of the solvent under reduced pressure the crude product was subjected to the next reaction step without further purification.

Yield: 604 mg.

(iv) 1-[5-(5-Chloro-thiophen-2-yl)-isoxazol-3-ylmethyl]-1H-benzoimidazole-2-carboxylic acid (1-isopropyl-piperidin-4-yl)-amide To a solution of 200 mg 1H-Benzoimidazole-2-carboxylic acid (1-isopropyl-piperidin-4-yl)-amide in 2 mL DMF, 227 mg Cs$_2$CO$_3$ and 194 mg 3-Bromomethyl-5-(5-Chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2] were added at RT and the mixture was stirred for 16 h. After addition of 5 mL water the mixture was filtered through a chem elut® cartridge by elution with ethyl acetate. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 29 mg MS (ES$^+$): m/e=484, chloro pattern.

Example 2

1-[(4-Chloro-phenylcarbamoyl)-methyl]-1H-benzoimidazole-2-carboxylic acid (1-isopropyl-piperidin-4-yl)-amide (i) 2-Bromo-N-(4-Chloro-phenyl)-acetamide
To a solution of 5 g 4-Chloro-phenylamine and 1.5 mL pyridine in 30 mL toluene, 8 g bromo-acetyl bromide dissolved in 10 mL toluene were added dropwise under ice cooling. After 2 h the precipitate was isolated by filtration and recrystallized from toluene to yield a white solid.
Yield: 10 g.

(ii) 1-[(4-Chloro-phenylcarbamoyl)-methyl]-1H-benzoimidazole-2-carboxylic acid (1-isopropyl-piperidin-4-yl)-amide
To a solution of 200 mg 1H-Benzoimidazole-2-carboxylic acid (1-isopropyl-piperidin-4-yl)-amide in 2 mL DMF, 227 mg Cs$_2$CO$_3$ and 173 mg 2-Bromo-N-(4-Chloro-phenyl)-acetamide were added at RT and the mixture was stirred for 16 h. After addition of 5 mL water the mixture was filtered through a chem elut® cartridge by elution with ethyl acetate. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 63 mg MS (ES$^+$): m/e=454, chloro pattern.

Example 3

1-[(5-Chloro-pyridin-2-ylcarbamoyl)-methyl]-1H-benzoimidazole-2-carboxylic acid (1-isopropyl-piperidin-4-yl)-amide (i) 2-Bromo-N-(5-Chloro-pyridin-2-yl)-acetamide
To a solution of 5 g 5-Chloro-pyridin-2-ylamine and 1.5 mL pyridine in 30 mL toluene, 8 g bromo-acetyl bromide dissolved in 10 mL toluene were added dropwise under ice cooling. After 2 h the precipitate was isolated by filtration and recrystallized from toluene to yield a white solid.
Yield: 12 g.

(ii) 1-[(5-Chloro-pyridin-2-ylcarbamoyl)-methyl]-1H-benzoimidazole-2-carboxylic acid (1-isopropyl-piperidin-4-yl)-amide
To a solution of 200 mg 1H-Benzoimidazole-2-carboxylic acid (1-isopropyl-piperidin-4-yl)-amide in 2 mL DMF, 227 mg Cs$_2$CO$_3$ and 174 mg 2-Bromo-N-(5-Chloro-pyridin-2-yl)-acetamide were added at RT and the mixture was stirred for 16 h. After addition of 5 mL water the mixture was filtered through a chem elut® cartridge by elution with ethyl acetate. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 34 mg MS (ES$^+$): m/e=455, chloro pattern.

Example 4

1-[5-(5-Chloro-thiophen-2-yl)-isoxazol-3-ylmethyl]-1H-benzoimidazole-2-carboxylic acid (1-pyrimidin-4-yl-piperidin-4-yl)-amide (i) (1-Pyrimidin-4-yl-piperidin-4-yl)-carbamic acid tert-butyl ester
To a solution of 395 mg [1-(2-Chloro-pyrimidin-4-yl)-piperidin-4-yl]-carbamic acid tert-butyl ester in 10 mL ethanol and 0.3 mL acetic acid, 20 mg Pd/C (10%) were added and the mixture purged with argon for 10 min. Then the mixture was stirred under a hydrogen atmosphere for 5 h at RT. After addition of 10 mL ethyl acetate the reaction mixture was filtered through a pad of celite. The solvent was evaporated under reduced pressure and the residue codistilled twice with toluene to give the product as a white solid. Yield: 468 mg.

(ii) 1-Pyrimidin-4-yl-piperidin-4-ylamine
To a solution of 468 mg (1-Pyrimidin-4-yl-piperidin-4-yl)-carbamic acid tert-butyl ester in 2 mL DCM, 2 mL TFA were added and the mixture was stirred for 2 h at RT. Then, 10 mL toluene were added and the solvents were removed under reduced pressure. The residue was codistilled twice with toluene to yield a yellow oil. The product was obtained as its trifluoroacetate salt.
Yield: 703 mg.

(iii) 1H-Benzoimidazole-2-carboxylic acid (1-pyrimidin-4-yl-piperidin-4-yl)-amide
To a solution of 80 mg 1H-Benzoimidazole-2-carboxylic acid in 1 mL DMF and 0.2 mL NEt$_3$, 200 mg 1-Pyrimidin-4-yl-piperidin-4-ylamine trifluoroacetate and 125 mg BOP-Cl were added and the mixture was stirred for 3 h. Finally, 3 mL saturated NaHCO$_3$ solution were added and the mixture was filtered through a chem elut® cartridge by elution with ethyl acetate. After removal of the solvent under reduced pressure the crude product was subjected to the next reaction step without further purification. Yield: 160 mg.

(iv) 1-[5-(5-Chloro-thiophen-2-yl)-isoxazol-3-ylmethyl]-1H-benzoimidazole-2-carboxylic acid (1-pyrimidin-4-yl-piperidin-4-yl)-amide
To a solution of 160 mg 1H-Benzoimidazole-2-carboxylic acid (1-pyrimidin-4-yl-piperidin-4-yl)-amide in 2 mL DMF, 161 mg Cs$_2$CO$_3$ and 138 mg 3-Bromomethyl-5-(5-Chloro-thiophen-2-yl)-isoxazole were added at RT and the mixture was stirred for 16 h. After addition of 5 mL water the mixture was filtered through a chem elut® cartridge by elution with ethyl acetate. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 114 mg MS (ES$^+$): m/e=520, chloro pattern.

Example 5 a) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid methyl ester b) 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid methyl ester (i) Methyl-2-trichloromethyl-1H-benzoimidazole-5-carboxylate 2.00 g (12.0 mmol) Methyl-3,4-diamino-benzoate were dissolved in 50 mL concentrated acetic acid. Then 2.09 mL (1.4 equiv.) methyl-2,2,2-trichloroacetimidate were added slowly and the resulting mixture was stirred at room temperature for 2 h. The mixture was diluted with 100 mL toluene and the solvent was removed under reduced pressure. The residue was taken up in dichloromethane and washed once with a saturated NaHCO$_3$-solution and once with brine. The organic layer was dried over MgSO$_4$ and the solvent was removed under reduced pressure to give pure methyl-2-trichloromethyl-1H-benzoimidazole-5-carboxylate as a light brown amorphous solid. Yield: 3.64 g MS (ES$^+$): m/e=293, chloro pattern.

(ii) 2-(1-Isopropyl-piperidin-4-ylcarbamoyl)-1H-benzoimidazole-5-carboxylic acid methyl ester 500 mg (1.7 mmol) Methyl-2-trichloromethyl-1H-benzoimidazole-5-carboxylate were added to a mixture of 548 mg (1.8 equiv.) 1-isopropyl-piperidine-4-ylamine-dihydrochloride and 1.43 g (10 equiv.) NaHCO$_3$ in 15 mL THF and 7.5 mL H$_2$O and stirred vigorously for 4 h at room temperature. The reaction mixture was diluted with dichloromethane and washed with a saturated NaHCO$_3$-solution and brine. The organic layer was dried over MgSO$_4$ and concentrated. Preparative HPLC (CH$_3$CN/H$_2$O gradient+0.05% formic acid) gave pure 2-(1-isopropyl-piperidin-4-ylcarbamoyl)-1H-benzoimidazole-5-carboxylic acid methyl ester as a white solid.

Yield: 300 mg MS (ES$^+$): m/e=345.

(iii) a) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid methyl ester b) 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid methyl ester 115 mg (0.33 mmol) 2-(1-Isopropyl-piperidin-4-ylcarbamoyl)-1H-benzoimidazole-5-carboxylic acid methyl ester were dissolved in 10 mL DMF. Subsequently 69.2 mg (1.5 equiv.) K$_2$CO$_3$ and 111.6 mg (1.2 equiv.) 3-bromomethyl-5-(5-Chloro-thiophen-2-yl)-isoxazole were added and the resulting mixture was stirred for 2 h at 80° C. The reaction mixture was diluted with toluene and washed twice with a saturated NaHCO$_3$-solution and once with brine, dried over anhydrous MgSO$_4$ and concentrated under reduced pressure. Preparative RP-HPLC (CH$_3$CN/H$_2$O gradient+0.05% formic acid) gave a 6:4 mixture of both isomers described in the title. These isomers could be separated by NP-HPLC using a chiral stationary phase and a mixture of heptane, ethanol, methanol and diethyl amine as solvent. Structural assignment of both isomers was achieved by NOE-spectroscopy.

Yield of 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid methyl ester: 52 mg; MS (ES$^+$): m/e=542, chloro pattern.

Yield of 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid methyl ester: 34 mg; MS (ES$^+$): m/e=542, chloro pattern.

Example 6

1-[5-(5-Chloro-thiophen-2-yl)-isoxazol-3-ylmethyl]-2-(1-isopropyl-piperidin-4-ylcarbamoyl)-1H-benzoimidazole-5-carboxylic acid To a suspension of 43.6 mg (0.080 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid methyl ester in 4 mL MeOH 0.4 mL of a 1 M aqueous LiOH-solution were added and the resulting mixture was stirred at 60° C. for 5 h. The mixture was acidified by the addition of a 1 M HCl-solution (pH≈2-3) and concentrated under reduced pressure. Final purification by preparative RP-HPLC (CH$_3$CN/H$_2$O gradient+0.05% formic acid) gave pure 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid. The corresponding dihydrochloride was obtained by treatment of the product with a 0.1 M HCl-solution followed by lyophilization. Yield: 43 mg MS (ES$^+$): m/e=528, chloro pattern.

Example 7

3-[5-(5-Chloro-thiophen-2-yl)-isoxazol-3-ylmethyl]-2-(1-isopropyl-piperidin-4-ylcarbamoyl)-3H-benzoimidazole-5-carboxylic acid 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid was prepared as described in example 6 from 20 mg (0.037 mmol) 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid methyl ester.

Yield: 18 mg MS (ES$^+$): m/e=528, chloro pattern.

Example 8 a) 1-[2-(5-Chloro-thiophen-2-yl)-thiazol-5-ylmethyl]-2-(1-isopropyl-piperidin-4-ylcarbamoyl)-1H-benzoimidazole-5-carboxylic acid methyl ester b) 3-[2-(5-Chloro-thiophen-2-yl)-thiazol-5-ylmethyl]-2-(1-isopropyl-piperidin-4-ylcarbamoyl)-3H-benzoimidazole-5-carboxylic acid methyl ester To a solution of 80.0 mg (0.23 mmol) 2-(1-isopropyl-piperidin-4-ylcarbamoyl)-1H-benzoimidazole-5-carboxylic acid methyl ester in 5 mL DMF 9.3 mg sodium hydride (60% suspension in mineral oil) were added. The mixture was stirred for 30 min at room temperature and subsequently 68.4 mg (0.23 mmol) 5-bromomethyl-2-(5-Chloro-thiophen-2-yl)-thiazole [prepared by adopting a procedure described by Ewing, William R. et al.; PCT Int. Appl. (2001), 460 pp. WO 0107436 A2] were added. After 1 h another 17.1 mg (0.25 equiv.) 5-bromomethyl-2-(5-Chloro-thiophen-2-yl)-thiazole were added and the reaction mixture was stirred for further 2 h. The reaction was stopped by the careful addition of MeOH and water. The solvent was removed under reduced pressure and the residue was purified by preparative RP-HPLC (CH$_3$CN/H$_2$O gradient+0.05% formic acid). The two isomers were then separated using NP-HPLC on a chiral stationary phase with a mixture of heptane, ethanol, methanol and diethyl amine as solvent. Structural assignment of both isomers was achieved by NOE-spectroscopy.

Yield of 1-[2-(5-Chloro-thiophen-2-yl)-thiazol-5-ylmethyl]-2-(1-isopropyl-piperidin-4-ylcarbamoyl)-1H-benzoimidazole-5-carboxylic acid methyl ester: 40 mg; MS (ES$^+$): m/e=558, chloro pattern.

Yield of 3-[2-(5-Chloro-thiophen-2-yl)-thiazol-5-ylmethyl]-2-(1-isopropyl-piperidin-4-ylcarbamoyl)-3H-benzoimidazole-5-carboxylic acid methyl ester: 26 mg; MS (ES$^+$): m/e=558, chloro pattern.

Example 9

1-[2-(5-Chloro-thiophen-2-yl)-thiazol-5-ylmethyl]-2-(1-isopropyl-piperidin-4-ylcarbamoyl)-1H-benzoimidazole-5-carboxylic acid 1-[2-(5-Chloro-thiophen-2-yl)-thiazol-5-ylmethyl]-2-(1-isopropyl-piperidin-4-ylcarbamoyl)-1H-benzoimidazole-5-carboxylic acid was prepared by a procedure according to example 6 starting from 40 mg (0.072 mmol) 1-[2-(5-Chloro-thiophen-2-yl)-thiazol-5-ylmethyl]-2-(1-isopropyl-piperidin-4-ylcarbamoyl)-1H-benzoimidazole-5-carboxylic acid methyl ester. The title compound was obtained as its dihydrochloride. Yield: 23 mg MS (ES$^+$): m/e=544, chloro pattern.

Example 10

3-[2-(5-Chloro-thiophen-2-yl)-thiazol-5-ylmethyl]-2-(1-isopropyl-piperidin-4-ylcarbamoyl)-3H-benzoimidazole-5-carboxylic acid 3-[2-(5-Chloro-thiophen-2-yl)-thiazol-5-ylmethyl]-2-(1-isopropyl-piperidin-4-ylcarbamoyl)-3H-benzoimidazole-5-carboxylic acid was prepared by a procedure according to example 6 starting from 26 mg (0.047 mmol) 3-[2-(5-Chloro-thiophen-2-yl)-thiazol-5-ylmethyl]-2-(1-isopropyl-piperidin-4-ylcarbamoyl)-3H-benzoimidazole-5-carboxylic acid methyl ester. The title compound was obtained as its dihydrochloride. Yield: 19 mg MS (ES$^+$): m/e=544, chloro pattern.

Example 11 a) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid methyl ester b) 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid methyl ester (i) Methyl-2,3-diamino-benzoate 3.0 g (15.3 mmol) Methyl-2-amino-3-nitro-benzoate were dissolved in 200 mL abs. MeOH. The solution was evacuated and rinsed with argon several times. 300 mg palladium on charcoal (10%) were added and again the mixture was evacuated and rinsed with argon a several times. Finally argon was exchanged by hydrogen (balloon filled with hydrogen) and the mixture was stirred for 4 h at room temperature. The reaction mixture was filtered over "Celite" and the filter residue was washed with 150 mL methanol. The filtrate was concentrated under reduced pressure to give pure methyl-2,3-diamino-benzoate as a brown oil. Yield: 2.53 g MS (ES$^+$): m/e=167.

(ii) Methyl-2-trichloromethyl-1H-benzoimidazole-4-carboxylate

Methyl-2-trichloromethyl-1H-benzoimidazole-4-carboxylate was prepared similarly to methyl-2-trichloromethyl-1H-benzoimidazole-5-carboxylate as described in example 5 i) starting from 2.53 g (15.1 mmol) methyl-2,3-diamino-benzoate. Yield: 4.15 g MS (ES$^+$): m/e=293, chloro pattern.

(iii) 2-(1-Isopropyl-piperidin-4-ylcarbamoyl)-1H-benzoimidazole-4-carboxylic acid methyl ester 2-(1-Isopropyl-piperidin-4-ylcarbamoyl)-1H-benzoimidazole-4-carboxylic acid methyl ester was prepared from 1.82 g (6.2 mmol) methyl-2-trichloromethyl-1H-benzoimidazole-4-carboxylate as described in example 5 ii). Yield: 1.10 g MS (ES$^+$): m/e=345.

(iv) a) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid methyl ester b) 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid methyl ester Both isomers were obtained by an analogous procedure as described for example 5 iii) starting from 150.0 mg (0.44 mmol) 2-(1-isopropyl-piperidin-4-ylcarbamoyl)-1H-benzoimidazole-4-carboxylic acid methyl ester and 145.6 mg (1.2 equiv.) 3-bromomethyl-5-(5-Chloro-thiophen-2-yl)-isoxazole. In this case the ratio of both isomers was 3:1. As described in example 5 iii) the isomers were separated by NP-HPLC using a chiral stationary phase and a mixture of heptane, ethanol, methanol and diethyl amine as solvent. Again structural assignment of both isomers was achieved by NOE-spectroscopy.

Yield of 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid methyl ester: 105 mg; MS (ES$^+$): m/e=542, chloro pattern. Yield of 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid methyl ester: 45 mg; MS (ES$^+$): m/e=542, chloro pattern.

Example 12

1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid was prepared from 60 mg (0.111 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid methyl ester as described in example 6. The title compound was obtained as its dihydrochloride.

Yield: 34 mg MS (ES$^+$): m/e=528, chloro pattern.

Example 13

3-[5-(5-Chloro-thiophen-2-yl)-isoxazol-3-ylmethyl]-2-(1-isopropyl-piperidin-4-ylcarbamoyl)-3H-benzoimidazole-4-carboxylic acid 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid was prepared from 20 mg (0.037 mmol) 3-[5-(5-Chloro-thiophen-2-yl)-isoxazol-3-ylmethyl]-2-(1- isopropyl-piperidin-4-ylcarbamoyl)-3H-benzoimidazole-4-carboxylic acid methyl ester as described in example 6. The title compound was obtained as its dihydrochloride.

Yield: 16 mg MS (ES$^+$): m/e=528, chloro pattern.

Example 14

3-[5-(5-Chloro-thiophen-2-yl)-isoxazol-3-ylmethyl]-3H-imidazo[4,5-b]pyridine-2-carboxylic acid (1-isopropyl-piperidin-4-yl)-amide (i) 3H-Imidazo[4,5-b]pyridine-2-carboxylic acid methyl ester 1.76 g (9.16 mmol) methyl-dichloro-methoxy-acetate were added to a solution of 1.00 g (9.16 mmol) 2,3-diaminopyridine in 40 mL methanol and stirred at room temperature. 1.85 g (18.32 mmol) triethyl amine were added dropwise. After complete addition the reaction mixture was stirred for 15 h at 80° C. The reaction was not complete resulting in the addition of another 1.76 g methyl-dichloro-methoxy-acetate and 1.85 g triethyl amine. Again the reaction mixture was stirred for 8 h at 80° C. The mixture was concentrated under reduced pressure and the residue was digerated sequentially with diethyl ether and a saturated NaHCO$_3$-solution and then washed with water yielding almost pure 3H-imidazo[4,5-b]pyridine-2-carboxylic acid methyl ester.

Yield: 210 mg MS (ES$^+$): m/e=178.

(ii) 3-[5-(5-Chloro-thiophen-2-yl)-isoxazol-3-ylmethyl]-3H-imidazo[4,5-b]pyridine-2-carboxylic acid methyl ester 100 mg (0.56 mmol) 3H-Imidazo[4,5-b]pyridine-2-carboxylic acid methyl ester were dissolved in 3 mL DMF. 22.6 mg (0.56 mmol) sodium hydride (60% in mineral oil) were added and the mixture was stirred 30 minutes at room temperature. 157.2 mg (0.56 mmol) 3-Bromomethyl-5-(5-Chloro-thiophen-2-yl)-isoxazole were added and the resulting mixture was stirred for 1 h at 80° C. The reaction mixture was cooled to room temperature and after the addition of a few drops of water concentrated under reduced pressure. HPLC-MS-analysis showed the presence of another isomer (ratio of isomers≈7:1). Final purification by preparative RP-HPLC (CH$_3$CN/H$_2$O gradient+0.05% formic acid) gave pure 3-[5-(5-Chloro-thiophen-2-yl)-isoxazol-3-ylmethyl]-3H-imidazo[4,5-b]pyridine-2-carboxylic acid methyl ester as a brown amorphous solid.

Yield: 203 mg MS (ES$^+$): m/e=375, chloro pattern.

(iii) 3-[5-(5-Chloro-thiophen-2-yl)-isoxazol-3-ylmethyl]-3H-imidazo[4,5-b]pyridine-2-carboxylic acid 175.0 mg (0.46 mmol) 3-[5-(5-Chloro-thiophen-2-yl)-isoxazol-3-ylmethyl]-3H-imidazo[4,5-b]pyridine-2-carboxylic acid methyl ester were added to a solution of 19.6 mg (0.82 mmol) LiOH in 6 mL THF and 2 mL H$_2$O. The reaction mixture was stirred for 2 h at 60° C., cooled to room temperature and acidified (pH=2) by the addition of a half concentrated HCl-solution. The precipitate was filtered off and washed with water to give pure 3-[5-(5-Chloro-thiophen-2-yl)-isoxazol-3-ylmethyl]-3H-imidazo[4,5-b] pyridine-2-carboxylic acid as a brown crystalline solid.

Yield: 150 mg MS (ES$^+$): m/e=361, chloro pattern.

(iv) 3-[5-(5-Chloro-thiophen-2-yl)-isoxazol-3-ylmethyl]-3H-imidazo[4,5-b]pyridine-2-carboxylic acid (1-isopropyl-piperidin-4-yl)-amide 150.0 mg (0.41 mmol) 3-[5-(5-Chloro-thiophen-2-yl)-isoxazol-3-ylmethyl]-3H-imidazo[4,5-b] pyridine-2-carboxylic acid were dissolved in 4 mL DMF. Sequentially 142 µl DIPEA and 151.8 mg (0.41 mmol) HATU were added and the mixture was stirred for 20 min at room temperature. 74.3 mg (0.41 mmol) 1-Isopropyl-piperidine-4-ylamine-hydrochloride and another 71 µl DIPEA were added and the resulting mixture was stirred 3 h at room temperature. Concentration under reduced pressure and final purification by preparative RP-HPLC (CH$_3$CN/H$_2$O gradient+0.05% formic acid) gave pure 3-[5-(5-Chloro-thiophen-2-yl)-isoxazol-3-ylmethyl]-3H-imidazo[4,5-b]pyridine-2-carboxylic acid (1-isopropyl-piperidin-4-yl)-amide as a light brown amorphous solid. The title compound was obtained as its hydroformiate.

Yield: 17 mg MS (ES$^+$): m/e=485, chloro pattern.

Example 15

1-[(5-Chloro-pyridin-2-ylcarbamoyl)-methyl]-2-(1-isopropyl-piperidin-4-ylcarbamoyl)-1H-benzoimidazole-4-carboxylic acid methyl ester 100.8 mg (0.29 mmol) 2-(Isopropyl-piperidin-4-ylcarbamoyl)-1H-benzoimidazole-4-carboxylic acid methyl ester were dissolved in 6 mL DMF. Subsequently 60.6 mg (0.44 mmol) K$_2$CO$_3$ and 87.5 mg (0.35 mmol) 2-bromo-N-(5-Chloro-pyridin-2-yl-)-acetamide were added and the resulting mixture was stirred for 3 h at 80° C. The reaction mixture was diluted with 60 mL toluene and washed with a sat. NaHCO$_3$ solution and brine. The organic layer was dried over MgSO$_4$ and the solvent was removed under reduced pressure. The residue was purified by preparative HPLC (CH$_3$CN/H$_2$O gradient+0.05% formic acid) to give 1-[(5-Chloro-pyridin-2-ylcarbamoyl)-methyl]-2-(1-isopropyl-piperidin-4-ylcarbamoyl)-1H-benzoimidazole-4-carboxylic acid methyl ester as a white amorphous solid. The product was obtained as its hydroformiate.

Yield: 106 mg MS (ES$^+$): m/e=513, chloro pattern.

Example 16

1-[(5-Chloro-pyridin-2-ylcarbamoyl)-methyl]-2-(1-isopropyl-piperidin-4-ylcarbamoyl)-1H-benzoimidazole-4-carboxylic acid 30 mg (0.058 mmol) 1-[(5-Chloro-pyridin-2-ylcarbamoyl)-methyl]-2-(1-isopropyl-piperidin-4-ylcarbamoyl)-1H-benzoimidazole-4-carboxylic acid methyl ester were dissolved in 3 mL dichloromethane and cooled to 0° C. 234 µl of a 1 M BBr$_3$-solution (4 equiv.) in dichloromethane were carefully added and the resulting mixture was stirred at room temperature for 16 h. Under cooling 3 mL water were added dropwise followed by the addition of 0.7 mL of a 1 M NaOH-solution. The mixture was concentrated under reduced pressure. Purification by preparative HPLC (CH$_3$CN/H$_2$O gradient+0.05% formic acid) gave pure 1-[(5-Chloro-pyridin-2-ylcarbamoyl)-methyl]-2-(1-isopropyl-piperidin-4-ylcarbamoyl)-1H-benzoimidazole-4-carboxylic acid. The corresponding dihydrochloride was obtained by treatment of the product with a 0.1 M HCl-solution and following lyophilization. Yield: 26 mg MS (ES$^+$): m/e=499, chloro pattern.

Example 17 a) 1-[(5-Chloro-pyridin-2-ylcarbamoyl)-methyl]-2-(1-isopropyl-piperidin-4-ylcarbamoyl)-1H-benzoimidazole-5-carboxylic acid methyl ester b) 3-[(5-Chloro-pyridin-2-ylcarbamoyl)-methyl]-2-(1-isopropyl-piperidin-4-ylcarbamoyl)-3H-benzoimidazole-5-carboxylic acid methyl ester 102.3 mg (0.297 mmol) 2-(Isopropyl-piperidin-4-ylcarbamoyl)-1H-benzoimidazole-5-carboxylic acid methyl ester were dissolved in 6 mL DMF. Subsequently 61.6 mg (0.446 mmol) $K_2CO_3$ and 88.9 mg (0.356 mmol) 2-bromo-N-(5-Chloro-pyridin-2-yl-)-acetamide were added and the resulting mixture was stirred for 2 h at 80° C. The reaction mixture was diluted with 60 mL toluene and washed with sat. $NaHCO_3$ solution and brine. The organic layer was dried over $MgSO_4$ and the solvent was removed under reduced pressure. The residue was purified by preparative HPLC ($CH_3CN/H_2O$ gradient+0.05% formic acid) to give both isomers described in the title in a 1.3:1 ratio. Both isomers could be separated by NP-HPLC using a chiral stationary phase and a mixture of heptane, ethanol and methanol as solvent. Structural assignment of both isomers was achieved by NOE-spectroscopy. Both isomers were transformed into their dihydrochloride by treatment with a 0.1 M HCl-solution and following lyophilization.

Yield of 1-[(5-Chloro-pyridin-2-ylcarbamoyl)-methyl]-2-(1-isopropyl-piperidin-4-ylcarbamoyl)-1H-benzoimidazole-5-carboxylic acid methyl ester: 50 mg MS ($ES^+$): m/e=513, chloro pattern.

Yield of 3-[(5-Chloro-pyridin-2-ylcarbamoyl)-methyl]-2-(1-isopropyl-piperidin-4-ylcarbamoyl)-3H-benzoimidazole-5-carboxylic acid methyl ester: 51 mg MS ($ES^+$): m/e=513, chloro pattern.

Example 18

1-[(5-Chloro-pyridin-2-ylcarbamoyl)-methyl]-2-(1-isopropyl-piperidin-4-ylcarbamoyl)-1H-benzoimidazole-5-carboxylic acid 1-[(5-Chloro-pyridin-2-ylcarbamoyl)-methyl]-2-(1-isopropyl-piperidin-4-ylcarbamoyl)-1H-benzoimidazole-5-carboxylic acid was prepared by a procedure according to example 16 starting from 27.8 mg (0.047 mmol) 1-[(5-Chloro-pyridin-2-ylcarbamoyl)-methyl]-2-(1-isopropyl-piperidin-4-ylcarbamoyl)-1H-benzoimidazole-5-carboxylic acid methyl ester. The title compound was obtained as its dihydrochloride. Yield: 15 mg MS ($ES^+$): m/e=499, chloro pattern.

Example 19

3-[(5-Chloro-pyridin-2-ylcarbamoyl)-methyl]-2-(1-isopropyl-piperidin-4-ylcarbamoyl)-3H-benzoimidazole-5-carboxylic acid 3-[(5-Chloro-pyridin-2-ylcarbamoyl)-methyl]-2-(1-isopropyl-piperidin-4-ylcarbamoyl)-3H-benzoimidazole-5-carboxylic acid was prepared by a procedure according to example 16 starting from 28 mg (0.048 mmol) 3-[(5-Chloro-pyridin-2-ylcarbamoyl)-methyl]-2-(1-isopropyl-piperidin-4-ylcarbamoyl)-3H-benzoimidazole-5-carboxylic acid methyl ester. The title compound was obtained as its dihydrochloride. Yield: 22 mg MS ($ES^+$): m/e=499, chloro pattern.

Example 20

1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-ethoxycarbonyloxy-ethyl ester 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid were dissolved in 3 mL DMF. Subsequently 27.6 mg (0.16 mmol) KI, 46 mg (0.33 mmol) $K_2CO_3$ and 45 µl (0.32 mmol) 1-chloroethyl-ethylcarbonate were added and the reaction mixture was stirred at 60° C. for 4 h. The reaction mixture was concentrated and the resulting residue purified by preparative HPLC ($CH_3CN/H_2O$ gradient+0.05% formic acid) to give pure 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-ethoxycarbonyloxy-ethyl ester as a white amorphous solid. The corresponding dihydrochloride was obtained by treatment with a 0.1 M HCl-solution and following lyophilization.

Yield: 46 mg MS ($ES^+$): m/e=644, chloro pattern.

Example 21

1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-cyclohexyloxycarbonyloxy-ethyl ester 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-cyclohexyloxycarbonyloxy-ethyl ester was prepared by adopting the procedure described for example 20 starting from 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid and 61 µl (0.32 mmol) cyclohexyl-1-chloroethyl carbonate. The title compound was obtained as its dihydrochloride.

Yield: 47 mg MS ($ES^+$): m/e=698, chloro pattern.

Example 22

1-[5-(5-Chloro-thiophen-2-yl)-isoxazol-3-ylmethyl]-1H-benzoimidazole-2,4-dicarboxylic acid 4-[(2-hydroxy-ethyl)-amide] 2-[(1-isopropyl-piperidin-4-yl)-amide]

30 mg (0.057 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid were dissolved in 3 mL DMF. Subsequently 29 µl (0.171 mmol) DIPEA and 21.6 mg (0.057 mmol) HATU were added. After 30 minutes 3.5 µl (0.057 mmol) 2-amino-ethanol and 10 µl DIPEA were added and the resulting mixture was stirred at room temperature for 16 h. The reaction mixture was concentrated and the residue was purified by preparative HPLC ($CH_3CN/H_2O$ gradient+0.05% formic acid). The title compound was obtained as its hydroformiate in form of a white amorphous solid.

Yield: 29 mg MS ($ES^+$): m/e=571, chloro pattern.

Example 23

1-[5-(5-Chloro-thiophen-2-yl)-isoxazol-3-ylmethyl]-4-(3-hydroxy-azetidine-1-carbonyl)-1H-benzoimidazole-2-carboxylic acid (1-isopropyl-piperidin-4-yl)-amide 1-[5-(5-Chloro-thiophen-2-yl)-isoxazol-3-ylmethyl]-4-(3-hydroxy-azetidine-1-carbonyl)-1H-benzoimidazole-2-carboxylic acid (1-isopropyl-piperidin-4-yl)-amide was prepared by a procedure according to example 22 starting from 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid and 6.7 mg (0.09 mmol) 3-hydroxy-acetidine. The title compound was obtained as its hydroformiate in form of a white amorphous solid. Yield: 51 mg MS (ES$^+$): m/e=583, chloro pattern.

Example 24

1-[5-(5-Chloro-thiophen-2-yl)-isoxazol-3-ylmethyl]-1H-benzoimidazole-2,4-dicarboxylic acid 4-[(2-hydroxy-ethyl)-methyl-amide] 2-[(1-isopropyl-piperidin-4-yl)-amide]

1-[5-(5-Chloro-thiophen-2-yl)-isoxazol-3-ylmethyl]-1H-benzoimidazole-2,4-dicarboxylic acid 4-[(2-hydroxy-ethyl)-methyl-amide] 2-[(1-isopropyl-piperidin-4-yl)-amide] was prepared by a procedure according to example 22 starting from 40 mg (0.067 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid and 5.6 mg (0.075 mmol) N-methyl-2-aminoethanol. The title compound was obtained as its hydroformiate in form of a white amorphous solid.

Yield: 35 mg MS (ES$^+$): m/e=585, chloro pattern.

Example 25

1-[5-(5-Chloro-thiophen-2-yl)-isoxazol-3-ylmethyl]-1H-benzoimidazole-2,5-dicarboxylic acid 5-[(2-hydroxy-ethyl)-methyl-amide] 2-[(1-isopropyl-piperidin-4-yl)-amide]

1-[5-(5-Chloro-thiophen-2-yl)-isoxazol-3-ylmethyl]-1H-benzoimidazole-2,5-dicarboxylic acid 5-[(2-hydroxy-ethyl)-methyl-amide] 2-[(1-isopropyl-piperidin-4-yl)-amide] was prepared by a procedure according to example 22 starting from 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid and 6.8 mg (0.09 mmol) N-methyl-2-aminoethanol. The title compound was obtained as its hydroformiate in form of a white amorphous solid.

Yield: 43 mg MS (ES$^+$): m/e=585, chloro pattern.

Example 26

1-[5-(5-Chloro-thiophen-2-yl)-isoxazol-3-ylmethyl]-5-(3-hydroxy-azetidine-1-carbonyl)-1H-benzoimidazole-2-carboxylic acid (1-isopropyl-piperidin-4-yl)-amide 1-[5-(5-Chloro-thiophen-2-yl)-isoxazol-3-ylmethyl]-5-(3-hydroxy-azetidine-1-carbonyl)-1H-benzoimidazole-2-carboxylic acid (1-isopropyl-piperidin-4-yl)-amide was prepared by a procedure according to example 22 starting from 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid and 6.7 mg (0.09 mmol) 3-hydroxy-acetidine. The title compound was obtained as its hydroformiate in form of a white amorphous solid. Yield: 37 mg MS (ES$^+$): m/e=583, chloro pattern.

Example 27

1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-ethoxycarbonyloxy-ethyl ester 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-ethoxycarbonyloxy-ethyl ester was prepared by adopting the procedure described for example 20 starting from 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid and 45 µl (0.32 mmol) 1-chloroethyl-ethylcarbonate. The title compound was obtained as its dihydrochloride. Yield: 57 mg MS (ES$^+$): m/e=644, chloro pattern.

Example 28

1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-cyclohexyloxycarbonyloxy-ethyl ester 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-cyclohexyloxycarbonyloxy-ethyl ester was prepared by adopting the procedure described for example 20 starting from 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid and 61 µl (0.32 mmol) cyclohexyl-1-chloroethyl carbonate. The title compound was obtained as its dihydrochloride. Yield: 59 mg MS (ES$^+$): m/e=698, chloro pattern.

Example 29 a) 1-[5-(5-Chloro-thiophen-2-yl)-isoxazol-3-ylmethyl]-5-(2-hydroxy-ethanesulfony)-1H-benzoimidazole-2-carboxylic acid (1-isopropyl-piperidin-4-yl)-amide b) 1-[5-(5-Chloro-thiophen-2-yl)-isoxazol-3-ylmethyl]-6-(2-hydroxy-ethanesulfonyl)-1H-benzoimidazole-2-carboxylic acid (1-isopropyl-piperidin-4-yl)-amide (i) 2-(2-Trichloromethyl-1H-benzoimidazole-5-sulfonyl)-ethanol 500 mg (2.31 mmol) 3,4-diamino-benzene-sulfonylethan-2-ol were dissolved in 10 mL concentrated acetic acid. 0.4 mL (1.4 equiv.) methyl-2,2,2-trichloroacetimidate were added slowly and the resulting mixture was stirred at room temperature for 4 h. The mixture was diluted with 100 mL toluene and the solvent was removed under reduced pressure. The residue was rinsed with toluene, filtered and dried under vacuo to give a brown crystalline solid pure enough for all further reactions. Yield: 680 mg MS (ES$^+$): m/e=345, chloro pattern.

(ii) 5-(2-Hydroxy-ethanesulfonyl)-1H-benzoimidazole-2-carboxylic acid (1-isopropyl-piperidin-4-yl)-amide 360 mg (1.05 mmol) 2-(2-Trichloromethyl-1H-benzoimidazole-5-sulfonyl)-ethanol were added to a mixture of 225.4 mg (1.05 equiv.) 1-isopropyl-piperidine-4-ylamine-dihydrochloride and 880 mg (10 equiv.) NaHCO$_3$ in 6 mL THF and 3 mL H$_2$O and stirred vigorously for 2 h at room temperature. The reaction mixture was diluted with dichloromethane and washed with a saturated NaHCO$_3$-solution and brine. The organic layer was dried over MgSO$_4$ and concentrated. The obtained product was pure enough for further reactions.

Yield: 207 mg MS (ES$^+$): m/e=395.

(iii) a) 1-[5-(5-Chloro-thiophen-2-yl)-isoxazol-3-ylmethyl]-5-(2-hydroxy-ethanesulfonyl)-1H-benzoimidazole-2-carboxylic acid (1-isopropyl-piperidin-4-yl)-amide b) 1-[5-(5-Chloro-thiophen-2-yl)-isoxazol-3-ylmethyl]-6-(2-hydroxy-ethanesulfonyl)-1H-benzoimidazole-2-carboxylic acid (1-isopropyl-piperidin-4-yl)-amide 126.2 mg (0.32 mmol) 5-(2-Hydroxy-ethanesulfonyl)-1H-benzoimidazole-2-carboxylic acid (1-isopropyl-piperidin-4-yl)-amide were dissolved in 10 mL DMF. Subsequently 48.6 mg (1.1 equiv.) K$_2$CO$_3$ and 89.0 mg (1.0 equiv.) 3-bromomethyl-5-(5-Chloro-thiophen-2-yl)-isoxazole were added and the resulting mixture was stirred for 3 h at 55° C. The reaction mixture was diluted with toluene and washed twice with a saturated NaHCO$_3$-solution and once with brine, dried over anhydrous MgSO$_4$ and concentrated under reduced pressure. Preparative RP-HPLC (CH$_3$CN/H$_2$O gradient+0.05% formic acid) gave a 6:4 mixture of both isomers described in the title. These isomers could be separated by NP-HPLC using a chiral stationary phase and a mixture of heptane, ethanol, methanol and diethyl amine as solvent. Structural assignment of both isomers was achieved by NOE-spectroscopy.

Yield of 1-[5-(5-Chloro-thiophen-2-yl)-isoxazol-3-ylmethyl]-5-(2-hydroxy-ethanesulfonyl)-1H-benzo-imidazole-2-carboxylic acid (1-isopropyl-piperidin-4-yl)-amide: 79 mg MS (ES$^+$): m/e=591, chloro pattern.

Yield of 1-[5-(5-Chloro-thiophen-2-yl)-isoxazol-3-ylmethyl]-6-(2-hydroxy-ethanesulfonyl)-1H-benzo-imidazole-2-carboxylic acid (1-isopropyl-piperidin-4-yl)-amide: 59 mg MS (ES$^+$): m/e=591, chloro pattern.

Example 30

1-[(5-Chloro-pyridin-2-ylcarbamoyl)-methyl]-1H-benzoimidazole-2,4-dicarboxylic acid 4-[(2-hydroxy-ethyl)-amide] 2-[(1-isopropyl-piperidin-4-yl)-amide]

1-[(5-Chloro-pyridin-2-ylcarbamoyl)-methyl]-1H-benzoimidazole-2,4-dicarboxylic acid 4-[(2-hydroxy-ethyl)-amide] 2-[(1-isopropyl-piperidin-4-yl)-amide] was prepared by a procedure according to example 22 starting from 40 mg (0.08 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 5.4 mg (0.088 mmol) 2-aminoethanol. The title compound was obtained as its hydroformiate in form of a white amorphous solid. Yield: 34 mg MS (ES$^+$): m/e=542, chloro pattern.

Example 31

1-[(5-Chloro-pyridin-2-ylcarbamoyl)-methyl]-1H-benzoimidazole-2,4-dicarboxylic acid 4-[(2-hydroxy-ethyl)-methyl-amide] 2-[(1-isopropyl-piperidin-4-yl)-amide]

1-[(5-Chloro-pyridin-2-ylcarbamoyl)-methyl]-1H-benzoimidazole-2,4-dicarboxylic acid 4-[(2-hydroxy-ethyl)-methyl-amide]2-[(1-isopropyl-piperidin-4-yl)-amide] was prepared by a procedure according to example 22 starting from 50 mg (0.10 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 8.3 mg (0.11 mmol) N-methyl-2-amino-ethanol. The title compound was obtained as its hydroformiate in form of a white amorphous solid. Yield: 30 mg MS (ES$^+$): m/e=556, chloro pattern.

Example 32

1-[(5-Chloro-pyridin-2-ylcarbamoyl)-methyl]-4-(3-hydroxy-azetidine-1-carbonyl)-1H-benzoimidazole-2-carboxylic acid (1-isopropyl-piperidin-4-yl)-amide 1-[(5-Chloro-pyridin-2-ylcarbamoyl)-methyl]-4-(3-hydroxy-azetidine-1-carbonyl)-1H-benzoimidazole-2-carboxylic acid (1-isopropyl-piperidin-4-yl)-amide was prepared by a procedure according to example 22 starting from 50 mg (0.10 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 8.1 mg (0.11 mmol) 3-hydroxy-acetidine. The title compound was obtained as its hydroformiate in form of a white amorphous solid. Yield: 28 mg MS (ES$^+$): m/e=554, chloro pattern.

Example 33

1-[(5-Chloro-pyridin-2-ylcarbamoyl)-methyl]-2-(1-isopropyl-piperidin-4-ylcarbamoyl)-1H-benzoimidazole-4-carboxylic acid 1-ethoxycarbonyloxy-ethyl ester 1-[(5-Chloro-pyridin-2-ylcarbamoyl)-methyl]-2-(1-isopropyl-piperidin-4-ylcarbamoyl)-1H-benzoimidazole-4-carboxylic acid 1-ethoxycarbonyloxy-ethyl ester was prepared by a procedure according to example 20 starting from 50 mg (0.10 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 61.2 mg (0.401 mmol) 1-Chloro-ethyl-ethylcarbonate. The title compound was obtained as its hydroformiate in form of a white amorphous solid.

Yield: 38 mg MS (ES$^+$): m/e=615, chloro pattern.

Example 34

1-[(5-Chloro-pyridin-2-ylcarbamoyl)-methyl]-2-(1-isopropyl-piperidin-4-ylcarbamoyl)-1H-benzoimidazole-4-carboxylic acid 1-cyclohexyloxycarbonyloxy-ethyl ester 1-[(5-Chloro-pyridin-2-ylcarbamoyl)-methyl]-2-(1-isopropyl-piperidin-4-ylcarbamoyl)-1H-benzoimidazole-4-carboxylic acid 1-cyclohexyloxycarbonyloxy-ethyl ester was prepared by a procedure according to example 20 starting from 50 mg (0.10 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 82.8 mg (0.401 mmol) cyclohexyl-1-chloroethyl carbonate. The title compound was obtained as its hydroformiate in form of a white amorphous solid.

Yield: 46 mg MS (ES$^+$): m/e=669, chloro pattern.

Example 35

1-[(5-Chloro-pyridin-2-ylcarbamoyl)-methyl]-1H-benzoimidazole-2-carboxylic acid [4-(3-oxo-morpholin-4-yl)-phenyl]-amide (i) 4-(4-Nitro-phenyl)-morpholine A mixture of 24.5 g morpholine and 13.3 g 1-Fluoro-4-nitro-benzene in 30 mL DMSO was heated to 100° C. for 4 h. This solution was poured on to 300 mL of water and the resulting precipitate was collected by filtration to yield a bright yellow crystalline product, which was dried under reduced pressure. Yield: 19.7 g.

(ii) 4-(4-Nitro-phenyl)-morpholin-3-one

To a solution of 10 g 4-(4-Nitro-phenyl)-morpholine in 200 mL DCM, 32 g Benzyl-triethyl-ammonium chloride and 22.7 g potassium permanganate (325 mesh) were cautiously added at RT. After stirring for 1 h at RT the reaction mixture was heated to reflux for 10 h. Then a solution of 95 g Na$_2$SO$_3$ in 450 mL water were added under ice cooling and vigourous stirring. The mixture was filtered trough a pad of celite and the filtrate was concentrated under reduced pressure. The yellow solid was stirred with 250 mL water and the precipitated product was collected by filtration. This crude product was purified by chromatography on silica gel eluting with a gradient of DCM/MeOH 100%->50%. The fractions containing the product were combined and the solvent evaporated under reduced pressure. Yield: 2.6 g.

(iii) 4-(4-Amino-phenyl)-morpholin-3-one

To a solution of 2.6 g 4-(4-Nitro-phenyl)-morpholin-3-one in 350 mL ethyl acetate and 17 mL ethanol, 13.2 g SnCl$_2$ dihydrate were added and the reaction mixture was heated to reflux for 2 h. Then, after cooling to RT the mixture was stirred for 16 h. The precipitated product was collected by filtration and was pure enough for the next reaction step. Yield: 2.07 g.

(iv) 1H-Benzoimidazole-2-carboxylic acid [4-(3-oxo-morpholin-4-yl)-phenyl]-amide To a solution of 100 mg 1H-Benzoimidazole-2-carboxylic acid and 118 mg 4-(4-Amino-phenyl)-morpholin-3-one in 2 mL DCM, 157 mg BOP-Cl and 0.3 mL NEt$_3$ were added and the mixture was stirred for 16 h at RT. Then, after the reaction mixture was diluted with 20 mL water, the precipitated product was collected by filtration. The crude product was subjected to the next reaction step without further purification. Yield: 122 mg.

(v) 1-[(5-Chloro-pyridin-2-ylcarbamoyl)-methyl]-1H-benzoimidazole-2-carboxylic acid [4-(3-oxo-morpholin-4-yl)-phenyl]-amide To a solution of 50 mg 1H-Benzoimidazole-2-carboxylic acid [4-(3-oxo-morpholin-4-yl)-phenyl]-amide in 2 mL DMF, 49 mg Cs$_2$CO$_3$ and 37 mg 2-Bromo-N-(5-Chloro-pyridin-2-yl)-acetamide were added at RT and the reaction mixture was stirred for 2 h. Then, additional 20 mg Cs$_2$CO$_3$ and 30 mg 2-Bromo-N-(5-Chloro-pyridin-2-yl)-acetamide were added at RT and the reaction mixture was stirred for additional 2 h. The reaction mixture was diluted with 20 mL water and the precipitated product was collected by filtration. The product was taken-up in 3 mL diluted HCl and lyophilized to yield a white solid. The product was obtained as its hydrochloride. Yield: 128 mg MS (ES$^+$): m/e=505, chloro pattern.

Example 36

1-[(5-Chloro-pyridin-2-ylcarbamoyl)-methyl]-2-[4-(3-oxo-morpholin-4-yl)-phenylcarbamoyl]-1H-benzoimidazole-4-carboxylic acid methyl ester (i) 2-[4-(3-Oxo-morpholin-4-yl)-phenylcarbamoyl]-1H-benzoimidazole-4-carboxylic acid methyl ester A solution of 69.4 mg (0.236 mmol) methyl-2-trichloromethyl-1H-benzoimidazole-4-carboxylate in 2 mL THF were slowly added to a mixture containing 50 mg (0.26 mmol) 4-(4-amino-phenyl)-morpholin-3-one, 220 mg (2.62 mmol) NaHCO$_3$, 8 mL THF and 3 mL H$_2$O. The mixture was stirred vigorously for 3 h at room temperature, diluted with 50 mL CH$_2$Cl$_2$ and washed with 30 mL of a saturated NaHCO$_3$-solution. The aqueous solution was extracted with 50 mL CH$_2$Cl$_2$ and the combined organic layers were dried over MgSO$_4$ and concentrated under reduced pressure to give a brown solid, which was pure enough for the following reactions.

Yield: 72 mg MS (ES$^+$): m/e=395.

(ii) 1-[(5-Chloro-pyridin-2-ylcarbamoyl)-methyl]-2-[4-(3-oxo-morpholin-4-yl)-phenylcarbamoyl]-1H-benzoimidazole-4-carboxylic acid methyl ester 72.0 mg (0.183 mmol) 2-[4-(3-Oxo-morpholin-4-yl)-phenylcarbamoyl]-1H-benzoimidazole-4-carboxylic acid methyl ester were dissolved in 7 mL DMF. Sequentially 37.8 mg (0.274 mmol) K$_2$CO$_3$ and 54.6 mg (0.219 mmol) 2-bromo-N-(5-Chloro-pyridin-2-yl-)-acetamide were added and the resulting mixture was stirred for 4 h at 80°. The mixture was diluted with 200 mL toluene and washed with 50 mL of a saturated NaHCO$_3$-solution. The product was not completely soluble in toluene, so ethyl acetate had to be added. The organic layer was washed with brine, dried over anhydrous MgSO$_4$ and concentrated under reduced pressure. The residue was purified by preparative HPLC (CH$_3$CN/H$_2$O gradient+0.05% formic acid) to give 1-[(5-Chloro-pyridin-2-ylcarbamoyl)-methyl]-2-[4-(3-oxo-morpholin-4-yl)-phenylcarbamoyl]-1H-benzoimidazole-4-carboxylic acid methyl ester as a light brown amorphous solid.

Yield: 46 mg MS (ES$^+$): m/e=563, chloro pattern.

Example 37

1-[5-(5-Chloro-thiophen-2-yl)-isoxazol-3-ylmethyl]-1H-benzoimidazole-2-carboxylic acid [4-(4-oxo-4H-pyridin-1-yl)-phenyl]-amide (i) 1-(4-Nitro-phenyl)-1H-pyridin-4-one A mixture of 10.1 g Pyridin-4-ol and 10 g 1-Fluoro-4-nitro-benzene and 46.1 g Cs$_2$CO$_3$ in 30 mL DMF was stirred at RT for 2 h. This solution was poured on to 300 mL of water and the resulting precipitate was collected by filtration to yield a bright yellow crystalline product, which was dried under reduced pressure. Yield: 11.2 g.

(ii) 1-(4-Amino-phenyl)-1H-pyridin-4-one

To a solution of 10 g 1-(4-Nitro-phenyl)-1H-pyridin-4-one in 510 mL ethyl acetate and 26 mL ethanol, 52.1 g SnCl$_2$ dihydrate were added and the reaction mixture was heated to reflux for 6 h. Then, after cooling to RT the solvents were removed under reduced pressure. The residue was taken-up in 100 mL aqueous NaHCO$_3$ solution and 200 mL ethyl acetate were added. The inorganic precipitate was filtered off and the solids were washed with ethyl acetate. After separation of the organic layer, the aqueous layer of the filtrate was extracted with ethyl acetate (2×100 ml) and with DCM (3×150 ml). The combined organic layers were dried over $Na_2SO_4$ and the solvents were removed under reduced pressure. The remaining product was pure enough for the next reaction step. Yield: 6 g.

(iii) 2-Trichloromethyl-1H-benzoimidazole

To a solution of 10 g Benzene-1,2-diamine in 250 mL acetic acid, 22.8 g 2,2,2-Trichloro-acetimidic acid methyl ester were added drop wise at RT. After 2 h 500 mL toluene were added and the solvents were removed under reduced pressure. The residue was codestilled additional two times with toluene. After drying under reduced pressure the product was pure enough for the next reaction step.

Yield: 25 g.

(iv) 1H-Benzoimidazole-2-carboxylic acid [4-(4-oxo-4H-pyridin-1-yl)-phenyl]-amide A solution of 769 mg 2-Trichloromethyl-1H-benzoimidazole in 10 mL THF were slowly added to a mixture containing 304 mg 1-(4-Amino-phenyl)-1H-pyridin-4-one, 1.3 g $NaHCO_3$, 40 mL THF and 15 mL $H_2O$. The mixture was stirred vigorously for 3 h at room temperature, diluted with 200 mL $CH_2Cl_2$ and washed with 40 mL of a saturated $NaHCO_3$-solution. The aqueous solution was extracted with $CH_2Cl_2$ (3×200 ml) and the combined organic layers were dried over $MgSO_4$ and concentrated under reduced pressure to give a brown solid, which was pure enough for the following reactions.

Yield: 598 mg.

(v) 1-[5-(5-Chloro-thiophen-2-yl)-isoxazol-3-ylmethyl]-1H-benzoimidazole-2-carboxylic acid [4-(4-oxo-4H-pyridin-1-yl)-phenyl]-amide To a solution of 192 mg 1H-Benzoimidazole-2-carboxylic acid [4-(4-oxo-4H-pyridin-1-yl)-phenyl]-amide in 10 mL DMF, 120 mg $K_2CO_3$ and 194 mg 3-Bromomethyl-5-(5-Chloro-thiophen-2-yl)-isoxazole were added at RT and the mixture was heated for 2 h at 70° C. After addition of 30 mL of water the mixture was extracted with ethyl acetate (3×100 ml). After drying the combined organic phases over $Na_2SO_4$, the solvent was removed under reduced pressure and the residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.

Yield: 70 mg MS ($ES^+$): m/e=528, chloro pattern.

Example 38

1-(3-Methoxy-benzyl)-1H-benzoimidazole-2-carboxylic acid [4-(4-oxo-4H-pyridin-1-yl)-phenyl]-amide The title compound was prepared analogously to example 37 with the difference that 1-Bromomethyl-3-methoxy-benzene was used instead of 3-Bromomethyl-5-(5-Chloro-thiophen-2-yl)-isoxazole in the alkylation step. MS ($ES^+$): m/e=451.

Example 39

1-[(5-Chloro-pyridin-2-ylcarbamoyl)-methyl]-1H-benzoimidazole-2-carboxylic acid [4-(4-oxo-4H-pyridin-1-yl)-phenyl]-amide The title compound was prepared analogously to example 37 with the difference that 2-Bromo-N-(5-chloro-pyridin-2-yl)-acetamide was used instead of 3-Bromomethyl-5-(5-Chloro-thiophen-2-yl)-isoxazole in the alkylation step. MS ($ES^+$): m/e=499, chloro pattern.

Example 40

1-[5-(5-Chloro-thiophen-2-yl)-isoxazol-3-ylmethyl]-1H-benzoimidazole-2-carboxylic acid (8-methyl-8-aza-bicyclo[3.2.1]oct-3-yl)-amide The title compound was prepared analogously to example 37 with the difference that 8-Methyl-8-aza-bicyclo[3.2.1]oct-3-ylamine hydrochloride was used instead of 1-(4-Amino-phenyl)-1H-pyridin-4-one in step (iv). MS ($ES^+$): m/e=482, chloro pattern.

Example 41

1-[5-(5-Chloro-thiophen-2-yl)-isoxazol-3-ylmethyl]-1H-benzoimidazole-2-carboxylic acid [4-(2,4-dioxo-3,4-dihydro-2H-pyrimidin-1-yl)-phenyl]-amide (i) 1-(4-Nitro-phenyl)-1H-pyrimidine-2,4-dione A mixture of 3.5 g 1H-Pyrimidine-2,4-dione and 3 g 1-Fluoro-4-nitro-benzene and 13.8 g $Cs_2CO_3$ in 60 mL DMF was heated to 80° C. for 12 h. This solution was poured on to 200 mL of water and the resulting precipitate was collected by filtration to yield a bright yellow crystalline product, which was dried under reduced pressure. Yield: 2.6 g.

(ii) 1-(4-Amino-phenyl)-1H-pyrimidine-2,4-dione

To a solution of 1.4 g 1-(4-Nitro-phenyl)-1H-pyrimidine-2,4-dione in 120 mL MeOH, 15 g Raney Nickel (washed three times with MeOH) were introduced under a nitrogen atmosphere. Then 15 mL of a 7 M solution of $NH_3$ in MeOH were added. The nitrogen atmosphere was replaced by a hydrogen atmosphere and the mixture was hydrogenated under normal pressure at RT. After 2 h the reaction mixture was filtered through a pad of celite. The solvents were removed under reduced pressure and the residue was subjected to the next reaction step without further purification. Yield: 502 mg.

(iii) 1H-Benzoimidazole-2-carboxylic acid [4-(2,4-dioxo-3,4-dihydro-2H-pyrimidin-1-yl)-phenyl]-amide The title compound was prepared analogously to example 37, step (iv) with the difference that 1-(4-Amino-phenyl)-1H-pyrimidine-2,4-dione was used instead of 1-(4-Amino-phenyl)-1H-pyridin-4-one.

MS ($ES^+$): m/e=348.

(iv) 1-[5-(5-Chloro-thiophen-2-yl)-isoxazol-3-ylmethyl]-1H-benzoimidazole-2-carboxylic acid [4-(2,4-dioxo-3,4-dihydro-2H-pyrimidin-1-yl)-phenyl]-amide The title compound was prepared analogously to example 37, step (iv) with the difference that 1H-Benzoimidazole-2-carboxylic acid [4-(2,4-dioxo-3,4-dihydro-2H-pyrimidin-1-yl)-phenyl]-amide was used instead of 1H-Benzoimidazole-2-carboxylic acid [4-(4-oxo-4H-pyridin-1-yl)-phenyl]-amide. MS ($ES^+$): m/e=545, chloro pattern.

Example 42

1-[5-(5-Chloro-thiophen-2-yl)-isoxazol-3-ylmethyl]-1H-benzoimidazole-2-carboxylic acid [4-(2-oxo-oxazolidin-3-yl)-phenyl]-amide The title compound was prepared analogously to example 41 with the difference that Oxazolidin-2-one and was used instead of 1H-Pyrimidine-2,4-dione in step (i).
MS (ES$^+$): m/e=520, chloro pattern.

Example 43

1-[(5-Chloro-pyridin-2-ylcarbamoyl)-methyl]-1H-benzoimidazole-2-carboxylic acid [4-(2-oxo-oxazolidin-3-yl)-phenyl]-amide The title compound was prepared analogously to example 41 with the difference that Oxazolidin-2-one and 2-Bromo-N-(5-chloro-pyridin-2-yl)-acetamide was used instead of 1H-Pyrimidine-2,4-dione (step (i)) and 3-Bromomethyl-5-(5-chloro-thiophen-2-yl)-isoxazole (step (iv)).
MS (ES$^+$): m/e=490, chloro pattern.

Example 44

1-[(5-Chloro-pyridin-2-ylcarbamoyl)-methyl]-1H-benzoimidazole-2-carboxylic acid [4-(2,4-dioxo-3,4-dihydro-2H-pyrimidin-1-yl)-phenyl]-amide The title compound was prepared analogously to example 41 with the difference that 2-Bromo-N-(5-chloro-pyridin-2-yl)-acetamide was used instead of 3-Bromomethyl-5-(5-chloro-thiophen-2-yl)-isoxazole in the alkylation step. MS (ES$^+$): m/e=516, chloro pattern.

Example 45

1-[5-(5-Chloro-thiophen-2-yl)-isoxazol-3-ylmethyl]-1H-benzoimidazole-2-carboxylic acid [4-(4-oxo-piperidin-1-yl)-phenyl]-amide The title compound was prepared analogously to example 41 with the difference that Piperidin-4-one hydrochloride was used instead of 1H-Pyrimidine-2,4-dione in step (i).
MS (ES$^+$): m/e=532, chloro pattern.

Example 46

1-[5-(5-Chloro-thiophen-2-yl)-isoxazol-3-ylmethyl]-1H-benzoimidazole-2-carboxylic acid [4-(1,1-dioxo-1λ6-thiomorpholin-4-yl)-phenyl]-amide (i) [4-(1,1-Dioxo-1λ6-thiomorpholin-4-yl)-phenyl]-carbamic acid tert-butyl ester A solution of 408 mg (4-Amino-phenyl)-carbamic acid tert-butyl ester and 254 mg Ethenesulfonyl-ethene in 4 mL EtOH were heated for 30 min at 140° C. under microwave irradiation (100 W, CEM Discover™ apparatus). Then, after cooling to RT the solvents were removed under reduced pressure and the residue was dried in vacuo. The crude product was subjected to the next reaction step.
Yield: 0.64 g.

(ii) 4-(1,1-Dioxo-1λ6-thiomorpholin-4-yl)-phenylamine

A solution of 640 mg [4-(1,1-Dioxo-1λ6-thiomorpholin-4-yl)-phenyl]-carbamic acid tert-butyl ester in 30 mL DCM and 30 mL TFA were allowed to stand for 16 h at RT. Then, after addition of 100 mL toluene the solvents were removed under reduced pressure and the residue was dried in vacuo. The product was obtained as its trifluoro acetate. Yield: 0.44 g.

(iii) 1H-Benzoimidazole-2-carboxylic acid [4-(1,1-dioxo-1λ6-thiomorpholin-4-yl)-phenyl]-amide The title compound was prepared analogously to example 37, step (iv) with the difference that 14-(1,1-Dioxo-1λ6-thiomorpholin-4-yl)-phenylamine was used instead of 1-(4-Amino-phenyl)-1H-pyridin-4-one.

(iv) 1-[5-(5-Chloro-thiophen-2-yl)-isoxazol-3-ylmethyl]-1H-benzoimidazole-2-carboxylic acid [4-(1,1-dioxo-1λ6-thiomorpholin-4-yl)-phenyl]-amide The title compound was prepared analogously to example 37, step (v) with the difference that 1H-Benzoimidazole-2-carboxylic acid [4-(1,1-dioxo-1λ6-thiomorpholin-4-yl)-phenyl]-amide was used instead of 1H-Benzoimidazole-2-carboxylic acid [4-(4-oxo-4H-pyridin-1-yl)-phenyl]-amide.
MS (ES$^+$): m/e=568, chloro pattern.

Example 47

1-[(5-Chloro-pyridin-2-ylcarbamoyl)-methyl]-1H-benzoimidazole-2-carboxylic acid [4-(1,1-dioxo-1λ6-thiomorpholin-4-yl)-phenyl]-amide The title compound was prepared analogously to example 46 with the difference that 2-Bromo-N-(5-chloro-pyridin-2-yl)-acetamide was used instead of 3-Bromomethyl-5-(5-chloro-thiophen-2-yl)-isoxazole (step (iv)). MS (ES$^+$): m/e=500, chloro pattern.

Example 48

1-[5-(5-Chloro-thiophen-2-yl)-isoxazol-3-ylmethyl]-1H-benzoimidazole-2-carboxylic acid [4-(2-oxo-2H-pyrazin-1-yl)-phenyl]-amide (i) 1-(4-Nitro-phenyl)-1H-pyrazin-2-one A mixture of 632 mg Sodium pyrazin-2-olate and 720 mg 1-Fluoro-4-nitro-benzene and 3.3 g Cs$_2$CO$_3$ in 13 mL DMF was heated to 35° C. for 6 h. This solution was poured on to 300 mL of water and the resulting precipitate was collected by filtration to yield a bright yellow crystalline product, which was dried under reduced pressure. Yield: 545 mg.

(ii) 1-(4-Amino-phenyl)-1H-pyrazin-2-one

To a solution of 520 mg 1-(4-Nitro-phenyl)-1H-pyrazin-2-one in 26 mL ethyl acetate and 1.3 mL ethanol, 2.7 g SnCl$_2$ dihydrate were added and the reaction mixture was heated to reflux for 6 h. Then, after cooling to RT the mixture was stirred for 16 h. The precipitated product was collected by filtration and was pure enough for the next reaction step.
Yield: 450 mg.

(iii) 1H-Benzoimidazole-2-carboxylic acid [4-(2-oxo-2H-pyrazin-1-yl)-phenyl]-amide The title compound was prepared analogously to example 37, step (iv) with the difference that 1-(4-Amino-phenyl)-1H-pyrazin-2-one was used instead of 1-(4-Amino-phenyl)-1H-pyridin-4-one.
Yield: 513 mg.

(iv) 1-[5-(5-Chloro-thiophen-2-yl)-isoxazol-3-ylmethyl]-1H-benzoimidazole-2-carboxylic acid [4-(2-oxo-2H-pyrazin-1-yl)-phenyl]-amide The title compound was prepared analogously to example 37, step (v) with the difference that 1H-Benzoimidazole-2-carboxylic acid [4-(2-oxo-2H-pyrazin-1-yl)-phenyl]-amide was used instead of 1H-Benzoimidazole-2-carboxylic acid [4-(4-oxo-4H-pyridin-1-yl)-phenyl]-amide.

MS (ES$^+$): m/e=529, chloro pattern.

Example 49

1-[(5-Chloro-pyridin-2-ylcarbamoyl)-methyl]-1H-benzoimidazole-2-carboxylic acid [4-(2-oxo-2H-pyrazin-1-yl)-phenyl]-amide The title compound was prepared analogously to example 48 with the difference that 2-Bromo-N-(5-chloro-pyridin-2-yl)-acetamide was used instead of 3-Bromomethyl-5-(5-chloro-thiophen-2-yl)-isoxazole. MS (ES$^+$): m/e=500, chloro pattern.

Example 50

1-[5-(5-Chloro-thiophen-2-yl)-isoxazol-3-ylmethyl]-1H-benzoimidazole-2-carboxylic acid [4-(2-oxo-piperazin-1-yl)-phenyl]-amide (i) 1-(4-Amino-phenyl)-piperazin-2-one To a solution of 670 mg 1-(4-Nitro-phenyl)-1H-pyrazin-2-one in 100 mL MeOH, 8 g Raney Nickel (washed three times with MeOH) were introduced under a nitrogen atmosphere. Then 10 mL of a 7 M solution of NH$_3$ in MeOH were added. The nitrogen atmosphere was replaced by a hydrogen atmosphere and the mixture was hydrogenated under normal pressure at RT. After 2 h the reaction mixture was filtered through a pad of celite. The solvents were removed under reduced pressure and the residue was subjected to the next reaction step without further purification.

Yield: 464 mg.

(ii) 4-(4-Amino-phenyl)-3-oxo-piperazine-1-carboxylic acid tert-butyl ester

To a solution of 464 mg 1-(4-Amino-phenyl)-piperazin-2-one and 30 mg DMAP in 15 mL acetonitrile, 794 mg Di-tert-butyldicarbonate were added at RT. After 2 h the solvents were removed under reduced pressure and the residue was taken-up in 200 mL ethyl acetate. The organic phase was washed with water and brine, dried over Na$_2$SO$_4$ and the solvent was removed under reduced pressure.

Yield: 547 mg.

(iii) 4-{4-[(1H-Benzoimidazole-2-carbonyl)-amino]-phenyl}-3-oxo-piperazine-1-carboxylic acid tert-butyl ester The title compound was prepared analogously to example 37, step (iv) with the difference that 4-(4-Amino-phenyl)-3-oxo-piperazine-1-carboxylic acid tert-butyl ester was used instead of 1-(4-Amino-phenyl)-1H-pyridin-4-one. Yield: 160 mg.

(iv) 4-[4-({1-[5-(5-Chloro-thiophen-2-yl)-isoxazol-3-ylmethyl]-1H-benzoimidazole-2-carbonyl}-amino)-phenyl]-3-oxo-piperazine-1-carboxylic acid tert-butyl ester The title compound was prepared analogously to example 37, step (v) with the difference that 4-{4-[(1H-Benzoimidazole-2-carbonyl)-amino]-phenyl}-3-oxo-piperazine-1-carboxylic acid tert-butyl ester was used instead of 1H-Benzoimidazole-2-carboxylic acid [4-(4-oxo-4H-pyridin-1-yl)-phenyl]-amide. MS (ES$^+$): m/e=633, chloro pattern.

(v) 1-[5-(5-Chloro-thiophen-2-yl)-isoxazol-3-ylmethyl]-1H-benzoimidazole-2-carboxylic acid [4-(2-oxo-piperazin-1-yl)-phenyl]-amide A solution of 150 mg 4-[4-({1-[5-(5-Chloro-thiophen-2-yl)-isoxazol-3-ylmethyl]-1H-benzoimidazole-2-carbonyl}-amino)-phenyl]-3-oxo-piperazine-1-carboxylic acid tert-butyl ester in 30 mL DCM and 10 mL TFA were allowed to stand for 16 h at RT. Then, after addition of 100 mL toluene the solvents were removed under reduced pressure and the residue was purified by preparative HPLC (C 18 reverse phase column, elution with a H$_2$O/MeCN gradient with 0.1% TFA). The fractions containing the product were evaporated and lyophilized to yield a white solid. The product was obtained as its trifluoroacetate salt. Yield: 84 mg MS (ES$^+$): m/e=533, chloro pattern.

Example 51

1-[(5-Chloro-pyridin-2-ylcarbamoyl)-methyl]-1H-benzoimidazole-2-carboxylic acid [4-(2-oxo-piperazin-1-yl)-phenyl]-amide The title compound was prepared analogously to example 50 with the difference that 2-Bromo-N-(5-chloro-pyridin-2-yl)-acetamide was used instead of 3-Bromomethyl-5-(5-chloro-thiophen-2-yl)-isoxazole. MS (ES$^+$): m/e=504, chloro pattern.

Example 52

1-[(5-Chloro-pyridin-2-ylcarbamoyl)-methyl]-4-(2-methoxy-ethoxy)-1H-benzoimidazole-2-carboxylic acid [4-(3-oxo-morpholin-4-yl)-phenyl]-amide (i) 2-(2-Methoxy-ethoxy)-6-nitro-phenylamine A solution of 5 g 2-Amino-3-nitro-phenol, 4.5 g 1-Bromo-2-methoxy-ethane, 4.4 g K$_2$CO$_3$ in 50 mL DMF were heated to 60° C. for 16 h. Then 50 mL of water were added and the mixture was extracted with ethyl acetate (3×100 ml). The combined organic layers were dried over MgSO$_4$, and the solvents were removed under reduced pressure. The remaining product was pure enough for the next reaction step. Yield: 5.8 g.

(ii) 3-(2-Methoxy-ethoxy)-benzene-1,2-diamine

To a solution of 1 g 2-(2-Methoxy-ethoxy)-6-nitro-phenylamine in 10 mL ethyl acetate and 3 mL ethanol, 4.4 g SnCl$_2$ dihydrate were added and the reaction mixture was heated to reflux for 6 h. Then, after cooling 50 mL 2 M NaOH were added and the inorganic precipitate was filtered and washed extensivley with ethyl acetate. The filtrate was extracted with exthyl acetate (3×100 ml), the combined organic layers were dried over MgSO$_4$, and the solvents were removed under reduced pressure. The remaining product was pure enough for the next reaction step.

Yield: 640 mg.

(iii) 4-(2-Methoxy-ethoxy)-2-trichloromethyl-1H-benzoimidazole

The title compound was prepared analogously to example 37, step (iii) with the difference that 3-(2-Methoxy-ethoxy)-benzene-1,2-diamine was used instead of Benzene-1,2-diamine.

(iv) 4-(2-Methoxy-ethoxy)-1H-benzoimidazole-2-carboxylic acid [4-(3-oxo-morpholin-4-yl)-phenyl]-amide The title compound was prepared analogously to example 37, step (iv) with the difference that 4-(2-Methoxy-ethoxy)-2-trichloromethyl-1H-benzoimidazole was used instead of 2-Trichloromethyl-1H-benzoimidazole. MS (ES$^+$): m/e=411.

(v) 1-[(5-Chloro-pyridin-2-ylcarbamoyl)-methyl]-4-(2-methoxy-ethoxy)-1H-benzoimidazole-2-carboxylic acid [4-(3-oxo-morpholin-4-yl)-phenyl]-amide The title compound was prepared analogously to example 35, step (v) with the difference that 4-(2-Methoxy-ethoxy)-1H-benzoimidazole-2-carboxylic acid [4-(3-oxo-morpholin-4-yl)-phenyl]-amide was used instead of 1H-Benzoimidazole-2-carboxylic acid [4-(3-oxo-morpholin-4-yl)-phenyl]-amide.

MS (ES$^+$): m/e=579, chloro pattern.

Example 53

1-[(5-Chloro-pyridin-2-ylcarbamoyl)-methyl]-2-[4-(3-oxo-morpholin-4-yl)-phenylcarbamoyl]-1H-benzoimidazole-4-carboxylic acid 127 mg (0.20 mmol) 1-[(5-Chloro-pyridin-2-ylcarbamoyl)-methyl]-2-[4-(3-oxo-morpholin-4-yl)-phenylcarbamoyl]-1H-benzoimidazole-4-carboxylic acid methyl ester were dissolved in 15 mL CH$_2$Cl$_2$. At 0° C. 1.8 mL (1.8 mmol) of a 1 M BBr$_3$-solution were added. The reaction mixture was stirred for 24 h at room temperature. Because of incomplete conversion further 0.9 mL (0.9 mmol) of a 1 M BBr$_3$-solution were added. After stirring for 24 h at room temperature the reaction mixture was concentrated and purified by preparative HPLC (CH$_3$CN/H$_2$O gradient+0.05% formic acid). 1-[(5-Chloro-pyridin-2-ylcarbamoyl)-methyl]-2-[4-(3-oxo-morpholin-4-yl)-phenylcarbamoyl]-1H-benzoimidazole-4-carboxylic acid was obtained as a light brown, amorphous solid. Yield: 73 mg MS (ES$^+$): m/e=549, chloro pattern.

Example 54

1-[(5-Chloro-pyridin-2-ylcarbamoyl)-methyl]-5-(3-hydroxy-azetidine-1-carbonyl)-1H-benzoimidazole-2-carboxylic acid (1-isopropyl-piperidin-4-yl)-amide 1-[(5-Chloro-pyridin-2-ylcarbamoyl)-methyl]-5-(3-hydroxy-azetidine-1-carbonyl)-1H-benzoimidazole-2-carboxylic acid (1-isopropyl-piperidin-4-yl)-amide was prepared by a procedure according to example 22 starting from 50 mg (0.10 mmol) 1-[(5-chloro-pyridin-2-ylcarbamoyl)-methyl]-2-(1-isopropyl-piperidin-4-ylcarbamoyl)-1H-benzoimidazole-5-carboxylic acid and 8.1 mg (0.11 mmol) 3-hydroxy-acetidine. The title compound was obtained as its formiate in form of a white amorphous solid. Yield: 10 mg MS (ES$^+$): m/e=552, chloro pattern.

Example 55

1-[(5-Chloro-pyridin-2-ylcarbamoyl)-methyl]-6-(3-hydroxy-azetidine-1-carbonyl)-1H-benzoimidazole-2-carboxylic acid (1-isopropyl-piperidin-4-yl)-amide 1-[(5-Chloro-pyridin-2-ylcarbamoyl)-methyl]-6-(3-hydroxy-azetidine-1-carbonyl)-1H-benzoimidazole-2-carboxylic acid (1-isopropyl-piperidin-4-yl)-amide was prepared by a procedure according to example 22 starting from 50 mg (0.10 mmol) 3-[(5-chloro-pyridin-2-ylcarbamoyl)-methyl]-2-(1-isopropyl-piperidin-4-ylcarbamoyl)-3H-benzoimidazole-5-carboxylic acid and 8.1 mg (0.11 mmol) 3-hydroxy-acetidine. The title compound was obtained as its formiate in form of a white amorphous solid. Yield: 27 mg MS (ES$^+$): m/e=552, chloro pattern.

Example 56

1-[(5-Chloro-pyridin-2-ylcarbamoyl)-methyl]-1H-benzoimidazole-2,5-dicarboxylic acid 5-[(2-hydroxy-ethyl)-amide]2-[(1-isopropyl-piperidin-4-yl)-amide]1-[(5-Chloro-pyridin-2-ylcarbamoyl)-methyl]-1H-benzoimidazole-2,5-dicarboxylic acid 5-[(2-hydroxy-ethyl)-amide]2-[(1-isopropyl-piperidin-4-yl)-amide] was prepared by a procedure according to example 22 starting from 50 mg (0.10 mmol) 1-[(5-chloro-pyridin-2-ylcarbamoyl)-methyl]-2-(1-isopropyl-piperidin-4-ylcarbamoyl)-1H-benzoimidazole-5-carboxylic acid and 6.8 mg (0.11 mmol) 2-amino-ethanol. The title compound was obtained as its formiate in form of a white amorphous solid.

Yield: 4 mg MS (ES$^+$): m/e=542, chloro pattern.

Example 57

3-[(5-Chloro-pyridin-2-ylcarbamoyl)-methyl]-3H-benzoimidazole-2,5-dicarboxylic acid 5-[(2-hydroxy-ethyl)-amide]2-[(1-isopropyl-piperidin-4-yl)-amide]3-[(5-Chloro-pyridin-2-ylcarbamoyl)-methyl]-3H-benzoimidazole-2,5-dicarboxylic acid 5-[(2-hydroxy-ethyl)-amide]2-[(1-isopropyl-piperidin-4-yl)-amide] was prepared by a procedure according to example 22 starting from 50 mg (0.10 mmol) 3-[(5-chloro-pyridin-2-ylcarbamoyl)-methyl]-2-(1-isopropyl-piperidin-4-ylcarbamoyl)-3H-benzoimidazole-5-carboxylic acid and 6.7 mg (0.11 mmol) 2-amino-ethanol. The title compound was obtained as its formiate in form of a white amorphous solid.

Yield: 18 mg MS (ES$^+$): m/e=542, chloro pattern.

Example 58

1-[(5-Chloro-pyridin-2-ylcarbamoyl)-methyl]-1H-benzoimidazole-2,5-dicarboxylic acid 5-[(2-hydroxy-ethyl)-methyl-amide]2-[(1-isopropyl-piperidin-4-yl)-amide]1-[(5-Chloro-pyridin-2-ylcarbamoyl)-methyl]-1H-benzoimidazole-2,5-dicarboxylic acid 5-[(2-hydroxy-ethyl)-methyl-amide]2-[(1-isopropyl-piperidin-4-yl)-amide] was prepared by a procedure according to example 22 starting from 50 mg (0.10 mmol) 1-[(5-chloro-pyridin-2-ylcarbamoyl)-methyl]-2-(1-isopropyl-piperidin-4-ylcarbamoyl)-1H-benzoimidazole-5-carboxylic acid and 8.3 mg (0.11 mmol) N-methyl-2-aminoethanol. The title compound was obtained as its formiate in form of a white amorphous solid. Yield: 23 mg MS (ES$^+$): m/e=556, chloro pattern.

Example 59

3-[(5-Chloro-pyridin-2-ylcarbamoyl)-methyl]-3H-benzoimidazole-2,5-dicarboxylic acid 5-[(2-hydroxy-ethyl)-methyl-amide]2-[(1-isopropyl-piperidin-4-yl)-amide]3-[(5-Chloro-pyridin-2-ylcarbamoyl)-methyl]-3H-benzoimidazole-2,5-dicarboxylic acid 5-[(2-hydroxy-ethyl)-methyl-amide]2-[(1-isopropyl-piperidin-4-yl)- amide] was prepared by a procedure according to example 22 starting from 50 mg (0.10 mmol) 3-[(5-chloro-pyridin-2-yl-carbamoyl)-methyl]-2-(1-isopropyl-piperidin-4-ylcarbamoyl)-3H-benzoimidazole-5-carboxylic acid and 8.3 mg (0.11 mmol) N-methyl-2-aminoethanol. The title compound was obtained as its formiate in form of a white amorphous solid.
Yield: 32 mg MS (ES+): m/e=556, chloro pattern.

Example 60

1-[(5-Chloro-pyridin-2-ylcarbamoyl)-methyl]-2-(1-isopropyl-piperidin-4-ylcarbamoyl)-1H-benzoimidazole-5-carboxylic acid 1-cyclohexyloxycarbonyloxy-ethyl ester 1-[(5-Chloro-pyridin-2-ylcarbamoyl)-methyl]-2-(1-isopropyl-piperidin-4-ylcarbamoyl)-1H-benzoimidazole-5-carboxylic acid 1-cyclohexyloxycarbonyloxy-ethyl ester was prepared by a procedure according to example 20 starting from 50 mg (0.10 mmol) 1-[(5-chloro-pyridin-2-ylcarbamoyl)-methyl]-2-(1-isopropyl-piperidin-4-ylcarbamoyl)-1H-benzoimidazole-5-carboxylic acid and 82.8 mg (0.40 mmol) cyclohexyl-1-chloroethyl carbonate. The title compound was obtained as its dihydrochloride in form of a white amorphous solid.
Yield: 27 mg MS (ES+): m/e=669, chloro pattern.

Example 61

3-[(5-Chloro-pyridin-2-ylcarbamoyl)-methyl]-2-(1-isopropyl-piperidin-4-ylcarbamoyl)-3H-benzoimidazole-5-carboxylic acid 1-cyclohexyloxycarbonyloxy-ethyl ester 3-[(5-Chloro-pyridin-2-ylcarbamoyl)-methyl]-2-(1-isopropyl-piperidin-4-ylcarbamoyl)-3H-benzoimidazole-5-carboxylic acid 1-cyclohexyloxycarbonyloxy-ethyl ester was prepared by a procedure according to example 20 starting from 50 mg (0.10 mmol) 3-[(5-chloro-pyridin-2-ylcarbamoyl)-methyl]-2-(1-isopropyl-piperidin-4-ylcarbamoyl)-3H-benzoimidazole-5-carboxylic acid and 82.8 mg (0.40 mmol) cyclohexyl-1-chloroethyl carbonate. The title compound was obtained as its dihydrochloride in form of a white amorphous solid.
Yield: 49 mg MS (ES+): m/e=669, chloro pattern.

Example 62

1-[(5-Chloro-pyridin-2-ylcarbamoyl)-methyl]-2-(1-isopropyl-piperidin-4-ylcarbamoyl)-1H-benzoimidazole-5-carboxylic acid 1-ethoxycarbonyloxy-ethyl ester 1-[(5-Chloro-pyridin-2-ylcarbamoyl)-methyl]-2-(1-isopropyl-piperidin-4-ylcarbamoyl)-1H-benzoimidazole-5-carboxylic acid 1-ethoxycarbonyloxy-ethyl ester was prepared by a procedure according to example 20 starting from 50 mg (0.10 mmol) 1-[(5-chloro-pyridin-2-ylcarbamoyl)-methyl]-2-(1-isopropyl-piperidin-4-ylcarbamoyl)-1H-benzoimidazole-5-carboxylic acid and 61.2 mg (0.40 mmol) 1-chloroethyl ethylcarbonate. The title compound was obtained as its dihydrochloride in form of a white amorphous solid.
Yield: 21 mg MS (ES+): m/e=615, chloro pattern.

Example 63

3-[(5-Chloro-pyridin-2-ylcarbamoyl)-methyl]-2-(1-isopropyl-piperidin-4-ylcarbamoyl)-3H-benzoimidazole-5-carboxylic acid 1-ethoxycarbonyloxy-ethyl ester 3-[(5-Chloro-pyridin-2-ylcarbamoyl)-methyl]-2-(1-isopropyl-piperidin-4-ylcarbamoyl)-3H-benzoimidazole-5-carboxylic acid 1-ethoxycarbonyloxy-ethyl ester was prepared by a procedure according to example 20 starting from 50 mg (0.10 mmol) 3-[(5-chloro-pyridin-2-ylcarbamoyl)-methyl]-2-(1-isopropyl-piperidin-4-ylcarbamoyl)-3H-benzoimidazole-5-carboxylic acid and 61.2 mg (0.40 mmol) 1-chloroethyl ethylcarbonate. The title compound was obtained as its dihydrochloride in form of a white amorphous solid.
Yield: 42 mg MS (ES+): m/e=615, chloro pattern.

Example 64

1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 2-hydroxy-ethyl ester 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid were dissolved in 4 mL DMF. Subsequently 20 mg DMAP, 34.3 mg (0.16 mmol) DCC and 46 µl (0.83 mmol) ethylene glycol were added. The resulting mixture was stirred for 8 h at 60° C. and then concentrated under removed pressure. The remaining residue was purified by preparative HPLC (CH$_3$CN/H$_2$O gradient+ 0.05% formic acid) to give pure 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 2-hydroxy-ethyl ester as a white amorphous solid. The corresponding dihydrochloride was obtained by treatment with a 0.1 M HCl-solution and following lyophilization. Yield: 22 mg MS (ES+): m/e=572, chloro pattern.

Example 65

3-[5-(5-Chloro-thiophen-2-yl)-isoxazol-3-ylmethyl]-2-(1-isopropyl-piperidin-4-ylcarbamoyl)-3H-benzoimidazole-5-carboxylic acid 2-hydroxy-ethyl ester 50 mg (0.08 mmol) 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid were dissolved in 10 mL CH$_2$Cl$_2$. Subsequently 3 mg DMAP, 23 mg (0.11 mmol) DCC and 46 µl (0.83 mmol) ethylene glycol were added. The resulting mixture was stirred at room temperature for 16 h and then concentrated under removed pressure. The remaining residue was purified by preparative HPLC (CH$_3$CN/H$_2$O gradient+0.05% formic acid) to give pure 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid 2-hydroxy-ethyl ester as a white amorphous solid. The corresponding dihydrochloride was obtained by treatment with a 0.1 M HCl-solution and following lyophilization.
Yield: 44 mg MS (ES+): m/e=572, chloro pattern.

Example 66

1-[5-(5-Chloro-thiophen-2-yl)-isoxazol-3-ylmethyl]-2-(1-isopropyl-piperidin-4-ylcarbamoyl)-1H-benzoimidazole-4-carboxylic acid carboxymethyl ester 50 mg (0.08 mmol) 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid were dissolved in 6 mL DMF. Subsequently 27.6 mg KI, 126.5 mg (0.88 mmol) K$_2$CO$_3$ and 62.8 mg (0.64 mmol) chloro-acetic acid were added. The resulting mixture was stirred for 8 h at 60° C. Further 92 mg K$_2$CO$_3$ and 62.8 mg (0.64 mmol) chloro-acetic acid were added. After further 8 h at 60° C. the reaction mixture was concentrated under removed pressure. The remaining residue was purified by preparative HPLC (CH$_3$CN/H$_2$O gradient+0.05% formic acid) to give pure 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid carboxymethyl ester as a white amorphous solid. The corresponding dihydrochloride was obtained by treatment with a 0.1 M HCl-solution and following lyophilization.

Yield: 21 mg MS (ES$^+$): m/e=586, chloro pattern.

Example 67

1-(3-Methoxy-benzyl)-2-[4-(3-oxo-morpholin-4-yl)-phenylcarbamoyl]-1H-benzoimidazole-4-carboxylic acid (i) 1-(3-Methoxy-benzyl)-2-[4-(3-oxo-morpholin-4-yl)-phenylcarbamoyl]-1H-benzoimidazole-4-carboxylic acid methyl ester 366.5.0 mg (0.929 mmol) 2-[4-(3-Oxo-morpholin-4-yl)-phenylcarbamoyl]-1H-benzoimidazole-4-carboxylic acid methyl ester were dissolved in 15 mL DMF. Sequentially 192.6 mg (1.394 mmol) K$_2$CO$_3$ and 156.1 μl (1.394 mmol) 1-bromomethyl-3-methoxy-benzene were added and the resulting mixture was stirred for 4 h at 80°. The mixture was diluted with 300 mL toluene and washed with 50 mL of a saturated NaHCO$_3$-solution. The product was not completely soluble in toluene, so ethyl acetate had to be added. The organic layer was washed with brine, dried over anhydrous MgSO$_4$ and concentrated under reduced pressure. The residue was purified by preparative HPLC (CH$_3$CN/H$_2$O gradient+0.05% formic acid) (separation of isomers) to give 1-(3-Methoxy-benzyl)-2-[4-(3-oxo-morpholin-4-yl)-phenylcarbamoyl]-1H-benzoimidazole-4-carboxylic acid methyl ester as a light brown amorphous solid.

Yield: 150 mg MS (ES$^+$): m/e=515.

(ii) 1-(3-Methoxy-benzyl)-2-[4-(3-oxo-morpholin-4-yl)-phenylcarbamoyl]-1H-benzoimidazole-4-carboxylic acid 20 mg (0.04 mmol) 1-(3-Methoxy-benzyl)-2-[4-(3-oxo-morpholin-4-yl)-phenylcarbamoyl]-1H-benzoimidazole-4-carboxylic acid methyl ester were suspended in 5 mL MeOH. 194 μl (0.19 mmol) of an aqueous 1 M LiOH-solution were added and the resulting mixture was stirred for 8 h at 60° C. After acidification with a 1 M HCL-solution the mixture was concentrated. The resulting residue was purified by preparative HPLC (CH$_3$CN/H$_2$O gradient+0.05% formic acid) to give pure 1-(3-Methoxy-benzyl)-2-[4-(3-oxo-morpholin-4-yl)-phenylcarbamoyl]-1H-benzoimidazole-4-carboxylic acid as a colorless amorphous solid. Yield: 44 mg MS (ES$^+$): m/e=501.

Example 68 a) 1-[(5-Chloro-pyridin-2-ylcarbamoyl)-methyl]-5-(2-hydroxy-ethanesulfonyl)-1H-benzoimidazole-2-carboxylic acid (1-isopropyl-piperidin-4-yl)-amide b) 1-[(5-Chloro-pyridin-2-ylcarbamoyl)-methyl]-6-(2-hydroxy-ethanesulfonyl)-1H-benzoimidazole-2-carboxylic acid (1-isopropyl-piperidin-4-yl)-amide 1-[(5-Chloro-pyridin-2-ylcarbamoyl)-methyl]-5-(2-hydroxy-ethanesulfonyl)-1H-benzoimidazole-2-carboxylic acid (1-isopropyl-piperidin-4-yl)-amide and 1-[(5-Chloro-pyridin-2-ylcarbamoyl)-methyl]-6-(2-hydroxy-ethanesulfonyl)-1H-benzoimidazole-2-carboxylic acid (1-isopropyl-piperidin-4-yl)-amide were prepared by a procedure according to example 29 starting from 1 g (2.5 mmol) crude 5-(2-hydroxy-ethanesulfonyl)-1H-benzoimidazole-2-carboxylic acid (1-isopropyl-piperidin-4-yl)-amide and 758.9 mg (3.04 mmol) 2-bromo-N-(5-chloro-pyridin-2-yl)-acetamide. Preparative RP-HPLC (CH$_3$CN/H$_2$O gradient+0.05% formic acid) gave a 1:1 mixture of both isomers described in the title. These isomers could be separated by NP-HPLC using a chiral stationary phase and a mixture of heptane, ethanol, methanol and diethyl amine as solvent. Structural assignment of both isomers was achieved by NOE-spectroscopy.

Yield of 1-[(5-Chloro-pyridin-2-ylcarbamoyl)-methyl]-5-(2-hydroxy-ethanesulfonyl)-1H-benzoimidazole-2-carboxylic acid (1-isopropyl-piperidin-4-yl)-amide: 79 mg MS (ES$^+$): m/e=563, chloro pattern. Yield of 1-[(5-Chloro-pyridin-2-ylcarbamoyl)-methyl]-6-(2-hydroxy-ethanesulfonyl)-1H-benzoimidazole-2-carboxylic acid (1-isopropyl-piperidin-4-yl)-amide is 44 mg MS (ES$^+$): m/e=563, chloro pattern.

Example 69

1-[(5-Chloro-pyridin-2-ylcarbamoyl)-methyl]-2-(1-isopropyl-piperidin-4-ylcarbamoyl)-1H-benzoimidazole-4-carboxylic acid cyclopropylmethyl ester 325.1 mg (0.57 mmol) 1-[(5-Chloro-pyridin-2-ylcarbamoyl)-methyl]-2-(1-isopropyl-piperidin-4-ylcarbamoyl)-1H-benzoimidazole-4-carboxylic acid were dissolved in 20 mL CH$_2$Cl$_2$. Subsequently 470 μl (5.7 mmol) cyclopropyl-methanol, 152.2 mg (0.74 mmol) DCC and 6.9 mg DMAP were added. The resulting mixture was stirred at room temperature for 16 h. The next day further 100 μl (2.28 mmol) cyclopropyl-methanol, 58.6 mg (0.29 mmol) DCC and 20 mg DMAP were added and the reaction mixture was stirred for 48 h. The solvent was removed under vacuo. Final purification by preparative RP-HPLC (CH$_3$CN/H$_2$O gradient+0.05% formic acid) gave 1-[(5-Chloro-pyridin-2-ylcarbamoyl)-methyl]-2-(1-isopropyl-piperidin-4-ylcarbamoyl)-1H-benzoimidazole-4-carboxylic acid cyclopropylmethyl ester as a white amorphous solid. The corresponding acetate was obtained by the following procedure: The above described material was dissolved in CH$_2$Cl$_2$ and washed with a saturated NaHCO$_3$-solution. The organic layer was dried over anhydrous MgSO$_4$ and concentrated. The resulting residue was diluted in 20 mL water containing 4 equiv. AcOH and lyophilized.

Yield: 231 mg MS (ES$^+$): m/e=553, chloro pattern.

Example 70

1-[(5-Chloro-pyridin-2-ylcarbamoyl)-methyl]-2-(1-isopropyl-piperidin-4-ylcarbamoyl)-1H-benzoimidazole-4-carboxylic acid 2-methoxy-ethyl ester 1-[(5-Chloro-pyridin-2-ylcarbamoyl)-methyl]-2-(1-isopropyl-piperidin-4-ylcarbamoyl)-1H-benzoimidazole-4-carboxylic acid 2-methoxy-ethyl ester was prepared by a procedure according to example 69 starting from 112 mg (0.22 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 177 µl (2.2 mmol) 2-methoxy-ethanol. The title compound was obtained as its dihydrochloride in form of a white amorphous solid. Yield: 66 mg MS (ES+): m/e=557, chloro pattern.

Example 71

1-[(5-Chloro-pyridin-2-ylcarbamoyl)-methyl]-4-hydroxymethyl-1H-benzoimidazole-2-carboxylic acid (1-isopropyl-piperidin-4-yl)-amide 85.0 mg (0.166 mmol) 1-[(5-Chloro-pyridin-2-ylcarbamoyl)-methyl]-2-(1-isopropyl-piperidin-4-ylcarbamoyl)-1H-benzoimidazole-4-carboxylic acid methyl ester were dissolved in 3 mL abs. THF. Under argon 0.25 mL (0.497 mmol) of a 2 M LiBH$_4$-solution in THF were added. After stirring for 1.5 h at room temperature 0.5 mL water were added and the reaction mixture was concentrated. The residue was purified by preparative RP-HPLC (CH$_3$CN/H$_2$O gradient+0.05% formic acid) to give 1-[(5-Chloro-pyridin-2-ylcarbamoyl)-methyl]-4-hydroxymethyl-1H-benzoimidazole-2-carboxylic acid (1-isopropyl-piperidin-4-yl)-amide as a white amorphous solid. The title compound was obtained as its formiate. Yield: 20 mg MS (ES+): m/e=485, chloro pattern.

Example 72

1-[(5-Chloro-pyridin-2-ylcarbamoyl)-methyl]-4-(2-methoxy-ethoxymethyl)-1H-benzoimidazole-2-carboxylic acid (1-isopropyl-piperidin-4-yl)-amide 81.6 mg (0.065 mmol) 1-[(5-Chloro-pyridin-2-ylcarbamoyl)-methyl]-4-hydroxymethyl-1H-benzoimidazole-2-carboxylic acid (1-isopropyl-piperidin-4-yl)-amide were dissolved in 5 mL abs. DMF. At 0° C. 21.9 mg (0.195 mmol) potassium tert.butylate were added. After 5 min 12 µl (0.13 mmol) 1-bromo-2-methoxy-ethane were added and the reaction mixture was allowed to come to room temperature. After 3 h further 12 µl (0.13 mmol) 1-bromo-2-methoxy-ethane were added and the reaction mixture was stirred for 16 h. The solvent was distilled off and the resulting residue was purified by preparative RP-HPLC (CH$_3$CN/H$_2$O gradient+0.05% formic acid) to give 1-[(5-Chloro-pyridin-2-ylcarbamoyl)-methyl]-4-(2-methoxy-ethoxymethyl)-1H-benzoimidazole-2-carboxylic acid (1-isopropyl-piperidin-4-yl)-amide as a light brown amorphous solid. The title compound was obtained as its formiate. Yield: 12 mg MS (ES+): m/e=543, chloro pattern.

Example 73

1-[(5-Chloro-pyridin-2-ylcarbamoyl)-methyl]-4-(morpholine-4-carbonyl)-1H-benzoimidazole-2-carboxylic acid (1-isopropyl-piperidin-4-yl)-amide 1-[(5-Chloro-pyridin-2-ylcarbamoyl)-methyl]-4-(morpholine-4-carbonyl)-1H-benzoimidazole-2-carboxylic acid (1-isopropyl-piperidin-4-yl)-amide was prepared by a procedure according to example 22 starting from 450 mg (0.90 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 87 µl (2.70 mmol) morpholine. The title compound was obtained as its formiate. Subsequent transformation to the corresponding acetate gave a white amorphous solid.

Yield: 456 mg MS (ES+): m/e=568, chloro pattern.

Example 74

1-[(5-Chloro-pyridin-2-ylcarbamoyl)-methyl]-4-([1,4]oxazepane-4-carbonyl)-1H-benzoimidazole-2-carboxylic acid (1-isopropyl-piperidin-4-yl)-amide 1-[(5-Chloro-pyridin-2-ylcarbamoyl)-methyl]-4-([1,4]oxazepane-4-carbonyl)-1H-benzoimidazole-2-carboxylic acid (1-isopropyl-piperidin-4-yl)-amide was prepared by a procedure according to example 22 starting from 423 mg (0.85 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 128.3 mg (0.94 mmol) homomorpholine-hydrochloride. The title compound was obtained as its formiate. Subsequent transformation to the corresponding acetate gave a white amorphous solid.

Yield: 370 mg MS (ES+): m/e=582, chloro pattern.

Example 75

1-[(5-Chloro-pyridin-2-ylcarbamoyl)-methyl]-4-(2,6-dimethyl-piperidine-1-carbonyl)-1H-benzoimidazole-2-carboxylic acid (1-isopropyl-piperidin-4-yl)-amide 1-[(5-Chloro-pyridin-2-ylcarbamoyl)-methyl]-4-(2,6-dimethyl-piperidine-1-carbonyl)-1H-benzoimidazole-2-carboxylic acid (1-isopropyl-piperidin-4-yl)-amide was prepared by a procedure according to example 22 starting from 100 mg (0.20 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 50.0 µl (0.40 mmol) 2,6-dimethyl-piperidine. The title compound was obtained as its formiate in form of a white amorphous solid. Yield: 72 mg MS (ES+): m/e=594, chloro pattern.

Example 76

1-[(5-Chloro-pyridin-2-ylcarbamoyl)-methyl]-4-(4,4-difluoro-piperidine-1-carbonyl)-1H-benzoimidazole-2-carboxylic acid (1-isopropyl-piperidin-4-yl)-amide 1-[(5-Chloro-pyridin-2-ylcarbamoyl)-methyl]-4-(4,4-difluoro-piperidine-1-carbonyl)-1H-benzoimidazole-2-carboxylic acid (1-isopropyl-piperidin-4-yl)-amide was prepared by a procedure according to example 22 starting from 870 mg (1.70 mmol) 1-[(5-Chloro-pyridin-2-ylcarbamoyl)-methyl]-2-(1-isopropyl-piperidin-4-ylcarbamoyl)-1H-benzoimidazole-4-carboxylic acid and 302.3 mg (1.87 mmol) 4,4-difluoro-piperidine-hydrochloride. The title compound was obtained as its formiate. Subsequent transformation to the corresponding acetate gave a white amorphous solid.

Yield: 700 mg MS (ES+): m/e=602, chloro pattern.

Example 77

1-[(5-Chloro-pyridin-2-ylcarbamoyl)-methyl]-5-([1,4]oxazepane-4-carbonyl)-1H-benzoimidazole-2-carboxylic acid (1-isopropyl-piperidin-4-yl)-amide 1-[(5-Chloro-pyridin-2-ylcarbamoyl)-methyl]-5-([1,4]oxazepane-4-carbonyl)-1H-benzoimidazole-2-carboxylic acid (1-isopropyl-piperidin-4-yl)-amide was prepared by a procedure according to example 22 starting from 147.8 mg (0.296 mmol) 1-[(5-Chloro-pyridin-2-ylcarbamoyl)-methyl]-2-(1-isopropyl-piperidin-4-ylcarbamoyl)-1H-benzoimidazole-5-carboxylic acid and 44.8 mg (0.326 mmol) homomorpholine-hydrochloride. The title compound was obtained as its formiate. Subsequent transformation to the corresponding acetate gave a white amorphous solid.
Yield: 113 mg MS (ES$^+$): m/e=582, chloro pattern.

Example 78

1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 2-hydroxy-ethyl ester 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 2-hydroxy-ethyl ester was prepared by a procedure according to example 65 starting from 100 mg (0.17 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid and 93 µl (1.7 mmol) ethylene glycol. The title compound was obtained as its dihydrochloride in form of a white amorphous solid. Yield: 86 mg MS (ES$^+$): m/e=572, chloro pattern.

Example 79

1-[5-(5-Chloro-thiophen-2-yl)-isoxazol-3-ylmethyl]-2-(1-isopropyl-piperidin-4-ylcarbamoyl)-1H-benzoimidazole-5-carboxylic acid carboxymethyl ester 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid carboxymethyl ester was prepared by a procedure according to example 66 starting from 100 mg (0.17 mmol) 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid and 62.9 mg (0.68 mmol) chloro-acetic acid. The title compound was obtained as its dihydrochloride in form of a white amorphous solid. Yield: 44 mg MS (ES$^+$): m/e=586, chloro pattern.

Example 80

1-[5-(5-Chloro-thiophen-2-yl)-isoxazol-3-ylmethyl]-4-(3-methoxy-azetidine-1-carbonyl)-1H-benzoimidazole-2-carboxylic acid (1-isopropyl-piperidin-4-yl)-amide 1-[5-(5-Chloro-thiophen-2-yl)-isoxazol-3-ylmethyl]-4-(3-methoxy-azetidine-1-carbonyl)-1H-benzoimidazole-2-carboxylic acid (1-isopropyl-piperidin-4-yl)-amide was prepared by a procedure according to example 22 starting from 205 mg (0.34 mmol) 1-[5-(5-chloro-thiophen-2-yl)-isoxazol-3-ylmethyl]-2-(1-isopropyl-piperidin-4-ylcarbamoyl)-1H-benzoimidazole-4-carboxylic acid and 46.6 mg (0.37 mmol) 3-methoxy-azetidine-hydrochloride. The title compound was obtained as its formiate. Subsequent transformation to the corresponding acetate gave a white amorphous solid. Yield: 190 mg MS (ES$^+$): m/e=597, chloro pattern.

Example 81 a) 2-(1-Isopropyl-piperidin-4-ylcarbamoyl)-1-(3-methoxy-benzyl)-1H-benzoimidazole-4-carboxylic acid b) 2-(1-Isopropyl-piperidin-4-ylcarbamoyl)-3-(3-methoxy-benzyl)-3H-benzoimidazole-4-carboxylic acid 1.45 g (4.21 mmol) 2-(1-Isopropyl-piperidin-4-ylcarbamoyl)-1H-benzoimidazole-4-carboxylic acid methyl ester were dissolved in 45 mL DMF. Subsequently 698.2 mg (5.05 mmol) K$_2$CO$_3$ and 888.8 mg (4.42 mmol) 1-bromomethyl-3-methoxy-benzene were added and the resulting mixture was stirred for 2 h at 60° C. The solvent was distilled off. The residue was taken up in 300 mL ethyl acetate and washed once with a saturated NaHCO$_3$-solution and with brine. The organic layer was dried over anhydrous MgSO$_4$, concentrated under reduced pressure and purified by flash chromatography on silica gel using an ethyl acetate-methanol mixture as eluent to give 1.19 g of a 4:1-mixture of 2-(1-Isopropyl-piperidin-4-ylcarbamoyl)-1-(3-methoxy-benzyl)-1H-benzoimidazole-4-carboxylic acid methyl ester and 2-(1-Isopropyl-piperidin-4-ylcarbamoyl)-3-(3-methoxy-benzyl)-3H-benzoimidazole-4-carboxylic acid methyl ester. That mixture of isomers was dissolved in 100 mL MeOH. 12.8 mL (12.8 mmol) of a 1 M aqueous LiOH-solution were added and the resulting suspension was stirred for 3 h at 60° C. The mixture was acidified by the addition of a 1M HCl-solution and concentrated under reduced pressure. Final purification by preparative RP-HPLC (CH$_3$CN/H$_2$O gradient+0.05% formic acid) gave both isomers a) 2-(1-Isopropyl-piperidin-4-ylcarbamoyl)-1-(3-methoxy-benzyl)-1H-benzoimidazole-4-carboxylic acid and b) 2-(1-Isopropyl-piperidin-4-ylcarbamoyl)-3-(3-methoxy-benzyl)-3H-benzoimidazole-4-carboxylic acid as white amorphous solids. Both isomers were transformed to the corresponding dihydrochlorides.
Yield of 2-(1-Isopropyl-piperidin-4-ylcarbamoyl)-1-(3-methoxy-benzyl)-1H-benzoimidazole-4-carboxylic acid: 890 mg MS (ES$^+$): m/e=451. Yield of 2-(1-Isopropyl-piperidin-4-ylcarbamoyl)-3-(3-methoxy-benzyl)-3H-benzoimidazole-4-carboxylic acid: 250 mg MS (ES$^+$): m/e=451.

Example 82 a) 1-[2-(4-Chloro-phenyl)-ethyl]-2-(1-isopropyl-piperidin-4-ylcarbamoyl)-1H-benzoimidazole-4-carboxylic acid b) 3-[2-(4-Chloro-phenyl)-ethyl]-2-(1-isopropyl-piperidin-4-ylcarbamoyl)-3H-benzoimidazole-4-carboxylic acid 1.45 g (4.21 mmol) 2-(1-Isopropyl-piperidin-4-ylcarbamoyl)-1H-benzoimidazole-4-carboxylic acid methyl ester were dissolved in 45 mL DMF. Subsequently 989.1 mg (7.16 mmol) K$_2$CO$_3$ and 1.11 g (6.32 mmol) 1-chloro-4-(2-chloroethyl)-benzene were added and the resulting mixture was stirred for 24 h at 80° C. The solvent was distilled off. The residue was taken up in 300 mL ethyl acetate and washed once with a saturated NaHCO$_3$-solution and with brine. The organic layer was dried over anhydrous MgSO$_4$, concentrated and purified by flash chromatography using an ethyl acetate-methanol mixture as eluent to give 1.30 g of a 3:1-mixture of 1-[2-(4-Chloro-phenyl)-ethyl]-2-(1-isopropyl-piperidin-4-ylcarbamoyl)-1H-benzoimidazole-4-carboxylic acid methyl ester and 3-[2-(4-Chloro-phenyl)-ethyl]-2-(1-isopropyl-piperidin-4-ylcarbamoyl)-3H-benzoimidazole-4-carboxylic acid methyl ester. That mixture of isomers was dissolved in 100 mL MeOH. 16.2 mL (16.2 mmol) of a 1 M aqueous LiOH-solution were added and the resulting suspension was stirred for 3 h at 60° C. The mixture was acidified by the addition of a 1 M HCl-solution and concentrated under reduced pressure. Final purification by preparative RP-HPLC ($CH_3CN/H_2O$ gradient+0.05% formic acid) gave both isomers a) 1-[2-(4-Chloro-phenyl)-ethyl]-2-(1-isopropyl-piperidin-4-ylcarbamoyl)-1H-benzoimidazole-4-carboxylic acid and b) 3-[2-(4-Chloro-phenyl)-ethyl]-2-(1-isopropyl-piperidin-4-ylcarbamoyl)-3H-benzoimidazole-4-carboxylic acid as white amorphous solids. Both isomers were isolated as their formiates.

Yield of 1-[2-(4-Chloro-phenyl)-ethyl]-2-(1-isopropyl-piperidin-4-ylcarbamoyl)-1H-benzoimidazole-4-carboxylic acid: 800 mg MS ($ES^+$): m/e=468, chloro pattern.

Yield of 3-[2-(4-Chloro-phenyl)-ethyl]-2-(1-isopropyl-piperidin-4-ylcarbamoyl)-3H-benzoimidazole-4-carboxylic acid: 250 mg MS ($ES^+$): m/e=468, chloro pattern.

Example 83

4-(3-Hydroxy-azetidine-1-carbonyl)-1-(3-methoxy-benzyl)-1H-benzoimidazole-2-carboxylic acid (1-isopropyl-piperidin-4-yl)-amide 4-(3-Hydroxy-azetidine-1-carbonyl)-1-(3-methoxy-benzyl)-1H-benzoimidazole-2-carboxylic acid (1-isopropyl-piperidin-4-yl)-amide was prepared by a procedure according to example 22 starting from 150 mg (0.287 mmol) 2-(1-Isopropyl-piperidin-4-ylcarbamoyl)-1-(3-methoxy-benzyl)-1H-benzoimidazole-4-carboxylic acid and 23.0 mg (0.315 mmol) 3-hydroxy-azetidine. The title compound was obtained as its formiate in form a white amorphous solid.

Yield: 62 mg MS ($ES^+$): m/e=506.

Example 84

1-[2-(4-Chloro-phenyl)-ethyl]-4-(3-hydroxy-azetidine-1-carbonyl)-1H-benzoimidazole-2-carboxylic acid (1-isopropyl-piperidin-4-yl)-amide 1-[2-(4-Chloro-phenyl)-ethyl]-4-(3-hydroxy-azetidine-1-carbonyl)-1H-benzoimidazole-2-carboxylic acid (1-isopropyl-piperidin-4-yl)-amide was prepared by a procedure according to example 22 starting from 150 mg (0.29 mmol) 1-[2-(4-Chloro-phenyl)-ethyl]-2-(1-isopropyl-piperidin-4-ylcarbamoyl)-1H-benzoimidazole-4-carboxylic acid and 23.4 mg (0.32 mmol) 3-hydroxy-azetidine. The title compound was obtained as its formiate in form a white amorphous solid.

Yield: 62 mg MS ($ES^+$): m/e=524, chloro pattern.

Example 85

1-[2-(4-Chloro-phenyl)-ethyl]-4-(3-methoxy-azetidine-1-carbonyl)-1H-benzoimidazole-2-carboxylic acid (1-isopropyl-piperidin-4-yl)-amide 1-[2-(4-Chloro-phenyl)-ethyl]-4-(3-methoxy-azetidine-1-carbonyl)-1H-benzoimidazole-2-carboxylic acid (1-isopropyl-piperidin-4-yl)-amide was prepared by a procedure according to example 22 starting from 50 mg (0.097 mmol) 1-[2-(4-Chloro-phenyl)-ethyl]-2-(1-isopropyl-piperidin-4-ylcarbamoyl)-1H-benzoimidazole-4-carboxylic acid and 13.5 mg (0.015 mmol) 3-methoxy-azetidine. The title compound was obtained as its formiate in form a white amorphous solid.

Yield: 35 mg MS ($ES^+$): m/e=538, chloro pattern.

Example 86 a) 2-(1-Isopropyl-piperidin-4-ylcarbamoyl)-1-(3-methoxy-benzyl)-1H-benzoimidazole-5-carboxylic acid methyl ester b) 2-(1-Isopropyl-piperidin-4-ylcarbamoyl)-3-(3-methoxy-benyl)-3H-benzoimidazole-5-carboxylic acid methyl ester 2-(1-Isopropyl-piperidin-4-ylcarbamoyl)-1-(3-methoxy-benzyl)-1H-benzoimidazole-5-carboxylic acid methyl ester and 2-(1-Isopropyl-piperidin-4-ylcarbamoyl)-3-(3-methoxy-benyl)-3H-benzoimidazole-5-carboxylic acid methyl ester were prepared by a procedure according to example 5 iii) starting from 300 mg (0.87 mmol) 2-(1-Isopropyl-piperidin-4-ylcarbamoyl)-1H-benzoimidazole-5-carboxylic acid methyl ester and 210.2 mg (1.04 mmol) 1-bromomethyl-3-methoxy-benzene. Preparative RP-HPLC ($CH_3CN/H_2O$ gradient+0.05% formic acid) gave a 1:1 mixture of both isomers described in the title. These isomers could be separated by NP-HPLC using a chiral stationary phase and a mixture of heptane, ethanol, methanol and diethyl amine as solvent. Structural assignment of both isomers was achieved by NOE-spectroscopy.

Yield of 2-(1-Isopropyl-piperidin-4-ylcarbamoyl)-1-(3-methoxy-benzyl)-1H-benzoimidazole-5-carboxylic acid methyl ester: 65 mg MS ($ES^+$): m/e=465.

Yield of 2-(1-Isopropyl-piperidin-4-ylcarbamoyl)-3-(3-methoxy-benzyl)-3H-benzoimidazole-5-carboxylic acid methyl ester: 70 mg MS ($ES^+$): m/e=465.

Example 87 a) 1-[2-(4-Chloro-phenyl)-ethyl]-2-(1-isopropyl-piperidin-4-ylcarbamoyl)-1H-benzoimidazole-5-carboxylic acid methyl ester b) 3-[2-(4-Chloro-phenyl)-ethyl]-2-(1-isopropyl-piperidin-4-ylcarbamoyl)-3H-benzoimidazole-5-carboxylic acid methyl ester 1-[2-(4-Chloro-phenyl)-ethyl]-2-(1-isopropyl-piperidin-4-ylcarbamoyl)-1H-benzoimidazole-5-carboxylic acid methyl ester and 3-[2-(4-Chloro-phenyl)-ethyl]-2-(1-isopropyl-piperidin-4-ylcarbamoyl)-3H-benzoimidazole-5-carboxylic acid methyl ester were prepared by a procedure according to example 5 iii) starting from 300 mg (0.87 mmol) 2-(1-Isopropyl-piperidin-4-ylcarbamoyl)-1H-benzoimidazole-5-carboxylic acid methyl ester and 365.9 mg (2.09 mmol) 1-chloro-4-(2-chloro-ethyl)-benzene. Since 1-chloro-4-(2-chloro-ethyl)-benzene is less reactive the reaction time had to be extended to 10 h. Preparative RP-HPLC ($CH_3CN/H_2O$ gradient+0.05% formic acid) gave a 4:3 mixture of both isomers described in the title. These isomers could be separated by NP-HPLC using a chiral stationary phase and a mixture of heptane, ethanol and methanol as solvent. Structural assignment of both isomers was achieved by NOE-spectroscopy.

Yield of 1-[2-(4-Chloro-phenyl)-ethyl]-2-(1-isopropyl-piperidin-4-ylcarbamoyl)-1H-benzoimidazole-5-carboxylic acid methyl ester: 102 mg MS (ES$^+$): m/e=483, chloro pattern.

Yield of 3-[2-(4-Chloro-phenyl)-ethyl]-2-(1-isopropyl-piperidin-4-ylcarbamoyl)-3H-benzoimidazole 5-carboxylic acid methyl ester: 74 mg MS (ES$^+$): m/e=483, chloro pattern.

Example 88

1-[2-(4-Chloro-phenyl)-ethyl]-2-(1-isopropyl-piperidin-4-ylcarbamoyl)-1H-benzoimidazole-5-carboxylic acid 1-[2-(4-Chloro-phenyl)-ethyl]-2-(1-isopropyl-piperidin-4-ylcarbamoyl)-1H-benzoimidazole-5-carboxylic acid was prepared by a procedure according to example 6 starting from 100 mg (0.21 mmol) 1-[2-(4-Chloro-phenyl)-ethyl]-2-(1-isopropyl-piperidin-4-ylcarbamoyl)-1H-benzoimidazole-5-carboxylic acid methyl ester and 1.04 mL (1.04 mmol) of a 1 M LiOH-solution. The title compound was obtained as its dihydrochloride in form a white amorphous solid.

Yield: 54 mg MS (ES$^+$): m/e=469, chloro pattern.

Example 89 a) 1-(5-Chloro-benzo[b]thiophen-2-ylmethyl)-2-(1-isopropyl-piperidin-4-ylcarbamoyl)-1H-benzoimidazole-4-carboxylic acid b) 3-(5-Chloro-benzo[b]thiophen-2-ylmethyl)-2-(1-isopropyl-piperidin-4-ylcarbamoyl)-3H-benzoimidazole-4-carboxylic acid 1-(5-Chloro-benzo[b]thiophen-2-ylmethyl)-2-(1-isopropyl-piperidin-4-ylcarbamoyl)-1H-benzoimidazole-4-carboxylic acid and 3-(5-Chloro-benzo[b]thiophen-2-ylmethyl)-2-(1-isopropyl-piperidin-4-ylcarbamoyl)-3H-benzoimidazole-4-carboxylic acid were prepared by a procedure according to example 81 starting from 200 mg (0.58 mmol) 2-(1-Isopropyl-piperidin-4-ylcarbamoyl)-1H-benzoimidazole-4-carboxylic acid methyl ester and 151.9 mg (0.58 mmol) 2-bromomethyl-5-chloro-benzo[b]thiophene. Hydrolysis of the resulting esters and purification by preparative RP-HPLC (CH$_3$CN/H$_2$O gradient+0.05% formic acid) gave the title compounds as their formiates in form of white amorphous solids.

Yield of 1-(5-Chloro-benzo[b]thiophen-2-ylmethyl)-2-(1-isopropyl-piperidin-4-ylcarbamoyl)-1H-benzoimidazole-4-carboxylic acid: 134 mg MS (ES$^+$): m/e=511, chloro pattern.

Yield of 3-(5-Chloro-benzo[b]thiophen-2-ylmethyl)-2-(1-isopropyl-piperidin-4-ylcarbamoyl)-3H-benzoimidazole-4-carboxylic acid: 49 mg MS (ES$^+$): m/e=511, chloro pattern.

Example 90

1-(5-Chloro-1H-indazol-3-ylmethyl)-2-(1-isopropyl-piperidin-4-ylcarbamoyl)-1H-benzoimidazole-4-carboxylic acid 1-(5-Chloro-1H-indazol-3-ylmethyl)-2-(1-isopropyl-piperidin-4-ylcarbamoyl)-1H-benzoimidazole-4-carboxylic acid was prepared by a procedure according to example 81 starting from 200 mg (0.58 mmol) 2-(1-isopropyl-piperidin-4-ylcarbamoyl)-1H-benzoimidazole-4-carboxylic acid methyl ester and 116.8 mg (0.58 mmol) 5-chloro-3-chloromethyl-1H-indazole. Hydrolysis of the resulting ester and purification by preparative RP-HPLC (CH$_3$CN/H$_2$O gradient+ 0.05% formic acid) gave the title compound as its formiate in form of a white amorphous solid.

Yield: 20 mg MS (ES$^+$): m/e=495, chloro pattern.

Example 91

1-[5-(5-Chloro-thiophen-2-yl)-isoxazol-3-ylmethyl]-4-(4-hydroxy-piperidine-1-carbonyl)-1H-benzoimidazole-2-carboxylic acid (1-isopropyl-piperidin-4-yl)-amide 1-[5-(5-Chloro-thiophen-2-yl)-isoxazol-3-ylmethyl]-4-(4-hydroxy-piperidine-1-carbonyl)-1H-benzoimidazole-2-carboxylic acid (1-isopropyl-piperidin-4-yl)-amide was prepared by a procedure according to example 22 starting from 670 mg (1.10 mmol) 1-[5-(5-chloro-thiophen-2-yl)-isoxazol-3-ylmethyl]-2-(1-isopropyl-piperidin-4-ylcarbamoyl)-1H-benzoimidazole-4-carboxylic acid and 124.0 mg (1.21 mmol) piperidin-4-ol. The title compound was obtained as its formiate. Subsequent transformation to the corresponding acetate gave a white amorphous solid.

Yield: 538 mg MS (ES$^+$): m/e=611, chloro pattern.

Example 92

7-[5-(5-Chloro-thiophen-2-yl)-isoxazol-3-ylmethyl]-1,3-dimethyl-2,6-dioxo-2,3,6,7-tetrahydro-1H-purine-8-carboxylic acid (1-isopropyl-piperidin-4-yl)-amide (i) 1,3-Dimethyl-2,6-dioxo-2,3,6,7-tetrahydro-1H-purine-8-carboxylic acid 5.00 g (24.0 mmol) 8-Hydroxymethyl-1,3-dimethyl-3,7-dihydro-purine-2,6-dione were suspended in 15 mL water. 16.8 mL (33.6 mmol) of a 2 N NaOH-solution were added. The resulting mixture was cooled to 5° C. At that temperature a solution of 5.05 g (32.2 mmol) KMnO$_4$ in 86 mL water was added. After stirring at room temperature for 4 h the reaction mixture was filtered over Celite. After addition of activated carbon the filtrate was again filtered over Celite. The filtrate was concentrated to a volume of 200 mL and 5 mL of conc. HCl-solution were added. After standing at 4° C. for 16 h the crystaline product was filtered off, washed twice with cold water and acetone and dried under reduced pressure at 40° C.

Yield: 5.18 g MS (ES$^+$): m/e=225.

(ii) 1,3-Dimethyl-2,6-dioxo-2,3,6,7-tetrahydro-1H-purine-8-carboxylic acid (1-isopropyl-piperidin-4-yl)-amide 100 mg (0.45 mmol) 1,3-Dimethyl-2,6-dioxo-2,3,6,7-tetrahydro-1H-purine-8-carboxylic acid were dissolved in 5 mL DMF. Subsequently 227 µl (1.35 mmol) DIPEA and 186.5 mg (0.495 mmol) HATU were added. After 1 h 105.6 mg (0.495 mmol) 1-isopropyl-piperidine-4-ylamine-dihydrochloride and 227 µl (1.35 mmol) DIPEA were added and the resulting mixture was stirred at room temperature for 4 h. The reaction mixture was concentrated and purified by preparative RP-HPLC (CH$_3$CN/H$_2$O gradient+0.05% formic acid) to give 1,3-dimethyl-2,6-dioxo-2,3,6,7-tetrahydro-1H-purine-8-carboxylic acid (1-isopropyl-piperidin-4-yl)-amide as its formiate.

(iii) 7-[5-(5-Chloro-thiophen-2-yl)-isoxazol-3-ylmethyl]-1, 3-dimethyl-2,6-dioxo-2,3,6,7-tetrahydro-1H-purine-8-carboxylic acid (1-isopropyl-piperidin-4-yl)-amide 155 mg (0.45 mmol) 1,3-Dimethyl-2,6-dioxo-2,3,6,7-tetrahydro-1H-purine-8-carboxylic acid (1-isopropyl-piperidin-4-yl)- amide were dissolved in 5 mL DMF. Subsequently 184.4 mg (1.35 mmol) $K_2CO_3$ and 111.5 mg (0.405 mmol) 3-bromomethyl-5-(5-chloro-thiophen-2-yl)-isoxazole were added and the resulting mixture was stirred at 80° C. for 1 h. The mixture was concentrated and purified by preparative RP-HPLC ($CH_3CN/H_2O$ gradient+0.05% formic acid) to give 7-[5-(5-Chloro-thiophen-2-yl)-isoxazol-3-ylmethyl]-1,3-dimethyl-2,6-dioxo-2,3,6,7-tetrahydro-1H-purine-8-carboxylic acid (1-isopropyl-piperidin-4-yl)-amide. The corresponding dihydrochloride was obtained by treatment of the product with a 0.1 M HCl-solution and following lyophilization.

Yield: 55 mg MS ($ES^+$): m/e=546, chloro pattern.

Example 93 a) 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid methyl ester b) 3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid methyl ester (i) (1-Cyclopropyl-piperidin-4-yl)-carbamic acid tert-butyl ester To a solution of 14.0 g (0.0699 mol) piperidin-4-yl-carbamic acid tert-butyl ester in 500 mL abs. MeOH 250 g of dried molecular sieves 3 Å were added. Under argon 39.9 mL (0.699 mol) acetic acid and 52.5 mL (0.262 mol) (1-ethoxy-cyclopropoxy)-trimethyl-silane were added. Finally 314.5 mL (0.3145 mol) of a 1 M $NaCNBH_3$-solution in THF were added dropwise. After 20 min at room temperature the reaction mixture was stirred for 6 h at 60° C. The mixture was filtered over "Celite". The filtrate was concentrated under reduced pressure. The resulting residue was taken up in 700 mL ethyl acetate and washed with 250 mL of a 1 M NaOH-solution. The aqueous layer was extracted with 300 mL ethyl acetate. The combined organic layers were washed with brine, dried over anhydrous $MgSO_4$ and concentrated under vacuo to give crude (1-cyclopropyl-piperidin-4-yl)-carbamic acid tert-butyl ester as a colorless solid.

Yield: 23.0 g MS ($ES^+$): m/e=241.

(ii) 1-Cyclopropyl-piperidin-4-ylamine dihydrochloride 23.0 g of above described crude (1-cyclopropyl-piperidin-4-yl)-carbamic acid tert-butyl ester were dissolved in 350 mL TFA and stirred for 45 minutes at room temperature. The reaction mixture was concentrated under reduced pressure and the resulting residue was dissolved in water. After addition of 23.1 mL of a conc. HCl-solution the mixture was lyophilized to yield a white amorphous solid. That solid was suspended in 300 mL ethyl acetate and treated for 45 minutes under ultrasonic conditions. That procedure was repeated twice. Finally, the filtered crystalline solid was dried at 45° C. under reduced pressure.

Yield: 15.9 g MS ($ES^+$): m/e=141.

(iii) 2-Trichloromethyl-1H-benzoimidazole-5-carboxylic acid methyl ester

To a solution of 10.0 g (0.060 mol) 3,4-diaminobenzoic acid methyl ester in 260 mL acetic acid 10.47 mL (0.084 mol) 2,2,2-trichloro-acetimidic acid methyl ester were added. After stirring for 2 h at room temperature the acetic acid was evaporated. The residue was dissolved in $CH_2Cl_2$, washed with brine, dried over $MgSO_4$ and concentrated under reduced pressure to give crude 2-Trichloromethyl-1H-benzoimidazole-5-carboxylic acid methyl ester as a brown rubbery material.

Yield: 20.5 g MS ($ES^+$): m/e=293, chloro pattern.

(iv) 2-(1-Cyclopropyl-piperidin-4-ylcarbamoyl)-1H-benzoimidazole-5-carboxylic acid methyl ester To a mixture of 7.53 g (35.3 mmol) 1-cyclopropyl-piperidin-4-ylamine-dihydrochloride and 32.39 g (0.386 mol) $NaHCO_3$ in 1300 mL THF and 370 mL water was added a solution of 11.79 g (32.1 mmol) 2-trichloromethyl-1H-benzoimidazole-5-carboxylic acid methyl ester in 360 mL THF. The reaction mixture was stirred vigorously for 2 h at room temperature. The THF was evaporated. The precipitate was filtered off and treated twice with approx. 300 mL of a saturated $NaHCO_3$-solution under ultrasonic conditions. After filtration the resulting solid was washed twice with 150 mL water and dried under vacuo at 45° C. to give pure 2-(1-cyclopropyl-piperidin-4-ylcarbamoyl)-1H-benzoimidazole-5-carboxylic methyl ester in form of a light brown crystalline material. Yield: 9.9 g MS ($ES^+$): m/e=343.

(v) 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid methyl ester 17.3 g (50.52 mmol) 2-(1-Cyclopropyl-piperidin-4-ylcarbamoyl)-1H-benzoimidazole-5-carboxylic acid methyl ester were dissolved in 800 mL DMF. Subsequently 10.47 g (75.8 mmol) $K_2CO_3$ and 14.84 g (50.52 mmol) methanesulfonic acid 5-(5-chloro-thiophen-2-yl)-isoxazol-3-ylmethyl ester were added and the resulting mixture was stirred for 2 h at 80° C. The mixture was concentrated under reduced pressure. The residue was suspended in 800 mL ethyl acetate. The next day the resulting precipitate was filtered off and washed with 100 mL ethyl acetate to give 3-[5-(5-chloro-thiophen-2-yl)-isoxazol-3-ylmethyl]-2-(1-cyclopropyl-piperidin-4-ylcarbamoyl)-3H-benzoimidazole-5-carboxylic acid methyl ester. The filtrate was concentrated to a volume of approx. 100 mL. Again the formed precipitate was filtered off. That procedure was repeated once again. The remaining filtrate was concentrated under reduced pressure and finally purified by flash-chromatography on silica gel using ethyl acetate as eluent. The product containing fractions were concentrated under vacuo to give pure (>98%) 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid methyl ester as a light brown crystalline solid.

Yield: 7.9 g MS ($ES^+$): m/e=540, chloro pattern.

(vi) 3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid methyl ester 1.0 g of crude 3-[5-(5-chloro-thiophen-2-yl)-isoxazol-3-ylmethyl]-2-(1-cyclopropyl-piperidin-4-ylcarbamoyl)-3H-benzoimidazole-5-carboxylic acid methyl ester was recrystallized from ethyl acetate.

Yield: 500 mg MS ($ES^+$): m/e=540, chloro pattern.

Example 94

1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid 7.84 g (14.52 mmol) 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid methyl ester were dissolved in 400 mL MEOH. 72.59 mL (72.59 mmol) of a 1 M aqueous LiOH-solution were added and the resulting mixture was stirred for 7 h at 60° C. The solution was concentrated to a volume of approx. 200 mL and acidified by the addition of a 4 M aqueous HCl-solution until pH≈1 was reached. After 30 minutes the resulting precipitate was filtered off and washed several times with cold MeOH. Recrystallization from MEOH gave pure 1-[5-(5-chloro-thiophen-2-yl)-isoxazol-3-ylmethyl]-2-(1-cyclopropyl-piperidin-4-ylcarbamoyl)-1H-benzoimidazole-5-carboxylic acid in form of a colorless, crystalline solid. The title compound was obtained as its monohydrochloride.

Yield: 7.3 g MS (ES$^+$): m/e=526, chloro pattern.

4.0 g (7.11 mmol) of the above described product were transformed into its sodium salt by suspension in 10 mL water, addition of 100.15 mL of a 0.2 M aqueous NaOH-solution and following extraction with 100 mL n-butanol (2×). The combined butanol layers were reextracted with 20 mL water (3×) and co-distilled with 200 mL water (3×). The resulting solution was lyophilized to give the title compound as its sodium salt in form of a white amorphous material.

Yield: 3.49 g

1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid was also prepared by a selective synthesis:

(i) C-[5-(5-Chloro-thiophen-2-yl)-isoxazol-3-yl]-methylamine 1.00 g (3.59 mmol) 3-Bromomethyl-5-(5-chloro-thiophen-2-yl)-isoxazole and 503.3 mg (3.59 mmol) urotropin were dissolved in 40 mL EtOH. The reaction mixture was stirred at room temperature for 16 h. The next day 3 mL of a conc. HCl-solution were added and the resulting mixture was refluxed for 45 minutes. After cooling the precipitate was filtered off and washed with water. The white crystalline material was dried under reduced pressure at 40° C.

Yield: 806 mg (ii) 4-{[5-(5-Chloro-thiophen-2-yl)-isoxazol-3-ylmethyl]-amino}-3-nitro-benzoic acid methyl ester To a solution of 634.4 mg (3.19 mmol) 4-Fluoro-3-nitro-benzoic acid methyl ester in 12 mL DMF were added 800.0 mg (3.19 mmol) C-[5-(5-Chloro-thiophen-2-yl)-isoxazol-3-yl]-methylamine and 0.88 mL (6.37 mmol) triethylamine. The reaction mixture was stirred at room temperature for 16 h. 12 mL water was added. The precipitate was filtered off and washed with water. The yellow crystalline material was dried under reduced pressure at 40° C.

Yield: 1.03 g MS (ES$^+$): m/e=394, chloro pattern.

(iii) 3-Amino-4-{[5-(5-chloro-thiophen-2-yl)-isoxazol-3-ylmethyl]-amino}-benzoic acid methyl ester 97.1 mg (0.41 mmol) NiCl$_2$.6H$_2$O were dissolved in 10 mL MeOH and treated under ultrasonic conditions. 46.4 mg (1.24 mmol) NaBH$_4$ were added. After 15 minutes a solution of 214.0 mg (0.54 mmol) 4-{[5-(5-Chloro-thiophen-2-yl)-isoxazol-3-ylmethyl]-amino}-3-nitro-benzoic acid methyl ester in 20 mL CH$_2$Cl$_2$ was added. After further 15 minutes 55.6 mg (1.48 mmol) NaBH$_4$ were added in three portions. The reaction mixture was treated under ultrasonic conditions for 2 h. Addition of NaBH$_4$ (55.6 mg each time) and treatment under ultrasonic conditions had to be repeated three times to achieve complete conversion. The reaction mixture was filtered over "Celite" and the filtrate was concentrated under reduced pressure. The residue was suspended in 30 mL MeOH. After filtration the filtrate was concentrated under vacuo and the residue was taken up in 100 mL CH$_2$Cl$_2$. The organic layer was washed four times with water, dried over anhydrous MgSO$_4$ and concentrated under reduced pressure to afford crude 3-Amino-4-{[5-(5-chloro-thiophen-2-yl)-isoxazol-3-ylmethyl]-amino}-benzoic acid methyl ester as a brown oil.

Yield: 83 mg MS (ES$^+$): m/e=364, chloro pattern.

(iv) 1-[5-(5-Chloro-thiophen-2-yl)-isoxazol-3-ylmethyl]-2-trichloromethyl-1H-benzoimidazole-5-carboxylic acid methyl ester 36.0 mg (0.098 mmol) 3-Amino-4-{[5-(5-chloro-thiophen-2-yl)-isoxazol-3-ylmethyl]-amino}-benzoic acid methyl ester were dissolved in 3 mL acetic acid. 17.4 µl (0.14 mmol) 2,2,2-trichloro-acetimidic acid methyl ester were added and the resulting mixture was stirred at room temperature for 3 h. The reaction mixture was concentrated under reduced pressure and the residue was co-distilled twice with 15 mL toluene to give crude 1-[5-(5-Chloro-thiophen-2-yl)-isoxazol-3-ylmethyl]-2-trichloromethyl-1H-benzoimidazole-5-carboxylic acid methyl ester as a brown solid. Yield: 49 mg MS (ES$^+$): m/e=491, chloro pattern.

(v) 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid 21.0 mg (0.098 mmol) (1-Cyclopropyl-piperidin-4-ylamine-dihydrochloride were dissolved in 3 mL CH$_3$CN and 3 mL water. 82.3 mg (0.98 mmol, 10 equiv.) NaHCO$_3$ were added. Finally, a solution of 48.1 mg (0.098 mmol) 1-[5-(5-Chloro-thiophen-2-yl)-isoxazol-3-ylmethyl]-2-trichloromethyl-1H-benzoimidazole-5-carboxylic acid methyl ester in 2 mL CH$_3$CN was added and the resulting mixture was stirred vigorously for 3 h under reflux. The mixture was concentrated under reduced pressure. The residue was purified by preparative RP-HPLC (CH$_3$CN/H$_2$O gradient+0.05% formic acid) to give pure 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid in form of a colorless amorphous solid.

Yield: 26 mg (50%) MS (ES$^+$): m/e=526, chloro pattern.

(Under the described conditions the methyl ester was hydrolyzed simultaneously)

Example 95

3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid 3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid was prepared by a procedure according to example 94 starting from 250.0 mg (0.46 mmol) 3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid methyl ester. The title compound was isolated as its monohydrochloride in form of a colorless crystalline material.

Yield: 135 mg MS (ES$^+$): m/e=526, chloro pattern.

Example 96 a) 1-[5-(5-Chloro-thiophen-2-yl)-isoxazol-3-ylmethyl]-2-(1-cyclopropyl-piperidin-4-ylcarbamoyl)-1H-benzoimidazole-4-carboxylic acid b) 3-[5-(5-Chloro-thiophen-2-yl)-isoxazol-3-ylmethyl]-2-(1-cyclopropyl-piperidin-4-ylcarbamoyl)-3H-benzoimidazole-4-carboxylic acid (i) 2-(1-Cyclopropyl-piperidin-4-ylcarbamoyl)-1H-benzoimidazole-4-carboxylic acid methyl ester 2-(1-Cyclopropyl-piperidin-4-ylcarbamoyl)-1H-benzoimidazole-4-carboxylic acid methyl ester was prepared by a procedure according to example 93 (iv) starting from 1.62 g (5.52 mmol) 2-trichloromethyl-1H-benzoimidazole-4-carboxylic acid methyl ester and 1.29 g (6.07 mmol) 1-cyclopropyl-piperidin-4-ylamine dihydrochloride.

Yield: 1.62 g MS (ES+): m/e=343.

(ii) a) 1-[5-(5-Chloro-thiophen-2-yl)-isoxazol-3-ylmethyl]-2-(1-cyclopropyl-piperidin-4-ylcarbamoyl)-1H-benzoimidazole-4-carboxylic acid b) 3-[5-(5-Chloro-thiophen-2-yl)-isoxazol-3-ylmethyl]-2-(1-cyclopropyl-piperidin-4-ylcarbamoyl)-3H-benzoimidazole-4-carboxylic acid 1-[5-(5-Chloro-thiophen-2-yl)-isoxazol-3-ylmethyl]-2-(1-cyclopropyl-piperidin-4-ylcarbamoyl)-1H-benzoimidazole-4-carboxylic acid and 3-[5-(5-Chloro-thiophen-2-yl)-isoxazol-3-ylmethyl]-2-(1-cyclopropyl-piperidin-4-ylcarbamoyl)-3H-benzoimidazole-4-carboxylic acid were prepared by a procedure according to example 81 starting from 248.0 mg (0.72 mmol) 2-(1-cyclopropyl-piperidin-4-ylcarbamoyl)-1H-benzoimidazole-4-carboxylic acid methyl ester and 221.9 mg (0.79 mmol) 3-bromomethyl-5-(5-chloro-thiophen-2-yl)-isoxazole. Hydrolysis of the resulting esters and purification by preparative RP-HPLC ($CH_3CN/H_2O$ gradient+0.05% formic acid) gave the title compounds as their formiates in form of white amorphous solids. The corresponding hydrochlorides were obtained by treatment of both products with a 0.1 M HCl-solution and following lyophilization. Yield of 1-[5-(5-chloro-thiophen-2-yl)-isoxazol-3-ylmethyl]-2-(1-cyclopropyl-piperidin-4-ylcarbamoyl)-1H-benzoimidazole-4-carboxylic acid: 119 mg MS (ES+): m/e=526, chloro pattern.

Yield of 3-[5-(5-Chloro-thiophen-2-yl)-isoxazol-3-ylmethyl]-2-(1-cyclopropyl-piperidin-4-ylcarbamoyl)-3H-benzoimidazole-4-carboxylic acid: 39 mg MS (ES+): m/e=526, chloro pattern.

Example 97

1-[(5-Chloro-pyridin-2-ylcarbamoyl)-methyl]-2-(1-cyclopropyl-piperidin-4-ylcarbamoyl)-1H-benzoimidazole-4-carboxylic acid methyl ester 1-[(5-Chloro-pyridin-2-ylcarbamoyl)-methyl]-2-(1-cyclopropyl-piperidin-4-ylcarbamoyl)-1H-benzoimidazole-4-carboxylic acid methyl ester was prepared by a procedure according to example 15 starting from 1.40 g (4.09 mmol) 2-(1-cyclopropyl-piperidin-4-ylcarbamoyl)-1H-benzoimidazole-4-carboxylic acid methyl ester and 1.02 g (4.09 mmol) 2-bromo-N-(5-chloro-pyridin-2-yl)-acetamide.

Yield: 1.90 g MS (ES+): m/e=511, chloro pattern.

Example 98

1-[(5-Chloro-pyridin-2-ylcarbamoyl)-methyl]-2-(1-cyclopropyl-piperidin-4-ylcarbamoyl)-1H-benzoimidazole-4-carboxylic acid 1-[(5-Chloro-pyridin-2-ylcarbamoyl)-methyl]-2-(1-cyclopropyl-piperidin-4-ylcarbamoyl)-1H-benzoimidazole-4-carboxylic acid was prepared by a procedure according to example 16 starting from 1.89 g (3.70 mmol) 1-[(5-chloro-pyridin-2-ylcarbamoyl)-methyl]-2-(1-cyclopropyl-piperidin-4-ylcarbamoyl)-1H-benzoimidazole-4-carboxylic acid methyl ester.

Yield: 1.90 g MS (ES+): m/e=497, chloro pattern.

Example 99

1-[(5-Chloro-pyridin-2-ylcarbamoyl)-methyl]-2-(1-cyclopropyl-piperidin-4-ylcarbamoyl)-1H-benzoimidazole-4-carboxylic acid cyclopropylmethyl ester 1-[(5-Chloro-pyridin-2-ylcarbamoyl)-methyl]-2-(1-cyclopropyl-piperidin-4-ylcarbamoyl)-1H-benzoimidazole-4-carboxylic acid cyclopropylmethyl ester was prepared by a procedure according to example 69 starting from 589.0 mg (1.19 mmol) 1-[(5-chloro-pyridin-2-ylcarbamoyl)-methyl]-2-(1-cyclopropyl-piperidin-4-ylcarbamoyl)-1H-benzoimidazole-4-carboxylic acid and 1.92 mL (23.8 mmol) cyclopropyl-methanol.

Yield: 362 mg MS (ES+): m/e=551, chloro pattern.

Example 100 a) 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid b) 3-[5-(5-Chloro-thiophen-2-yl)-isoxazol-3-ylmethyl]-2-(1-isopropyl-piperidin-4-ylcarbamoyl)-3H-thieno[3,4-d]imidazole-4-carboxylic acid (i) 2-Trichloromethyl-3H-thieno[3,4-d]imidazole-6-carboxylic acid methyl ester To a solution of 2.00 g (11.6 mmol) 3,4-diamino-thiophene-2-carboxylic acid methyl ester in 50 mL acetic acid 2.06 mL (16.24 mmol) 2,2,2-trichloro-acetimidic acid methyl ester were added. After stirring for 2 h at 95° C. the mixture was concentrated and co-distilled twice with 100 mL toluene.

The residue was dried under vacuo to afford a brown rubbery material.

Yield: 4.2 g MS (ES+): m/e=300, chloro pattern.

(ii) 2-(1-Isopropyl-piperidin-4-ylcarbamoyl)-3H-thieno[3,4-d]imidazole-6-carboxylic acid methyl ester 2-(1-Isopropyl-piperidin-4-ylcarbamoyl)-3H-thieno[3,4-d]imidazole-6-carboxylic acid methyl ester was prepared by a procedure according to example 93 (iv) starting from 3.48 g (11.6 mmol) 2-trichloromethyl-3H-thieno[3,4-d]imidazole-6-carboxylic acid methyl ester and 2.50 g (11.6 mmol) 1-isopropyl-piperidin-4-ylamine-dihydrochloride.

Yield: 3.7 g MS (ES+): m/e=351.

(iii) a) 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid b) 3-[5-(5-Chloro-thiophen-2-yl)-isoxazol-3-ylmethyl]-2-(1-isopropyl-piperidin-4-ylcarbamoyl)-3H-thieno[3,4-d]imidazole-4-carboxylic acid 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid and 3-[5-(5-Chloro-thiophen-2-yl)-isoxazol-3-ylmethyl]-2-(1-isopropyl-piperidin-4-ylcarbamoyl)-3H-thieno[3,4-d]imidazole-4-carboxylic acid were prepared by a procedure according to example 81 starting from 500 mg (1.40 mmol) 2-(1-isopropyl-piperidin-4-ylcarbamoyl)-3H-thieno[3,4-d]imidazole-6-carboxylic acid methyl ester and 397.4 mg (1.40 mmol) 3-bromomethyl-5-(5-chloro-thiophen-2-yl)-isoxazole. Hydrolysis of the resulting esters and purification by preparative RP-HPLC ($CH_3CN/H_2O$ gradient+0.05% formic acid) gave the title compounds as their formiates in form of white amorphous solids. Structural assignment of both isomers was achieved by NOE-spectroscopy.

Yield of 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid: 113 mg MS (ES$^+$): m/e=534, chloro pattern.

Yield of 3-[5-(5-Chloro-thiophen-2-yl)-isoxazol-3-ylmethyl]-2-(1-isopropyl-piperidin-4-ylcarbamoyl)-3H-thieno[3,4-d]imidazole-4-carboxylic acid: 146 mg MS (ES$^+$): m/e=534, chloro pattern.

Example 101 a) 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid b) 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-4-carboxylic acid (i) 2-(1-Cyclopropyl-piperidin-4-ylcarbamoyl)-3H-thieno[3,4-d]imidazole-6-carboxylic acid methyl ester 2-(1-Cyclopropyl-piperidin-4-ylcarbamoyl)-3H-thieno[3,4-d]imidazole-6-carboxylic acid methyl ester was prepared by a procedure according to example 93 (iv) starting from 203.7 mg (0.68 mmol) 2-trichloromethyl-3H-thieno[3,4-d]imidazole-6-carboxylic acid methyl ester and 158.7 mg (0.75 mmol) 1-cyclopropyl-piperidin-4-ylamine-dihydrochloride.

Yield: 309 mg MS (ES$^+$): m/e=349.

(ii) a) 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid b) 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-4-carboxylic acid 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid and 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-4-carboxylic acid were prepared by a procedure according to example 81 starting from 236.0 mg (0.68 mmol) 2-(1-cyclopropyl-piperidin-4-ylcarbamoyl)-3H-thieno[3,4-d]imidazole-6-carboxylic acid methyl ester and 188.7 mg (0.68 mmol) 3-bromomethyl-5-(5-chloro-thiophen-2-yl)-isoxazole. Hydrolysis of the resulting esters and purification by preparative RP-HPLC (CH$_3$CN/H$_2$O gradient+0.05% formic acid) gave the title compounds as their formiates in form of white amorphous solids. Structural assignment of both isomers was achieved by NOE-spectroscopy.

Yield of 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid: 46 mg MS (ES$^+$): m/e=531, chloro pattern.

Yield of 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-4-carboxylic acid is 78 mg; MS (ES$^+$): m/e=531, chloro pattern.

Example 102

3-[5-(5-Chloro-thiophen-2-yl)-isoxazol-3-ylmethyl]-3H-thieno[3,4-d]imidazole-2,6-dicarboxylic acid 6-[(2-hydroxy-ethyl)-amide]2-[(1-isopropyl-piperidin-4-yl)-amide]

3-[5-(5-Chloro-thiophen-2-yl)-isoxazol-3-ylmethyl]-3H-thieno[3,4-d]imidazole-2,6-dicarboxylic acid 6-[(2-hydroxy-ethyl)-amide]2-[(1-isopropyl-piperidin-4-yl)-amide] was prepared by a procedure according to example 22 starting from 96 mg (0.18 mmol) 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid and 11.0 µl (0.18 mmol) 2-amino-ethanol. The title compound was obtained as its formiate in form of a white amorphous solid.

Yield: 55 mg MS (ES$^+$): m/e=577, chloro pattern.

Example 103 a) 3-[(5-Chloro-pyridin-2-ylcarbamoyl)-methyl]-2-(1-isopropyl-piperidin-4-ylcarbamoyl)-3H-thieno[3,4-d]imidazole-6-carboxylic acid b) 3-[(5-Chloro-pyridin-2-ylcarbamoyl)-methyl]-2-(1-isopropyl-piperidin-4-ylcarbamoyl)-3H-thieno[3,4-d]imidazole-4-carboxylic acid 3-[(5-Chloro-pyridin-2-ylcarbamoyl)-methyl]-2-(1-isopropyl-piperidin-4-ylcarbamoyl)-3H-thieno[3,4-d]imidazole-6-carboxylic acid and 3-[(5-Chloro-pyridin-2-ylcarbamoyl)-methyl]-2-(1-isopropyl-piperidin-4-ylcarbamoyl)-3H-thieno[3,4-d]imidazole-4-carboxylic acid were prepared by a procedure according to example 81 starting from 500 mg (1.40 mmol) 2-(1-isopropyl-piperidin-4-ylcarbamoyl)-3H-thieno[3,4-d]imidazole-6-carboxylic acid methyl ester and 356.0 mg (1.40 mmol) 2-bromo-N-(5-chloro-pyridin-2-yl)-acetamide. Hydrolysis of the resulting esters by treatment with BBr$_3$ according to example 16 and purification by preparative RP-HPLC (CH$_3$CN/H$_2$O gradient+0.05% formic acid) gave the title compounds as their formiates in form of white amorphous solids. Structural assignment of both isomers was achieved by NOE-spectroscopy.

Yield of 3-[(5-Chloro-pyridin-2-ylcarbamoyl)-methyl]-2-(1-isopropyl-piperidin-4-ylcarbamoyl)-3H-thieno[3,4-d]imidazole-6-carboxylic acid: 142 mg MS (ES$^+$): m/e=505, chloro pattern.

Yield of 3-[(5-Chloro-pyridin-2-ylcarbamoyl)-methyl]-2-(1-isopropyl-piperidin-4-ylcarbamoyl)-3H-thieno[3,4-d]imidazole-4-carboxylic acid: 58 mg MS (ES$^+$): m/e=505, chloro pattern.

Example 104

3-[(5-Chloro-pyridin-2-ylcarbamoyl)-methyl]-6-([1,4]oxazepane-4-carbonyl)-3H-thieno[3,4-d]imidazole-2-carboxylic acid (1-isopropyl-piperidin-4-yl)-amide 3-[(5-Chloro-pyridin-2-ylcarbamoyl)-methyl]-6-([1,4]oxazepane-4-carbonyl)-3H-thieno[3,4-d]imidazole-2-carboxylic acid (1-isopropyl-piperidin-4-yl)-amide was prepared by a procedure according to example 22 starting from 80 mg (0.158 mmol) 3-[(5-Chloro-pyridin-2-ylcarbamoyl)-methyl]-2-(1-isopropyl-piperidin-4-ylcarbamoyl)-3H-thieno[3,4-d]imidazole-6-carboxylic acid and 21.8 mg (0.158 mmol)

Example 105

3-[5-(5-Chloro-thiophen-2-yl)-isoxazol-3-ylmethyl]-
2-(1-isopropyl-piperidin-4-ylcarbamoyl)-6-(2,2,2-
trifluoro-ethoxy)-3H-thieno[3,4-d]imidazole-4-car-
boxylic acid methyl ester (i) 2-Trichloromethyl-6-(2,2,2-trifluoro-ethoxy)-3H-thieno [3,4-d]imidazole-4-carboxylic acid methyl ester 2-Trichloromethyl-6-(2,2,2-trifluoro-ethoxy)-3H-thieno [3,4-d]imidazole-4-carboxylic acid methyl ester was prepared by a procedure according to example 100 (i) from 500 mg (1.85 mmol) 3,4-diamino-5-(2,2,2-trifluoro-ethoxy)-thiophene-2-carboxylic acid methyl ester and 328.0 µl (2.59 mmol) 2,2,2-trichloro-acetimidic acid methyl ester.

Yield: 735 mg MS (ES$^+$): m/e=397, chloro pattern.

(ii) 2-(1-Isopropyl-piperidin-4-ylcarbamoyl)-6-(2,2,2-trifluoro-ethoxy)-3H-thieno[3,4-d]imidazole-4-carboxylic acid methyl ester 2-(1-Isopropyl-piperidin-4-ylcarbamoyl)-6-(2,2,2-trifluoro-ethoxy)-3H-thieno[3,4-d]imidazole-4-carboxylic acid methyl ester was prepared by a procedure according to example 93 (iv) starting from 735.0 mg (1.85 mmol) 2-trichloromethyl-6-(2,2,2-trifluoro-ethoxy)-3H-thieno[3,4-d]imidazole-4-carboxylic acid methyl ester and 397.8 mg (1.85 mmol) 1-isopropyl-piperidin-4-ylamine-dihydrochloride.

Yield: 71 mg MS (ES$^+$): m/e=449.

(iii) 3-[5-(5-Chloro-thiophen-2-yl)-isoxazol-3-ylmethyl]-2-(1-isopropyl-piperidin-4-ylcarbamoyl)-6-(2,2,2-trifluoro-ethoxy)-3H-thieno[3,4-d]imidazole-4-carboxylic acid methyl ester 3-[5-(5-Chloro-thiophen-2-yl)-isoxazol-3-ylmethyl]-2-(1-isopropyl-piperidin-4-ylcarbamoyl)-6-(2,2,2-trifluoro-ethoxy)-3H-thieno[3,4-d]imidazole-4-carboxylic acid methyl ester was prepared by a procedure according to example 81 starting from 68.0 mg (0.15 mmol) 2-(1-isopropyl-piperidin-4-ylcarbamoyl)-6-(2,2,2-trifluoro-ethoxy)-3H-thieno[3,4-d]imidazole-4-carboxylic acid methyl ester and 42.2 mg (0.15 mmol) 3-bromomethyl-5-(5-chloro-thiophen-2-yl)-isoxazole. Purification by preparative RP-HPLC (CH$_3$CN/H$_2$O gradient+0.05% formic acid) gave the title compound as its formiate in form of a white amorphous solid. Structural assignment was achieved by NOE-spectroscopy.

Yield: 19 mg MS (ES$^+$): m/e=646, chloro pattern.

Example 106 a) 1-[3-(5-Chloro-thiophen-2-yl)-isoxazol-5-ylmethyl]-2-(1-cyclopropyl-piperidin-4-ylcarbamoyl)-1H-benzoimidazole-5-carboxylic acid b) 3-[3-(5-Chloro-thiophen-2-yl)-isoxazol-5-ylmethyl]-2-(1-cyclopropyl-piperidin-4-ylcarbamoyl)-3H-benzoimidazole-5-carboxylic acid 1-[3-(5-Chloro-thiophen-2-yl)-isoxazol-5-ylmethyl]-2-(1-cyclopropyl-piperidin-4-ylcarbamoyl)-1H-benzoimidazole-5-carboxylic acid and 3-[3-(5-Chloro-thiophen-2-yl)-isoxazol-5-ylmethyl]-2-(1-cyclopropyl-piperidin-4-ylcarbamoyl)-3H-benzoimidazole-5-carboxylic acid were prepared by a procedure according to example 81 starting from 240 mg (0.70 mmol) 2-(1-Cyclopropyl-piperidin-4-ylcarbamoyl)-1H-benzoimidazole-5-carboxylic acid methyl ester and 201.3 mg (0.70 mmol) 5-bromomethyl-3-(5-chloro-thiophen-2-yl)-isoxazole. Hydrolysis of the resulting esters and purification by preparative RP-HPLC (CH$_3$CN/H$_2$O gradient+0.05% formic acid) gave the title compounds as their formiates in form of white amorphous solids. Structural assignment of both isomers was achieved by NOE-spectroscopy.

Yield of 1-[3-(5-Chloro-thiophen-2-yl)-isoxazol-5-ylmethyl]-2-(1-cyclopropyl-piperidin-4-ylcarbamoyl)-1H-benzoimidazole-5-carboxylic acid: 93 mg MS (ES$^+$): m/e=526, chloro pattern.

Yield of 3-[3-(5-Chloro-thiophen-2-yl)-isoxazol-5-ylmethyl]-2-(1-cyclopropyl-piperidin-4-yl-carbamoyl)-3H-benzoimidazole-5-carboxylic acid is 60 mg; MS (ES$^+$): m/e=526, chloro pattern.

Example 107 a) 1-[5-(5-Chloro-thiophen-2-yl)-[1,3,4]thiadiazol-2-ylmethyl]-2-(1-cyclopropyl-piperidin-4-ylcarbamoyl)-1H-benzoimidazole-5-carboxylic acid b) 3-[5-(5-Chloro-thiophen-2-yl)-[1,3,4]thiadiazol-2-ylmethyl]-2-(1-cyclopropyl-piperidin-4-ylcarbamoyl)-3H-benzoimidazole-5-carboxylic acid 1-[5-(5-Chloro-thiophen-2-yl)-[1,3,4]thiadiazol-2-ylmethyl]-2-(1-cyclopropyl-piperidin-4-ylcarbamoyl)-1H-benzoimidazole-5-carboxylic acid and 3-[5-(5-Chloro-thiophen-2-yl)-[1,3,4]thiadiazol-2-ylmethyl]-2-(1-cyclopropyl-piperidin-4-ylcarbamoyl)-3H-benzoimidazole-5-carboxylic acid were prepared by a procedure according to example 81 starting from 200 mg (0.58 mmol) 2-(1-Cyclopropyl-piperidin-4-ylcarbamoyl)-1H-benzoimidazole-5-carboxylic acid methyl ester and 181.8 mg (0.58 mmol) 2-bromomethyl-5-(5-chloro-thiophen-2-yl)-[1,3,4]thiadiazole. Hydrolysis of the resulting esters and purification by preparative RP-HPLC (CH$_3$CN/H$_2$O gradient+0.05% formic acid) gave the title compounds as their formiates in form of white amorphous solids. Structural assignment of both isomers was achieved by NOE-spectroscopy.

Yield of 1-[5-(5-Chloro-thiophen-2-yl)-[1,3,4]thiadiazol-2-ylmethyl]-2-(1-cyclopropyl-piperidin-4-yl-carbamoyl)-1H-benzoimidazole-5-carboxylic acid is 18 mg; MS (ES$^+$): m/e=543, chloro pattern.

Yield of 3-[5-(5-Chloro-thiophen-2-yl)-[1,3,4]thiadiazol-2-ylmethyl]-2-(1-cyclopropyl-piperidin-4-yl-carbamoyl)-3H-benzoimidazole-5-carboxylic acid is 6 mg; MS (ES$^+$): m/e=543, chloro pattern.

Example 108

1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide (i) 1-(2-Methoxy-ethoxy)-2,3-dinitro-benzene 1.50 g (8.15 mmol) 2,3-Dinitro-phenol were dissolved in 75 mL acetone. Subsequently 1.69 g (12.22 mol) K$_2$CO$_3$, 135.3 mg KI (0.81 mmol) and 0.93 mL (9.77 mmol) 1-bromo-2-methoxy-ethane were added. The reaction mixture was refluxed for 8 h. After that time further 1.69 g (12.22 mol)

(Previous content: homomorpholine-hydrochloride. The title compound was obtained as its formiate in form of a white amorphous solid. Yield: 70 mg MS (ES$^+$): m/e=588, chloro pattern.)

K₂CO₃, 400 mg KI and 0.93 mL (9.77 mmol) 1-bromo-2-methoxy-ethane were added. The resulting mixture was refluxed for 16 h and then concentrated under reduced pressure. The residue was dissolved in warm ethyl acetate and purified by flash-chromatography on silica gel using an ethyl acetate/heptane-mixture as eluent to afford 1-(2-Methoxy-ethoxy)-2,3-dinitro-benzene as an orange crystalline material. Yield: 1.35 g MS (ES$^+$): m/e=243.

(ii) 3-(2-Methoxy-ethoxy)-benzene-1,2-diamine 1.80 g (7.43 mmol) 1-(2-Methoxy-ethoxy)-2,3-dinitro-benzene were dissolved in 250 mL MeOH. The solution was evacuated and rinsed with argon several times. 250 mg palladium on charcoal (10%) were added and again the mixture was evacuated and rinsed with argon several times. Finally argon was exchanged by hydrogen (balloon filled with hydrogen) and the mixture was stirred for 2 h at room temperature. The reaction mixture was filtered over "Celite" and the filter residue was washed with 100 mL MeOH. The filtrate was concentrated under vacuo to give pure 3-(2-Methoxy-ethoxy)-benzene-1,2-diamine as a brown oil. Yield: 1.33 g MS (ES$^+$): m/e=183.

(iii) 4-(2-Methoxy-ethoxy)-2-trichloromethyl-1H-benzoimidazole 1.33 g (7.30 mmol) 3-(2-Methoxy-ethoxy)-benzene-1,2-diamine were dissolved in 35 mL acetic acid. 1.25 mL (10.22 mmol) 2,2,2-trichloro-acetimidic acid methyl ester were added and the resulting mixture was stirred for 2 h at room temperature. The mixture was concentrated under reduced pressure and the residue was co-distilled twice with 20 mL toluene to give crude 4-(2-Methoxy-ethoxy)-2-trichloromethyl-1H-benzoimidazole as a brown solid.

Yield: 2.25 g MS (ES$^+$): m/e=309, chloro pattern.

(iv) 4-(2-Methoxy-ethoxy)-1H-benzoimidazole-2-carboxylic acid (1-isopropyl-piperidin-4-yl)-amide 4-(2-Methoxy-ethoxy)-1H-benzoimidazole-2-carboxylic acid (1-isopropyl-piperidin-4-yl)-amide was prepared by a procedure according to example 5 (ii) starting from 1.91 g (6.18 mmol) 4-(2-Methoxy-ethoxy)-2-trichloromethyl-1H-benzoimidazole and 1.46 g (6.79 mmol) 1-isopropyl-piperidin-4-ylamine-dihydrochloride. Final purification was achieved by flash-chromatography on silica gel using an ethyl acetate/MeOH-mixture as eluent. Yield: 660 mg MS (ES$^+$): m/e=361.

(v) 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide was prepared by a procedure according to example 5 (iii) starting from 650.0 mg (1.80 mmol) 4-(2-Methoxy-ethoxy)-1H-benzoimidazole-2-carboxylic acid (1-isopropyl-piperidin-4-yl)-amide and 449.9 mg (1.80 mmol) 2-bromo-N-(5-chloro-pyridin-2-yl)-acetamide. Purification by flash-chromatography on silica gel using a ethyl acetate/heptane-mixture as eluent gave a 9:1 mixture of 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide and 1-[(5-Chloro-pyridin-2-ylcarbamoyl)-methyl]-7-(2-methoxy-ethoxy)-1H-benzoimidazole-2-carboxylic acid (1-isopropyl-piperidin-4-yl)-amide. These isomers were separated by NP-HPLC using a chiral stationary phase and a mixture of heptane, ethanol, methanol and diethyl amine as solvent. The title compound was transformed into its acetate affording a colorless amorphous material.

Yield of 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide is 500 mg; MS (ES$^+$): m/e=529, chloro pattern.

Example 109

1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide (i) 1-(2-Ethoxy-ethoxy)-2,3-dinitro-benzene 1-(2-Ethoxy-ethoxy)-2,3-dinitro-benzene was prepared by a procedure according to example 108 (i) starting from 500 mg (2.72 mmol) 2,3-dinitro-phenol and 0.72 mL (6.52 mmol) 1-chloro-2-ethoxy-ethane. Yield: 450 mg MS (ES$^+$): m/e=257.

(ii) 3-(2-Ethoxy-ethoxy)-benzene-1,2-diamine 3-(2-Ethoxy-ethoxy)-benzene-1,2-diamine was prepared by a procedure according to example 108 (ii) starting from 450 mg (1.76 mmol) 1-(2-Ethoxy-ethoxy)-2,3-dinitro-benzene.

Yield: 345 mg MS (ES$^+$): m/e=197.

(iii) 4-(2-Ethoxy-ethoxy)-2-trichloromethyl-1H-benzoimidazole 4-(2-Ethoxy-ethoxy)-2-trichloromethyl-1H-benzoimidazole was prepared by a procedure according to example 108 (iii) starting from 345 mg (1.76 mmol) 3-(2-Ethoxy-ethoxy)-benzene-1,2-diamine and 0.30 mL (2.46 mmol) 2,2,2-trichloro-acetimidic acid methyl ester.

Yield: 568 mg MS (ES$^+$): m/e=323, chloro pattern.

(iv) 4-(2-Ethoxy-ethoxy)-1H-benzoimidazole-2-carboxylic acid (1-isopropyl-piperidin-4-yl)-amide 4-(2-Ethoxy-ethoxy)-1H-benzoimidazole-2-carboxylic acid (1-isopropyl-piperidin-4-yl)-amide was prepared by a procedure according to example 108 (iv) starting from 569.6 mg (1.76 mmol) 4-(2-Ethoxy-ethoxy)-2-trichloromethyl-1H-benzoimidazole and 454.4 mg (2.11 mmol) 1-isopropyl-piperidin-4-ylamine-dihydrochloride. Yield: 540 mg MS (ES$^+$): m/e=375.

(v) 1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide 1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide was prepared by a procedure according to example 108 (v) starting from 540.0 mg (1.44 mmol) 4-(2-Ethoxy-ethoxy)-1H-benzoimidazole-2-carboxylic acid (1-isopropyl-piperidin-4-yl)-amide and 359.8 mg (1.44 mmol) 2-bromo-N-(5-chloro-pyridin-2-yl)-acetamide. The title compound was transformed into its acetate affording a colorless amorphous material.

Yield of 1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide: 201 mg MS (ES$^+$): m/e=543, chloro pattern.

Example 110

1-[(5-Chloro-pyridin-2-ylcarbamoyl)-methyl]-4-(2-hydroxy-ethoxy)-1H-benzoimidazole-2-carboxylic acid (1-isopropyl-piperidin-4-yl)-amide (i) tert-Butyl-[2-(2,3-dinitro-phenoxy)-ethoxy]-dimethyl-silane tert-Butyl-[2-(2,3-dinitro-phenoxy)-ethoxy]-dimethyl-silane was prepared by a procedure according to example 108 (i) starting from 500 mg (2.72 mmol) 2,3-dinitro-phenol and 1.00 g (4.18 mmol) (2-Bromo-ethoxy)-tert-butyl-dimethyl-silane.

Yield: 610 mg MS (ES$^+$): m/e=343.

(ii) 3-[2-(tert-Butyl-dimethyl-silanyloxy)-ethoxy]-benzene-1,2-diamine

3-[2-(tert-Butyl-dimethyl-silanyloxy)-ethoxy]-benzene-1,2-diamine was prepared by a procedure according to example 108 (ii) starting from 610 mg (1.78 mmol) tert-Butyl-[2-(2,3-dinitro-phenoxy)-ethoxy]-dimethyl-silane. Yield: 503 mg MS (ES$^+$): m/e=283.

(iii) 4-[2-(tert-Butyl-dimethyl-silanyloxy)-ethoxy]-2-trichloromethyl-1H-benzoimidazole 4-[2-(tert-Butyl-dimethyl-silanyloxy)-ethoxy]-2-trichloromethyl-1H-benzoimidazole was prepared by a procedure according to example 108 (iii) starting from 503 mg (1.78 mmol) 3-[2-(tert-Butyl-dimethyl-silanyloxy)-ethoxy]-benzene-1,2-diamine and 0.31 mL (2.49 mmol) 2,2,2-trichloro-acetimidic acid methyl ester. Yield: 680 mg MS (ES$^+$): m/e=409, chloro pattern.

(iv) 4-[2-(tert-Butyl-dimethyl-silanyloxy)-ethoxy]-1H-benzoimidazole-2-carboxylic acid (1-isopropyl-piperidin-4-yl)-amide 4-[2-(tert-Butyl-dimethyl-silanyloxy)-ethoxy]-1H-benzoimidazole-2-carboxylic acid (1-isopropyl-piperidin-4-yl)-amide was prepared by a procedure according to example 108 (iv) starting from 680.0 mg (1.66 mmol) 4-[2-(tert-Butyl-dimethyl-silanyloxy)-ethoxy]-2-trichloromethyl-1H-benzoimidazole and 428.4 mg (1.99 mmol) 1-isopropyl-piperidin-4-ylamine-dihydrochloride.

Yield: 670 mg MS (ES$^+$): m/e=461.

(v) 4-[2-(tert-Butyl-dimethyl-silanyloxy)-ethoxy]-1-[(5-chloro-pyridin-2-ylcarbamoyl)-methyl]-1H-benzoimidazole-2-carboxylic acid (1-isopropyl-piperidin-4-yl)-amide 4-[2-(tert-Butyl-dimethyl-silanyloxy)-ethoxy]-1-[(5-chloro-pyridin-2-ylcarbamoyl)-methyl]-1H-benzoimidazole-2-carboxylic acid (1-isopropyl-piperidin-4-yl)-amide was prepared by a procedure according to example 108 (v) starting from 670.0 mg (1.45 mmol) 4-[2-(tert-Butyl-dimethyl-silanyloxy)-ethoxy]-1H-benzoimidazole-2-carboxylic acid (1-isopropyl-piperidin-4-yl)-amide and 362.8 mg (1.45 mmol) 2-bromo-N-(5-chloro-pyridin-2-yl)-acetamide. Final purification by flash-chromatography on silica gel using ethyl acetate as eluent gave the title compound as a brown oil.

Yield: 350 mg MS (ES$^+$): m/e=629, chloro pattern.

(vi) 1-[(5-Chloro-pyridin-2-ylcarbamoyl)-methyl]-4-(2-hydroxy-ethoxy)-1H-benzoimidazole-2-carboxylic acid (1-isopropyl-piperidin-4-yl)-amide 250 mg (0.40 mmol) 4-[2-(tert-Butyl-dimethyl-silanyloxy)-ethoxy]-1-[(5-chloro-pyridin-2-ylcarbamoyl)-methyl]-1H-benzoimidazole-2-carboxylic acid (1-isopropyl-piperidin-4-yl)-amide were dissolved in 15 mL THF. 435 µl of a 1 M TBAF-solution in THF and 26 µl acetic acid were added. The resulting mixture was stirred for 48 h at room temperature. The reaction mixture was concentrated under reduced pressure. The residue was taken up in 50 mL CH$_2$Cl$_2$ and washed once with a saturated NaHCO$_3$-solution and five times with water. The organic layer was dried over anhydrous MgSO$_4$ and concentrated under vacuo. Final purification by preparative RP-HPLC (CH$_3$CN/H$_2$O gradient+0.05% formic acid) gave pure 1-[(5-Chloro-pyridin-2-ylcarbamoyl)-methyl]-4-(2-hydroxy-ethoxy)-1H-benzoimidazole-2-carboxylic acid (1-isopropyl-piperidin-4-yl)-amide as its formiate in form of a colorless amorphous material. The title compound was transformed into its acetate. Yield: 132 mg MS (ES$^+$): m/e=515, chloro pattern.

Example 111

1-[(5-Chloro-pyridin-2-ylcarbamoyl)-methyl]-2-[2-fluoro-4-(pyrrolidine-1-carbonyl)-phenylcarbamoyl]-1H-benzoimidazole-4-carboxylic acid methyl ester (i) (3-Fluoro-4-nitro-phenyl)-pyrrolidin-1-yl-methanone 1.00 g (5.40 mmol) 3-Fluoro-4-nitro-benzoic acid were suspended in 55 mL benzene. 1 mL Thionyl chloride and 7 drops DMF were added. The resulting mixture was stirred of 5 h at 70° C. and then concentrated under reduced pressure. The residue was dissolved in 40 mL CH$_2$Cl$_2$. Subsequently 0.75 mL (5.40 mmol) triethylamine and 0.45 mL (5.40 mmol) pyrrolidine were added and the resulting solution was stirred for 1 h at room temperature. The mixture was diluted with CH$_2$Cl$_2$ and washed subsequently with a 0.1 N HCl-solution, with a saturated NaHCO$_3$-solution and with brine. The organic layer was dried over anhydrous MgSO$_4$ and concentrated under vacuo to give crude (3-Fluoro-4-nitro-phenyl)-pyrrolidin-1-yl-methanone as an orange solid.

Yield: 1.35 g MS (ES$^+$): m/e=239.

(ii) (4-Amino-3-fluoro-phenyl)-pyrrolidin-1-yl-methanone 515.0 mg (2.16 mmol) (3-Fluoro-4-nitro-phenyl)-pyrrolidin-1-yl-methanone were dissolved in 20 mL MeOH. The solution was evacuated and rinsed with argon several times. 150 mg palladium on charcoal (10%) were added and again the mixture was evacuated and rinsed with argon several times. Finally argon was exchanged by hydrogen (balloon filled with hydrogen) and the mixture was stirred for 2 h at room temperature. The reaction mixture was filtered over "Celite" and the filter residue was washed with 30 mL MeOH. The filtrate was concentrated under vacuo to give pure (4-Amino-3-fluoro-phenyl)-pyrrolidin-1-yl-methanone as a colorless oil.

Yield: 448 mg MS (ES$^+$): m/e=209.

(iii) 2-[2-Fluoro-4-(pyrrolidine-1-carbonyl)-phenylcarbamoyl]-1H-benzoimidazole-4-carboxylic acid methyl ester 59.0 mg (0.28 mmol) (4-Amino-3-fluoro-phenyl)-pyrrolidin-1-yl-methanone were dissolved in 6 mL THF and 3 mL water. 238.0 mg (2.83 mmol) NaHCO$_3$ were added. Finally 75.6 mg (0.26 mmol) 2-Trichloromethyl-1H-benzoimidazole-4-carboxylic acid methyl ester were added and the resulting mixture was stirred vigorously for 3 h at room temperature. The mixture was diluted with CH$_2$Cl$_2$ and washed with a saturated NaHCO$_3$-solution and with brine. The organic layer was dried over anhydrous MgSO$_4$ and concentrated under reduced pressure. Final purification by preparative RP-HPLC (CH$_3$CN/H$_2$O gradient+0.05% formic acid) gave pure 2-[2-Fluoro-4-(pyrrolidine-1-carbonyl)-phenylcarbamoyl]-1H-benzoimidazole-4-carboxylic acid methyl ester in form of a colorless amorphous solid. Yield: 69 mg MS (ES$^+$): m/e=411.

(iv) 1-[(5-Chloro-pyridin-2-ylcarbamoyl)-methyl]-2-[2-fluoro-4-(pyrrolidine-1-carbonyl)-phenylcarbamoyl]-1H-benzoimidazole-4-carboxylic acid methyl ester 1-[(5-Chloro-pyridin-2-ylcarbamoyl)-methyl]-2-[2-fluoro-4-(pyrrolidine-1-carbonyl)-phenylcarbamoyl]-1H-benzoimidazole-4-carboxylic acid methyl ester was prepared by a procedure according to example 36 (ii) starting from 40.0 mg (0.10 mmol) 2-[2-Fluoro-4-(pyrrolidine-1-carbonyl)-phenylcarbamoyl]-1H-benzoimidazole-4-carboxylic acid methyl ester and 29.2 mg (0.12 mmol) 2-bromo-N-(5-chloro-pyridin-2-yl)-acetamide. Final purification by preparative RP-HPLC (CH$_3$CN/H$_2$O gradient+0.05% formic acid) gave pure 1-[(5-Chloro-pyridin-2-ylcarbamoyl)-methyl]-2-[2-fluoro-4-(pyrrolidine-1-carbonyl)-phenylcarbamoyl]-1H-benzoimidazole-4-carboxylic acid methyl ester as a colorless amorphous solid.

Yield: 13 mg MS (ES$^+$): m/e=579, chloro pattern.

Example 112 a) 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid b) 3-[5-(5-Chloro-thiophen-2-yl)-isoxazol-3-ylmethyl]-2-(1-cyclopropyl-piperidin-4-ylcarbamoyl)-7-methyl-3H-benzoimidazole-5-carboxylic acid (i) 4-Amino-3-methyl-5-nitro-benzoic acid 4-Amino-3-methyl-5-nitro-benzoic acid was prepared as described by Bolhofer et al. in U.S. Pat. No. 3,691,166.

(ii) 4-Amino-3-methyl-5-nitro-benzoic acid methyl ester 500 mg (2.50 mmol) 4-Amino-3-methyl-5-nitro-benzoic acid were dissolved in a mixture of 8 mL CH$_2$Cl$_2$ and 2 mL MeOH. At 0° C. 1.3 mL of a 2 M trimethylsilyldiazomethane-solution in hexane were added. After 1 h at 0° C. the reaction mixture was allowed to warm to room temperature. The next day further 1.3 mL of a 2 M trimethylsilyldiazomethane-solution in hexane were added. After stirring for 3 h at room temperature a solution of 0.22 mL acetic acid in 1.8 mL CH$_2$Cl$_2$ was added dropwise to destroy excess trimethylsilyl-diazomethane. The reaction mixture was concentrated under reduced pressure. The residue was digerated with heptane and the crystalline material was filtered off to give pure 4-Amino-3-methyl-5-nitro-benzoic acid methyl ester. Yield: 496 mg MS (ES$^+$): m/e=211.

(iii) 3,4-Diamino-5-methyl-benzoic acid methyl ester 3,4-Diamino-5-methyl-benzoic acid methyl ester was prepared by a procedure according to example 11 (i) starting from 495.0 mg (2.36 mmol) 4-Amino-3-methyl-5-nitro-benzoic acid methyl ester.

Yield: 404 mg MS (ES$^+$): m/e=181.

(iv) 7-Methyl-2-trichloromethyl-1H-benzoimidazole-5-carboxylic acid methyl ester 7-Methyl-2-trichloromethyl-1H-benzoimidazole-5-carboxylic acid methyl ester was prepared by a procedure according to example 5 (i) starting from 404.0 mg (2.20 mmol) 3,4-Diamino-5-methyl-benzoic acid methyl ester and 0.39 mL (3.08 mmol) 2,2,2-trichloro-acetimidic acid methyl ester.

Yield: 869 mg MS (ES$^+$): m/e=307, chloro pattern.

(v) 2-(1-Cyclopropyl-piperidin-4-ylcarbamoyl)-7-methyl-1H-benzoimidazole-5-carboxylic acid methyl ester 2-(1-Cyclopropyl-piperidin-4-ylcarbamoyl)-7-methyl-1H-benzoimidazole-5-carboxylic acid methyl ester was prepared by a procedure according to example 93 (iv) starting from 685.0 mg (2.20 mmol) 7-Methyl-2-trichloromethyl-1H-benzoimidazole-5-carboxylic acid methyl ester and 474.4 mg (2.20 mmol) 1-cyclopropyl-piperidin-4-ylamine -dihydro-chloride.

Yield: 730 mg MS (ES$^+$): m/e=357.

(vi) a) 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid b) 3-[5-(5-Chloro-thiophen-2-yl)-isoxazol-3-ylmethyl]-2-(1-cyclopropyl-piperidin-4-ylcarbamoyl)-7-methyl-3H-benzoimidazole-5-carboxylic acid 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid and 3-[5-(5-Chloro-thiophen-2-yl)-isoxazol-3-ylmethyl]-2-(1-cyclopropyl-piperidin-4-ylcarbamoyl)-7-methyl-3H-benzoimidazole-5-carboxylic acid were prepared by a procedure according to example 81 starting from 200 mg (0.56 mmol) 2-(1-Cyclopropyl-piperidin-4-ylcarbamoyl)-7-methyl-1H-benzoimidazole-5-carboxylic acid methyl ester and 164.8 mg (0.56 mmol) methanesulfonic acid 5-(5-chloro-thiophen-2-yl)-isoxazol-3-ylmethyl ester. Hydrolysis of the resulting esters by treatment with LiOH and purification by preparative RP-HPLC (CH$_3$CN/H$_2$O gradient+0.05% formic acid) gave the title compounds as their formiates in form of white amorphous solids. Structural assignment of both isomers was achieved by NOE-spectroscopy.

Yield of 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid is 7 mg; MS (ES$^+$): m/e=540, chloro pattern.

Yield of 3-[5-(5-Chloro-thiophen-2-yl)-isoxazol-3-ylmethyl]-2-(1-cyclopropyl-piperidin-4-ylcarbamoyl)-7-methyl-3H-benzoimidazole-5-carboxylic acid is 111 mg; MS (ES$^+$): m/e=540, chloro pattern.

Example 113

1-[5-(5-Chloro-thiophen-2-yl)-isoxazol-3-ylmethyl]-5-fluoro-2-(1-isopropyl-piperidin-4-ylcarbamoyl)-1H-benzoimidazole-4-carboxylic acid (i) 2,3-Diamino-6-fluoro-benzoic acid ethyl ester 2,3-Diamino-6-fluoro-benzoic acid ethyl ester was prepared by a procedure according to example 11 (i) starting from 200.0 mg (0.88 mmol) 2-Amino-6-fluoro-3-nitro-benzoic acid ethyl ester.

Yield: 157 mg MS (ES$^+$): m/e=229.

(ii) 5-Fluoro-2-trichloromethyl-1H-benzoimidazole-4-carboxylic acid ethyl ester

5-Fluoro-2-trichloromethyl-1H-benzoimidazole-4-carboxylic acid ethyl ester was prepared by a procedure according to example 5 (i) starting from 150.0 mg (0.76 mmol) 2,3-Diamino-6-fluoro-benzoic acid ethyl ester and 133 μl (1.06 mmol) 2,2,2-trichloro-acetimidic acid methyl ester.

Yield: 280 mg MS (ES$^+$): m/e=325, chloro pattern.

(iii) 5-Fluoro-2-(1-isopropyl-piperidin-4-ylcarbamoyl)-1H-benzoimidazole-4-carboxylic acid ethyl ester 5-Fluoro-2-(1-isopropyl-piperidin-4-ylcarbamoyl)-1H-benzoimidazole-4-carboxylic acid ethyl ester was prepared by a procedure according to example 93 (iv) starting from 240.0 mg (0.74 mmol) 5-Fluoro-2-trichloromethyl-1H-benzoimidazole-4-carboxylic acid ethyl ester and 158.6 mg (0.74 mmol) 1-Isopropyl-piperidin-4-ylamine-dihydrochloride.

Yield: 232 mg MS (ES$^+$): m/e=377.

(iv) 1-[5-(5-Chloro-thiophen-2-yl)-isoxazol-3-ylmethyl]-5-fluoro-2-(1-isopropyl-piperidin-4-ylcarbamoyl)-1H-benzoimidazole-4-carboxylic acid 1-[5-(5-Chloro-thiophen-2-yl)-isoxazol-3-ylmethyl]-5-fluoro-2-(1-isopropyl-piperidin-4-ylcarbamoyl)-1H-benzoimidazole-4-carboxylic acid was prepared by a procedure according to example 81 starting from 230 mg (0.60 mmol) 5-Fluoro-2-(1-isopropyl-piperidin-4-ylcarbamoyl)-1H-benzoimidazole-4-carboxylic acid ethyl ester and 179.5 mg (0.60 mmol) methanesulfonic acid 5-(5-chloro-thiophen-2-yl)-isoxazol-3-ylmethyl ester. Hydrolysis of the resulting ethyl ester by treatment with LiOH and purification by preparative RP-HPLC (CH$_3$CN/H$_2$O gradient+0.05% formic acid) gave the title compound as its formiate in form of a white amorphous solid.

Yield: 87 mg MS (ES$^+$): m/e=546, chloro pattern.

Example 114

1-[5-(5-Chloro-thiophen-2-yl)-isoxazol-3-ylmethyl]-2-(1-isopropyl-piperidin-4-ylcarbamoyl)-5-(2,2,2-trifluoro-ethoxy)-1H-benzoimidazole-4-carboxylic acid (i) 2-Amino-3-nitro-6-(2,2,2-trifluoro-ethoxy)-benzoic acid ethyl ester 420 mg NaH (60% suspension in oil) were added to a solution of 2.16 mL (29.8 mmol) 2,2,2-trifluoro-ethanol in 5 mL THF. When the gas evolution ceased, 1.0 g (4.38 mmol) 2-Amino-6-fluoro-3-nitro-benzoic acid ethyl ester was added. The resulting mixture was stirred at 0° C. for 30 minutes and at room temperature for further 30 minutes. To this mixture were added 2 mL of a 6 M aqueous HCl-solution, and most of the solvent was removed under reduced pressure. The residue was mixed with 20 mL water and the resulting solid was collected and washed with water and then hexane. The obtained yellow crystalline material was dried under reduced pressure at 35° C. Yield: 1.22 g.

(ii) 2,3-Diamino-6-(2,2,2-trifluoro-ethoxy)-benzoic acid ethyl ester 2,3-Diamino-6-(2,2,2-trifluoro-ethoxy)-benzoic acid ethyl ester was prepared by a procedure according to example 11 (i) starting from 1.22 g (3.96 mmol) 2-Amino-3-nitro-6-(2,2,2-trifluoro-ethoxy)-benzoic acid ethyl ester. Yield: 1.07 g MS (ES$^+$): m/e=279.

(iii) 2-Trichloromethyl-5-(2,2,2-trifluoro-ethoxy)-1H-benzoimidazole-4-carboxylic acid ethyl ester 2-Trichloromethyl-5-(2,2,2-trifluoro-ethoxy)-1H-benzoimidazole-4-carboxylic acid ethyl ester was prepared by a procedure according to example 5 (i) starting from 200.0 mg (0.72 mmol) 2,3-Diamino-6-fluoro-benzoic acid ethyl ester and 128 µl (1.01 mmol) 2,2,2-trichloro-acetimidic acid methyl ester.

Yield: 340 mg MS (ES$^+$): m/e=405, chloro pattern.

(iv) 2-(1-Isopropyl-piperidin-4-ylcarbamoyl)-5-(2,2,2-trifluoro-ethoxy)-1H-benzoimidazole-4-carboxylic acid ethyl ester 2-(1-Isopropyl-piperidin-4-ylcarbamoyl)-5-(2,2,2-trifluoro-ethoxy)-1H-benzoimidazole-4-carboxylic acid ethyl ester was prepared by a procedure according to example 93 (iv) starting from 290.0 mg (0.72 mmol) 2-Trichloromethyl-5-(2,2,2-trifluoro-ethoxy)-1H-benzoimidazole-4-carboxylic acid ethyl ester and 153.8 mg (0.72 mmol) 1-Isopropyl-piperidin-4-ylamine-dihydrochloride. Yield: 299 mg MS (ES$^+$): m/e=457.

(v) 1-[5-(5-Chloro-thiophen-2-yl)-isoxazol-3-ylmethyl]-2-(1-isopropyl-piperidin-4-ylcarbamoyl)-5-(2,2,2-trifluoro-ethoxy)-1H-benzoimidazole-4-carboxylic acid 1-[5-(5-Chloro-thiophen-2-yl)-isoxazol-3-ylmethyl]-2-(1-isopropyl-piperidin-4-ylcarbamoyl)-5-(2,2,2-trifluoro-ethoxy)-1H-benzoimidazole-4-carboxylic acid was prepared by a procedure according to example 81 starting from 299.0 mg (0.66 mmol) 2-(1-Isopropyl-piperidin-4-ylcarbamoyl)-5-(2,2,2-trifluoro-ethoxy)-1H-benzoimidazole-4-carboxylic acid ethyl ester and 192.4 mg (0.66 mmol) methanesulfonic acid 5-(5-chloro-thiophen-2-yl)-isoxazol-3-ylmethyl ester. Hydrolysis of the resulting ethyl ester by treatment with LiOH in MeOH and purification by preparative RP-HPLC (CH$_3$CN/H$_2$O gradient+0.05% formic acid) gave the title compound as its formiate in form of a white amorphous solid.

Yield: 90 mg MS (ES$^+$): m/e=626, chloro pattern.

Example 115

1-[5-(5-Chloro-thiophen-2-yl)-isoxazol-3-ylmethyl]-4-(3-hydroxy-azetidine-1-carbonyl)-5-(2,2,2-trifluoro-ethoxy)-1H-benzoimidazole-2-carboxylic acid (1-isopropyl-piperidin-4-yl)-amide 1-[5-(5-Chloro-thiophen-2-yl)-isoxazol-3-ylmethyl]-4-(3-hydroxy-azetidine-1-carbonyl)-5-(2,2,2-trifluoro-ethoxy)-1H-benzoimidazole-2-carboxylic acid (1-isopropyl-piperidin-4-yl)-amide was prepared by a procedure according to example 22 starting from 50.0 mg (0.08 mmol) 1-[5-(5-Chloro-thiophen-2-yl)-isoxazol-3-ylmethyl]-2-(1-isopropyl-piperidin-4-ylcarbamoyl)-5-(2,2,2-trifluoro-ethoxy)-1H-benzoimidazole-4-carboxylic acid and 8.7 mg (0.12 mmol) azetidin-3-ol. The title compound was obtained as its formiate in form of a white amorphous solid.

Yield: 18 mg MS (ES$^+$): m/e=681, chloro pattern.

Example 116

1-[5-(5-Chloro-thiophen-2-yl)-isoxazol-3-ylmethyl]-2-(1-cyclopropyl-piperidin-4-ylcarbamoyl)-7-fluoro-1H-benzoimidazole-5-carboxylic acid The title compound can be prepared by adapting the methodology described above.

Example 117

7-Chloro-1-[5-(5-chloro-thiophen-2-yl)-isoxazol-3-ylmethyl]-2-(1-cyclopropyl-piperidin-4-ylcarbamoyl)-1H-benzoimidazole-5-carboxylic acid The title compound can be prepared by adapting the methodology described above.

Example 118

1-[5-(5-Chloro-thiophen-2-yl)-isoxazol-3-ylmethyl]-7-cyclopropyl-2-(1-cyclopropyl-piperidin-4-ylcarbamoyl)-1H-benzoimidazole-5-carboxylic acid The title compound can be prepared by adapting the methodology described above.

Example 119

1-[5-(5-Chloro-thiophen-2-yl)-isoxazol-3-ylmethyl]-2-(1-cyclopropyl-piperidin-4-ylcarbamoyl)-7-ethyl-1H-benzoimidazole-5-carboxylic acid The title compound can be prepared by adapting the methodology described above.

Example 120

1-[3-(5-Chloro-thiophen-2-yl)-isoxazol-5-ylmethyl]-2-(1-cyclopropyl-piperidin-4-ylcarbamoyl)-7-methyl-1H-benzoimidazole-5-carboxylic acid The title compound can be prepared by adapting the methodology described above.

Example 121

1-[3-(5-Chloro-thiophen-2-yl)-isoxazol-5-ylmethyl]-2-(1-cyclopropyl-piperidin-4-ylcarbamoyl)-7-fluoro-1H-benzoimidazole-5-carboxylic acid The title compound can be prepared by adapting the methodology described above.

Example 122

7-Chloro-1-[3-(5-chloro-thiophen-2yl)-isoxazol-5-ylmethyl]-2-(1-cyclopropyl-piperidin-4-ylcarbamoyl)-1H-benzoimidazole-5-carboxylic acid The title compound can be prepared by adapting the methodology described above.

Example 123

1-[3-(5-Chloro-thiophen-2-yl)-isoxazol-5-ylmethyl]-7-cyclopropyl-2-(1-cyclopropyl-piperidin-4-ylcarbamoyl)-1H-benzoimidazole-5-carboxylic acid The title compound can be prepared by adapting the methodology described above.

Example 124

1-[3-(5-Chloro-thiophen-2-yl)-isoxazol-5-ylmethyl]-2-(1-cyclopropyl-piperidin-4-ylcarbamoyl)-7-ethyl-1H-benzoimidazole-5-carboxylic acid The title compound can be prepared by adapting the methodology described above.

Example 125

1-[5-(5-Chloro-thiophen-2-yl)-[1,3,4]thiadiazol-2-ylmethyl]-2-(1-cyclopropyl-piperidin-4-ylcarbamoyl)-7-methyl-1H-benzoimidazole-5-carboxylic acid The title compound can be prepared by adapting the methodology described above.

Example 126

1-[5-(5-Chloro-thiophen-2-yl)-[1,3,4]thiadiazol-2-ylmethyl]-2-(1-cyclopropyl-piperidin-4-ylcarbamoyl)-7-fluoro-1H-benzoimidazole-5-carboxylic acid The title compound can be prepared by adapting the methodology described above.

Example 127

7-Chloro-1-[5-(5-chloro-thiophen-2-yl)-[1,3,4]thiadiazol-2-ylmethyl]-2-(1-cyclopropyl-piperidin-4-ylcarbamoyl)-1H-benzoimidazole-5-carboxylic acid The title compound can be prepared by adapting the methodology described above.

Example 128

1-[5-(5-Chloro-thiophen-2-yl)-[1,3,4]thiadiazol-2-ylmethyl]-2-(1-cyclopropyl-piperidin-4-ylcarbamoyl)-7-ethyl-1H-benzoimidazole-5-carboxylic acid The title compound can be prepared by adapting the methodology described above.

Example 129

1-[5-(5-Chloro-thiophen-2-yl)-[1,3,4]thiadiazol-2-ylmethyl]-7-cyclopropyl-2-(1-cyclopropyl-piperidin-4-ylcarbamoyl)-1H-benzoimidazole-5-carboxylic acid The title compound can be prepared by adapting the methodology described above.

Example 130

1-(6-Chloro-benzo[b]thiophen-2-ylmethyl)-2-(1-cyclopropyl-piperidin-4-ylcarbamoyl)-7-methyl-1H-benzoimidazole-5-carboxylic acid The title compound can be prepared by adapting the methodology described above.

Example 131

7-Chloro-1-(6-chloro-benzo[b]thiophen-2-ylmethyl)-2-(1-cyclopropyl-piperidin-4-ylcarbamoyl)-1H-benzoimidazole-5-carboxylic acid The title compound can be prepared by adapting the methodology described above.

Example 132

(1-(6-Chloro-benzo[b]thiophen-2-ylmethyl)-2-(1-cyclopropyl-piperidin-4-ylcarbamoyl)-7-fluoro-1H-benzoimidazole-5-carboxylic acid The title compound can be prepared by adapting the methodology described above.

Example 133

1-(6-Chloro-benzo[b]thiophen-2-ylmethyl)-7-cyclopropyl-2-(1-cyclopropyl-piperidin-4-ylcarbamoyl)-1H-benzoimidazole-5-carboxylic acid The title compound can be prepared by adapting the methodology described above.

Example 134

1-(6-Chloro-benzo[b]thiophen-2-ylmethyl)-2-(1-cyclopropyl-piperidin-4-ylcarbamoyl)-7-ethyl-1H-benzoimidazole-5-carboxylic acid The title compound can be prepared by adapting the methodology described above.

Example 135

1-[5-(5-Chloro-thiophen-2-yl)-isoxazol-3-ylmethyl]-2-(1-cyclopropyl-piperidin-4-ylcarbamoyl)-7-methyl-1H-benzoimidazole-4-carboxylic acid The title compound can be prepared by adapting the methodology described above.

Example 136

(1-[5-(5-Chloro-thiophen-2-yl)-isoxazol-3-ylmethyl]-2-(1-cyclopropyl-piperidin-4-ylcarbamoyl)-7-fluoro-1H-benzoimidazole-4-carboxylic acid The title compound can be prepared by adapting the methodology described above.

Example 137

7-Chloro-1-[5-(5-chloro-thiophen-2-yl)-isoxazol-3-ylmethyl]-2-(1-cyclopropyl-piperidin-4-ylcarbamoyl)-1H-benzoimidazole-4-carboxylic acid The title compound can be prepared by adapting the methodology described above.

Example 138

1-[3-(5-Chloro-thiophen-2-yl)-isoxazol-5-ylmethyl]-2-(1-cyclopropyl-piperidin-4-ylcarbamoyl)-7-methyl-1H-benzoimidazole-4-carboxylic acid The title compound can be prepared by adapting the methodology described above.

Example 139

1-[3-(5-Chloro-thiophen-2-yl)-isoxazol-5-ylmethyl]-2-(1-cyclopropyl-piperidin-4-ylcarbamoyl)-7-fluoro-1H-benzoimidazole-4-carboxylic acid The title compound can be prepared by adapting the methodology described above.

Example 140

7-Chloro-1-[3-(5-chloro-thiophen-2-yl)-isoxazol-5-ylmethyl]-2-(1-cyclopropyl-piperidin-4-ylcarbamoyl)-1H-benzoimidazole-4-carboxylic acid The title compound can be prepared by adapting the methodology described above.

Example 141

1-[5-(5-Chloro-thiophen-2-yl)-[1,3,4]thiadiazol-2-ylmethyl]-2-(1-cyclopropyl-piperidin-4-ylcarbamoyl)-7-methyl-1H-benzoimidazole-4-carboxylic acid The title compound can be prepared by adapting the methodology described above.

Example 142

7-Chloro-1-[5-(5-chloro-thiophen-2-yl)-[1,3,4]thiadiazol-2-ylmethyl]-2-(1-cyclopropyl-piperidin-4-ylcarbamoyl)-1H-benzoimidazole-4-carboxylic acid The title compound can be prepared by adapting the methodology described above.

Example 143

1-[5-(5-Chloro-thiophen-2-yl)-[1,3,4]thiadiazol-2-ylmethyl]-2-(1-cyclopropyl-piperidin-4-ylcarbamoyl)-7-fluoro-1H-benzoimidazole-4-carboxylic acid The title compound can be prepared by adapting the methodology described above.

Example 144

1-[5-(5-Chloro-thiophen-2-yl)-isoxazol-3-ylmethyl]-5-fluoro-4-(3-hydroxy-azetidine-1-carbonyl)-1H-benzoimidazole-2-carboxylic acid (1-cyclopropyl-piperidin-4-yl)-amide The title compound can be prepared by adapting the methodology described above.

Example 145

1-[5-(5-Chloro-thiophen-2-yl)-isoxazol-3-ylmethyl]-5-fluoro-1H-benzoimidazole-2,4-dicarboxylic acid 4-[(2-hydroxy-ethyl)-amide]2-[(1-isopropyl-piperidin-4-yl)-amide]

The title compound can be prepared by adapting the methodology described above.

Example 146

1-[5-(5-Chloro-thiophen-2-yl)-isoxazol-3-ylmethyl]-5-(2,2,2-trifluoro-ethoxy)-1H-benzoimidazole-2,4-dicarboxylic acid 4-amide 2-[(1-isopropyl-piperidin-4-yl)-amide]

The title compound can be prepared by adapting the methodology described above.

Example 147

1-[5-(5-Chloro-thiophen-2-yl)-isoxazol-3-ylmethyl]-5-(2,2,2-trifluoro-ethoxy)-1H-benzoimidazole-2,4-dicarboxylic acid 4-[(2-hydroxy-ethyl)-amide]2-[(1-isopropyl-piperidin-4-yl)-amide]

The title compound can be prepared by adapting the methodology described above.

Example 148

1-[5-(5-Chloro-thiophen-2-yl)-isoxazol-3-ylmethyl]-5-(2,2,2-trifluoro-ethoxy)-1H-benzoimidazole-2,4-dicarboxylic acid 4-dimethylamide 2-[(1-isopropyl-piperidin-4-yl)-amide]

The title compound can be prepared by adapting the methodology described above.

Example 149

1-[5-(5-Chloro-thiophen-2-yl)-isoxazol-3-ylmethyl]-5-(2,2,2-trifluoro-ethoxy)-1H-benzoimidazole-2,4-dicarboxylic acid 2-[(1-isopropyl-piperidin-4-yl)-amide]4-(methyl-propyl-amide)

The title compound can be prepared by adapting the methodology described above.

Example 150

1-[5-(5-Chloro-thiophen-2-yl)-isoxazol-3-ylmethyl]-5-fluoro-7-methyl-1H-benzoimidazole-2,4-dicarboxylic acid 4-[(2-hydroxy-ethyl)-methyl-amide]2-[(1-isopropyl-piperidin-4-yl)-amide]

The title compound can be prepared by adapting the methodology described above.

Example 151

(1-[5-(5-Chloro-thiophen-2-yl)-isoxazol-3-ylmethyl]-5-fluoro-4-(3-hydroxy-azetidine-1-carbonyl)-7-methyl-1H-benzoimidazole-2-carboxylic acid (1-isopropyl-piperidin-4-yl)-amide The title compound can be prepared by adapting the methodology described above.

Example 152

1-[5-(5-Chloro-thiophen-2-yl)-[1,3,4]thiadiazol-2-ylmethyl]-5-fluoro-7-methyl-1H-benzoimidazole-2,4-dicarboxylic acid 4-[(2-hydroxy-ethyl)-methyl-amide]2-[(1-isopropyl-piperidin-4-yl)-amide]

The title compound can be prepared by adapting the methodology described above.

Example 153

(1-[5-(5-Chloro-thiophen-2-yl)-[1,3,4]thiadiazol-2-ylmethyl]-5-fluoro-4-(3-hydroxy-azetidine-1-carbonyl)-7-methyl-1H-benzoimidazole-2-carboxylic acid (1-isopropyl-piperidin-4-yl)-amide The title compound can be prepared by adapting the methodology described above.

Example 154

1-[2-(4-Chloro-phenyl)-ethyl]-4-(2-hydroxy-ethoxy)-1H-benzoimidazole-2-carboxylic acid (1-isopropyl-piperidin-4-yl)-amide The title compound can be prepared by adapting the methodology described above.

Example 155

1-(6-Chloro-benzo[b]thiophen-2-ylmethyl)-4-(2-hydroxy-ethoxy)-1H-benzoimidazole-2-carboxylic acid (1-isopropyl-piperidin-4-yl)-amide The title compound can be prepared by adapting the methodology described above.

Example 156

1-[5-(5-Chloro-thiophen-2-yl)-isoxazol-3-ylmethyl]-4-(3-hydroxy-azetidine-1-carbonyl)-1H-thieno[3,4-d]imidazole-2-carboxylic acid (1-isopropyl-piperidin-4-yl)-amide The title compound can be prepared by adapting the methodology described above.

Example 157

5-Chloro-1H-benzoimidazole-2-carboxylic acid benzylamide

A solution of 120.0 mg (0.45 mmol) 5-chloro-2-trichloromethyl-1H-benzoimidazole in 2 mL tetrahydrofuran (THF) was added slowly to a mixture of 53.5 µl (0.49 mmol) benzylamine and 373.8 mg (4.45 mmol, 10 equiv.) NaHCO$_3$ in 8 mL THF and 4 mL water. The reaction mixture was stirred for 2 h at room temperature (20° C. to 25° C. in the following RT). The suspension was filtered and the filtrate was concentrated under reduced pressure. After purification by preparative RP-HPLC (CH$_3$CN/H$_2$O gradient and 0.05% formic acid) pure 5-Chloro-1H-benzoimidazole-2-carboxylic acid benzylamide was obtained as a white amorphous solid.

Yield: 84 mg MS (ES$^+$): m/e: 286, chloro pattern.

Example 158

2-(1-Isopropyl-piperidin-4-ylcarbamoyl)-1H-benzoimidazole-4-carboxylic acid methyl ester A solution of 3.99 g (13.6 mmol) 2-trichloromethyl-1H-benzoimidazole-4-carboxylic acid methyl ester in 40 mL THF was added slowly to a mixture of 2.9 g (13.6 mmol) 1-isopropyl-piperidin-4-ylamine-dihydrochloride and 13.7 g (0.163 mol, 12 equivalents) NaHCO$_3$ in 200 mL THF and 120 mL water. The reaction mixture was stirred for 2 h at RT. The THF was distilled off. The resulting aqueous suspension was diluted with 200 mL CH$_2$Cl$_2$ and extracted twice with 150 mL water. The organic layer was concentrated under reduced pressure and the resulting residue was purified by flash-chromatography on silica gel using an ethyl acetate/methanol-(4:1)-mixture as eluent. The title compound was obtained as a light brown crystalline material.

Yield: 3.20 g MS (ES$^+$): m/e: 345.

Example 159

2-(1-Cyclopropyl-piperidin-4-ylcarbamoyl)-1H-benzoimidazole-5-carboxylic acid methyl ester To a mixture of 7.53 g (35.3 mmol) 1-cyclopropyl-piperidin-4-ylamine dihydrochloride and 32.39 g (0.386 mol) NaHCO$_3$ in 1300 mL THF and 370 mL water a solution of 11.79 g (32.1 mmol) 2-trichloromethyl-1H-benzoimidazole-5-carboxylic acid methyl ester in 360 mL THF was added. The reaction mixture was stirred vigorously for 2 h at RT. The THF was evaporated. The precipitate was filtered off and treated twice with about 300 mL of a saturated NaHCO$_3$-solution under ultrasonic conditions. After filtration the resulting solid was washed twice with 150 mL water and dried under reduced pressure at 45° C. to give pure 2-(1-cyclopropyl-piperidin-4-ylcarbamoyl)-1H-benzoimidazole-5-carboxylic methyl ester in form of a light brown crystalline material.

Yield: 9.9 g (90%) MS (ES$^+$): m/e=343.

Example 160

5-Chloro-1H-benzoimidazole-2-carboxylic acid diisopropylamide

A solution of 500.0 mg (1.85 mmol) 5-Chloro-2-trichloromethyl-1H-benzoimidazole in 20 mL THF was added slowly to a mixture of 286 µl (2.04 mmol) diisopropyl-amine and 1.55 g (18.5 mmol, 10 equivalents) NaHCO$_3$ in 70 mL THF and 20 mL water. The reaction mixture was stirred for 2 h at RT. The organic solvent was evaporated. The formed crystalline material was filtered off and treated once with about 50 mL of a saturated NaHCO$_3$-solution under ultrasonic conditions. The crystalline residue was filtered off again and washed twice with 20 mL water. Drying under reduced pressure at 35° C. gave pure 5-Chloro-1H-benzoimidazole-2-carboxylic acid diisopropylamide in form of a light brown crystalline solid.

Yield: 321 mg MS (ES$^+$): m/e: 280, chloro pattern.

Example 161

(5-Chloro-1H-benzoimidazol-2-yl)-morpholin-4-yl-methanone (5-Chloro-1H-benzoimidazol-2-yl)-morpholin-4-yl-methanone was prepared by a procedure according to example 157 starting from 120.0 mg (0.45 mmol) 5-Chloro-2-trichloromethyl-1H-benzoimidazole and 42.6 µl (0.49 mmol) morpholine. The title compound was isolated as a colorless amorphous solid.

Yield: 95 mg (80%) MS (ES$^+$): m/e: 266, chloro pattern.

Example 162

5-Chloro-1H-benzoimidazole-2-carboxylic acid (4-methyl-piperazin-1-yl)-amide

5-Chloro-1H-benzoimidazole-2-carboxylic acid (4-methyl-piperazin-1-yl)-amide was prepared by a procedure according to example 157 starting from 120.0 mg (0.45 mmol) 5-Chloro-2-trichloromethyl-1H-benzoimidazole and 58.9 µl (0.49 mmol) 4-Methyl-piperazin-1-ylamine. The title compound was isolated as a colorless amorphous solid.

Yield: 89 mg MS (ES$^+$): m/e: 294, chloro pattern.

Example 163

5-Chloro-1H-benzoimidazole-2-carboxylic acid (4-cyano-phenyl)-amide

5-Chloro-1H-benzoimidazole-2-carboxylic acid (4-cyano-phenyl)-amide was prepared by a procedure according to example 160 starting from 500.0 mg (1.85 mmol) 5-Chloro-2-trichloromethyl-1H-benzoimidazole and 229.8 mg (1.95 mmol) 4-amino-benzonitrile. The title compound was isolated as a light brown crystalline solid.

Yield: 475 mg (86%) MS (ES$^+$): m/e: 297, chloro pattern.

Example 164

2-[4-(3-Oxo-morpholin-4-yl)-phenylcarbamoyl]-1H-benzoimidazole-4-carboxylic acid methyl ester 2-[4-(3-Oxo-morpholin-4-yl)-phenylcarbamoyl]-1H-benzoimidazole-4-carboxylic acid methyl ester was prepared by a procedure according to example 160 starting from 1.32 g (4.49 mmol) 2-trichloromethyl-1H-benzoimidazole-4-carboxylic acid methyl ester and 950.0 mg (4.94 mmol) 4-(4-Amino-phenyl)-morpholin-3-one. The title compound was isolated as a light brown crystalline solid.

Yield: 1.44 g (81%) MS (ES$^+$): m/e: 395.

Example 165

2-[2-Fluoro-4-(pyrrolidine-1-carbonyl)-phenylcarbamoyl]-1H-benzo-imidazole-4-carboxylic acid methyl ester 59.0 mg (0.28 mmol) (4-Amino-3-fluoro-phenyl)-pyrrolidin-1-yl-methanone was dissolved in 6 mL THF and 3 mL water. 238.0 mg (2.83 mmol) NaHCO$_3$ were added. Finally 75.6 mg (0.26 mmol) 2-Trichloromethyl-1H-benzoimidazole-4-carboxylic acid methyl ester were added and the resulting mixture was stirred vigorously for 3 h at RT. The mixture was diluted with 25 mL CH$_2$Cl$_2$ and washed with a saturated NaHCO$_3$-solution and with brine. The organic layer was dried over anhydrous MgSO$_4$ and concentrated under reduced pressure. After purification by preparative RP-HPLC (CH$_3$CN/H$_2$O gradient and 0.05% formic acid) pure 2-[2-Fluoro-4-(pyrrolidine-1-carbonyl)-phenylcarbamoyl]-1H-benzoimidazole-4-carboxylic acid methyl ester was obtained in form of a colorless amorphous solid.

Yield: 69 mg (65%) MS (ES$^+$): m/e=411.

Example 166

5-Chloro-1H-benzoimidazole-2-carboxylic acid isoquinolin-4-ylamide

5-Chloro-1H-benzoimidazole-2-carboxylic acid isoquinolin-4-ylamide was prepared by a procedure according to example 160 starting from 100.0 mg (0.37 mmol) 5-chloro-2-trichloromethyl-1H-benzoimidazole and 56.1 mg (0.39 mmol) isoquinolin-4-ylamine. The title compound was isolated as a light brown crystalline solid.

Yield: 113 mg (94%) MS (ES$^+$): m/e: 323, chloro pattern.

Example 167

2-[(5-Chloro-1H-benzoimidazole-2-carbonyl)-amino]-3-nitro-benzoic acid methyl ester 2-[(5-Chloro-1H-benzoimidazole-2-carbonyl)-amino]-3-nitro-benzoic acid methyl ester was prepared by a procedure according to example 160 starting from 200.0 mg (0.74 mmol) 5-chloro-2-trichloromethyl-1H-benzoimidazole and 152.6 mg (0.78 mmol) 2-amino-3-nitro-benzoic acid methyl ester. The title compound was isolated as a yellow crystalline solid.

Yield: 218 mg (79%)

Example 168

2-(1-Isopropyl-piperidin-4-ylcarbamoyl)-1H-thieno[3,4-d]imidazole-4-carboxylic acid methyl ester 2-(1-Isopropyl-piperidin-4-ylcarbamoyl)-1H-thieno[3,4-d]imidazole-4-carboxylic acid methyl ester was prepared by a procedure according to example 158 starting from 1.74 g (5.80 mmol) 2-trichloromethyl-3H-thieno[3,4-d]imidazole-6-carboxylic acid methyl ester and 1.25 g (5.80 mmol) 1-isopropyl-piperidin-4-ylamine-dihydrochloride. The title compound was isolated as a light brown crystalline solid. Yield: 1.75 g (86%) MS (ES$^+$): m/e: 351.

Example 169

1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid 21.0 mg (0.098 mmol) (1-Cyclopropyl-piperidin-4-ylamine-dihydrochloride were dissolved in 3 mL CH$_3$CN and 3 mL water. 82.3 mg (0.98 mmol, 10 equivalents) NaHCO$_3$ were added. Then, a solution of 48.1 mg (0.098 mmol) 1-[5-(5-chloro-thiophen-2-yl)-isoxazol-3-ylmethyl]-2-trichloromethyl-1H-benzoimidazole-5-carboxylic acid methyl ester in 2 mL CH$_3$CN was added and the resulting mixture was stirred vigorously for 3 h under reflux. The mixture was concentrated under reduced pressure. The residue was purified by preparative RP-HPLC (CH$_3$CN/H$_2$O gradient and 0.05% formic acid) to give pure 1-[5-(5-chloro-thiophen-2-yl)-isoxazol-3-ylmethyl]-2-(1-cyclopropyl-piperidin-4-yl-carbamoyl)-1H-benzoimidazole-5-carboxylic acid in form of a colorless amorphous solid. (Under these conditions the methyl ester was hydrolyzed simultaneously!)

Yield: 26 mg (50%) MS (ES$^+$): m/e=526, chloro pattern.

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i. e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formula I. For calculating the inhibition constant Ki, the IC50 value was corrected for competition with substrate using the formula $Ki = IC50/\{1+(\text{substrate concentration}/Km)\}$ wherein Km is the Michaelis-Menten constant (Chen and Prusoff, Biochem. Pharmacol. 22 (1973) 3099-3108; I. H. Segal, Enzyme Kinetics, 1975, John Wiley & Sons, New York, 100-125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN3) was used. The IC50 was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV9OOHDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM CaCl$_2$, 0.05% PEG 8000, pH 8.15). Following a 15 minutes preincubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki(FXa) [µM] |
|---|---|
| 1 | 0,0007 |
| 2 | 0,0031 |
| 3 | 0,0014 |
| 4 | 0,0592 |
| 5a | 0,0025 |
| 5b | 0,1750 |
| 6 | 0,0030 |
| 7 | 0,0165 |
| 9 | 0,0940 |
| 10 | 1,357 |

TABLE 1-continued

| Example | Ki(FXa) [µM] |
|---|---|
| 11a | 0,004 |
| 11b | 0,001 |
| 12 | 0,0030 |
| 13 | 0,2990 |
| 14 | 2,3900 |
| 15 | 0,0115 |
| 16 | 0,0110 |
| 17a | 0,0195 |
| 17b | 0,3710 |
| 18 | 0,0225 |
| 19 | 0,0235 |
| 20 | 0,0085 |
| 21 | 0,0310 |
| 22 | 0,0007 |
| 23 | 0,0080 |
| 24 | 0,0260 |
| 25 | 0,0650 |
| 26 | 0,0185 |
| 27 | 0,0125 |
| 28 | 0,0480 |
| 29a | 0,0255 |
| 29b | 0,0115 |
| 30 | 0,0090 |
| 31 | 0,0155 |
| 32 | 0,0105 |
| 33 | 0,0125 |
| 34 | 0,0195 |
| 35 | 0,041 |
| 36 | 0,0315 |
| 37 | 0,012 |
| 39 | 0,047 |
| 40 | 0,020 |
| 41 | 0,006 |
| 42 | 0,462 |
| 43 | 0,840 |
| 44 | 0,028 |
| 45 | 0,210 |
| 48 | 0,002 |
| 49 | 0,015 |
| 50 | 0,141 |
| 51 | 0,510 |
| 52 | 0,014 |
| 53 | 0,040 |
| 54 | 0,031 |
| 55 | 1.30 pM |
| 57 | 0,585 |
| 60 | 0,035 |
| 61 | 0,867 |
| 62 | 0,019 |
| 63 | 0,687 |
| 64 | 0,002 |
| 65 | 0,121 |
| 66 | 0,003 |
| 68 a) | 0,070 |
| 68 b) | 0,226 |
| 69 | 0,015 |
| 70 | 0,015 |
| 71 | 0,007 |
| 72 | 0,0125 |
| 73 | 0,019 |
| 74 | 0,0105 |
| 75 | 0,0026 |
| 76 | 0,0085 |
| 77 | 0,0525 |
| 78 | 0,0035 |
| 79 | 0,001 |
| 80 | 0,007 |
| 81 a) | 0,558 |
| 82 a) | 0,064 |
| 91 | 0,021 |
| 92 | 0,0225 |
| 94 | 0,0245 |
| 96 a) | 0,0305 |
| 100 a) | 0,005 |
| 102 | 0,0025 |
| 103 a) | 0,022 |
| 103 b) | 0,088.5 |
| 104 | 0,020 |
| 105 | 0,054.5 |
| 106 a) | 0,022 |
| 106 b) | 0,188 |
| 108 | 0,0065 |
| 109 | 0,0035 |
| 110 | 0,004 |
| 112 a) | 0,0008 |

We claim:

1. A compound of formula I

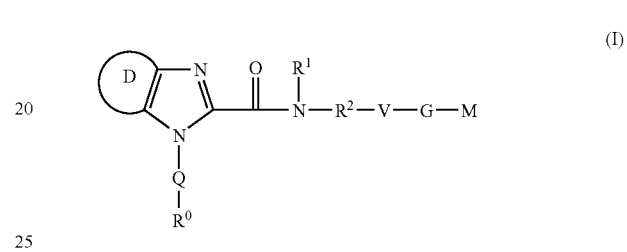

wherein

R⁰ is 1) a heterocyclyl selected from the group consisting of benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl and 1,4,5,6-tetrahydro-pyridazinyl, wherein the heterocyclyl is unsubstituted or mono-, di- or trisubstituted independently of one another by R8, or 2) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen that is unsubstituted or mono-, di- or trisubstituted independently of one another by R8;

R8 is 1) halogen,
2) —NO₂,
3) —CN,
4) —C(O)—NH₂,
5) —OH,
6) —NH₂,
7) —O—CF₃
8) a monocyclic or bicyclic 6- to 14-membered aryl, wherein the aryl is mono-, di- or trisubstituted independently of one another by halogen or —O—(C₁-C₈)-alkyl,
9) —(C₁-C₈)-alkyl, wherein the alkyl is unsubstituted or mono-, di- or trisubstituted independently of one another by halogen, NH₂, —OH or methoxy,
10) —O—(C₁-C₈)-alkyl, wherein alkyl is unsubstituted or mono-, di- or trisubstituted independently of one another by halogen, NH₂, —OH or methoxy, 11) —SO$_2$—CH$_3$ or
12) —SO$_2$—CF$_3$,
the substructure

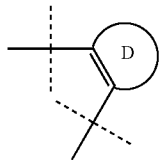

in formula I is a 4-to 8 membered saturated, partially unsaturated or aromatic cyclic group containing zero, 1, 2, 3 or 4 heteroatoms chosen from nitrogen, sulfur or oxygen and is unsubstituted or substituted 1, 2, 3, 4, 5 or 6 times by R3 or is substituted 1 or 2 times by =O;

Q is —(C$_0$-C$_2$)-alkylene-C(O)—NR$^{10}$—, —NR$^{10}$—C(O)—NR$^{10}$—, —NR$^{10}$—C(O)—, —SO$_2$—, methylene, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—S—(CH$_2$)$_n$—, —(CH$_2$)$_m$—C(O)—(CH$_2$)$_n$—, —(CH$_2$)$_m$—SO$_2$—NR$^{10}$—(CH$_2$)$_n$—, —(CH$_2$)$_m$—NR$^{10}$—SO$_2$—(CH$_2$)$_n$—, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—O—C(O)—NR$^{10}$—(CH$_2$)$_n$—, —(C$_2$-C$_3$)-alkylene-O—(C$_0$-C$_3$)-alkylene-, —(C$_2$-C$_3$)-alkylene—S(O)—, —(C$_2$-C$_3$)-alkylene-S(O)$_2$—, —(CH$_2$)$_m$—NR$^{10}$—C(O)—O—(CH$_2$)$_n$—, —(C$_2$-C$_3$)-alkylene-S(O)$_2$—NH—(R$^{10}$)—,
—(C$_2$-C$_3$)-alkylene-N(R$^{10}$)— or —(C$_0$-C$_3$)-alkylene-C(O)—O—(CH$_2$)$_m$—,
wherein —(CH$_2$)$_m$— or —(CH$_2$)$_n$— are alkylene that is unsubstituted or mono-, di- or trisubstituted independently of one another by halogen, —NH$_2$ or —OH, or —(C$_3$-C$_6$)-cycloalkylene, that is unsubstituted or mono-, di- or trisubstituted independently of one another by halogen, —NH$_2$ or —OH;

R$^1$ is hydrogen, —(C$_1$-C$_4$)-alkyl, wherein the alkyl is unsubstituted or substituted one to three times by R13, —(C$_1$-C$_3$)-alkylene-C(O)—NH—R$^0$, —(C$_1$-C$_3$)-alkylene-C(O)—O—R$^{15}$, a monocyclic or bicyclic 6- to 14-membered aryl, wherein the aryl is mono-, di- or trisubstituted independently of one another by R8, a monocyclic or bicyclic 4- to 15-membered heterocyclyl, containing one, two, three or four heteroatoms chosen from nitrogen, sulfur or oxygen, —(C$_1$-C$_3$)-perfluoroalkylene, —(C$_1$-C$_3$)-alkylene -S(O)—(C$_1$-C$_4$)-alkyl, —(C$_1$-C$_3$)-alkylene-S(O)$_2$—(C$_1$-C$_3$)-alkyl, —(C$_1$-C$_3$)-alkylene-S(O)$_2$—N(R$^{4'}$)—R$^{5'}$, —(C$_1$-C$_3$)-alkylene-O—(C$_1$-C$_4$)-alkyl, —(C$_0$-C$_3$)-alkylene-(C$_3$-C$_8$)-cycloalkyl, or —(C$_0$-C$_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R$^{4'}$ and R$^{5'}$ are independent of one another are identical or different and are hydrogen or —(C$_1$-C$_4$)-alkyl,
R$^2$ is a direct bond;
R14 is halogen, —OH, =O, —(C$_1$-C$_8$)-alkyl, —(C$_1$-C$_4$)-alkoxy, —NO$_2$, —C(O)—OH, —CN, —NH$_2$, —C(O)—O—(C$_1$-C$_4$)-alkyl, —(C$_0$-C$_8$)-alkyl—SO$_2$—(C$_1$-C$_4$)-alkyl, —(C$_0$-C$_8$)-alkyl—SO$_2$—(C$_1$-C$_3$)-perfluoroalkyl, —(C$_0$-C$_8$)-alkyl—SO$_2$-N(R$^{18}$)—R$^{21}$, —C(O)—NH—(C$_1$-C$_8$)-alkyl, —C(O)—N—[(C$_1$-C$_8$)-alkyl]$_2$, —NR$^{18}$—C(O)—NH—(C$_1$-C$_8$)-alkyl, —C(O)—NH$_2$, —S—R$^{18}$, or —NR$^{18}$—C(O)—NH—[(C$_1$-C$_8$)-alkyl]$_2$,
wherein R$^{18}$ and R$^{21}$ are independently from each other hydrogen, —(C$_1$-C$_3$)-perfluoroalkyl or —(C$_1$-C$_6$)-alkyl, V is 1) a 6- to 14-membered aryl, wherein the aryl is unsubstituted or mono-, di- or trisubstituted independently of one another by R14, or
2) a heterocyclyl selected from the group consisting of acridinyl, 8-aza-bicyclo[3.2.1]oct-3-yl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,4-triazolyl, 1,2,5-triazolyl, 1,3,4-triazolyl and xanthenyl, wherein the heterocyclyl is unsubstituted or mono-, di- or trisubstituted independently of one another by R14;

G is a direct bond, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—, —(CH$_2$)$_m$—O—(CH$_2$)$_n$—, —(CH$_2$)$_m$—C(O)—NR$^{10}$—(CH$_2$)$_n$—, —(CH$_2$)—SO$_2$—(CH$_2$)$_n$—, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—C(O)—(CH$_2$)$_n$—, —(CH$_2$)—S—(CH$_2$)$_n$—, —(CH$_2$)$_m$—SO$_2$—NR$^{10}$—(CH$_2$)$_n$—, —(CH$_2$)$_m$—NR$^{10}$—SO$_2$—

$-(CH_2)_n-$, $-(CH_2)_m-NR^{10}-$, $-(CH_2)_m-O-C(O)-NR^{10}-(CH_2)_n-$ or $-(CH_2)_m-NR^{10}-C(O)-O-(CH_2)_n-$;

n and m are independently of one another identical or different and are zero, 1, 2, 3, 4, 5 or 6;

M is 1) hydrogen,
2) $-(C_1-C_8)$-alkyl, wherein the alkyl is unsubstituted or mono-, di- or trisubstituted independently of one another by R14,
3) $-C(O)-N(R11)-R12$,
4) $-(CH_2)_m-NHR^{10}$,
5) a 6- to 14-membered aryl, wherein the aryl is unsubstituted or mono-, di- or trisubstituted independently of one another by R14,
6) a monocyclic or bicyclic 4- to 15-membered heterocyclyl, wherein the heterocyclyl is unsubstituted or mono-, di- or trisubstituted independently of one another by R14,
7) $-(C_3-C_8)$-cycloalkyl, wherein the cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein the cyclic residue is unsubstituted or mono-, di- or trisubstituted independently of one another by R14;

R3 is 1) hydrogen,
2) halogen,
3) $-(C_1-C_4)$-alkyl, wherein the alkyl is unsubstituted or mono-, di- or trisubstituted independently of one another by R13,
4) $-(C_1-C_3)$-perfluoroalkyl,
5) phenyl, wherein the phenyl is unsubstituted or mono-, di- or trisubstituted independently of one another by R13,
6) $-(C_0-C_4)$-alkylene-O—R19,
7) $-NO_2$,
8) $-CN$,
9) $-SO_s-R^{11}$, wherein s is 1 or 2,
10) $-SO_t-N(R^{11})-R^{12}$, wherein t is 1 or 2,
11) $-(C_0-C_4)$-alkylene-C(O)—$R^{11}$,
12) $-(C_0-C_4)$-alkylene-C(O)—O—$R^{11}$,
13) $-(C_0-C_4)$-alkylene-C(O)—N($R^{11}$)—$R^{12}$,
14) $-(C_0-C_4)$-alkylene-N($R^{11}$)—$R^{12}$,
15) $-NR^{10}-SO_2-R^{10}$,
16) $-S-R^{10}$,
17) $-(C_0-C_2)$alkylene-C(O)—O—$(C_2-C_4)$-alkylene-O—C(O)—$(C_1-C_4)$-alkyl,
18) $-C(O)-O-C(R15, R16)-O-C(O)-R17$,
19) $-(C_0-C_2)$alkylene-C(O)—O—$(C_2-C_4)$-alkylene-O—C(O)—O—$(C_1-C_6)$-alkyl,
20) $-C(O)-O-C(R15, R16)-O-C(O)-O-R17$,
21) $-(C_0-C_4)$-alkylene-$(C_6-C_{14})$-aryl, wherein the aryl is mono-, di- or trisubstituted independently of one another by R13,
22) $-(C_0-C_4)$-alkylene-$(C_4-C_{15})$-heterocyclyl, wherein the heterocyclyl is unsubstituted or mono-, di- or trisubstituted independently of one another by R13
23) $-(C_0-C_4)$-alkylene-$(C_3-C_8)$-cycloalkyl, wherein the cycloalkyl is unsubstituted or mono-, di- or trisubstituted independently of one another by R13,
24) $-(C_0-C_4)$-alkylene-het, wherein the het is unsubstituted or mono-, di- or trisubstituted independently of one another by R13,
25) $-(C_0-C_4)$-alkylene-O—$CH_2$—$(C_1-C_3)$-perfluoroalkylene-$CH_2$—O—$(C_1-C_4)$-alkyl,
26) $-SO_w-N(R^{11})-R^{13}$, wherein w is 1 or 2,
27) $-(C_0-C_4)$-alkylene-C(O)—N($R^{11}$)—$R^{13}$,
28) $-(C_0-C_4)$-alkylene-N($R^{11}$)—$R^{13}$, or
29) a residue selected from the group consisting of

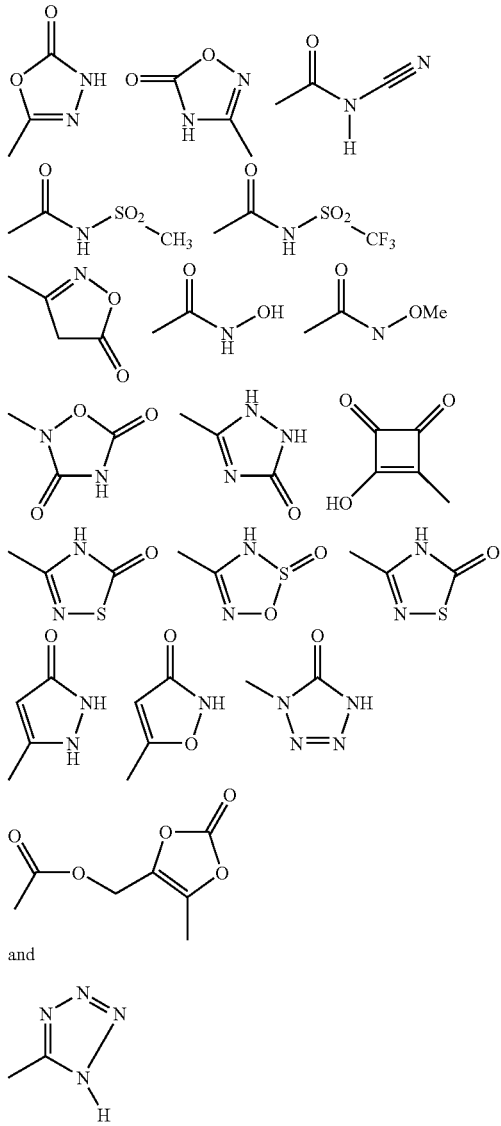

and wherein Me is methyl;

R19 is a) hydrogen,
b) $-(C_1-C_4)$-alkyl, wherein alkyl is unsubstituted or mono-, di- or trisubstituted independently of one another by R13, or
c) phenyl, wherein the phenyl is unsubstituted or mono-, di- or trisubstituted independently of one another by R13,
d) $-CF_3$, or
e) $-CHF_2$, or two —OR19 residues and adjacent atoms through which they are attached form together with the atoms which they are attached to a 5- or 6- membered ring, which is unsubstituted or substituted one, two, three or four times by R13;

R11 and R12 are independently of one another identical or different and are 1) hydrogen,
2) —($C_1$-$C_6$)-alkyl, wherein the alkyl is unsubstituted or mono-, di- or trisubstituted independently of one another by R13,
3) —($C_0$-$C_6$)-alkyl-($C_3$-$C_8$)-cycloalkyl,
4) —$SO_t$-$R^{10}$, wherein t is 1 or 2,
5) —($C_0$-$C_6$)-alkyl-($C_6$-$C_{14}$)-aryl, wherein the alkyl and aryl independently from one another are unsubstituted or mono-, di- or trisubstituted by R13,
6) —($C_1$-$C_3$)-perfluoroalkyl,
7) —O—$R^{17}$, or
8) —($C_0$-$C_6$)-alkyl—($C_4$-$C_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13;

R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$,
—($C_3$-$C_8$)-cycloalkyl, —($C_0$-$C_3$)-alkylene-O—$R^{10}$, —Si—($CH_3$)$_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$-$C_8$)-alkyl, —($C_1$-$C_8$)-alkoxy, phenyl, phenyloxy, —O—$CF_3$,
—($C_0$-$C_4$)-alkyl-C(O)—O—C(R15, R16)—O—C(O)—R17, —($C_1$-$C_4$)-alkoxy-phenyl, —($C_0$-$C_4$)-alkyl-C(O)—O—C(R15, R16)—O—C(O)—O—R17, —($C_1$-$C_3$)-perfluoroalkyl, —O—R15, —NH—C(O)—NH—$R^{10}$, —NH—C(O)—O—$R^{10}$, or a residue selected from the group consisting of

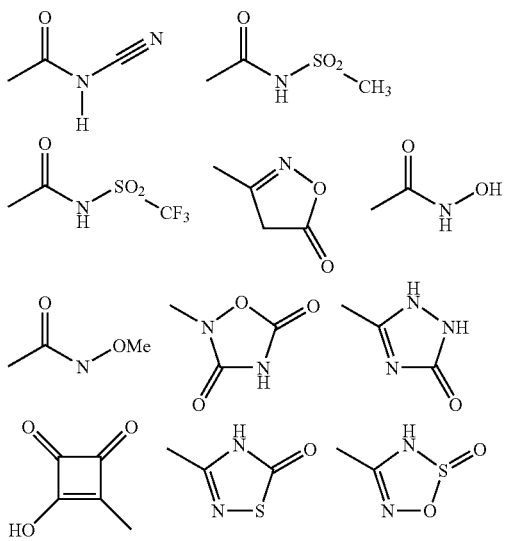

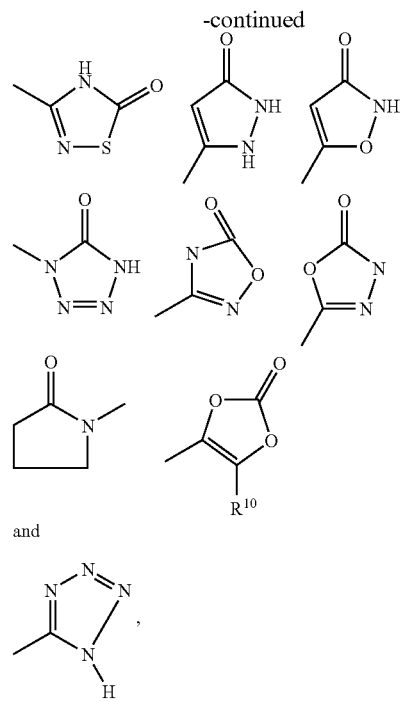

and wherein Me is methyl;
$R^{10}$ and $R^{20}$ are independently of one another hydrogen, —($C_1$-$C_6$)-alkyl, —($C_0$-$C_4$)-alkyl-OH, —($C_0$-$C_4$)-alkyl-O—($C_1$-$C_4$)-alkyl or —($C_1$-$C_3$)-perfluoroalkyl;
R15 and R16 are independently of one another hydrogen, —($C_1$-$C_6$)-alkyl, or together with the carbon atom to which they are bonded they can form a 3- to 6 membered carbocyclic ring which is unsubstituted or substituted one to three times by $R^{10}$; and
R17 is —($C_1$-$C_6$)-alkyl, —($C_1$-$C_6$)-alkyl-OH, —($C_1$-$C_6$)-alkyl-O—($C_1$-$C_4$)-alkyl, —($C_3$-$C_8$)-cycloalkyl, —($C_1$-$C_6$)-alkyl-O—($C_1$-$C_8$)-alkyl—($C_3$-$C_8$)-cycloalkyl, or —($C_1$-$C_6$)-alkyl-($C_3$-$C_8$)-cycloalkyl, wherein the cycloalkyl is unsubstituted or substituted one, two or three times by —OH, —O—($C_1$-$C_4$)-alkyl or $R^{10}$;
or a stereoisomer or a mixture of stereoisomers thereof in any ratio, or a physiologically tolerable salt thereof.

2. The compound according to claim 1, wherein the compound is
1-[5-(5-Chloro-thiophen-2-yl)-isoxazol-3-ylmethyl]-1H-benzoimidazole-2-carboxylic acid (1-isopropyl-piperidin-4-yl)-amide,
1-[(5-Chloro-pyridin-2-ylcarbamoyl)-methyl]-1H-benzoimidazole-2-carboxylic acid (1-isopropyl-piperidine4-yl)-amide,
1-[5-(5-Chloro-thiophen-2-yl)-isoxazol-3-ylmethyl]-1H-benzoimidazole-2-carboxylic acid (1-pyrimidine-4-yl-piperidine4-yl)-amide,
1-[5-(5-Chloro-thiophen-2-yl)-isoxazol-3-ylmethyl]-2-(1-isopropyl-piperidin-4-ylcarbamoyl)-1H-benzoimidazole-5-carboxylic acid methyl ester,
3-[5-(5-Chloro-thiophen-2-yl)-isoxazol-3-ylmethyl]-2-(1-isopropyl-piperidin-4-ylcarbamoyl)-3H-benzoimidazole-5-carboxylic acid methyl ester,
1-[5-(5-Chloro-thiophen-2-yl)-isoxazol-3-ylmethyl]-2-(1-isopropyl-piperidin-4-ylcarbamoyl)-1H-benzoimidazole-5-carboxylic acid, 3-[5-(5-Chloro-thiophen-2-yl)-isoxazol-3-ylmethyl]-2-(1-isopropyl-piperidin-4-ylcarbamoyl)-3H-benzoimidazole-5-carboxylic acid, 1-[2-(5-Chloro-thiophen-2-yl)-thiazol-5-ylmethyl]-2-(1-isopropyl-piperidin4-ylcarbamoyl)-1H-benzoimidazole-5-carboxylic acid methyl ester, 3-[2-(5-Chloro-thiophen-2-yl)-thiazol-5-ylmethyl]-2-(1-isopropyl-piperidin4-ylcarbamoyl)-3H-benzoimidazole-5-carboxylic acid methyl ester, 1-[2-(5-Chloro-thiophen-2-yl)-thiazol-5-ylmethyl]-2-(1-isopropyl-piperidin4-ylcarbamoyl)-1H-benzoimidazole-5-carboxylic acid, 3-[2-(5-Chloro-thiophen-2-yl)-thiazol-5-ylmethyl]-2-(1-isopropyl-piperidin4-ylcarbamoyl)-3H-benzoimidazole-5-carboxylic acid, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid methyl ester, 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid methyl ester, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid, 3-[5-(5-Chloro-thiophen-2-yl)-isoxazol-3-ylmethyl]-2-(1-isopropyl-piperidin-4-ylcarbamoyl)-3H-benzoimidazole-4-carboxylic acid, 3-[5-(5-Chloro-thiophen-2-yl)-isoxazol-3-ylmethyl]-3H-imidazo[4,5-b]pyridine-2-carboxylic acid (1-isopropyl-piperidin-4-yl)-amide, 1-[(5-Chloro-pyridin-2-ylcarbamoyl)-methyl]-2-(1-isopropyl-piperidin-4-ylcarbamoyl)-1H-benzoimidazole-4-carboxylic acid methyl ester, 1-[(5-Chloro-pyridin-2-ylcarbamoyl)-methyl]-2-(1-isopropyl-piperidin-4-ylcarbamoyl)-1H-benzoimidazole-4-carboxylic acid, 1-[(5-Chloro-pyridin-2-ylcarbamoyl)-methyl]-2-(1-isopropyl-piperidin-4-ylcarbamoyl)-1H-benzoimidazole-5-carboxylic acid methyl ester, 3-[(5-Chloro-pyridin-2-ylcarbamoyl)-methyl]-2-(1-isopropyl-piperidin-4-ylcarbamoyl)-3H-benzoimidazole-5-carboxylic acid methyl ester, 1-[(5-Chloro-pyridin-2-ylcarbamoyl)-methyl]-2-(1-isopropyl-piperidin-4-ylcarbamoyl)-1H-benzoimidazole-5-carboxylic acid, 3-[(5-Chloro-pyridin-2-ylcarbamoyl)-methyl]-2-(1-isopropyl-piperidin-4-ylcarbamoyl)-3H-benzoimidazole-5-carboxylic acid, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-ethoxycarbonyloxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 1-cyclohexyloxycarbonyloxy-ethyl ester, 1-[5-(5-Chloro-thiophen-2-yl)-isoxazol-3-ylmethyl]-1H-benzoimidazole-2,4-dicarboxylic acid 4-[(2-hydroxy-ethyl)-amide]2-[(1-isopropyl-piperidin-4-yl)-amide], 1-[5-(5-Chloro-thiophen-2-yl)-isoxazol-3-ylmethyl]-4-(3-hydroxy-azetidine-1-carbonyl)-1H-benzoimidazole-2-carboxylic acid (1-isopropyl-piperidin-4-yl)-amide, 1-[5-(5-Chloro-thiophen-2-yl)-isoxazol-3-ylmethyl]-1H-benzoimidazole-2,4-dicarboxylic acid 4-[(2-hydroxy-ethyl)-methyl-amide]-2-[(1-isopropyl-piperidin-4-yl)-amide], 1-[5-(5-Chloro-thiophen-2-yl)-isoxazol-3-ylmethyl]-1H-benzoimidazole-2,5-dicarboxylic acid 5-[(2-hydroxy-ethyl)-methyl-amide]2-[(1-isopropyl-piperidin-4-yl)-amide], 1-[5-(5-Chloro-thiophen-2-yl)-isoxazol-3-ylmethyl]-5-(3-hydroxy-azetidine-1-carbonyl)-1H-benzoimidazole-2-carboxylic acid (1-isopropyl-piperidin-4-yl)-amide, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-ethoxycarbonyloxy-ethyl ester, 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 1-cyclohexyloxycarbonyloxy-ethyl ester, 1-[5-(5-Chloro-thiophen-2-yl)-isoxazol-3-ylmethyl]-5-(2-hydroxy-ethanesulfonyl)-1H-benzoimidazole-2-carboxylic acid (1-isopropyl-piperidin-4-yl)-amide, 1-[5-(5-Chloro-thiophen-2-yl)-isoxazol-3-ylmethyl]-6-(2-hydroxy-ethanesulfonyl)-1H-benzoimidazole-2-carboxylic acid (1-isopropyl-piperidin-4-yl)-amide, 1-[(5-Chloro-pyridin-2-ylcarbamoyl)-methyl]-1H-benzoimidazole-2,4-dicarboxylic acid 4-[(2-hydroxy-ethyl)-amide]2-[(1-isopropyl-piperidin-4-yl)-amide], 1-[(5-Chloro-pyridin-2-ylcarbamoyl)-methyl]-1H-benzoimidazole-2,4-dicarboxylic acid 4-[(2-hydroxy-ethyl)-methyl-amide]2-[(1-isopropyl-piperidin-4-yl)-amide], 1-[(5-Chloro-pyridin-2-ylcarbamoyl)-methyl]-4-(3-hydroxy-azetidine-1-carbonyl)-1H-benzoimidazole-2-carboxylic acid (1-isopropyl-piperidin-4-yl)-amide, 1-[(5-Chloro-pyridin-2-ylcarbamoyl)-methyl]-2-(1-isopropyl-piperidin-4-ylcarbamoyl)-1H-benzoimidazole-4-carboxylic acid 1-ethoxycarbonyloxy-ethyl ester, 1-[(5-Chloro-pyridin-2-ylcarbamoyl)-methyl]-2-(1-isopropyl-piperidin-4-ylcarbamoyl)-1H-benzoimidazole-4-carboxylic acid 1-cyclohexyloxycarbonyloxy-ethyl ester, 1-[(5-Chloro-pyridin-2-ylcarbamoyl)-methyl]-1H-benzoimidazole-2-carboxylic acid [4-(3-oxo-morpholin-4yl)-phenyl]-amide, 1-[(5-Chloro-pyridin-2-ylcarbamoyl)-methyl]-2-[4-(3-oxo-morpholin-4-yl)-phenylcarbamoyl]-H-benzoimidazole-4-carboxylic acid methyl ester, 1-[5-(5-Chloro-thiophen-2-yl)-isoxazol-3-ylmethyl]-1H-benzoimidazole-2-carboxylic acid [4-(4-oxo-4H-pyridin-1-yl)-phenyl]-amide, 1-[(5-Chloro-pyridin-2-ylcarbamoyl)-methyl]-1H-benzoimidazole-2-carboxylic acid [4-(4-oxo-4H-pyridin-1-yl)-phenyl]-amide, 1-[5-(5-Chloro-thiophen-2-yl)-isoxazol-3-ylmethyl]-1H-benzoimidazole-2-carboxylic acid (8-methyl-8-aza-bicyclo[3.2.1]oct-3-yl)-amide, 1-[5-(5-Chloro-thiophen-2-yl)-isoxazol-3-ylmethyl]-1H-benzoimidazole-2-carboxylic acid [4-(2,4-dioxo-3,4-dihydro-2H-pyrimidin-1-yl)-phenyl]-amide, 1-[5-(5-Chloro-thiophen-2-yl)-isoxazol-3-ylmethyl]-1H-benzoimidazole-2-carboxylic acid [4-(2-oxo-oxazolidin-3-yl)-phenyl]-amide, 1-[(5-Chloro-pyridin-2-ylcarbamoyl)-methyl]-1H-benzoimidazole-2-carboxylic acid [4-(2-oxo-oxazolidin-3-yl)-phenyl]-amide, 1-[(5-Chloro-pyridin-2-ylcarbamoyl)-methyl]-1H-benzoimidazole-2-carboxylic acid [4-(2,4-dioxo-3,4-dihydro-2H-pyrimidin-1-yl)-phenyl]-amide, 1-[5-(5-Chloro-thiophen-2-yl)-isoxazol-3-ylmethyl]-1H-benzoimidazole-2-carboxylic acid [4-(4-oxo-piperidin-1-yl)-phenyl]-amide,
1-[5-(5-Chloro-thiophen-2-yl)-isoxazol-3-ylmethyl]-1H-benzoimidazole-2-carboxylic acid [4-(2-oxo-2H-pyrazin-1-yl)-phenyl]-amide,
1-[(5-Chloro-pyridin-2-ylcarbamoyl)-methyl]-1H-benzoimidazole-2-carboxylic acid [4-(2-oxo-2H-pyrazin-1-yl)-phenyl]-amide,
1-[5-(5-Chloro-thiophen-2-yl)-isoxazol-3-ylmethyl]-1H-benzoimidazole-2-carboxylic acid [4-(2-oxo-piperazin-1-yl)-phenyl]-amide,
1-[(5-Chloro-pyridin-2-ylcarbamoyl)-methyl]-1H-benzoimidazole-2-carboxylic acid [4-(2-oxo-piperazin-1-yl)-phenyl]-amide,
1-[(5-Chloro-pyridin-2-ylcarbamoyl)-methyl]-4-(2-methoxy-ethoxy)-1H-benzoimidazole-2-carboxylic acid [4-(3-oxo-morpholin-4-yl)-phenyl]-amide,
1-[(5-Chloro-pyridin-2-ylcarbamoyl)-methyl]-2-[4-(3-oxo-morpholin-4-yl)-phenylcarbamoyl]-1H-benzoimidazole-4-carboxylic acid,
1-[(5-Chloro-pyridin-2-ylcarbamoyl)-methyl]-5-(3-hydroxy-azetidine-1-carbonyl)-1H-benzoimidazole-2-carboxylic acid (1-isopropyl-piperidin-4-yl)-amide,
1-[(5-Chloro-pyridin-2-ylcarbamoyl)-methyl]-6-(3-hydroxy-azetidine-1-carbonyl)-1H-benzoimidazole-2-carboxylic acid (1-isopropyl-piperidin-4-yl)-amide,
1-[(5-Chloro-pyridin-2-ylcarbamoyl)-methyl]-1H-benzoimidazole-2,5-dicarboxylic acid 5-[(2-hydroxy-ethyl)-amide]2-[(1-isopropyl-piperidin-4-yl)-amide],
3-[(5-Chloro-pyridin-2-ylcarbamoyl)-methyl]-3H-benzoimidazole-2,5-dicarboxylic acid 5-[(2-hydroxy-ethyl)-amide]2-[(1-isopropyl-piperidin-4-yl)-amide],
1-[(5-Chloro-pyridin-2-ylcarbamoyl)-methyl]-1H-benzoimidazole-2,5-dicarboxylic acid 5-[(2-hydroxy-ethyl)-methyl-amide]-2-[(1-isopropyl-piperidin-4-yl)-amide],
3-[(5-Chloro-pyridin-2-ylcarbamoyl)-methyl]-3H-benzoimidazole-2,5-dicarboxylic acid 5-[(2-hydroxy-ethyl)-methyl-amide]2-[(1-isopropyl-piperidin-4-yl)-amide],
1-[(5-Chloro-pyridin-2-ylcarbamoyl)-methyl]-2-(1-isopropyl-piperidin-4-ylcarbamoyl)-1H-benzoimidazole-5-carboxylic acid 1-cyclohexyloxycarbonyloxy-ethyl ester,
3-[(5-Chloro-pyridin-2-ylcarbamoyl)-methyl]-2-(1-isopropyl-piperidin-4-ylcarbamoyl)-3H-benzoimidazole-5-carboxylic acid 1-cyclohexyloxycarbonyloxy-ethyl ester,
1-[(5-Chloro-pyridin-2-ylcarbamoyl)-methyl]-2-(1-isopropyl-piperidin-4-ylcarbamoyl)-1H-benzoimidazole-5-carboxylic acid 1-ethoxycarbonyloxy-ethyl ester,
3-[(5-Chloro-pyridin-2-ylcarbamoyl)-methyl]-2-(1-isopropyl-piperidin-4-ylcarbamoyl)-3H-benzoimidazole-5-carboxylic acid 1-ethoxycarbonyloxy-ethyl ester,
1-[5-(5-Chloro-thiophen-2-yl)-isoxazol-3-ylmethyl]-2-(1-isopropyl-piperidin-4-ylcarbamoyl)-1H-benzoimidazole-4-carboxylic acid 2-hydroxy-ethyl ester,
3-[5-(5-Chloro-thiophen-2-yl)-isoxazol-3-ylmethyl]-2-(1-isopropyl-piperidin-4-ylcarbamoyl)-3H-benzoimidazole-5-carboxylic acid 2-hydroxy-ethyl ester,
1-[5-(5-Chloro-thiophen-2-yl)-isoxazol-3-ylmethyl]-2-(1-isopropyl-piperidin-4-ylcarbamoyl)-1H-benzoimidazole-4-carboxylic acid carboxymethyl ester,
1-[(5-Chloro-pyridin-2-ylcarbamoyl)-methyl]-5-(2-hydroxy-ethanesulfonyl)-1H-benzoimidazole-2-carboxylic acid (1-isopropyl-piperidin-4-yl)-amide,
1-[(5-Chloro-pyridin-2-ylcarbamoyl)-methyl]-6-(2-hydroxy-ethanesulfonyl)-1H-benzoimidazole-2-carboxylic acid (1-isopropyl-piperidin-4-yl)-amide,
1-[(5-Chloro-pyridin-2-ylcarbamoyl)-methyl]-2-(1-isopropyl-piperidin-4-ylcarbamoyl)-1H-benzoimidazole-4-carboxylic acid cyclopropylmethyl ester,
1-[(5-Chloro-pyridin-2-ylcarbamoyl)-methyl]-2-(1-isopropyl-piperidin-4-ylcarbamoyl)-1H-benzoimidazole-4-carboxylic acid 2-methoxy-ethyl ester,
1-[(5-Chloro-pyridin-2-ylcarbamoyl)-methyl]-4-hydroxymethyl-1H-benzoimidazole-2-carboxylic acid (1-isopropyl-piperidin-4-yl)-amide,
1-[(5-Chloro-pyridin-2-ylcarbamoyl)-methyl]-4-(2-methoxy-ethoxymethyl)-1H-benzoimidazole-2-carboxylic acid (1-isopropyl-piperidin-4-yl)-amide,
1-[(5-Chloro-pyridin-2-ylcarbamoyl)-methyl]-4-(morpholine4-carbonyl)-1H-benzoimidazole-2-carboxylic acid (1-isopropyl-piperidin-4-yl)-amide,
1-[(5-Chloro-pyridin-2-ylcarbamoyl)-methyl]-4-([1,4]oxazepane-4-carbonyl)-1H-benzoimidazole-2-carboxylic acid (1-isopropyl-piperidin-4-yl)-amide,
1-[(5-Chloro-pyridin-2-ylcarbamoyl)-methyl]-4-(2,6-dimethyl-piperidine-1-carbonyl)-1H-benzoimidazole-2-carboxylic acid (1-isopropyl-piperidin-4-yl)-amide,
1-[(5-Chloro-pyridin-2-ylcarbamoyl)-methyl]-4-(4,4-difluoro-piperidine-1-carbonyl)-1H-benzoimidazole-2-carboxylic acid (1-isopropyl-piperidin-4-yl)-amide,
1-[(5-Chloro-pyridin-2-ylcarbamoyl)-methyl]-5-([1,4]oxazepane-4-carbonyl)-1H-benzoimidazole-2-carboxylic acid (1-isopropyl-piperidin-4-yl)-amide,
1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 2-hydroxy-ethyl ester,
1-[5-(5-Chloro-thiophen-2-yl)-isoxazol-3-ylmethyl]-2-(1-isopropyl-piperidin-4-ylcarbamoyl)-1H-benzoimidazole-5-carboxylic acid carboxymethyl ester,
1-[5-(5-Chloro-thiophen-2-yl)-isoxazol-3-ylmethyl]4-(3-methoxy-azetidine-1-carbonyl)-1H-benzoimidazole-2-carboxylic acid (1-isopropyl-piperidin-4-yl)-amide,
1-(5-Chloro-benzo[b]thiophen-2-ylmethyl)-2-(1-isopropyl-piperidin-4-ylcarbamoyl)-1H-benzoimidazole-4-carboxylic acid,
3-(5-Chloro-benzo[b]thiophen-2-ylmethyl)-2-(1-isopropyl-piperidin-4-ylcarbamoyl)-3H-benzoimidazole-4-carboxylic acid,
1-(5-Chloro-1H-indazol-3-ylmethyl)-2-(1-isopropyl-piperidin-4-ylcarbamoyl)-1H-benzoimidazole-4-carboxylic acid,
1-[5-(5-Chloro-thiophen-2-yl)-isoxazol-3-ylmethyl]-4-(4-hydroxy-piperidine-1-carbonyl)-1H-benzoimidazole-2-carboxylic acid (1-isopropyl-piperidin-4-yl)-amide,
7-[5-(5-Chloro-thiophen-2-yl)-isoxazol-3-ylmethyl]-1,3-dimethyl-2,6-dioxo-2,3,6,7-tetrahydro-1H-purine-8-carboxylic acid (1-isopropyl-piperidin-4-yl)-amide,
1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid methyl ester,
3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid methyl ester,
1-[5-(5-Chloro-thiophen-2-yl)-isoxazol-3-ylmethyl]-2-(1-cyclopropyl-piperidin4-ylcarbamoyl)-1H-benzoimidazole-5-carboxylic acid,
3-[5-(5-Chloro-thiophen-2-yl)-isoxazol-3-ylmethyl]-2-(1-cyclopropyl-piperidin-4-ylcarbamoyl)-3H-benzoimidazole-5-carboxylic acid, 1-[5-(5-Chloro-thiophen-2-yl)-isoxazol-3-ylmethyl]-2-(1-cyclopropyl-piperidin-4-ylcarbamoyl)-1H-benzoimidazole-4-carboxylic acid, 3-[5-(5-Chloro-thiophen-2-yl)-isoxazol-3-ylmethyl]-2-(1-cyclopropyl-piperidin-4-ylcarbamoyl)-3H-benzoimidazole-4-carboxylic acid, 1-[(5-Chloro-pyridin-2-ylcarbamoyl)-methyl]-2-(1-cyclopropyl-piperidin-4-ylcarbamoyl)-1H-benzoimidazole-4-carboxylic acid methyl ester, 1-[(5-(-Chloro-pyridin-2-ylcarbamoyl)-methyl]-2-(1-cyclopropyl-piperidin-4-ylcarbamoyl)-1H-benzoimidazole-4-carboxylic acid, 1-[(5-(-Chloro-pyridin-2-ylcarbamoyl)-methyl]-2-(1-cyclopropyl-piperidin-4-ylcarbamoyl)-1H-benzoimidazole-4-carboxylic acid cyclopropylmethyl ester, 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid, 3-[5-(5-Chloro-thiophen-2-yl)-isoxazol-3-ylmethyl]-2-(1-isopropyl-piperidin-4-ylcarbamoyl)-3H-thieno[3,4-d]imidazole-4-carboxylic acid, 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-6-carboxylic acid, 3-[5-(5-Chloro-thiophen-2-yl)-isoxazol-3-ylmethyl]-2-(1-cyclopropyl-piperidin-4-ylcarbamoyl)-3H-thieno[3,4-d]imidazole-4-carboxylic acid, 3-[5-(5-Chloro-thiophen-2-yl)-isoxazol-3-ylmethyl]-3H-thieno[3,4-d]imidazole-2,6-dicarboxylic acid 6-[(2-hydroxy-ethyl)-amide]2-[(1-isopropyl-piperidin-4-yl)-amide], 3-[(5-Chloro-pyridin-2-ylcarbamoyl)-methyl]-2-(1-isopropyl-piperidin-4-ylcarbamoyl)-3H-thieno[3,4-d]imidazole-6-carboxylic acid, 3-[(5-Chloro-pyridin-2-ylcarbamoyl)-methyl]-2-(1-isopropyl-piperidin-4-ylcarbamoyl)-3H-thieno[3,4-d]imidazole-4-carboxylic acid, 3-[(5-Chloro-pyridin-2-ylcarbamoyl)-methyl]-6-([1,4]oxazepane-4-carbonyl)-3H-thieno[3,4-d]imidazole-2-carboxylic acid (1-isopropyl-piperidin-4-yl)-amide, 3-[5-(5-Chloro-thiophen-2-yl)-isoxazol-3-ylmethyl]-2-(1-isopropyl-piperidin-4-ylcarbamoyl)-6-(2,2,2-trifluoro-ethoxy)-3H-thieno[3,4-d]imidazole-4-carboxylic acid methyl ester, 1-[3-(5-Chloro-thiophen-2-yl)-isoxazol-5-ylmethyl]-2-(1-cyclopropyl-piperidin-4-ylcarbamoyl)-1H-benzoimidazole-5-carboxylic acid, 3-[3-(5-Chloro-thiophen-2-yl)-isoxazol-5-ylmethyl]-2-(1-cyclopropyl-piperidin-4-ylcarbamoyl)-3H-benzoimidazole-5-carboxylic acid, 1-[5-(5-Chloro-thiophen-2-yl)-[1,3,4]thiadiazol-2-ylmethyl]-2-(1-cyclopropyl-piperidin-4-ylcarbamoyl)-1H-benzoimidazole-5-carboxylic acid, 3-[5-(5-Chloro-thiophen-2-yl)-[1,3,4]thiadiazol-2-ylmethyl]-2-(1-cyclopropyl-piperidin-4-ylcarbamoyl)-3H-benzoimidazole-5-carboxylic acid, 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide, 1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide, 1-[(5-Chloro-pyridin-2-ylcarbamoyl)-methyl]-4-(2-hydroxy-ethoxy)-1H-benzoimidazole-2-carboxylic acid (1-isopropyl-piperidin-4-yl)-amide, 1-[(5-Chloro-pyridin-2-ylcarbamoyl)-methyl]-2-[2-fluoro-4-(pyrrolidine-1-carbonyl)-phenylcarbamoyl]-1H-benzoimidazole-4-carboxylic acid methyl ester, 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid, 3-[5-(5-Chloro-thiophen-2-yl)-isoxazol-3-ylmethyl]-2-(1-cyclopropyl-piperidin-4-ylcarbamoyl)-7-methyl-3H-benzoimidazole-5-carboxylic acid, 1-[5-(5-Chloro-thiophen-2-yl)-isoxazol-3-ylmethyl]-5-fluoro-2-(1-isopropyl-piperidin-4-ylcarbamoyl)-1H-benzoimidazole-4-carboxylic acid, 1-[5-(5-Chloro-thiophen-2-yl)-isoxazol-3-ylmethyl]-2-(1-isopropyl-piperidin-4-ylcarbamoyl)-5-(2,2,2-trifluoro-ethoxy)-1H-benzoimidazole-4-carboxylic acid, or 1-[5-(5-Chloro-thiophen-2-yl)-isoxazol-3-ylmethyl]-4-(3-hydroxy-azetidine-1-carbonyl)-5-(2,2,2-trifluoro-ethoxy)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

3. A pharmaceutical composition comprising at least one compound according to claim 1 or a stereoisomer or a mixture of stereoisomers thereof in any ratio, or a physiologically tolerable salt thereof, and a pharmaceutically acceptable carrier.

4. The compound according to claim 1, which is 1-[5-(5-Chloro-thiophen-2-yl)-isoxazol-3-ylmethyl]-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

5. The compound according to claim 1, which is 1-[5-(5-Chloro-thiophen-2-yl)-isoxazol-3-ylmethyl]-2-(1-isopropyl-piperidin-4-ylcarbamoyl)-1H-benzoimidazole-4-carboxylic acid carboxymethyl ester, or a stereoisomer or a mixture of stereoisomers thereof in any ratio, or a physiologically tolerable salt thereof.

6. The compound according to claim 1, which is 1-[(5-Chloro-pyridin-2-ylcarbamoyl)-methyl]-4-hydroxymethyl-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

7. The compound according to claim 1, which is 1-[(5-Chloro-pyridin-2-ylcarbamoyl)-methyl]-4-(2,6-dimethyl-piperidine-1-carbonyl)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

8. The compound according to claim 1, which is 1-[(5-Chloro-pyridin-2-ylcarbamoyl)-methyl]-4-(4,4-difluoro-piperidine-1-carbonyl)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

9. The compound according to claim 1, which is 1-[5-(5-Chloro-thiophen-2-yl)-isoxazol-3-ylmethyl]-2-(1-isopropyl-piperidin-4-ylcarbamoyl)-1H-benzoimidazole-5-carboxylic acid 2-hydroxy-ethyl ester, or a stereoisomer or a mixture of stereoisomers thereof in any ratio, or a physiologically tolerable salt thereof.

10. The compound according to claim 1, which is 1-[5-(5-Chloro-thiophen-2-yl)-isoxazol-3-ylmethyl]-2-(1-isopropyl-piperidin-4-ylcarbamoyl)-1H-enzoimidazole-5-carboxylic acid carboxymethyl ester, or a stereoisomer or a mixture of stereoisomers thereof in any ratio, or a physiologically tolerable salt thereof.

11. The compound according to claim 1, which is 1-[5-(5-Chloro-thiophen-2-yl)-isoxazol-3-ylmethyl]-4-(3-methoxy-azetidine-1-carbonyl)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

12. The compound according to claim 1, which is 7-[5-(5-Chloro-thiophen-2-yl)-isoxazol-3-ylmethyl]-1,3-dimethyl-2,6-dioxo-2,3,6,7-tetrahydro-1H-purine-8-carboxylic acid (1-isopropyl-piperidin-4-yl)-amide, or a stereoisomer or a mixture of stereoisomers thereof in any ratio, or a physiologically tolerable salt thereof.

13. The compound according to claim 1, which is 1-[5-(5-Chloro-thiophen-2-yl)-isoxazol-3-ylmethyl]-2-(1-cyclopropyl-piperidin-4-ylcarbamoyl)-1H-benzoimidazole-5-carboxylic acid, or a stereoisomer or a mixture of stereoisomers thereof in any ratio, or a physiologically tolerable salt thereof.

14. The compound according to claim 1, which is 3-[5-(5-Chloro-thiophen-2-yl)-isoxazol-3-ylmethyl]-2-(1-isopropyl-piperidin-4-ylcarbamoyl)-3H-thieno[3,4-d]imidazole-6-carboxylic acid, or a stereoisomer or a mixture of stereoisomers thereof in any ratio, or a physiologically tolerable salt thereof.

15. The compound according to claim 1, which is 3-[5-(5-Chloro-thiophen-2-yl)-isoxazol-3-ylmethyl]-3H-thieno[3,4-d]imidazole-2,6-dicarboxylic acid 6-[(2-hydroxy-ethyl)-amide]2-[(1-isopropyl-piperidin-4-yl)-amide], or a stereoisomer or a mixture of stereoisomers thereof in any ratio, or a physiologically tolerable salt thereof.

16. The compound according to claim 1, which is 1-[(5-Chloro-pyridin-2-ylcarbamoyl)-methyl]-4-(2-methoxy-ethoxy)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

17. The compound according to claim 1, which is 1-[(5-Chloro-pyridin-2-ylcarbamoyl)-methyl]-4-(2-ethoxy-ethoxy)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

18. The compound according to claim 1, which is 1-[(5-Chloro-pyridin-2-ylcarbamoyl)-methyl]-4-(2-hydroxy-ethoxy)-1H-benzoimidazole-2-carboxylic acid (1-isopropyl-piperidin-4-yl)-amide, or a stereoisomer or a mixture of stereoisomers thereof in any ratio, or a physiologically tolerable salt thereof.

19. The compound according to claim 1, which is 1-[5-(5-Chloro-thiophen-2-yl)-isoxazol-3-ylmethyl]-2-(1-cyclopropyl-piperidin-4-ylcarbamoyl)-7-methyl-1H-benzoimidazole-5-carboxylic acid, or a stereoisomer or a mixture of stereoisomers thereof in any ratio, or a physiologically tolerable salt thereof.

* * * * *